US012343319B2

(12) United States Patent
Bowen et al.

(10) Patent No.: US 12,343,319 B2
(45) Date of Patent: Jul. 1, 2025

(54) COMPOSITIONS AND METHODS FOR TREATMENT OF DISEASES AND DISORDERS

(71) Applicant: Atai Therapeutics Inc., New York, NY (US)

(72) Inventors: Carrie Bowen, Encinitas, CA (US); Glenn F. Short, Encinitas, CA (US); Thomas Cameron Robertson, Encinitas, CA (US)

(73) Assignee: Atai Therapeutics, Inc., New York, NY (US)

( * ) Notice: Subject to any disclaimer, the term of this patent is extended or adjusted under 35 U.S.C. 154(b) by 0 days.

(21) Appl. No.: 18/652,721

(22) Filed: May 1, 2024

(65) Prior Publication Data

US 2024/0366531 A1 Nov. 7, 2024

Related U.S. Application Data

(60) Provisional application No. 63/567,737, filed on Mar. 20, 2024, provisional application No. 63/545,825, filed on Oct. 26, 2023, provisional application No. 63/463,202, filed on May 1, 2023.

(51) Int. Cl.
*A61K 31/137* (2006.01)
*A61P 25/20* (2006.01)
*A61P 25/24* (2006.01)

(52) U.S. Cl.
CPC ............ *A61K 31/137* (2013.01); *A61P 25/20* (2018.01); *A61P 25/24* (2018.01)

(58) Field of Classification Search
CPC ......... A61K 31/137; A61P 25/20; A61P 25/24
USPC ........................................................ 514/654
See application file for complete search history.

(56) References Cited

U.S. PATENT DOCUMENTS

| | | | |
|---|---|---|---|
| 4,239,903 A | 12/1980 | Isoda et al. |
| 5,807,897 A | 9/1998 | Warawa et al. |
| 6,201,025 B1 | 3/2001 | Dax et al. |
| 6,225,352 B1 | 5/2001 | Horwell et al. |
| 9,101,613 B2 | 8/2015 | Laudon et al. |
| 9,720,005 B2 | 8/2017 | McConnell et al. |
| 10,703,711 B2 | 7/2020 | Singh et al. |
| 11,306,059 B2 | 4/2022 | Weeber et al. |
| 11,629,127 B2 | 4/2023 | Weeber et al. |
| 11,827,580 B2 | 11/2023 | Short et al. |
| 11,827,582 B2 | 11/2023 | Singh et al. |
| 11,962,574 B2 | 4/2024 | Proulx et al. |
| 2002/0115715 A1 | 8/2002 | Dax et al. |
| 2003/0079301 A1 | 5/2003 | Sauter et al. |
| 2003/0199497 A1 | 10/2003 | Ruat et al. |
| 2005/0152858 A1 | 7/2005 | Bertz et al. |
| 2007/0099909 A1 | 5/2007 | Chen et al. |
| 2007/0196395 A1 | 8/2007 | Mackerell et al. |
| 2008/0248511 A1 | 10/2008 | Daily et al. |
| 2008/0318957 A1 | 12/2008 | Glinka et al. |
| 2009/0275563 A1 | 11/2009 | Bonaventure |
| 2010/0113539 A1 | 5/2010 | Scott et al. |
| 2010/0130742 A1 | 5/2010 | Harris, III et al. |
| 2012/0028995 A1 | 2/2012 | Ansorge et al. |
| 2012/0283298 A1 | 11/2012 | Crider et al. |
| 2015/0346226 A1 | 12/2015 | Mcconnell et al. |
| 2019/0315689 A1 | 10/2019 | Chen et al. |
| 2020/0325124 A1 | 10/2020 | Lavoie et al. |
| 2021/0052519 A1 | 2/2021 | Singh et al. |
| 2021/0145851 A1 | 5/2021 | Stamets |
| 2021/0315860 A1 | 10/2021 | Hopkins et al. |
| 2021/0403425 A1 | 12/2021 | Bryson |
| 2023/0138118 A1 | 5/2023 | Short et al. |
| 2023/0202965 A1 | 6/2023 | Short et al. |
| 2023/0331658 A1 | 10/2023 | Singh et al. |
| 2024/0254087 A1 | 8/2024 | Wallach et al. |
| 2024/0294461 A1 | 9/2024 | Short et al. |

(Continued)

FOREIGN PATENT DOCUMENTS

| | | |
|---|---|---|
| EP | 0883599 B1 | 6/2002 |
| JP | 2023531311 A | 7/2023 |
| WO | WO-9323364 A1 | 11/1993 |

(Continued)

OTHER PUBLICATIONS

Baker et al., "Neurochemical and neuropharmacological investigation of N-cyanoethyltryptamine, a potential prodrug of tryptamine", Proc West Pharmacol Soc., 1987; 30: 307-11.

Benneyworth et al., "Complex discriminative stimulus properties of (+)lysergic acid diethylamide (LSD) in C57Bl/6J mice," Psychopharmacology (2005) 179, 854-862.

Berge et al., "Pharmaceutical Salts," J. Pharmaceutical Sciences, 66(1), pp. 1-19 (Jan. 1977).

Brandt et al., "Analytical characterization of bioactive N-benzyl-substituted phenethylamines and 5-methoxytryptamines." Rapid Commun., Mass Spectrum, 2015, 29, pp. 573-584.

Carter et al., "Modulating the rate and rhythmicity of perceptual rivalry alternations with the mixed 5-HT2A and 5-HT1A agonist psilocybin," Neuropsychopharmacology, Jun. 2005, pp. 1154-1162.

(Continued)

Primary Examiner — Yevgeny Valenrod
(74) Attorney, Agent, or Firm — COOLEY LLP

(57) ABSTRACT

Provided herein are compounds of Formula (I), Formula (I-A), Formula (I-B), or pharmaceutically acceptable salt thereof, wherein R1, R2, R3, R4, R5, R6, R7, R8, R9, R10, R11, R12, R13, R14 are defined herein. Also provided herein are pharmaceutical compositions comprising a compound of Formula (I), Formula (I-A), Formula (I-B) or pharmaceutically acceptable salt thereof, and methods of using a compound of Formula (I), Formula (I-A), Formula (I-B) or pharmaceutically acceptable salt thereof. The current invention reports compounds to reduce REM sleep and/or non-REM sleep in a subject which can be effective in treating diseases or disorder where sleep is dysregulated. The methods of the disclosure include methods of treating sleep dysfunction, sleep disorder, stress related disorders, neuropsychiatric diseases, neurological conditions and/or neurodevelopmental disorders, using the compound of Formula (I), Formula (I-A), and/or Formula (I-B).

13 Claims, 61 Drawing Sheets

(56) References Cited

U.S. PATENT DOCUMENTS

| | | |
|---|---|---|
| 2024/0300885 A1 | 9/2024 | Short et al. |
| 2024/0366542 A1 | 11/2024 | Khan et al. |

FOREIGN PATENT DOCUMENTS

| | | |
|---|---|---|
| WO | WO-2019084338 A1 | 5/2019 |
| WO | WO-2019089066 A1 | 5/2019 |
| WO | WO-2020037372 A1 | 2/2020 |
| WO | WO-2021025723 A1 | 2/2021 |
| WO | WO-2022006186 A1 | 1/2022 |
| WO | WO-2022212854 A1 | 10/2022 |
| WO | WO-2022241006 A1 | 11/2022 |
| WO | WO-2022261240 A2 | 12/2022 |
| WO | WO-2022261263 A1 | 12/2022 |
| WO | WO-2023114320 A1 | 6/2023 |
| WO | WO-2023129909 A1 | 7/2023 |
| WO | WO-2024124056 A1 | 6/2024 |
| WO | WO-2024138032 A1 | 6/2024 |
| WO | WO-2024138041 A1 | 6/2024 |
| WO | WO-2024192150 A2 | 9/2024 |
| WO | WO-2024229149 | 11/2024 |

OTHER PUBLICATIONS

CAS Registry No. 1152718-19-8, Benzenemethanamine, N-[4-(1,1-dimethylethyl)cyclohexyl]-2,4-difluoro-α-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1,1-dimethylpropyl)cyclohexyl]-2,5-difluoro-, Jun. 9, 2009, 1 page.

CAS Registry No. 127456-43-3, Phenol, 2-[[[4-(1,1-dimethylethyl)cyclohexyl]amino]methyl]-4-(1, 1-dimethylpropyl)-, trans-(9CI), Jun. 1, 1990, 1 page.

CAS Registry No. 127456-44-4, 1H-Inden-5-ol, 6-[[[4-(1,1-dimethylethyl) cyclohexyl]amino]methyl]-2,3-dihydro-, trans-(9CI), Jun. 1, 1990, 1 page.

CAS Registry No. 127456-45-5, Phenol, 4-(1,1-dimethylethyl)-2-[[[4-(1,1-dimethylethyl)cyclohexyl]amino]methyl]-, trans-(9CI), Jun. 1, 1990, 1 page.

CAS Registry No. 127456-46-6, Phenol, 4-(1,1-dimethylethyl)-2-[[[4-(1,1-dimethylethyl)cyclohexyl]amino]methyl]-6-methyl-, hydrochloride, trans-(9CI), Jun. 1, 1990, 1 page.

CAS Registry No. 127456-52-4, Phenol, 2-[[[4-(1,1-dimethylethyl)cyclohexyl]amino]methyl]-4-(1-methylethyl)-, cis-(9CI), Jun. 1, 1990, 1 page.

CAS Registry No. 127456-56-8, Phenol, 4-chloro-2-[[[4-(1,1-dimethylethyl)cyclohexyl]amino]methyl]-, trans-(9CI), Jun. 1, 1990, 1 page.

CAS Registry No. 127456-57-9, Phenol, 2-[[[4-(1,1-dimethylethyl)cyclohexyl]amino]methyl]-4-fluoro-, trans-(9CI), Jun. 1, 1990, 1 page.

CAS Registry No. 1308467-14-2, 1,2-Benzenediol, 3-[[[4-(1,1-dimethylpropyl)cyclohexyl]amino]methyl]-, Jun. 10, 2011, 1 page.

CAS Registry No. 1405571-87-0, Benzenemethanamine, 2-bromo-N-[4-(1,1-dimethylpropyl)cyclohexyl]-5-fluoro-, Nov. 23, 2012, 1 page.

CAS Registry No. 1406541-63-6, Phenol, 2-chloro-4-[[[4-(1,1-dimethylpropyl)cyclohexyl]amino]methyl]-, Nov. 25, 2012, 1 page.

CAS Registry No. 1411655-23-6, Benzenemethanamine, N-[4-(1,1-dimethylpropyl)cyclohexyl]-2,3-difluoro-, Dec. 5, 2012, 1 page.

CAS Registry No. 1456349-79-3, Benzenemethanamine, 2,3-dichloro-N-[4-(1,1-dimethylpropyl)cyclohexyl]-, Oct. 6, 2013, 1 page.

CAS Registry No. 1458497-71-6, Benzenemethanamine, 2,4-dichloro-N-[4-(1,1-dimethylethyl)cyclohexyl]-α-methyl-, Oct. 15, 2013, 1 page.

CAS Registry No. 1459328-13-2, Phenol, 2-bromo-4-[[[4-(1,1-dimethylpropyl)cyclohexyl]amino]methyl]-, Oct. 16, 2013, 1 page.

CAS Registry No. 1490220-45-5, Benzenemethanamine, 2-bromo-5-chloro-N-[4-(1,1-dimethylpropyl)cyclohexyl]-, Dec. 8, 2013, 1 page.

CAS Registry No. 1515984-46-9, Benzamide, N-(4-aminocyclohexyl)-3-chloro-N,5-dimethyl-, Jan. 10, 2014, 1 page.

CAS Registry No. 1542027-51-9, Phenol, 3-chloro-2-[[[4-(1,1-dimethylpropyl)cyclohexyl]amino]methyl]-, Feb. 11, 2014, 1 page.

CAS Registry No. 1624268-56-9, Benzamide, 4-[[[4-(1,1-dimethylethyl)cyclohexyl]amino]methyl]-N-methyl-, Sep. 22, 2014, 1 page.

CAS Registry No. 1712122-27-4, Benzenemethanamine, 5-chloro-N-[4-(1,1-dimethylpropyl)cyclohexyl]-2-fluoro-, May 25, 2015, 1 page.

CAS Registry No. 1772618-27-5, Phenol, 3-[[[4-(1,1-dimethylpropyl)cyclohexyl]amino]methyl]-5-fluoro-, Jun. 3, 2015, 1 page.

CAS Registry No. 1775706-37-0, Phenol, 2-chloro-6-[[[4-(1,1-dimethylpropyl)cyclohexyl]amino]methyl]-, Jun. 8, 2015, 1 page.

CAS Registry No. 1858436-76-6, Bicyclo[3.1.0]hexan-2-amine, N-[(3-chloro-5-methylphenyl)methyl]-, Feb. 3, 2016, 1 page.

CAS Registry No. 1931388-10-1, Benzenemethanamine, 2,5-dichloro-N-[4-(1,1-dimethylpropyl)cyclohexyl]-, Jun. 14, 2016, 1 page.

CAS Registry No. 1939264-55-7, Phenol, 4-[[[4-(1,1-dimethylpropyl)cyclohexyl]amino]methyl]-2-fluoro-, Jun. 26, 2016, 1 page.

CAS Registry No. 1939792-99-0, Benzenemethanamine, 5-bromo-2-chloro-N-[4-(1,1-dimethylpropyl)cyclohexyl]-, Jun. 27, 2016, 1 page.

CAS Registry No. 1962333-15-8, Benzenemethanamine, N-[4-(1,1-dimethylpropyl)cyclohexyl]-5-fluoro-2-methyl-, Jul. 29, 2016, 1 page.

CAS Registry No. 2032268-58-7, Cyclohexanecarboxylic acid, 4-[[(3-chloro-5-methylphenyl)methyl]amino]-, Nov. 15, 2016, 1 page.

CAS Registry No. 2199998-08-6, Cyclohexanecarboxylic acid, 2-[[(3-chloro-5-methylphenyl)methyl]amino]-1-methyl-, Mar. 27, 2018, 1 page.

CAS Registry No. 2202151-69-5, Cyclohexanecarboxylic acid, 3-[[(3-chloro-5-methylphenyl)methyl]amino]-, Mar. 30, 2018, 1 page.

CAS Registry No. 2322790-81-6, Benzenemethanamine, N-[4-(1,1-dimethylethyl)cyclohexyl]-3-(trifluoromethyl)-, Jun. 2, 2019, 1 page.

CAS Registry No. 2419600-39-6, Benzenemethanamine, 3-chloro-N-[4-(1,1-dimethylpropyl)cyclohexyl]-5-methyl-, Jun. 5, 2020, 1 page.

CAS Registry No. 415970-94-4, Benzenemethanamine, N-[4-(1,1-dimethylethyl)cyclohexyl]-3,5-dimethoxy-, May 15, 2002, 1 page.

CAS Registry No. 744981-83-7, Phenol, 2,6-dibromo-4-[[[4-(1,1-dimethylethyl)cyclohexyl]amino]methyl]-, Sep. 15, 2004, 1 page.

CAS Registry No. 793633-39-3, Phenol, 4-(1, 1-dimethylethyl)-2-[[[trans-4-(1,1-dimethylethyl)cyclohexyl]amino]methyl]-6-methyl-, Dec. 6, 2004, 1 page.

Chen, et al., "Structure-activity relationships in a series of 5-[(2, 5-dihydroxybenzyl) amino] salicylate inhibitors of EGF-receptor-associated tyrosine kinase: importance of additional hydrophobic aromatic interactions", Journal of Medicinal Chemistry, Mar. 1994, pp. 845-859.

Cocchi et al., "Novel Psychoactive Phenethylamines: Impact on Genetic Material", International Journal of Molecular Sciences, 2020, 17 pages.

De Barros et al., "Synthesis of 25X-BOMes and 25X-NBOHs (X = H, I, Br) for pharmacological studies and as reference standards for forensic purposes," Tetrahedron Letters, Mar. 2021, 4 pages.

Demarinis, et al., alpha.—Adrenergic agents. 2. Synthesis and. alpha. 1—agonist activity of 2-aminotetralins, Journal of Medicinal Chemistry, Feb. 1982, pp. 136-141.

Glennon et al., "Influence of amine substituents on 5-HT2A versus 5-HT2C binding of phenylalkyl-and indolylalkylamines", Journal of Medicinal Chemistry, 1994, pp. 1929-1935.

Gonzalez-Maeso et al., "Hallucinogens Recruit Specific Cortical 5-HT2A Receptor-Mediated Signaling Pathways to Affect Behavior," Neuron, Feb. 2007, 53, 439-452.

Halberstadt, A. L., "Recent Advances in the Neuropsychopharmacology of Serotonergic Hallucinogens", Behav Brain Res. Jan. 15,

(56) References Cited

OTHER PUBLICATIONS

2015: 277: 99-120. doi: 10.1016/j.bbr.2014.07.016. Epub Jul. 15, 2014. Author manuscript; available in PMC Jan. 15, 2016. 60 pages.
Hamada et al., "Water-soluble prodrugs of dipeptide HIV protease inhibitors based on O-→N intramolecular acyl migration: Design, synthesis and kinetic study", Bioorg Med Chem., Jan. 2004, pp. 159-170.
Hansen et al., "Synthesis and pharmacological evaluation of N-benzyl substituted 4-bromo-2,5-dimethoxyphenethylamines as 5-HT2A/2C partial agonists", Bioorganic & Medicinal Chemistry, 2015, pp. 3933-3937.
Hansen et al., "Synthesis and Structure-Activity Relationships of N-Benzyl Phenethylamines as 5-HT2A/2C Agonists", ACS Chemical Neuroscience, 2014, pp. 243-249.
International Search Report and Written Opinion for International Application No. PCT/US2022/032715 mailed Nov. 17, 2022, 17 pages.
International Search Report and Written Opinion for International Application No. PCT/US2023/085505, mailed Apr. 8, 2024, 11 pages.
International Search Report and Written Opinion for International Application No. PCT/US2023/085521, mailed Apr. 8, 2024, 13 pages.
International Search Report and Written Opinion for International Application No. PCT/US2024/019770, mailed Aug. 12, 2024. 22 pages.
International Search Report and Written Opinion for International Application No. PCT/US23/82981, mailed Apr. 4, 2024. 24 pages.
International Search Report and Written Opinion for PCT Application No. PCT/US2024/027296 mailed Aug. 13, 2024, 18 pages.
International Search Report and Written Opinion for PCT/US2022/082403, mailed May 17, 2023, 15 pages.
Invitation to Pay Fee for International Application No. PCT/US2022/032715 dated Aug. 30, 2022, 2 pages.
Invitation to Pay Fee for International Application No. PCT/US2022/082403 mailed Mar. 8, 2023, 3 pages.
Kaminska et al., "25C-NBOMe short characterization", Forensic Toxicology, 2020, pp. 490-495.
Kehne et al., "Preclinical characterization of the potential of the putative atypical antipsychotic MDL 100,907 as a potent 5-HT2A antagonist with a favorable CNS safety profile." J Pharmacol Exp Ther. May 1996; 277(2): 968-81.
Kennett et al. "SB 242084, a selective and brain penetrant 5-HT2C receptor antagonist", Neuropharmacology, (1997); 36(4-5):609-620.
Klein et al., "Investigation of the Structure-Activity Relationships of Psilocybin Analogues." ACS Pharmacol. Transl. Sci. 2021, 4, 533-542.
Kraehenmann et al., "Dreamlike effects of LSD on waking imagery in humans depend on serotonin 2A receptor activation", Psychopharmacology, 2017, pp. 2031-2046.
Kraehenmann et al., "LSD Increases Primary Process Thinking via Serotonin 2A Receptor Activation", Front. Pharmacol., 2017, 9 pages.
Kucklander, et al., "Darstellung und Oxidation von 2-(2, 5-Dihydroxyphenyl)-ethylamin-Derivaten, II/Synthesis and Oxidation of 2-(2, 5-Dihydroxyphenyl)-ethylamine Derivatives, II", Zeitschrift für Naturforschung B, 1987, pp. 1567-1577 (with English abstract). 12 pages.
Li et al., "Treatment of breast and lung cancer cells with a N-7 benzyl guanosine monophosphate tryptamine phosphoramidate pronucleotide (4Ei-1) results in chemosensitization to gemcitabine and induced eIF4E proteasomal degradation", Mol Pharm., Feb. 2013, pp. 523-531.
Madsen et al., "Psychedelic effects of psilocybin correlate with serotonin 2A receptor occupancy and plasma psilocin levels," Neuropsychopharmacology (2019) 44: 1328-1334.
Milne et al., "Metabolic engineering of Saccharomyces cerevisiae for the de novo production of psilocybin and related tryptamine derivatives", Metabolic Engineering, Jul. 2020, pp. 25-36.

National Center for Biotechnology Information "2-(2,5-Dimethoxy-4-methylsulfanyl-phenyl)-N-[(2-methoxyphenyl)methyl]ethanamine: Pubchem CID 124518722" Pubchem entry (online), Apr. 10, 2017; Retrieved on Feb. 17, 2024 from the Internet: [URL:https://pubchem.ncbi.nlm.nih.gov/compound/124518722]; 13 pages.
National Center for Biotechnology Information 2-[2,5-dimethoxy-4-(methylsulfonimidoyl)phenyl]-N-[(3-fluoro-5-methylphenyl)methyl]ethanamine: Pubchem CID 167226743 Pubchem entry (online), pp. 1-9, Mar. 21, 2023, URL:https://pubchem.ncbi.nlm.nih.gov/compound/167226743.
National Center for Biotechnology Information, "2-(2,5-dimethoxyphenyl)-N-(pyridin-2-ylmethyl)ethanamine: Pubchem CID 39371636" Pubchem entry (online), created May 29, 2009, Modified Oct. 12, 2024, [URL: https://pubchem.ncbi.nlm.nih.gov/compound/39371636]; 7 pages.
National Center for Biotechnology Information "N-[(3-chloro-5-methylphenyl)methyl]-2-[2,5-dimethoxy-4-(methylsulfonimidoyl)phenyl]ethanamine Pubchem CID 167226858" Pubchem entry (online), pp. 1-8, Mar. 21, 2023, URL: https://pubchem.ncbi.nlm.nih.gov/compound/167226858.
National Center for Biotechnology Information "N-benzyl-2,5-dimethoxy-phenethylamine: Pubchem CID 13836160" PubChem entry (online), pp. 1-9, Feb. 8, 2007; URL: https://pubchem.ncbi.nlm.nih.gov/compound/13836160. 9 pages.
Nichols, et al., "Nonneurotoxic tetralin and indan analogs of 3,4-(methylenedioxy) amphetamine (MDA)", Journal of Medicinal Chemistry, Feb. 1990, pp. 703-710.
Nichols, et al., "Potential psychotomimetics. 21. Rigid analogs of 2,5-dimethoxy-4-methylphenylisopropylamine (DOM, STP)", Journal of Medicinal Chemistry, Feb. 1974, pp. 161-166.
Nichols, et al., "Structure-activity relationships of Phyenethylamine hallucinogens", Journal of Pharmaceutical Sciences, Aug. 1981, pp. 839-849.
Nichols, "Hallucinogens", Pharmacol. Ther., 2004, pp. 131-181.
Perez Custodio et al., "25B-NBOMe, a novel N-2-methoxybenzyl-phenethylamine (NBOMe) derivative, may induce rewarding and reinforcing effects via a dopaminergic mechanism: evidence of abuse potential", Addiction Biology, Nov. 2019, 12 pages.
Pokorny et al., Modulatory effect of the 5-HT1A agonist buspirone and the mixed non-hallucinogenic 5-HT1A/2A agonist ergotamine on psilocybin-induced psychedelic experience, Eur. Neuropsychopharmacol., Apr. 2016, pp. 756-766.
Pottie et al., "Identification of psychedelic new psychoactive substances (NPS) showing biased agonism at the 5-HT2AR through simultaneous use of β-arrestin 2 and miniGαq bioassays", Biochem Pharmacol. Dec. 2020: 182: 114251. Epub Sep. 28, 2020. 37 pages.
Poulie et al., "Discovery of β-Arrestin-Biased 25CN-NBOH-Derived 5-HT2A Receptor Agonists." J Med Chem. Sep. 22, 2022; 65(18): 12031-12043. doi:10.1021/acs.jmedchem.2c00702. Epub Sep. 13, 2022.
Preller et al., "Effects of serotonin 2A/1A receptor stimulation on social exclusion processing," PNAS, May 3, 2016, vol. 113, No. 18, 5119-5124.
Preller et al., "Role of the 5-HT2A Receptor in Self- and Other-Initiated Social Interaction in Lysergic Acid Diethylamide-Induced States: A Pharmacological fMRI Study," J. Neurosci., Apr. 2018, 38(14): 3603-3611.
Preller et al., The Fabric of Meaning and Subjective Effects in LSD-Induced States Depend on Serotonin 2A Receptor Activation, Current Biology, Feb. 2017, pp. 451-457.
Pubchem, SID 103414083, Modify Date: Feb. 17, 2021, 7 pages.
Pubchem, SID 103936367, deposit date Jan. 19, 2011. [Retrieved on Mar. 28, 2023]., Retrieved from the Internet [URL: https://pubchem.ncbi.nlm.nih.gov/substance/103936367], 6 pages.
Pubchem, SID 310331158, Modify Date: Feb. 15, 2015, 4 pages.
Pubchem, SID 369863280, Modify Date: May 25, 2018, 5 pages.
Pubchem, SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.
Pubchem SID 387777206, Modify Date: Dec. 6, 2019 Retrieved from the Internet URL: https://pubchem.ncbi.nlm.nih.gov/substance/387777206, 5 pages.

(56) References Cited

OTHER PUBLICATIONS

Pubchem, SID 472180752, Modify Date: Oct. 11, 2022 [retrieved on Feb. 21, 2024]. Retrieved from the Internet URL: https://pubchem.ncbi.nlm.nih.gov/substance/472180752, 5 pages.
Sargent et al., "Radiohalogen-Labeled Imaging Agents. 3. Compounds for Measurement of Brain Blood Flow by Emission Tomography," Journal of Medicinal Chemistry (1984), 27(8), 1071-1077.
Schifano et al., "New psychoactive substances (NPS) and serotonin syndrome onset: A systematic review", Exp Neurol. May 2021: 339: 113638. Epub Feb. 8, 2021. 29 pages.
Tirapegui et al., "Synthesis of N-(halogenated) benzyl analogs of superpotent serotonin ligands," J. Chil. Chem. Soc., (2014) 59, No. 3, pp. 2625-2627.
Titeler et al., "Radioligand binding evidence implicates the brain 5-HT2 receptor as a site of action for LSD and phenylisopropylamine hallucinogens," Psychopharmacology (1988) 94, 213-216.
Tomaszewski et al., "Benzofuran Bioisosteres of Hallucinogenic Tryptamines," J. Med. Chem., 1992, 35, pp. 2061-2064.
Valle et al., "Inhibition of alpha oscillations through serotonin-2A receptor activation underlies the visual effects of ayahuasca in humans", Eur Neuropsychopharmacol. Jul. 2016; 26(7): 1161-75. Epub Mar. 25, 2016.
Vollenweider et al., "Psilocybin induces schizophrenia-like psychosis in humans via a serotonin-2 agonist action," Neuroreport (1998) 9, 3897-3902 (8 pages).
Vollenweider et al., "Psychedelic drugs: neurobiology and potential for treatment of psychiatric disorders," Nature Reviews Neuroscience, Nov. 2020, vol. 21, pp. 611-624.
Winter, J.C. et al., "Psilocybin-induced stimulus control in the rat", Pharmacology Biochemistry and Behavior, 87(4): 472-480. NIH Public Access Author Manuscript; available in PMC Oct. 3, 2007, 18 pages.
Wood et al., "Prevalence of use and acute toxicity associated with the use of NBOMe drugs", Clin Toxicol (Phila). Feb. 2015; 53(2): 85-92. doi:10.3109/15563650.2015.1004179.
Braden M.R., et al., "Molecular Interaction of Serotonin 5-HT2A Receptor Residues Phe339(6.51) and Phe340(6.52) with Superpotent N-Benzyl Phenethylamine Agonists." Molecular Pharmacology, American Society for Pharmacology and Experimental Therapeutics, US, vol. 70, No. 6, Dec. 1, 2006 (Dec. 1, 2006), pp. 1956-1965.
Jensen A.A., et al., "Detailed Characterization of the In Vitro Pharmacological and Pharmacokinetic Properties of N-(2-Hydroxybenzyl)-2,5-Dimethoxy-4-Cyanophenylethylamine (25CN-NBOH), a Highly Selective and Brain-Penetrant 5-HT2A Receptor Agonist." J Pharmacol Exp Ther. Jun. 2017; 361(3): 441-453. doi:10.1124/jpet.117.239905. Epub Mar. 30, 2017.
Leth-Petersen S., et al., "Correlating the Metabolic Stability of Psychedelic 5-HT2A Agonists with Anecdotal Reports of Human Oral Bioavailability." Neurochem Res. Oct. 2014; 39(10): 2018-23. doi: 10.1007/s11064-014-1253-y. Epub Feb. 12, 2014.

REM SLEEP AMOUNT

NREM SLEEP AMOUNT

EFFECT ON WAKING

BRAIN OSCILLATIONS (1-4 Hz) DURING NREM

BRAIN OSCILLATIONS (4-7 Hz) DURING NREM

BRAIN OSCILLATIONS (8-12 Hz) DURING WAKING

BRAIN OSCILLATIONS (50-100 Hz) DURING WAKING

EFFECT ON LOCOMOTION

EFFECT ON BODY TEMPERATURE

EFFECT ON WAKING

EFFECT ON BRAIN OSCILLATION (8-12 Hz) DURING WAKING

EFFECT ON BRAIN OSCILLATION (50-100 Hz) DURING WAKING

EGX-12-1
Plasma concentration vs Receptor occupancy

EC50=584.5 ng/mL with 95% C.I. (461.5, 740.3)

Brain concentration vs Receptor occupancy

EC50=1608.4 ng/g with 95% C.I. (1341.9, 1927.7)

COMPOSITIONS AND METHODS FOR TREATMENT OF DISEASES AND DISORDERS

CROSS-REFERENCE TO RELATED APPLICATIONS

This application claims the benefit of U.S. Provisional Application No. 63/463,202 filed May 1, 2023, U.S. Provisional Application No. 63/545,825 filed Oct. 26, 2023, and U.S. Provisional Application No. 63/567,737 filed Mar. 20, 2024. The disclosures of each of these applications are incorporated herein by reference.

BACKGROUND OF THE INVENTION

Field of the Invention

The present invention generally relates to compounds for the treatment of diseases and/or disorders, and more specifically to using compounds of Formula (I), Formula (I-A), and Formula (I-B), described herein to treat sleep dysfunction, sleep disorders, stress related disorders, neuropsychiatric diseases, and/or neurodevelopmental disorders.

Background Information

Sleep is a universal function of living species, comprising one-third of human life. Changes in sleep, including excess or insufficient sleep have been associated with a wide variety of dysfunctions in most body systems, including endocrine, metabolic, higher cortical function, and neurological systems.

It is estimated that 40 million Americans suffer from various sleep disorders. Sleep disorders have various etiologies, including stress induced by environmental and lifestyle factors, physical factors, and psychiatric disorders, such as depression. Sleep disorders are often found in conjunction with other conditions, in particular inflammatory and neurological conditions, neuropathies, and neurodegenerative disorders such as Parkinson's Disease, Alzheimer's Disease, amyotrophic lateral sclerosis, multiple sclerosis and Huntington's Disease.

There remains a need for therapies which can reduce REM sleep and/or non-REM sleep in patients suffering from sleep disorders or dysfunctional sleep associated with other conditions or diseases.

SUMMARY OF THE INVENTION

The present invention is based on the discovery that compounds of the disclosure can reduce REM sleep and/or non-REM sleep. In some embodiments, the present disclosure provides a method of treating a sleep dysfunction or sleep disorder in a subject by administering to the subject a compound of Formula (I):

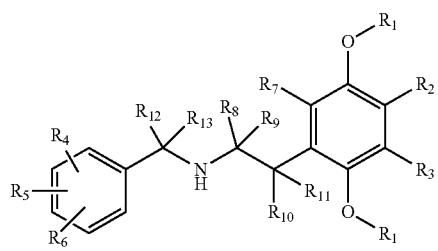

(I)

or a pharmaceutically acceptable salt thereof; wherein
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$ (C=O)($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;
$R_8$ and $R_9$ are independently hydrogen, $C_1$-$C_6$ alkyl, $C_1$-$C_4$ alkyl, $C_3$-$C_6$ cycloalkyl, $C_3$-$C_{11}$ cycloalkyl, $CH_2OH$, or $CH_2O$—$C_1$-$C_4$ alkyl;
$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;
$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and
$R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In some embodiments, the present disclosure provides a method of treating a stress related disorder, a neuropsychiatric disease, or a neurodevelopmental disorder, by administering to the subject a compound of Formula (I):

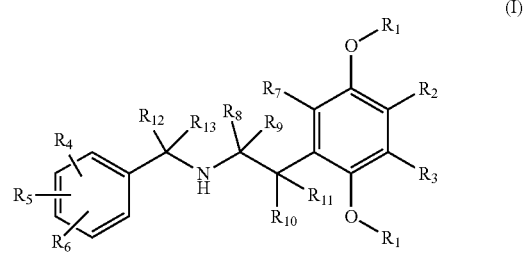

(I)

or a pharmaceutically acceptable salt thereof. In Formula (1) wherein
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$ (C=O)($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;
$R_8$ and $R_9$ are independently hydrogen, $C_1$-$C_6$ alkyl, $C_1$-$C_4$ alkyl, $C_3$-$C_6$ cycloalkyl, $C_3$-$C_{11}$ cycloalkyl, $CH_2OH$, or $CH_2O$—$C_1$-$C_4$ alkyl;
$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;
$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and
$R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In one embodiment, the sleep dysfunction or sleep disorder may be a hypersomnia or a circadian rhythm sleep disorder. In one embodiment, the stress related disorder may be depression, anxiety, or post-traumatic stress disorder.

In one embodiment, the compound of Formula (I) may be an agonist of a serotonin receptor. In one embodiment, the compound of Formula (I) may be an agonist of a 5-HT2A receptor. In one embodiment, the methods of treatment of sleep dysfunction or sleep disorder, a stress related disorder, a neuropsychiatric disease, or a neurodevelopmental disorder may include administering a compound having the structure of

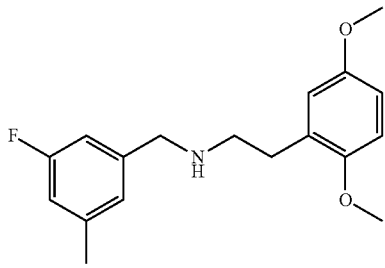

or a pharmaceutically acceptable salt thereof.

In one embodiment, the methods of treatment of sleep dysfunction or sleep disorder, a stress related disorder, a neuropsychiatric disease, or a neurodevelopmental disorder may include administering a compound having the structure of

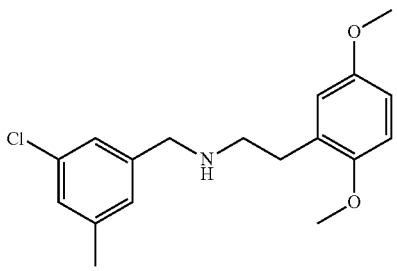 [SMILES: COc1ccc(OC)c(CCNCc2cc(C)cc(Cl)c2)c1]

or a pharmaceutically acceptable salt thereof.

In one embodiment, the compounds of the disclosure for the treatment of sleep dysfunction or sleep disorder, a stress related disorder, a neuropsychiatric disease, or a neurodevelopmental disorder may reduce a rapid eye movement (REM) sleep in the subject. In one embodiment, the compounds of the disclosure may increase a REM sleep latency and/or decrease a REM sleep duration in the subject.

In one embodiment, the compounds of the disclosure for the treatment of sleep dysfunction or sleep disorder, a stress related disorder, a neuropsychiatric disease, or a neurodevelopmental disorder may reduce a non-REM sleep in the subject. In one embodiment, the compounds of the disclosure may increase a non-REM sleep latency and/or decrease a non-REM sleep duration in the subject.

In one embodiment, the compounds of the disclosure for the treatment of sleep dysfunction or sleep disorder, a stress related disorder, a neuropsychiatric disease, or a neurodevelopmental disorder may increase the amount of time spent in wake by the subject.

In one embodiment, the compounds of the disclosure for the treatment of sleep dysfunction or sleep disorder, a stress related disorder, a neuropsychiatric disease, or a neurodevelopmental disorder may be administered by sublingual, intracutaneous, subcutaneous, intraperitoneal, intravenous, intraarterial, intradermal, transdermal, intramuscular, oral, buccal, or nasal route of administration.

In one embodiment, the compounds of the disclosure may be administered as a single dose or as multiple doses.

In some embodiments, the present disclosure provides a method of reducing rapid eye movement (REM) sleep in a subject by administering to the subject a compound of Formula (I):

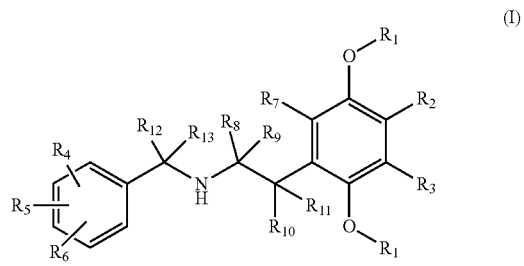

or a pharmaceutically acceptable salt thereof; wherein
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$ (C=O)($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;
$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl; $R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl; $R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and $R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In some embodiments, the disclosure provides a method of increasing a REM sleep latency in a subject by administering to the subject a compound of Formula (I):

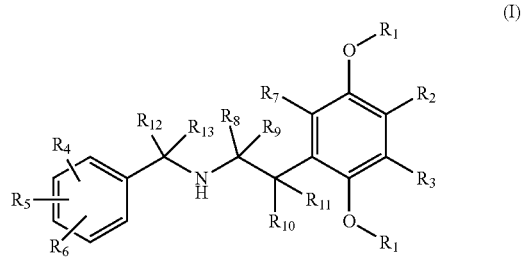

or a pharmaceutically acceptable salt thereof; wherein
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$ (C=O)($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;

$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and $R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In one embodiment, the compounds of the disclosure may reduce REM sleep by increasing a REM sleep latency and/or decreasing REM sleep duration in the subject. In one embodiment, the compounds of the disclosure may further reduce non-REM sleep in the subject. In one embodiment, reducing non-REM sleep may include increasing a non-REM sleep latency and/or decreasing non-REM sleep duration in the subject.

In one embodiment, the subject may have one or more of a sleep dysfunction, a sleep disorder, a stress related disorder, a neuropsychiatric disease, and a neurodevelopmental disorder. In one embodiment, the sleep dysfunction may be a hypersomnia or a circadian rhythm sleep disorder. In some embodiments, the stress related disorder may be depression, anxiety, or post-traumatic stress disorder. In one embodiment, the compound of the disclosure may be an agonist of a serotonin receptor. In one embodiment, the compound may be an agonist of 5-HT2A receptor.

In one embodiment, the compound may be

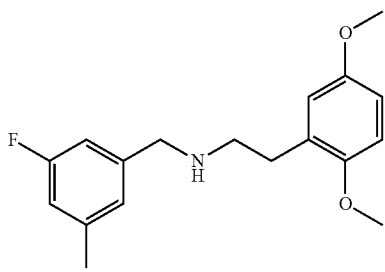

or a pharmaceutically acceptable salt thereof. In one embodiment, the compound may be

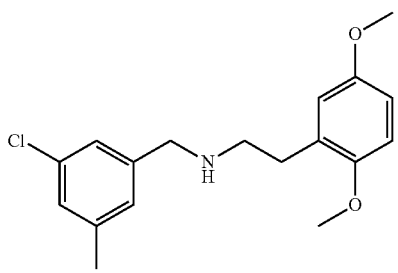 [SMILES: COc1ccc(OC)c(CCNCc2cc(C)cc(Cl)c2)c1]

or a pharmaceutically acceptable salt thereof. In one embodiment, the compounds of the disclosure may increase an amount of time spent in wake by the subject. In one embodiment, the compound is administered by a route such as, but not limited to, sublingual, intracutaneous, subcutaneous, intramuscular, intraperitoneal, intravenous, intraarterial, intradermal, transdermal, oral, buccal, or nasal route of administration. In one embodiment, the compounds of the disclosure may be administered as a single dose. In one embodiment, the compounds of the disclosure may be administered as multiple doses.

In some embodiments, the present disclosure provides methods of reducing non rapid eye movement (non-REM) sleep in a subject by administering to the subject a compound of Formula (I):

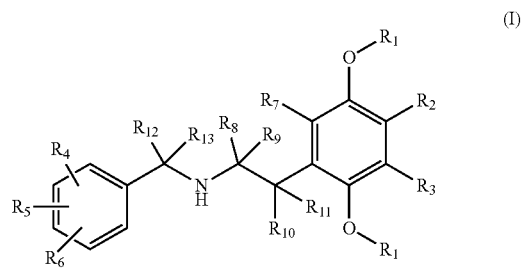

or a pharmaceutically acceptable salt thereof; wherein
$R_1$ is independently at each position hydrogen, $C_1$-$C_6$ alkyl, or $C_1$-$C_6$ haloalkyl;

$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$ $SR_1$ $(C=O)(R_{14})$, $O(C=O)(R_{14})$, $NO_2$, or $NH(C=O)(R_{14})$, wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;

$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and $R_{13}$ is hydrogen, $C_1$-$C_9$ alkyl, $C_3$-$C_{10}$ cycloalkyl, or $CH_2OH$, $CH_2O$—$C_1$-$C_4$ alkyl.

The present disclosure also provides methods of increasing a non-REM sleep latency in a subject by administering to the subject a compound of Formula (I):

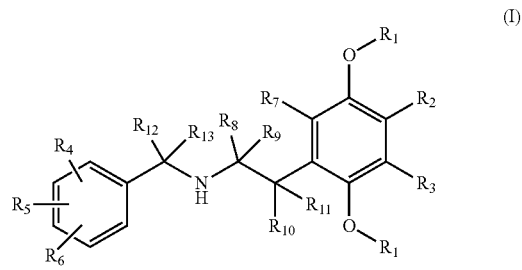

or a pharmaceutically acceptable salt thereof; wherein
$R_1$ is independently at each position hydrogen, $C_1$-$C_6$ alkyl, or $C_1$-$C_6$ haloalkyl;

$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$ $SR_1$ $(C=O)$ ($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;

$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and $R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In one embodiment, the compounds of the disclosure may reduce non-REM sleep by increasing a non-REM sleep latency and/or decreasing a non-REM sleep duration in the subject. In one embodiment, the compounds of the disclosure may further reduce REM sleep in the subject. In one embodiment, the compounds of the disclosure may reduce REM sleep by increasing a REM sleep latency and/or decreasing REM sleep duration in the subject. In one embodiment, the subject may have a sleep dysfunction, a sleep disorder, a stress related disorder, a neuropsychiatric disease, and a neurodevelopmental disorder. In one embodiment, the sleep dysfunction or sleep disorder may be a hypersomnia or a circadian rhythm sleep disorder. In one embodiment, the stress related disorder may be depression, anxiety, or post-traumatic stress disorder. In one embodiment, the compound may be an agonist of a serotonin receptor. In one embodiment, the compound may be agonist of a 5-HT2A receptor. In one embodiment, the compound may be

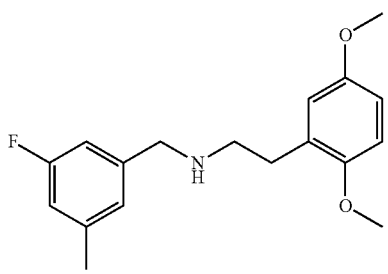

or a pharmaceutically acceptable salt thereof. In one embodiment, the compound may be

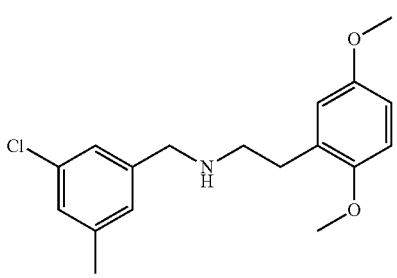 [SMILES: COc1ccc(OC)c(CCNCc2cc(C)cc(Cl)c2)c1]

or a pharmaceutically acceptable salt thereof. In one embodiment, the compound may increase the amount of time spent in wake by the subject. In one embodiment, the compound may be administered by a route such as, but not limited to sublingual, intracutaneous, subcutaneous, intramuscular, intraperitoneal, intravenous, intraarterial, intradermal, transdermal, oral, buccal, or nasal route of administration. In one embodiment, the compounds of the disclosure may be administered as a single dose or as multiple doses.

In some embodiments, the disclosure provides methods of promoting wakefulness in a subject, by administering to the subject a compound of Formula (I):

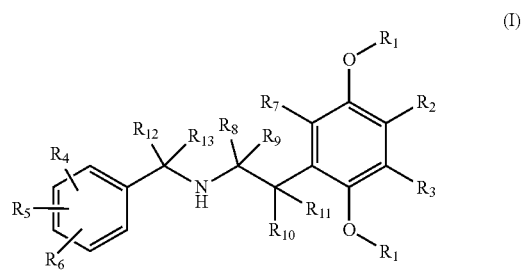

(I)

or a pharmaceutically acceptable salt thereof; wherein $R_1$ is independently at each position hydrogen, $C_1$-$C_6$ alkyl, or $C_1$-$C_6$ haloalkyl;

$R_2$, $R_3$ and $R_7$ are independently hydrogen, heterocycle, $C_1$-$C_6$ alkyl, $C_1$-$C_6$ haloalkyl, halogen, cyano, $OR_1$, S(O)(=NH)$R_1$, S(O)$_2R_1$, S(O)$R_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$ $SR_1$ (C=O)($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;

$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and $R_{13}$ is hydrogen, $C_1$-$C_9$ alkyl, $C_3$-$C_{10}$ cycloalkyl, or $CH_2OH$, $CH_2O$—$C_1$-$C_4$ alkyl.

In one embodiment, the compound may further reduce non-REM sleep. In one embodiment, the compound may reduce non-REM sleep by increasing a non-REM sleep latency and/or decreasing a non-REM sleep duration in the subject. In some embodiments, the compounds of the disclosure may further reduce REM sleep. In one embodiment, the compounds of the disclosure may reduce REM sleep by increasing a REM sleep latency and/or decreasing REM sleep duration in the subject. In one embodiment, the subject may have sleep dysfunction, a sleep disorder, a stress related disorder, a neuropsychiatric disease, and/or a neurodevelopmental disorder. In one embodiment, the sleep dysfunction or sleep disorder may be hypersomnia or a circadian rhythm sleep disorder. In one embodiment, the stress related disorder may be depression, anxiety, or post-traumatic stress disorder. In one embodiment, the compound may be serotonin receptor. In one embodiment, the compound may be an agonist of a 5-HT2A receptor. In one embodiment, the compound may be

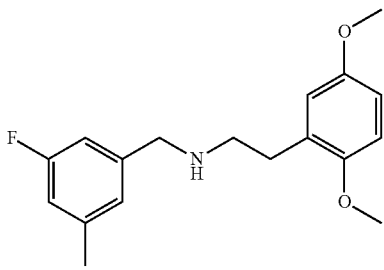

or a pharmaceutically acceptable salt thereof.

In one embodiment, the compound may be

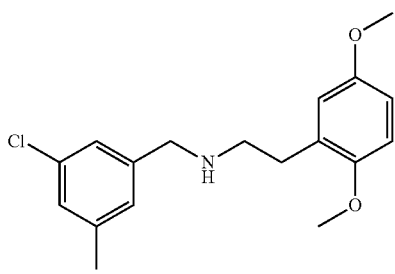 [SMILES: COc1ccc(OC)c(CCNCc2cc(C)cc(Cl)c2)c1]

or a pharmaceutically acceptable salt thereof.

In one embodiment, the compound may be administered via sublingual, intracutaneous, subcutaneous, intramuscular, intraperitoneal, intravenous, intraarterial, intradermal, transdermal, oral, buccal, or nasal route of administration. In one embodiment, the compound may be administered as a single dose or as multiple doses.

In some embodiments, the present disclosure provides methods of treating sleep dysfunction or a sleep disorder in a subject by administering to the subject, an effective amount of a compound, wherein the compound is:

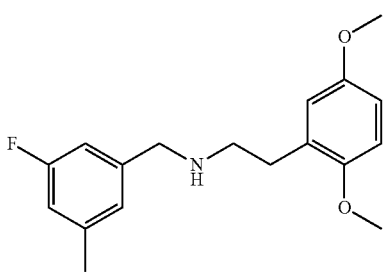

or a pharmaceutically acceptable salt thereof, and wherein the compound is administered sublingually.

In some embodiments, the present disclosure provides methods of treating sleep dysfunction or a sleep disorder in a subject by administering to the subject, an effective amount of a compound, wherein the compound is:

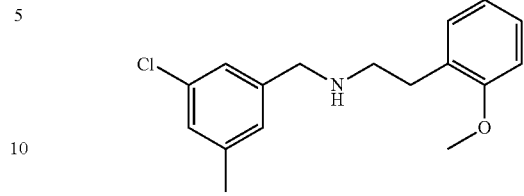

or a pharmaceutically acceptable salt thereof, and wherein the compound is administered sublingually.

In some embodiments, the present disclosure provides methods of treating a stress related disorder, a neuropsychiatric disease, or a neurodevelopmental disorder in a subject comprising administering to the subject, an effective amount of a compound, wherein the compound is:

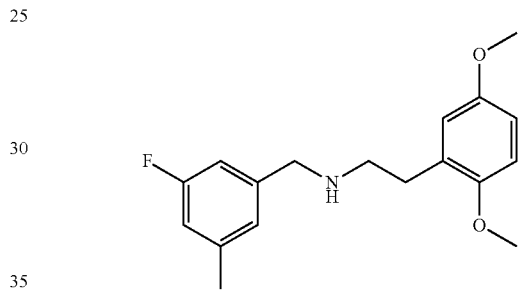

or a pharmaceutically acceptable salt thereof, and wherein the compound is administered sublingually.

In some embodiments, the present disclosure provides methods of treating a stress related disorder, a neuropsychiatric disease, or a neurodevelopmental disorder, in a subject comprising administering to the subject, an effective amount of a compound, wherein the compound is:

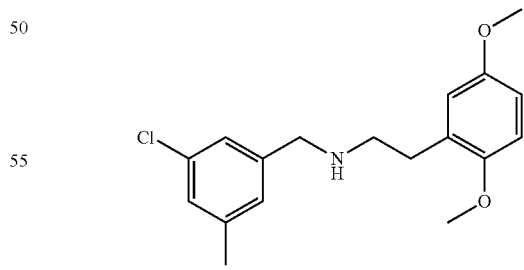

or a pharmaceutically acceptable salt thereof, and wherein the compound is administered sublingually.

In some embodiments, the present disclosure provides methods of reducing rapid eye movement (REM) sleep in a subject by administering to the subject, an effective amount of a compound, wherein the compound is:

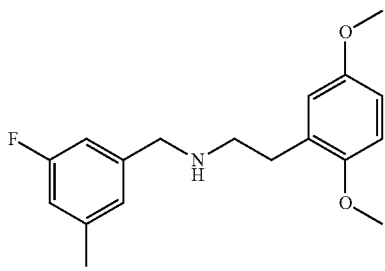

or a pharmaceutically acceptable salt thereof, and wherein the compound is administered sublingually.

In some embodiments, the present disclosure provides methods of reducing rapid eye movement (REM) sleep in a subject by administering to the subject, an effective amount of a compound, wherein the compound is:

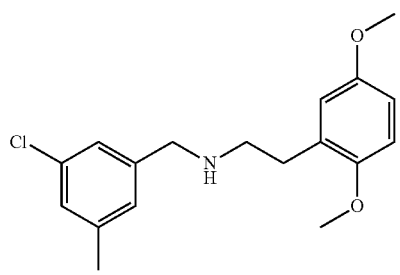 [SMILES: COc1ccc(OC)c(CCNCc2cc(C)cc(Cl)c2)c1]

or a pharmaceutically acceptable salt thereof, and wherein the compound is administered sublingually.

In some embodiments, the present disclosure provides methods of increasing a REM sleep latency in a subject by administering to the subject, an effective amount of a compound, wherein the compound is:

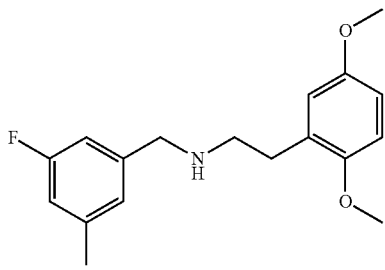

or a pharmaceutically acceptable salt thereof, and wherein the compound is administered sublingually.

In some embodiments, the present disclosure provides methods of increasing a REM sleep latency in a subject by administering to the subject, an effective amount of a compound, wherein the compound is:

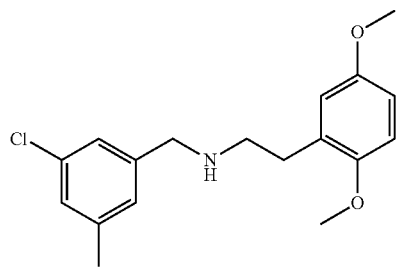 [SMILES: COc1ccc(OC)c(CCNCc2cc(C)cc(Cl)c2)c1]

or a pharmaceutically acceptable salt thereof, and wherein the compound is administered sublingually.

In some embodiments, the present disclosure provides methods of reducing non rapid eye movement (non-REM) sleep in a subject by administering to the subject, an effective amount of a compound, wherein the compound is:

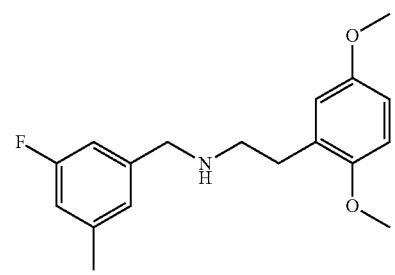

or a pharmaceutically acceptable salt thereof, and wherein the compound is administered sublingually.

In some embodiments, the present disclosure provides methods of reducing non rapid eye movement (non-REM) sleep in a subject by administering to the subject, an effective amount of a compound, wherein the compound is:

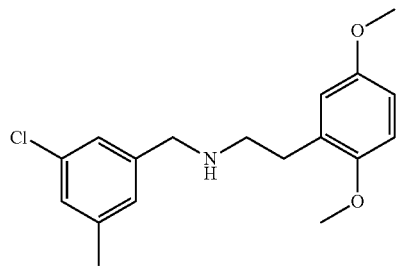 [SMILES: COc1ccc(OC)c(CCNCc2cc(C)cc(Cl)c2)c1]

or a pharmaceutically acceptable salt thereof, and wherein the compound is administered sublingually.

In some embodiments, the present disclosure provides methods of increasing a non-REM sleep latency in a subject by administering to the subject, an effective amount of a compound, wherein the compound is:

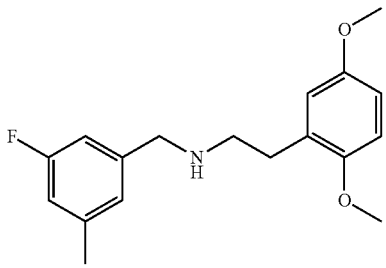

or a pharmaceutically acceptable salt thereof, and wherein the compound is administered sublingually.

In some embodiments, the present disclosure provides methods of increasing a non-REM sleep latency in a subject by administering to the subject, an effective amount of a compound, wherein the compound is:

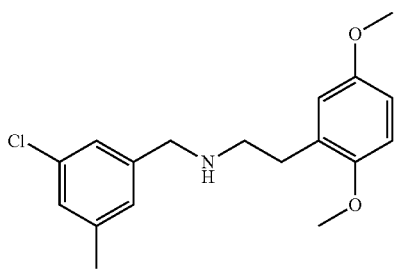 [SMILES: COc1ccc(OC)c(CCNCc2cc(C)cc(Cl)c2)c1]

or a pharmaceutically acceptable salt thereof, and wherein the compound is administered sublingually.

In some embodiments, the present disclosure provides methods of identifying a patient population for treatment with a compound of Formula (I):

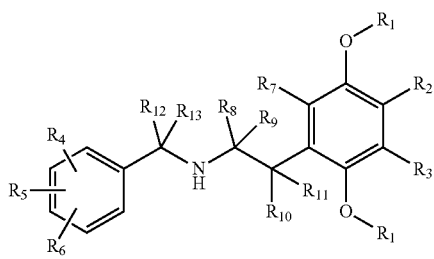

or a pharmaceutically acceptable salt thereof;
which includes measuring one or more of a REM sleep, a non-REM sleep, and
wakefulness in a subject, wherein
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$ (C=O)($R_{14}$), O(C=O)($R_{14}$), $NO_2$, or NH(C=O)($R_{14}$), wherein $R_{14}$ is $C_1$-$C_6$ alkyl, OH, or $OC_1$-$C_6$ alkyl;
$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;
$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;
$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and
$R_{13}$ is hydrogen, $C_1$-$C_9$ alkyl, $C_3$-$C_{10}$ cycloalkyl, or $CH_2OH$, $CH_2O$—$C_1$-$C_4$ alkyl, In one embodiment, measuring REM sleep may include measuring one or more of a REM sleep latency and a REM sleep duration. In one embodiment, measuring non-REM sleep may include measuring one or more of a non-REM sleep latency and a non-REM sleep duration.

DETAILED DESCRIPTION

Figure 1A:
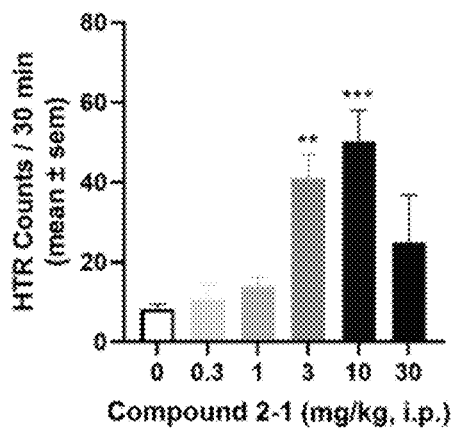
FIG. 1A is a graph showing mouse head twitch response (HTR) data following administration of compound 2-1 i.p. alone.

The present invention is based on the seminal discovery of the effect of compounds of Formula (I), Formula (I-A), Formula (I-B) described herein in reducing rapid eye movement (REM) sleep and/or non-REM sleep in subjects. Accordingly, the invention provides methods of treating stress-related disorders and any other disorder involving altered REM and/or non-REM sleep.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein may be used in the practice or testing of the invention, it will be understood that modifications and variations are encompassed within the spirit and scope of the instant disclosure. The preferred methods and materials are now described.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

As used herein, the term "and/or" includes any and all combinations of one or more of the associated listed items.

As used herein, the term "about" in association with a numerical value is meant to include any additional numerical value reasonably close to the numerical value indicated. For example, and based on the context, the value may vary up or down by 5-10%. For example, for a value of about 100, means 90 to 110 (or any value between 90 and 110).

In some embodiments, the present disclosure provides compounds which act as agonists of a serotonin receptor. In some embodiments, the present disclosure provides compounds which act as agonists of the 5-HT2A receptor. In one aspect, the compounds may be full agonists of the 5-HT2A receptor. In one embodiment, the compounds are partial agonists of the 5-HT2A receptor. In one embodiment, the compounds display selectivity for 5-HT2A receptor.

Activation of 5-HT2A receptors located in cortical and subcortical structures of the brain are thought to mediate the subjective, behavioral, and psychological effects of psychedelics in both animals and humans. In rodents, psychedelics have shown to elicit a 'head twitch response' which has been demonstrated to be a direct and selective consequence of 5-HT2A activation over other similar serotonin receptors including both 5-HT2C and 5-HT2B. Similar observations have been made in humans where the administration of ketanserin, a 5-HT2A receptor antagonist, blocked the majority of subjective effects induced by dimethyltryptamine (DMT), psilocybin and lysergic acid diethylamide (LSD). In addition, psychedelic effects elicited by psilocybin have correlated with 5-HT2A receptor occupancy as measured by positron emission tomography in the prefrontal cortex (PFC) and other cortical regions in humans. While 5-HT2A is the predominant driver of psychedelic effects in humans, other serotonin receptors, like 5-HT1A, are likely contributing to the overall psychedelic experience including both visual and attention-disrupting effects in humans.

In one aspect, provided herein is a compound of Formula (I):

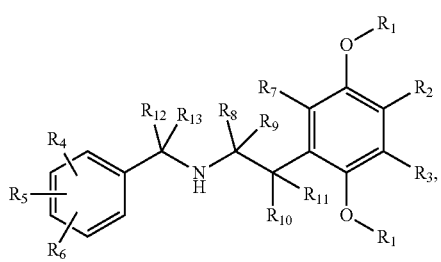

or a pharmaceutically acceptable salt thereof, wherein,
$R_1$ is independently at each position hydrogen, $C_1$-$C_6$ alkyl, or $C_1$-$C_6$ haloalkyl;
$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$ $(C=O)(R_{14})$, $O(C=O)(R_{14})$, $NO_2$, or $NH(C=O)(R_{14})$, wherein $R_{14}$ is $C_1$-$C_6$ alkyl, OH, or $OC_1$-$C_6$ alkyl;
$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;
$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;
$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and
$R_{13}$ is hydrogen, $C_1$-$C_9$ alkyl, $C_3$-$C_{10}$ cycloalkyl, or $CH_2OH$, $CH_2O$—$C_1$-$C_4$ alkyl, In one aspect, provided herein is a compound of Formula (I):

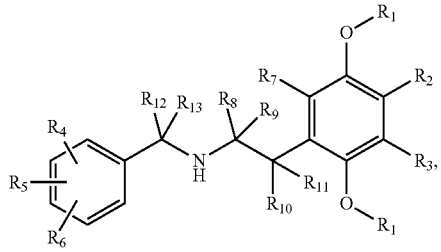

or a pharmaceutically acceptable salt thereof, wherein,
$R_1$ is independently at each position hydrogen, $C_1$-$C_6$ alkyl, or $C_1$-$C_6$ haloalkyl;
$R_2$, $R_3$ and $R_7$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, $OR_1$ $SR_1$, $O(C=O)(R_{14})$, or $NH(C=O)(R_{14})$, wherein $R_{14}$ is $C_1$-$C_6$ alkyl;
$R_8$ and $R_9$ are independently hydrogen or $C_1$-$C_6$ alkyl;
$R_{10}$, and $R_u$, are independently hydrogen, halogen or $C_1$-$C_6$ alkyl;

$R_{12}$ is hydrogen, $CH_2OH$, $CH_2O$—$C_1$-$C_9$ alkyl, $C_3$-$C_{10}$ cycloalkyl, $CH_2OH$, $CH_2O$—$C_1$ to $C_4$ alkyl; and
$R_{13}$ is hydrogen, $C_1$-$C_9$ alkyl, $C_3$-$C_{10}$ cycloalkyl, $CH_2OH$, $CH_2O$—$C_1$ to $C_4$ alkyl.

In some embodiment, the compound of Formula (I) is a compound of Formula (I-A):

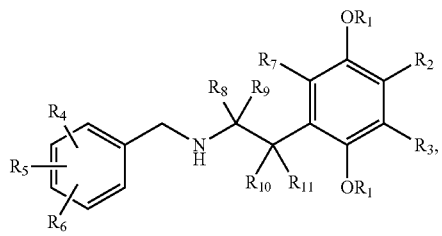

or a pharmaceutically acceptable salt thereof;
wherein,
$R_1$ is independently at each position hydrogen, $C_1$-$C_6$ alkyl, or $C_1$-$C_6$ haloalkyl;
$R_2$, $R_3$ and $R_7$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen;
$R_4$, $R_5$ and $R_6$ are independently hydrogen, $C_1$-$C_6$ alkyl, $C_1$-$C_6$ haloalkyl, halogen, cyano, ORI, SRI, $O(C=O)(R_{12})$, or $NH(C=O)(R_{12})$, wherein $R_{12}$ is $C_1$-$C_6$ alkyl;
$R_8$ and $R_9$ are independently hydrogen or $C_1$-$C_6$ alkyl; and
$R_{10}$ and $R_{12}$ are independently hydrogen, halogen or $C_1$-$C_6$ alkyl.

In some embodiments, the compound of Formula (I) is a compound of Formula (I-B):

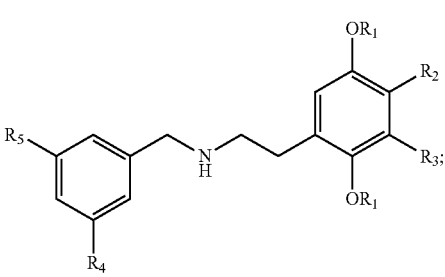

or a pharmaceutically acceptable salt thereof; wherein:
$R_1$, $R_2$, $R_3$ $R_4$, and $R_5$ are defined herein.

In some embodiments of the compounds of Formula (I), (I-A), or (I-B), $R_1$ is independently at each position hydrogen, $C_1$-$C_6$ alkyl, or $C_1$-$C_6$ haloalkyl.

In some embodiments of the compounds of Formula (I), (I-A), or (I-B), $R_1$ is independently at each position hydrogen or $C_1$-$C_6$ alkyl.

In some embodiments of the compounds of Formula (I), (I-A), or (I-B), $R_1$ is independently at each position $C_1$-$C_6$ alkyl.

In some embodiments of the compounds of Formula (I), (I-A), or (I-B), $R_1$ is independently at each position $C_1$-$C_3$ alkyl.

In some embodiments of the compounds of Formula (I), (I-A), or (I-B), $R_1$ is independently at each position methyl, ethyl, propyl, or isopropyl.

In some embodiments of the compounds of Formula (I), (I-A), or (I-B), $R_1$ is independently at each position $C_1$-$C_6$ haloalkyl. In some embodiments, $R_1$ is independently at each position $C_1$-$C_3$ haloalkyl. In some embodiments, $R_1$ is independently at each position $CF_3$.

In some embodiments of the compounds of Formula (I), (I-A), or (I-B), $R_1$ is methyl.

In some embodiments of the compounds of Formula (I), (I-A), or (I-B), $R_2$, and $R_3$ are independently hydrogen, $C_1$-$C_6$ alkyl, $C_1$-$C_6$ haloalkyl, halogen, cyano, $OR_1$ or $SR_1$, wherein at least one of $R_2$ and $R_3$ is hydrogen.

In some embodiments of the compounds of Formula (I), (I-A), or (I-B), $R_2$, and $R_3$ are independently hydrogen, $C_1$-$C_6$ alkyl, halogen, cyano, OR or $SR_1$, wherein at least one of $R_2$ and $R_3$ is hydrogen.

In some embodiments of the compounds of Formula (I), (I-A), or (I-B), $R_2$ and $R_3$ are independently hydrogen, halogen. $C_1$-$C_6$ alkyl, or $C_1$-$C_6$ haloalkyl, wherein at least one of $R_2$ and $R_3$ is hydrogen.

In some embodiments of the compounds of Formula (I), (I-A), or (I-B), $R_2$ and $R_3$ are independently hydrogen, halogen, $C_1$-$C_3$ alkyl, or $C_1$-$C_3$ haloalkyl, wherein at least one of $R_2$ and $R_3$ is hydrogen.

In some embodiments of the compounds of Formula (I), (I-A), or (I-B), $R_2$ and $R_3$ are independently hydrogen, $C_1$-$C_6$ alkyl, or $C_1$-$C_6$ haloalkyl, wherein at least one of $R_2$ and $R_3$ is hydrogen.

In some embodiments of the compounds of Formula (I), (I-A), or (I-B), $R_2$ and $R_3$ are independently hydrogen, $C_1$-$C_3$ alkyl, or $C_1$-$C_3$ haloalkyl, wherein at least one of $R_2$ and $R_3$ is hydrogen.

In some embodiments of the compounds of Formula (I), (I-A), or (I-B), $R_2$ and $R_3$ are independently hydrogen, or $C_1$-$C_6$ alkyl, wherein at least one of $R_2$ and $R_3$ is hydrogen.

In some embodiments of the compounds of Formula (I), (I-A), or (I-B). $R_2$ and $R_3$ are independently hydrogen, or $C_1$-$C_3$ alkyl, wherein at least one of $R_2$ and $R_3$ is hydrogen.

In some embodiments of the compounds of Formula (I), (I-A), or (I-B), $R_2$ and $R_3$ are independently hydrogen, —$CF_3$, methyl or ethyl, wherein at least one of $R_2$ and $R_3$ is hydrogen.

In some embodiments of the compounds of Formula (I), (I-A), or (I-B), $R_2$ and $R_3$ are independently hydrogen, methyl, or ethyl, wherein at least one of $R_2$ and $R_3$ is hydrogen.

In some embodiments of the compounds of Formula (I), (I-A), or (I-B), $R_2$ and $R_3$ are independently hydrogen or methyl, wherein at least one of $R_2$ and $R_3$ is hydrogen.

In some embodiments of the compounds of Formula (I), (I-A), or (I-B), $R_2$ is hydrogen, —$CF_3$, methyl or ethyl and $R_3$ is hydrogen.

In some embodiments of the compounds of Formula (I), (I-A), or (I-B), $R_2$ is hydrogen, methyl, or ethyl and $R_3$ is hydrogen.

In some embodiments of the compounds of Formula (I), (I-A), or (I-B), $R_3$ is hydrogen.

In some embodiments of the compounds of Formula (I), (I-A), or (I-B), $R_2$ is hydrogen.

In some embodiments of the compounds of Formula (I), (I-A), or (I-B), $R_2$ is hydrogen and $R_3$ is hydrogen, —$CF_3$, methyl or ethyl.

In some embodiments of the compounds of Formula (I), (I-A), or (I-B), $R_2$ is hydrogen and $R_3$ is hydrogen, methyl, or ethyl.

In some embodiments of the compounds of Formula (I), (I-A), or (I-B), $R_2$ and $R_3$ are hydrogen.

In some embodiments of the compounds of Formula (I), (I-A), or (I-B), $R_2$ is halogen and $R_3$ is hydrogen.

In some embodiments of the compounds of Formula (I), (I-A), or (I-B), $R_2$ is hydrogen and $R_3$ is halogen.

In some embodiments of the compounds of Formula (I), (I-A), or (I-B), $R_4$, $R_5$ and $R_6$ are independently hydrogen, $C_1$-$C_6$ alkyl, $C_1$-$C_6$ haloalkyl, halogen, cyano, $OR_1$, $SR_1$, $O(C=O)(R_{12})$, or $NH(C=O)(R_{12})$, wherein $R_{12}$ is $C_1$-$C_6$ alkyl.

In some embodiments of the compounds of Formula (I), (I-A), or (I-B), $R_4$ and $R_5$ are independently hydrogen, $C_1$-$C_6$ alkyl, halogen, cyano, $OR_1$, $SR_1$, $O(C=O)(R_{12})$, or $NH(C=O)(R_{12})$, wherein $R_{12}$ is $C_1$-$C_6$ alkyl.

In some embodiments of the compounds of Formula (I), (I-A), or (I-B), $R_4$ is $C_1$-$C_6$alkyl or $C_1$-$C_6$ haloalkyl.

In some embodiments of the compounds of Formula (I), (I-A), or (I-B), $R_4$ is $C_1$-$C_6$ alkyl.

In some embodiments of the compounds of Formula (I), (I-A), or (I-B), $R_4$ is —$CF_3$ or methyl.

In some embodiments of the compounds of Formula (I), (I-A), or (I-B), $R_4$ is methyl.

In some embodiments of the compounds of Formula (I), (I-A), or (I-B), $R_5$ is halogen.

In some embodiments of the compounds of Formula (I), (I-A), or (I-B), $R_5$ is chloro.

In some embodiments of the compounds of Formula (I) or (I-A), $R_6$ is hydrogen.

In some embodiments of the compounds of Formula (I) or (I-A), $R_7$ is hydrogen.

In some embodiments of the compounds of Formula (I) or (I-A), $R_8$ and $R_9$ are hydrogen.

In some embodiments of the compounds of Formula (I) or (I-A), $R_{10}$ and $R_{11}$ are hydrogen.

In some embodiments of the compounds of Formula (I) or (I-A), $R_{10}$ and $R_{11}$ are fluoro.

In some embodiments of the compounds of Formula (I), $R_{11}$ and $R_{12}$ are hydrogen.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" or "alkyl group" refers to a fully saturated, straight, or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group may be optionally substituted.

"Cycloalkyl" refers to a stable non-aromatic monocyclic or polycyclic fully saturated hydrocarbon consisting solely of carbon and hydrogen atoms, which may include fused, bridged, or spirocyclic ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Haloalkyl" refers to an alkyl, as defined above, that is substituted by one or more halo radicals, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen, and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl may be a monocyclic, bicyclic, tricyclic, or tetracyclic ring system, which may include fused, bridged, or spirocyclic ring systems; and the nitrogen, carbon, or sulfur atoms in the heterocyclyl may be optionally oxidized; the nitrogen atom may be optionally quaternized; and the heterocyclyl may be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group may be optionally substituted.

"The term "substituted" used herein means any of the groups described herein (e.g., alkyl, alkenyl, alkynyl, alkoxy, aryl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkyl, haloalkyl, haloalkenyl, haloalkynyl, heterocyclyl, 1-heterocyclyl, heterocyclylalkyl, heteroaryl, A-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkyl, haloalkyl, haloalkenyl, haloalkynyl, heterocyclyl, A-heterocyclyl, heterocyclylalkyl, heteroaryl, A-heteroaryl and/or heteroarylalkyl group. In addition, each of the foregoing substituents may also be optionally substituted with one or more of the above substituents.

Table 1 provides one or more compounds of the disclosure. In one embodiment, provided herein is one or more pharmaceutically acceptable salts of a compound in Table 1.

TABLE 1

Compounds of the Disclosure

| Compound | Name | Structure |
|---|---|---|
| 2-1 | N-(3-chloro-5-methylbenzyl)-2-(2,5-dimethoxyphenyl)ethan-1-amine | 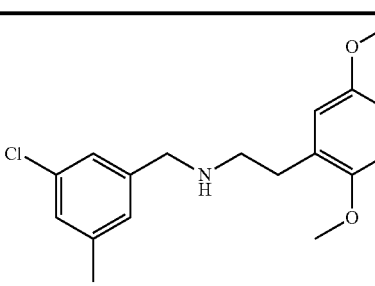 |

TABLE 1-continued

Compounds of the Disclosure

| Compound | Name | Structure |
|---|---|---|
| 2-2 | 2-(2,5-dimethoxyphenyl)-N-(3-fluoro-5-methylbenzyl)ethan-1-amine | 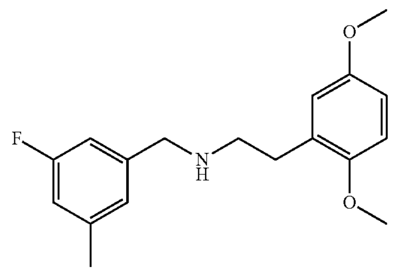 [SMILES: COc1ccc(OC)c(CCNCc2cc(C)cc(F)c2)c1] |
| 2-3 | N-(2-chloro-4-methylbenzyl)-2-(2,5-dimethoxyphenyl)ethan-1-amine | 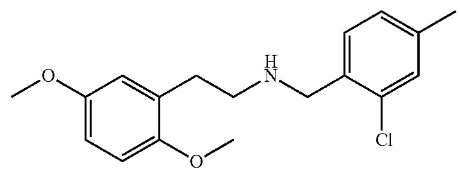 |
| 2-4 | N-(2-chloro-5-methylbenzyl)-2-(2,5-dimethoxyphenyl)ethan-1-amine | 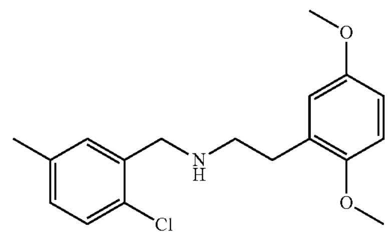 |
| 2-5 | N-(2,4-dichlorobenzyl)-2-(2,5-dimethoxyphenyl)ethan-1-amine | 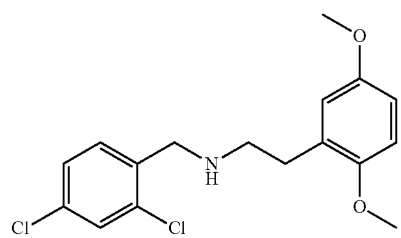 [SMILES: COc1ccc(OC)c(CCNCc2ccc(Cl)cc2Cl)c1] |
| 2-6 | N-(3,5-dichlorobenzyl)-2-(2,5-dimethoxyphenyl)ethan-1-amine | 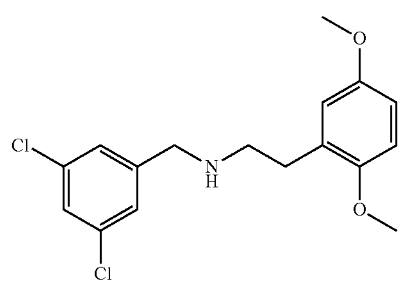 [SMILES: COc1ccc(OC)c(CCNCc2cc(Cl)cc(Cl)c2)c1] |
| 2-7 | N-(3,4-dichlorobenzyl)-2-(2,5-dimethoxyphenyl)ethan-1-amine | 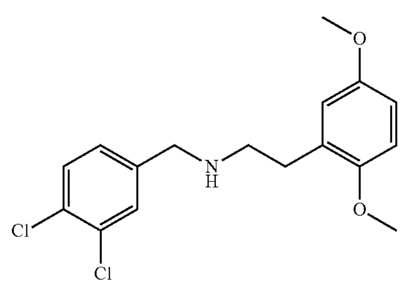 [SMILES: COc1ccc(OC)c(CCNCc2ccc(Cl)c(Cl)c2)c1] |

TABLE 1-continued

Compounds of the Disclosure

| Compound | Name | Structure |
| --- | --- | --- |
| 2-8 | N-(2,3-dichlorobenzyl)-2-(2,5-dimethoxyphenyl)ethan-1-amine | 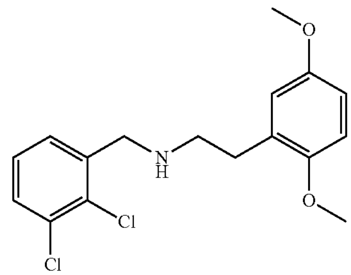 [SMILES: COc1ccc(OC)c(CCNCc2cccc(Cl)c2Cl)c1] |
| 2-9 | 2-(2,5-dimethoxyphenyl)-N-(3-methyl-5-nitrobenzyl)ethan-1-amine | 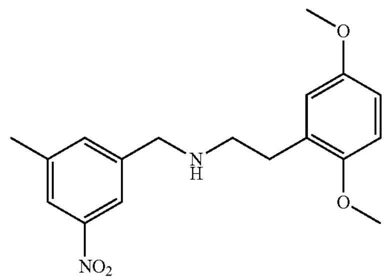 |
| 2-10 | N-(3-bromo-5-methylbenzyl)-2-(2,5-dimethoxyphenyl)ethan-1-amine | 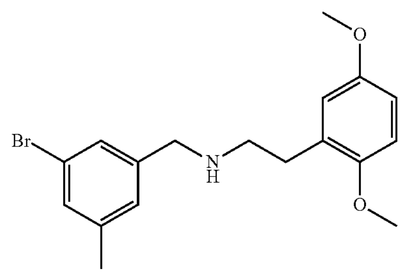 [SMILES: COc1ccc(OC)c(CCNCc2cc(C)cc(Br)c2)c1] |
| 2-11 | 2-(2,5-dimethoxyphenyl)-N-(3-iodo-5-methylbenzyl)ethan-1-amine | 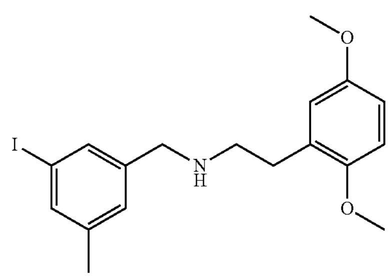 [SMILES: COc1ccc(OC)c(CCNCc2cc(C)cc(I)c2)c1] |
| 2-12 | N-(5-chloro-2-methylbenzyl)-2-(2,5-dimethoxyphenyl)ethan-1-amine | 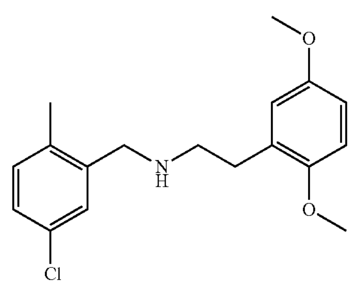 [SMILES: COc1ccc(OC)c(CCNCc2cc(Cl)ccc2C)c1] |

TABLE 1-continued

| Compounds of the Disclosure | | |
|---|---|---|
| Compound | Name | Structure |
| 2-13 | N-(3-chloro-4-methylbenzyl)-2-(2,5-dimethoxyphenyl)ethan-1-amine | |
| 2-14 | N-(4-chloro-3-methylbenzyl)-2-(2,5-dimethoxyphenyl)ethan-1-amine | |
| 2-15 | N-(3-chloro-2-methylbenzyl)-2-(2,5-dimethoxyphenyl)ethan-1-amine | |
| 2-16 | N-(2-chloro-3-methylbenzyl)-2-(2,5-dimethoxyphenyl)ethan-1-amine | |
| 2-17 | N-(4-chloro-2-methylbenzyl)-2-(2,5-dimethoxyphenyl)ethan-1-amine | |

TABLE 1-continued

Compounds of the Disclosure

| Compound | Name | Structure |
|---|---|---|
| 2-18 | N-(3-chloro-5-methylbenzyl)-2-(2,5-dimethoxy-4-methylphenyl)ethan-1-amine | 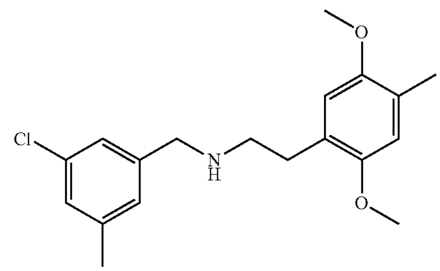 [SMILES: COc1cc(CCNCc2cc(C)cc(Cl)c2)c(OC)cc1C] |
| 2-19 | N-(3-chloro-5-methylbenzyl)-2-(4-ethyl-2,5-dimethoxyphenyl)ethan-1-amine | 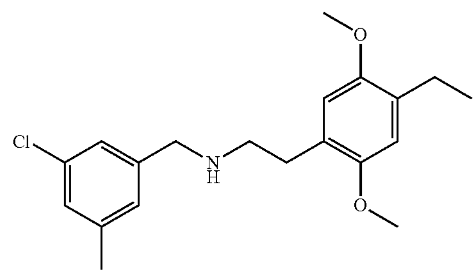 [SMILES: CCc1cc(OC)c(CCNCc2cc(C)cc(Cl)c2)cc1OC] |
| 2-20 | N-(3-chloro-5-methylbenzyl)-2-(4-fluoro-2,5-dimethoxyphenyl)ethan-1-amine | 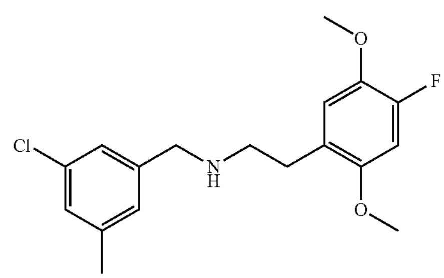 [SMILES: COc1cc(CCNCc2cc(C)cc(Cl)c2)c(OC)cc1F] |
| 2-21 | 2-(4-chloro-2,5-dimethoxyphenyl)-N-(3-chloro-5-methylbenzyl)ethan-1-amine | 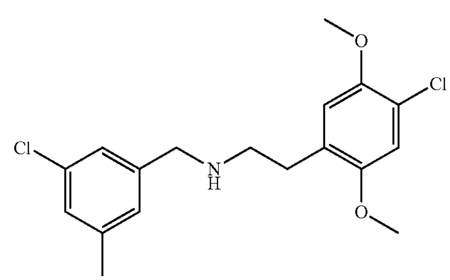 [SMILES: COc1cc(CCNCc2cc(C)cc(Cl)c2)c(OC)cc1Cl] |
| 2-22 | 2-(4-bromo-2,5-dimethoxyphenyl)-N-(3-chloro-5-methylbenzyl)ethan-1-amine | 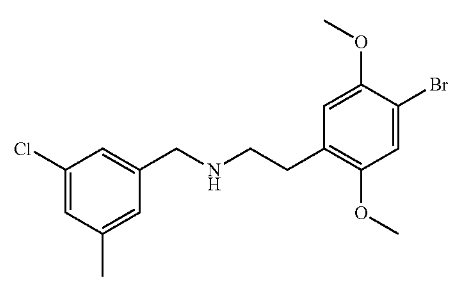 [SMILES: COc1cc(CCNCc2cc(C)cc(Cl)c2)c(OC)cc1Br] |

TABLE 1-continued

Compounds of the Disclosure

| Compound | Name | Structure |
|---|---|---|
| 2-23 | 4-(2-((3-chloro-5-methylbenzyl)amino)ethyl)-2,5-dimethoxybenzonitrile | 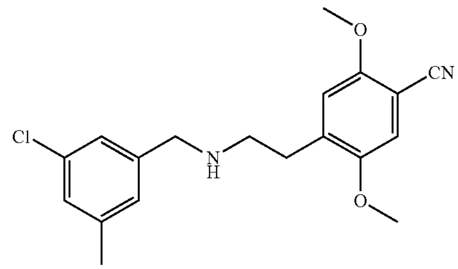 [SMILES: COc1cc(CCNCc2cc(C)cc(Cl)c2)c(OC)cc1C#N] |
| 2-24 | N-(3-chloro-5-methylbenzyl)-2-(2,5-dimethoxy-4-(methylthio)phenyl)ethan-1-amine | 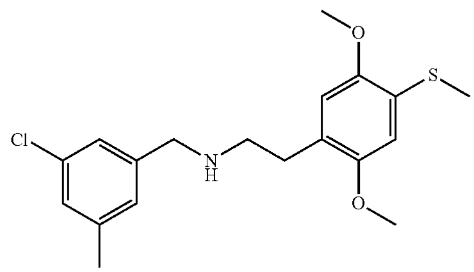 [SMILES: COc1cc(SC)c(OC)cc1CCNCc1cc(C)cc(Cl)c1] |
| 2-25 | N-(3-chloro-5-methylbenzyl)-2-(2,5-dimethoxy-4-(methylsulfinyl)phenyl)ethan-1-amine | 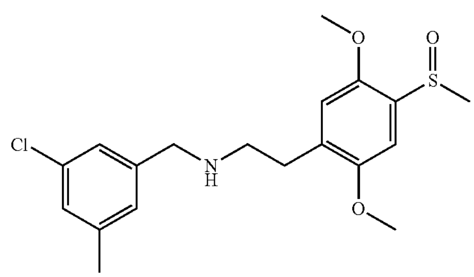 [SMILES: COc1cc(S(C)=O)c(OC)cc1CCNCc1cc(C)cc(Cl)c1] |
| 2-26 | N-(3-chloro-5-methylbenzyl)-2-(2,5-dimethoxy-4-(methylsulfonyl)phenyl)ethan-1-amine | 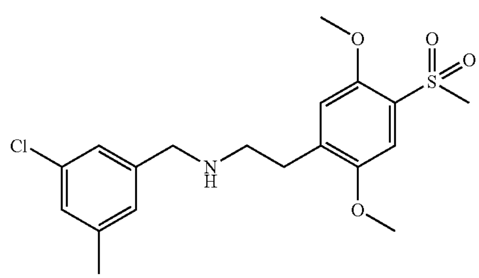 [SMILES: COc1cc(S(C)(=O)=O)c(OC)cc1CCNCc1cc(C)cc(Cl)c1] |
| 2-27 | N-(3-chloro-5-methylbenzyl)-1-(2,5-dimethoxy-4-methylphenyl)propan-2-amine | 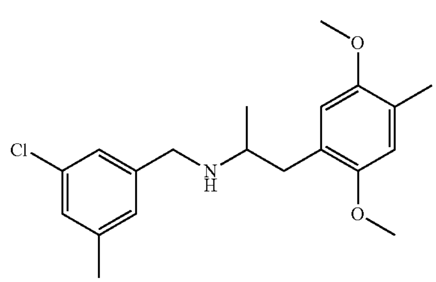 [SMILES: COc1cc(CC(C)NCc2cc(C)cc(Cl)c2)c(OC)cc1C] |

TABLE 1-continued

Compounds of the Disclosure

| Compound | Name | Structure |
| --- | --- | --- |
| 2-28 | N-(3-chloro-5-methylbenzyl)-1-(2,5-dimethoxy-3-methylphenyl)propan-2-amine | 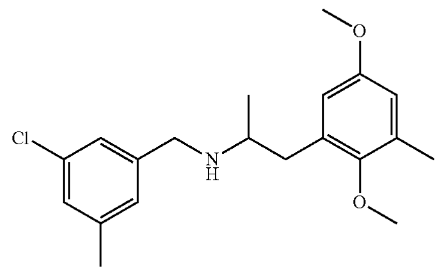 [SMILES: COc1cc(C)c(OC)c(CC(C)NCc2cc(C)cc(Cl)c2)c1] |
| 2-29 | 2-((3-chloro-5-methylbenzyl)amino)-3-(2,5-dimethoxyphenyl)propan-1-ol | 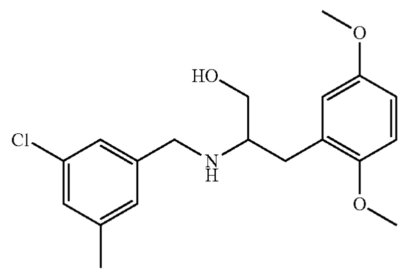 [SMILES: COc1ccc(OC)c(CC(CO)NCc2cc(C)cc(Cl)c2)c1] |
| 2-30 | 2-((3-chloro-5-methylbenzyl)amino)-1-(2,5-dimethoxyphenyl)ethan-1-ol | 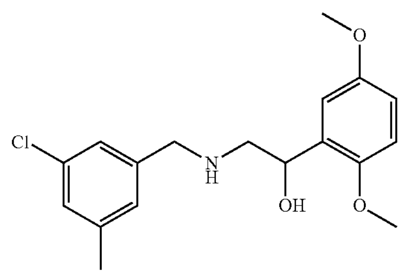 [SMILES: COc1ccc(OC)c(C(O)CNCc2cc(C)cc(Cl)c2)c1] |
| 2-31 | N-(3-chloro-5-methylbenzyl)-2-(2,5-dimethoxy-4-morpholinophenyl)ethan-1-amine | 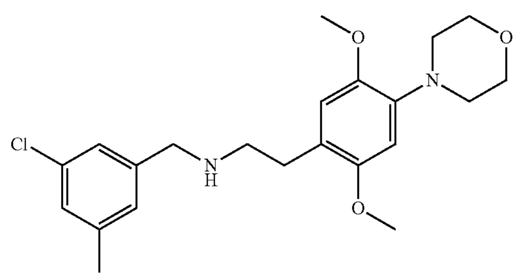 [SMILES: COc1cc(N2CCOCC2)c(OC)cc1CCNCc1cc(C)cc(Cl)c1] |
| 2-32 | (R)-2-((3-chloro-5-methylbenzyl)amino)-1-(2,5-dimethoxyphenyl)ethan-1-ol | 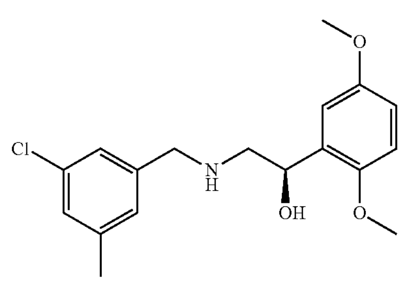 [SMILES: COc1ccc(OC)c([C@@H](O)CNCc2cc(C)cc(Cl)c2)c1] |

TABLE 1-continued

Compounds of the Disclosure

| Compound | Name | Structure |
|---|---|---|
| 2-33 | (S)-2-((3-chloro-5-methylbenzyl)amino)-1-(2,5-dimethoxyphenyl)ethan-1-ol | 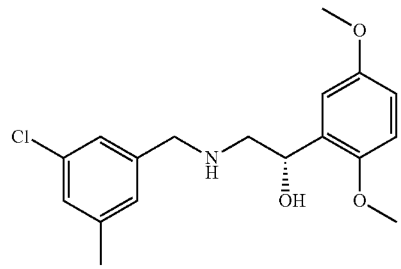 [SMILES: COc1ccc(OC)c([C@H](O)CNCc2cc(C)cc(Cl)c2)c1] |
| 2-34 | (4-(2-((3-chloro-5-methylbenzyl)amino)ethyl)-2,5-dimethoxyphenyl)(imino)(methyl)-$\lambda^6$-sulfanone | 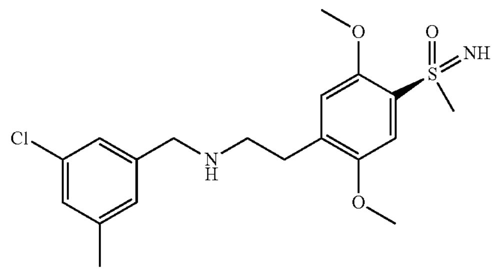 [SMILES: COc1cc([S@](C)(=N)=O)c(OC)cc1CCNCc1cc(C)cc(Cl)c1] |
| 2-35 | (4-(2-((3-chloro-5-methylbenzyl)amino)ethyl)-2,5-dimethoxyphenyl)(imino)(methyl)-$\lambda^6$-sulfanone | 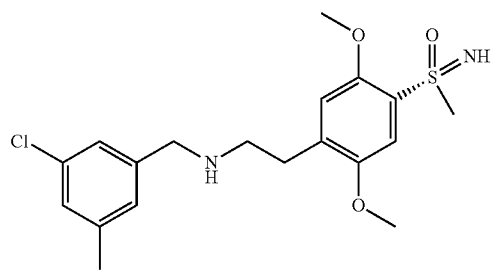 [SMILES: COc1cc([S@@](C)(=N)=O)c(OC)cc1CCNCc1cc(C)cc(Cl)c1] |
| 2-36 | 3-(((2,5-dimethoxyphenethyl)amino)methyl)-5-methylbenzonitrile | 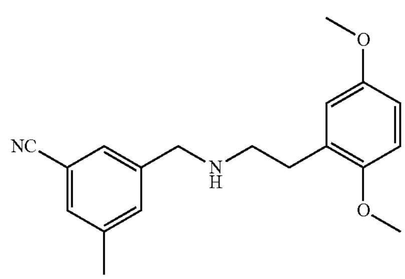 [SMILES: COc1ccc(OC)c(CCNCc2cc(C)cc(C#N)c2)c1] |
| 2-37 | 3-chloro-5-(((2,5-dimethoxyphenethyl)amino)methyl)benzonitrile | 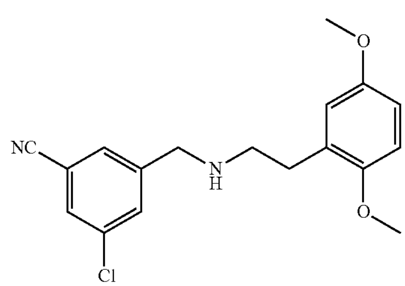 [SMILES: COc1ccc(OC)c(CCNCc2cc(Cl)cc(C#N)c2)c1] |

TABLE 1-continued

Compounds of the Disclosure

| Compound | Name | Structure |
|---|---|---|
| 2-38 | methyl 3-chloro-5-(((2,5-dimethoxyphenethyl)amino)methyl)benzoate | 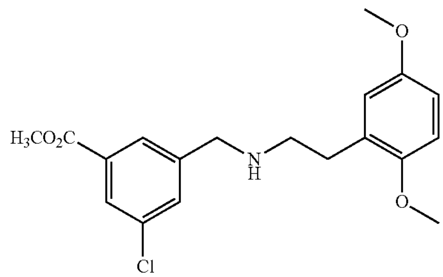 [SMILES: COC(=O)c1cc(Cl)cc(CNCCc2cc(OC)ccc2OC)c1] |
| 2-39 | 3-chloro-5-(((2,5-dimethoxyphenethyl)amino)methyl)benzoic acid | 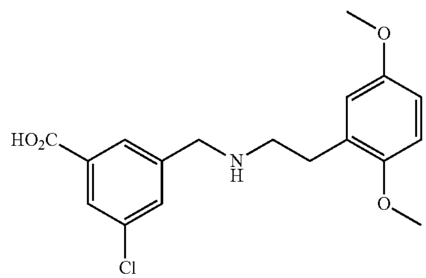 [SMILES: COc1ccc(OC)c(CCNCc2cc(Cl)cc(C(=O)O)c2)c1] |
| 2-40 | N-(3-chloro-5-methylbenzyl)-1-(4-iodo-2,5-dimethoxyphenyl)propan-2-amine | 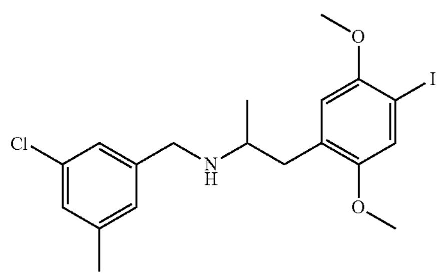 [SMILES: COc1cc(CC(C)NCc2cc(C)cc(Cl)c2)c(OC)cc1I] |
| 2-41 | (R)-1-(2,5-dimethoxyphenyl)-2-((3-fluoro-5-methylbenzyl)amino)ethan-1-ol | 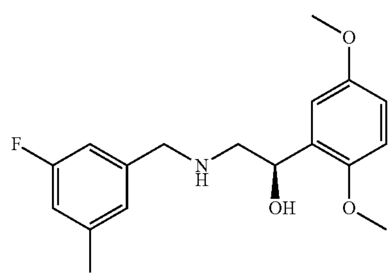 [SMILES: COc1ccc(OC)c([C@@H](O)CNCc2cc(C)cc(F)c2)c1] |
| 2-42 | (S)-1-(2,5-dimethoxyphenyl)-2-((3-fluoro-5-methylbenzyl)amino)ethan-1-ol | 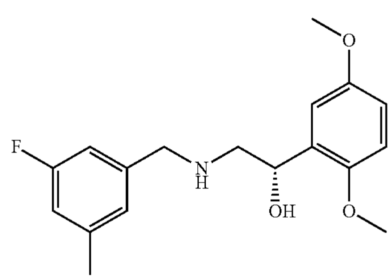 [SMILES: COc1ccc(OC)c([C@H](O)CNCc2cc(C)cc(F)c2)c1] |

In one embodiment, HCl salt forms of any of the compounds described in Table 1 can be used in the present disclosure.

In some embodiments, any of the compounds described in International Patent Publication WO2022/261240 are useful in the present disclosure. Methods of synthesizing compounds of the disclosure are also provided in in International Patent Publication WO2022/261240 (the contents of which are herein incorporated by reference in its entirety).

Provided herein are methods of treating a subject in need thereof using the compounds described herein.

The term "subject" as used herein refers to any individual or patient to which the subject methods are performed. Generally, the subject is human, although as will be appreciated by those in the art, the subject may be an animal. Thus, other animals, including vertebrate such as rodents (including mice, rats, hamsters, and guinea pigs), cats, dogs, rabbits, farm animals including cows, horses, goats, sheep, pigs, chickens, etc., and primates (including monkeys, chimpanzees, orangutans, and gorillas) are included within the definition of subject.

The term "treatment" is used interchangeably herein with the term "therapeutic method" and refers to both 1) therapeutic treatments or measures that cure, slow down, lessen symptoms of, and/or halt progression of a diagnosed pathologic conditions or disorder, and 2) and prophylactic/preventative measures. Those in need of treatment may include individuals already having a particular medical disorder as well as those who may ultimately acquire the disorder (i.e., those needing preventive measures).

The terms "therapeutically effective amount," "effective dose," "therapeutically effective dose," "effective amount," or the like refer to that amount of the subject compound that will elicit the biological or medical response of a tissue, system, animal, or human that is being sought by the researcher, veterinarian, medical doctor, or other clinician. Generally, the response is either amelioration of symptoms in a patient or a desired biological outcome (e.g., treating cancer).

In some embodiments, the compounds of the disclosure including compounds of Formula (I), Formula (I-A), Formula (I-B) and/or Table 1, may be useful in treating a disease or a disorder associated with sleep. In some embodiments, the compounds of the disclosure may be used to treat a sleep dysfunction or a sleep disorder.

In some embodiments, the sleep dysfunction or sleep disorder is a hypersomnia or a circadian rhythm sleep disorder.

In some embodiments, the sleep dysfunction or sleep disorder is a hypersomnia or a circadian rhythm sleep disorder.

In some embodiments, the hypersomnia is narcolepsy, long sleeper disorder, Kleine-Levine Syndrome, or a combination thereof.

In some embodiments, the hypersomnia is narcolepsy.

In some embodiments, the hypersomnia is long sleeper disorder.

In some embodiments, the hypersomnia is Kleine-Levine Syndrome.

In some embodiments, the circadian rhythm sleep disorder is delayed sleep-wake phase disorder, advanced sleep-wake phase disorder, a non-24 sleep wake rhythm, or a combination thereof.

In some embodiments, the circadian rhythm sleep disorder is delayed sleep-wake phase disorder.

In some embodiments, the circadian rhythm sleep disorder is advanced sleep-wake phase disorder.

In some embodiments, the circadian rhythm sleep disorder is a non-24 sleep wake rhythm.

The sleep disorder or sleep dysfunction may be characterized by increased REM sleep and/or increased non-REM sleep compared to healthy control subject. In some embodiments, the compounds of the disclosure may reduce REM sleep in a subject. In some embodiments, compounds of the disclosure may increase REM sleep latency and/or reduce REM sleep duration, thereby treating the sleep disorder or sleep dysfunction. In some embodiments, the compounds of the disclosure may reduce non-REM sleep in a subject. In some embodiments, compounds of the disclosure may increase non-REM sleep latency and/or reduce non-REM sleep duration, thereby treating the sleep disorder or sleep dysfunction.

In some embodiments, the compounds of the disclosure may be used to treat circadian rhythm sleep disorder such as, but not limited to, delayed sleep-wake phase disorder, advanced sleep-wake phase disorder, and/or a non-24 sleep wake rhythm. Circadian rhythm sleep disorders may occur due to a disruption in the timing of sleep and wakefulness caused by an imbalance of homeostatic factors, and/or endogenous circadian system.

In some embodiments, the compounds of the disclosure may be used to treat hypersomnia. Hypersomnia includes a group of sleep disorders that are characterized by excessive sleepiness, particularly during the day. Excessive sleepiness may occur even after long stretches of sleep. A subject with hypersomnia may fall asleep at times that are typically not suitable for sleep, such as, at work and/or while driving. In some embodiments, the compounds of the disclosure can be used to treat hypersomnia such as, but not limited to, insufficient sleep syndrome, narcolepsy, long sleeper disorder, insufficient sleep syndrome, Kleine-Levine Syndrome, and/or idiopathic hypersomnia. In some embodiments, the compounds of the disclosure can be used to treat hypersomnia associated with hypothyroidism, diabetes, chronic pain, depression and/or anxiety. In some embodiments, the compounds of the disclosure may be used to treat hypersomnia associated with mental illness, administration of a medication, or another sleep disorder.

In some embodiments, compounds of the disclosure may be used to modulate one or more stages of sleep. Sleep occurs in five stages: wake, N1, N2, N3, and REM. Stages N1 to N3 are considered non-rapid eye movement (non-REM or NREM herein) sleep, with each stage resulting in a progressively deeper sleep. Approximately 75% of sleep is spent in the NREM stages, with the majority spent in the N2 stage. In humans, a typical night's sleep consists of 4 to 5 sleep cycles, with the progression of sleep stages in the following order: N1, N2, N3, N2, REM. A complete sleep cycle in humans takes roughly 90 to 110 minutes. The first REM period may be short, and, as the night progresses, longer periods of REM and decreased time in deep sleep (NREM) may occur.

In some embodiments, the present disclosure provides methods of reducing REM sleep in a subject using the compounds of the disclosure. As used herein, "REM sleep" may be defined as a stage of sleep characterized by random rapid movement of the eyes, accompanied by low muscle tone throughout the body. Electroencephalogram (EEG) measurements taken during REM sleep may be typically associated with high gamma power. A variety of parameters may be used to measure REM sleep, including the time to onset, length, or duration of the REM stage, and/or amount of eye movement that occurs during REM.

In some embodiments, compounds of the disclosure may be used to increase REM sleep latency. As used herein, "REM sleep latency" refers to the amount of time elapsed between the onset of sleep to the first REM stage. In some embodiments, the compounds of the disclosure may be used to reduce REM density. As used herein, "REM density" refers to the number of eye movements during REM sleep. REM latency can also be characterized in terms of EEG parameters, as for example, REM latency can include the time after dosing at which the first occurrence of three consecutive epochs occurred, allowing for a single epoch of another type to interrupt the sequence, with epochs defined as non-overlapping 10-second time segments.

In some embodiments, the compounds may reduce REM sleep by about 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may reduce REM sleep duration by about 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may increase REM sleep latency by about 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may increase the REM sleep latency by about 0-10 minutes, about 5-15 minutes, about 10-20 minutes, about 15-25 minutes, about 20-30 minutes, about 25-35 minutes, about 30-40 minutes, about 35-45 minutes, about 40-50 minutes, about 45-55 minutes, about 50-60 minutes, about 55-65 minutes, about 1-2 hours, about 1.5-2.5 hours, about 2-3 hours, about 2.5-3.5 hours, about 3-4 hours, about 3.5-4.5 hours, about 4-5 hours, about 4.5-5.5 hours, about 5-6 hours, about 5.5-6.5 hours, about 6-7 hours, about 6.5-7.5 hours, about 7-8 hours, about 7.5-8.5 hours, about 8-9 hours, about 8.5-9.5 hours, about 9-10 hours, about 9.5-10.5 hours, about 10-11 hours, about 10.5-11.5 hours, about 11-12 hours, about 11.5-12.5 hours, about 12-13 hours, about 12.5-13.5 hours, about 13-14 hours, about 13.5-14.5 hours, about 14-15 hours, about 14.5-15.5 hours, about 15-16 hours or more. In some embodiments, the compounds may reduce REM sleep duration by about 0-10 minutes, about 5-15 minutes, about 10-20 minutes, about 15-25 minutes, about 20-30 minutes, about 25-35 minutes, about 30-40 minutes, about 35-45 minutes, about 40-50 minutes, about 45-55 minutes, about 50-60 minutes, about 55-65 minutes, about 1-2 hours, about 1.5-2.5 hours, about 2-3 hours, about 2.5-3.5 hours, about 3-4 hours, about 3.5-4.5 hours, about 4-5 hours, about 4.5-5.5 hours, about 5-6 hours, about 5.5-6.5 hours, about 6-7 hours, about 6.5-7.5 hours, about 7-8 hours, about 7.5-8.5 hours, about 8-9 hours, about 8.5-9.5 hours, about 9-10 hours, about 9.5-10.5 hours, about 10-11 hours, about 10.5-11.5 hours, about 11-12 hours, about 11.5-12.5 hours, about 12-13 hours, about 12.5-13.5 hours, about 13-14 hours, about 13.5-14.5 hours, about 14-15 hours, about 14.5-15.5 hours, about 15-16 hours or more.

In some embodiments, the present disclosure provides methods of reducing non-REM sleep in a subject using the compounds of the disclosure. As used herein, "non-REM sleep" may be defined as a stage of sleep characterized by synchronized EEG activity, muscle relaxation, and decreased heart rate, blood pressure, and tidal volume. In some embodiments, compounds of the disclosure may be used to increase non-REM sleep latency. As used herein, "non-REM sleep latency" refers to the amount of time elapsed between the onset of sleep to the first non-REM stage. Non-REM sleep latency may also be characterized in terms of EEG parameters, for example, non-REM sleep latency can refer to the time after dosing at which the first occurrence of 6 consecutive non-REM sleep epochs occurred, allowing for a single epoch of another type to interrupt the sequence, with epochs defined as non-overlapping 10-second time segments.

In some embodiments, the compounds may reduce non-REM sleep by about 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may reduce non-REM sleep duration by about 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may increase non-REM sleep latency by about 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may increase the non-REM sleep latency by about 0-10 minutes, about 5-15 minutes, about 10-20 minutes, about 15-25 minutes, about 20-30 minutes, about 25-35 minutes, about 30-40 minutes, about 35-45 minutes, about 40-50 minutes, about 45-55 minutes, about 50-60 minutes, about 55-65 minutes, about 1-2 hours, about 1.5-2.5 hours, about 2-3 hours, about 2.5-3.5 hours, about 3-4 hours, about 3.5-4.5 hours, about 4-5 hours, about 4.5-5.5 hours, about 5-6 hours, about 5.5-6.5 hours, about 6-7 hours, about 6.5-7.5 hours, about 7-8 hours, about 7.5-8.5 hours, about 8-9 hours, about 8.5-9.5 hours, about 9-10 hours, about 9.5-10.5 hours, about 10-11 hours, about 10.5-11.5 hours, about 11-12 hours, about 11.5-12.5 hours, about 12-13 hours, about 12.5-13.5 hours, about 13-14 hours, about 13.5-14.5 hours, about 14-15 hours, about 14.5-15.5 hours, about 15-16 hours or more. In some embodiments, the compounds may reduce non-REM sleep duration by about 0-10 minutes, about 5-15 minutes, about 10-20 minutes, about 15-25 minutes, about 20-30 minutes, about 25-35 minutes, about 30-40 minutes, about 35-45 minutes, about 40-50 minutes, about 45-55 minutes, about 50-60 minutes, about 55-65 minutes, about 1-2 hours, about 1.5-2.5 hours, about 2-3 hours, about 2.5-3.5 hours, about 3-4 hours, about 3.5-4.5 hours, about 4-5 hours, about 4.5-5.5 hours, about 5-6 hours, about 5.5-6.5 hours, about 6-7 hours, about 6.5-7.5 hours, about 7-8 hours, about 7.5-8.5 hours, about 8-9 hours, about 8.5-9.5 hours, about 9-10 hours, about 9.5-10.5 hours, about 10-11 hours, about 10.5-11.5 hours, about 11-12 hours, about 11.5-12.5 hours, about 12-13 hours, about 12.5-13.5 hours, about 13-14 hours, about 13.5-14.5 hours, about 14-15 hours, about 14.5-15.5 hours, about 15-16 hours or more.

In some embodiments, the compounds of the disclosure may promote being awake (or wakefulness) in a subject. The wake stage may be defined as the period prior to sleep or after sleep. The subject's eyes may be open during the wake stage, or they may be closed. In some embodiments, the subject may be drowsy but not asleep during wake stage. Brain activity may be recorded using electroencephalogram (EEG) and electromyography (EMG) during wake stage and "waking" may be defined as active movement, or high muscle tone (EMG) with high EEG gamma power. In some embodiments, the compounds may increase the amount of time spent in wake by 0-10%, about 5-15%, about 10-20%, about 15-25%, about 20-30%, about 25-35%, about 30-40%, about 35-45%, about 40-50%, about 45-55%, about 50-60%, about 55-65%, about 60-70%, about 65-75%, about 70-80%, about 75-85%, about 80-90% or more compared to an untreated control subject. In some embodiments, the compounds may increase the amount of time spent in wake by about 0-10 minutes, about 5-15 minutes, about 10-20 minutes, about 15-25 minutes, about 20-30 minutes, about 25-35 minutes, about 30-40 minutes, about 35-45 minutes, about 40-50 minutes, about 45-55 minutes, about 50-60 minutes, about 55-65 minutes, about 1-2 hours, about 1.5-2.5 hours, about 2-3 hours, about 2.5-3.5 hours, about 3-4 hours, about 3.5-4.5 hours, about 4-5 hours, about 4.5-5.5 hours, about 5-6 hours, about 5.5-6.5 hours, about 6-7 hours, about 6.5-7.5 hours, about 7-8 hours, about 7.5-8.5 hours, about 8-9 hours, about 8.5-9.5 hours, about 9-10 hours, about 9.5-10.5 hours, about 10-11 hours, about 10.5-11.5 hours, about 11-12 hours, about 11.5-12.5 hours, about 12-13 hours, about 12.5-13.5 hours, about 13-14 hours, about 13.5-14.5 hours, about 14-15 hours, about 14.5-15.5 hours, about 15-16 hours or more.

In some embodiments, the compounds of the disclosure including compounds of Formula (I), Formula (I-A), Formula (I-B) and/or Table 1, may be useful in treating a disease or a disorder associated with a stress related disorder, a neuropsychiatric disease, neurological condition or a neurodevelopmental disorder. The stress related disorder, neuropsychiatric disease, neurological condition or neurodevelopmental disorder may be characterized by increased REM sleep and/or increased non-REM sleep compared to healthy control subject. In some embodiments, the compounds of the disclosure may reduce REM sleep in the subject. In some embodiments, compounds of the disclosure may increase REM sleep latency and/or reduce REM sleep duration, thereby treating the stress related disorder, the neuropsychiatric disease, neurological condition or the neurodevelopmental disorder. In some embodiments, the compounds of the disclosure may reduce non-REM sleep in the subject. In some embodiments, compounds of the disclosure may increase non-REM sleep latency and/or reduce non-REM sleep duration, thereby treating the stress related disorder, the neuropsychiatric disease, neurological condition or the neurodevelopmental disorder.

In some embodiments, the stress related disorder is depression, anxiety, or post-traumatic stress disorder.

In some embodiments, the depression is major depressive disorder, treatment resistant depression disorder, or a combination thereof.

In some embodiments, the depression is major depressive disorder.

In some embodiments, the depression is treatment resistant depression disorder.

In some embodiments, the anxiety is generalized anxiety disorder, social anxiety disorder, or a combination thereof.

In some embodiments, the anxiety is generalized anxiety disorder.

In some embodiments, the anxiety is social anxiety disorder.

In some embodiments, the stress related disorder is post-traumatic stress disorder.

In some embodiments, the neuropsychiatric disease is alcohol use disorders, drug or substance use disorders, obsessive-compulsive disorder, eating disorders, or a combination thereof.

In some embodiments, the neuropsychiatric disease is alcohol use disorders.

In some embodiments, the neuropsychiatric disease drug or substance use disorders.

In some embodiments, the neuropsychiatric disease is obsessive-compulsive disorder.

In some embodiments, the neuropsychiatric disease is eating disorders.

In some embodiments, compounds of the disclosure may be used to treat stress related disorders. As used herein, a "stress related disorder" refers to any disorder characterized by an elevation in the level of one or more stress hormones. Non-limiting examples of stress hormones may include cortisol, corticotropin-releasing hormone (CRH) and/or adrenocorticotropic hormone (ACTH). Non-limiting examples of stress-related disorders that may be treated by compounds of the disclosure include, post-traumatic stress disorder (PTSD), acute stress disorder (ASD), adjustment disorders, reactive attachment disorder (RAD), disinhibited social engagement disorder (DSED) and/or unspecified traumatic stress disorder.

In some embodiments, the stress related disorder may be depression. In some embodiments, the compounds of the disclosure may be used in the treatment of depression. Depression may be characterized by low mood, lack of energy, sadness, changes in sleep, and an inability to enjoy life. Compounds of the disclosure can be used to treat any type of depression, including, major depressive disorder (MDD) (also known as clinical depression, unipolar depression), treatment resistant depression disorder (TRD), severe treatment resistant depression disorder, persistent depressive disorder, disruptive mood dysregulation disorder, melancholia, psychotic depression, premenstrual dysphoric disorder, antenatal depression, postnatal depression, bipolar disorder, bipolar type I disorder, bipolar type II disorder, unspecified bipolar disorder, cyclothymic disorder, dysthymic disorder, unspecified depressive disorder and/or seasonal affective disorder.

In some embodiments, the compounds of the disclosure may be used to treat anxiety. The term "anxiety" as used herein refers to a group of mental disorders characterized by feelings of fear. There are several types of anxiety disorders, including, but not limited to, generalized anxiety disorder, social anxiety disorder, separation anxiety disorder, panic disorder, selective mutism, unspecified anxiety disorder and/or various phobia-related disorders. The common types of phobia-related disorders include agoraphobia, social phobia, glossophobia, acrophobia, claustrophobia, aviophobia, dentophobia, hemophobia, arachnophobia, cynophobia, ophidiophobia and nyctophobia. Symptoms of anxiety disorders include, but are not limited to, excessive worrying, feeling agitated, restlessness, fatigue, difficulty in concentrating, irritability, trouble falling or staying asleep, panic attacks, avoiding social situations and irrational fears, cold, sweaty, numb, or tingling hands or feet, shortness of breath, heart palpitations, dry mouth, nausea and/or dizziness.

In some embodiments, the compounds of the disclosure may be used to treat neurological diseases. The term neurological disorder may encompass any disorder of the nervous system resulting from structural, biochemical, or electrical abnormalities in the brain, spinal cord, or nervous system. In one embodiment, the neurological disease may be associated with a sleep dysfunction. In one embodiment, the sleep dysfunction may be increased REM sleep and/or increased non-REM sleep in a subject suffering from a neurological disease. As a non-limiting example, the neurological disease may be Attention Deficit-Hyperactivity Disorder (ADHD), Adie's Pupil, Adie's Syndrome, Adrenoleukodystrophy, AIDS-Neurological Complications, Alzheimer's Disease, Amyotrophic Lateral Sclerosis (ALS), Aneurysm, Angelman Syndrome, Angiomatosis, Anoxia, Asperger Syndrome, Ataxia, Ataxia Telangiectasia, Ataxias and Cerebellar or Spinocerebellar Degeneration, Atrial Fibrillation and Stroke, Autism Spectrum Disorder, Autonomic Dysfunction, Back Pain, Brain and Spinal Tumors, Brain Aneurysm, Brain Injury, Bulbospinal Muscular Atrophy, Central Pain Syndrome, Cerebral Palsy, Chronic Pain, Cumulative Trauma Disorders, Dementia, Dementia-Multi-Infarct, Dementia-Semantic, Dementia-Subcortical, Dementia With Lewy Bodies, Dentate Cerebellar Ataxia, Dentatorubral Atrophy, Dermatomyositis, Encephaloceles, Encephalopathy, Encephalopathy (familial infantile), Epilepsy, Epileptic Hemiplegia, Erb's Palsy, Essential Tremor, Extrapontine Myelinolysis, Fabry Disease, Fahr's Syndrome, Fainting, Familial Periodic Paralyses, Familial Spastic Paralysis, Head Injury, Headache, Herpes Zoster, HTLV-1 Associated Myelopathy, Huntington's Disease, Hypersomnia, Lipid Storage Diseases, Lyme Disease-Neurological Complications, Meningitis and Encephalitis, Menkes Disease, Mucolipidoses, Mucopolysaccharidoses, Multiple Sclerosis, Multiple System Atrophy, Muscular Dystrophy, Myelinoclastic Diffuse Sclerosis, Myotonia, Neurological Complications of AIDS, Neurological Complications of Lyme Disease, Neurological Consequences of Cytomegalovirus Infection, Neurological Manifestations of Pompe Disease, Niemann-Pick Disease, Orofacial Pain, Pain-Chronic, Peripheral Neuropathy, Repetitive Motion Disorders, Repetitive Stress Injuries, Restless Legs Syndrome, Retrovirus-Associated Myelopathy, Rett Syndrome, Rheumatic Encephalitis, Seizure Disorder, Semantic Dementia, Shingles, Sleep Apnea, Sleeping Sickness, Spinal Cord Infarction, Spinal Cord Injury, Spinal Cord Tumors, Spinal Muscular Atrophy, Spinocerebellar Atrophy, Systemic Lupus Erythematosus, Tourette Syndrome, Transient Ischemic Attack, Transmissible Spongiform Encephalopathies, Transverse Myelitis, Traumatic Brain Injury, Tremor, Prader-Willi syndrome, Tuberous Sclerosis Complex, and/or Von Hippel-Lindau Disease (VHL).

In some embodiments, the compounds of the disclosure may be used to treat neurological disease such as, but not limited to, schizophrenia, alcohol use disorders, drug or substance use disorders, obsessive-compulsive disorder, body dysmorphic disorder, eating disorders, post-traumatic stress disorder (PTSD), panic disorder, as well as affective, cognitive and behavioral symptoms associated with neurological conditions including Parkinson's disease, migraine, and/or intellectual and developmental disabilities.

In some embodiments, the compounds of the disclosure may be used to treat neurological disease such as, but not limited to, developmental language disorder (DLD; formerly known as SLI—Specific Language Impairment), communication, speech, or language disorders, expressive language disorder, fluency disorder, social (pragmatic) communication disorder, and speech sound disorder, global developmental delay (GDD), motor disorders including developmental coordination disorder, stereotypic movement disorder, and tic disorders (such as Tourette's syndrome), and CAS—Apraxia of speech, neurogenetic disorders, such as Fragile X syndrome, Down syndrome, hypogonadotropic hypogonadal syndromes, specific learning disorders, like dyslexia or dyscalculia and/or fetal alcohol spectrum disorders (FASD).

In some embodiments, the compounds of the disclosure may be used in the treatment of neuropsychiatric diseases. As used herein, the term "neuropsychiatric disease" applies to diseases that affect cognition, and/or behavior that arise from overt disorder in cerebral function, or from indirect effects of extracerebral disease. In one embodiment, the neuropsychiatric disease may be associated with a sleep dysfunction. In one embodiment, the sleep dysfunction may be increased REM sleep and/or increased non-REM sleep in a subject suffering from a neuropsychiatric disease. Non-limiting examples of neuropsychiatric diseases that may be treated by the compounds of the disclosure include psychiatric conditions such as schizophrenia, alcohol use disorders, drug or substance use disorders, obsessive-compulsive disorder, body dysmorphic disorder, eating disorders, as well as affective, cognitive and behavioral symptoms associated with neurological conditions including epilepsy, Alzheimer's and other dementias, Parkinson's disease, multiple sclerosis, migraine, and/or intellectual and developmental disabilities.

In some embodiments, the compounds of the disclosure may be used to treat neurodevelopmental disorders. As used herein, the term "neurodevelopmental disorder" refers to any disorder characterized by an impairment in the growth and development of the brain and/or central nervous system. Neurodevelopmental disorders also include disorders of brain function that affects emotion, learning ability, self-control and memory which unfolds as an individual develops and grows. In one embodiment, the neurodevelopmental disorder may be associated with a sleep dysfunction. In one embodiment, the sleep dysfunction may be increased REM sleep and/or increased non-REM sleep in a subject suffering from a neurodevelopmental disorder. Non-limiting examples of neurodevelopmental disorders that may be treated by the compounds of the disclosure include, attention deficit hyperactivity disorder (ADHD), developmental language disorder (DLD; formerly known as SLI—Specific Language Impairment), communication, speech, or language disorders, expressive language disorder, fluency disorder, social (pragmatic) communication disorder, and speech sound disorder, Asperger syndrome, autism spectrum disorder (ASD), intellectual disabilities (IDs) or intellectual development disorder (IDD) and global developmental delay (GDD), motor disorders including developmental coordination disorder, stereotypic movement disorder, and tic disorders (such as Tourette's syndrome), and CAS—Apraxia of speech, neurogenetic disorders, such as Fragile X syndrome, Down syndrome, Rett syndrome, Angelman syndrome, Prader-Willi syndrome, Tuberous sclerosis complex, hypogonadotropic hypogonadal syndromes, specific learning disorders, like dyslexia or dyscalculia and/or fetal alcohol spectrum disorders (FASD).

In some embodiments, the compounds of the present disclosure are used for treating a mental health disease or disorder in a subject in need thereof, the method comprising administering to the subject a therapeutically effective amount of a compound of the present disclosure (e.g., a compound of Formula (I), (I-A), (I-B), or Table 1 or a pharmaceutically acceptable salt thereof) or a pharmaceutical composition comprising a compound of the present disclosure (e.g., a compound of Formula (I), (I-A), (I-B), or Table 1 or a pharmaceutically acceptable salt thereof) and a pharmaceutically acceptable excipient. In some embodiments, the mental health disease or disorder may be selected from the group consisting of depression, substance use disorders (SUD) and eating disorders. In some embodiments, the mental health disease or disorder may be an eating disorder. Eating disorders include illnesses such as anorexia nervosa, bulimia nervosa, and other disorders related to eating (e.g., binge eating). In some embodiments, the mental health disease or disorder may be a mood disorder. Mood disorders include e.g., depressive disorders, such as major depressive disorder or treatment resistant depression.

In some embodiments, the mental health disorder is a substance abuse disorder. In some embodiments, substance use related disorders are disorders of maladaptive patterns of substance use, and include criteria, such as recurrent substance use related problems, tolerance to a substance, withdrawal upon discontinuing use, an inability to cut down or control use of the substance, and giving up important social, occupational, or recreational activities because of using the substance. See e.g., the Diagnostic and Statistical Manual of Mental Disorders (DSM-5). In some embodiments, the substance use related disorder is a disorder resulting from the use of alcohol; caffeine; cannabis; hallucinogens (such as phencyclidine or similarly acting arylcyclohexylamines, and other hallucinogens, such as LSD); inhalants; opioids; sedatives, hypnotics, or anxiolytics; stimulants (including amphetamine-type substances, cocaine, and other stimulants); tobacco; and other substances.

In some embodiments, the present disclosure provides methods of identifying a patient population for treatment with the compounds of the disclosure. In one embodiment, measuring REM sleep may include measuring one or more of a REM sleep latency and a REM sleep duration. In one embodiment, measuring non-REM sleep may include measuring one or more of a non-REM sleep latency and a non-REM sleep duration. In one embodiment, the present disclosure provides a method of patient stratification based on measuring REM sleep and/or non-REM sleep. In one embodiment, the patient may be enrolled in a sleep study to measure REM and/or non-REM sleep patterns.

In some embodiments of the present disclosure, a pharmaceutical composition that includes a therapeutically effective amounts of one or more compounds of the present disclosure (e.g., a compound of Formula (I), Formula (I-A), Formula (I-B), or Table 1) or a pharmaceutically acceptable salt thereof and a pharmaceutically acceptable excipient is provided.

The term "pharmaceutically acceptable" refers to the fact that the carrier, diluent, or excipient must be compatible with the other ingredients of the formulation and not deleterious to the recipient thereof. For example, the carrier, diluent, or excipient or composition thereof may be administered to a subject along with a compound of the invention without causing any undesirable biological effects or interacting in an undesirable manner with any of the other components of the pharmaceutical composition in which it is contained. "Pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammoniumhydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Those skilled in the art will further recognize that acid addition salts may be prepared by reaction of the compounds with the appropriate inorganic or organic acid via any of a number of known methods.

The pharmaceutically acceptable excipients and adjuvants may be added to the compounds for a variety of purposes. In some embodiments, a pharmaceutical composition comprising one or more compounds disclosed herein, or a pharmaceutically acceptable salt thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable carriers include, but are not limited to, inert solid fillers or diluents and sterile aqueous or organic solutions. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, and the like.

The terms "administration of" and or "administering" should be understood to mean providing a pharmaceutical composition in a therapeutically effective amount to the subject in need of treatment. Administration routes may be enteral, topical, or parenteral. As such, administration routes include but are not limited to intracutaneous, subcutaneous, intramuscular, intravenous, intraperitoneal, intraarterial, intrathecal, intracapsular, intraorbital, intracardiac, intradermal, transdermal, transtracheal, subcuticular, subcapsular, subarachnoid, intraspinal and intrasternal, oral, sublingual, buccal, rectal, vaginal, nasal ocular administrations, as well infusion, inhalation, and nebulization.

For the purposes of this disclosure, the compounds of the present disclosure may be formulated for administration by a variety of means including sublingual, intracutaneous, subcutaneous, intramuscular, intraperitoneal, intravenous, intraarterial, intradermal, transdermal, oral, buccal, or nasal route of administration, in formulations containing pharmaceutically acceptable carriers, adjuvants and vehicles. The term parenteral as used herein includes subcutaneous, intravenous, intramuscular, intraperitoneal, transdermal, transmucosal, vaginal, and/or intraarterial administration. In some embodiments, the pharmaceutical compositions may be injected into a subject. Intraarterial and intravenous injection as used herein includes administration through catheters. In one embodiment, a pharmaceutical composition of the present disclosure may be formulated into tablets, dragees, capsules, or an oral liquid preparation for oral or sublingual administration.

Compounds of the disclosure may be administered to a subject e.g., a human, at a dose of from about 0.0025 to about 1500 mg per kg body weight of the mammal, or an equivalent amount of a pharmaceutically acceptable salt or solvate thereof. In some embodiments, the dose may be a dose per day. In one embodiment, the dose of the compound administered to a mammal is from about 0.0025 to about 50 mg per kg body weight of the mammal, or an equivalent amount of the pharmaceutically acceptable salt or solvate thereof.

A single dose of the compound may be administered to the subject. In some embodiments, multiple doses such as 2, 3, 4, 5, 6, 7, 8, 9, 10 or more may be administered to the subject. A unit dose includes from about 0.01 mg to about 1 g of the compound, e.g., about 0.01 mg to about 500 mg, about 0.01 mg to about 250 mg, about 0.01 mg to about 100 mg, 0.01 mg to about 50 mg, e.g., about 0.1 mg to about 10 mg of the compounds of the disclosure. The unit dose may be administered one or more times daily.

Presented below are examples discussing the utility of compounds of the invention contemplated for the discussed applications. The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

Primary In Vitro Pharmacology of Compound 2-1

In vitro pharmacology studies were performed to evaluate the effects of compound 2-1 on functional activity of several 5-HT receptors using recombinant target overexpression cell culture systems. The effect of compound 2-1 on G protein-dependent signaling was investigated at 5-HT2A, 5-HT2B, and 5-HT2C receptors with calcium mobilization and IPOne assays; and at 5-HT1A, 5-HT1B, 5-HT1F, 5-HT5A, and 5-HT7D receptors with a cAMP assay. G protein-independent signaling was investigated at the 5-HT2A receptor with a β-Arrestin assay.

As shown in Table 2, compound 2-1 demonstrated binding and full agonism in both G protein-dependent and -independent assays with nanomolar potency at the 5-HT2A receptor. Compound 2-1 also showed agonist activity at 5-HT2C, and binding and agonism at 5-HT2B, receptors with nanomolar potency in the assays tested, but demonstrated higher selectivity for the 5-HT2A receptor (5-HT2A/5-HT2C selectivity factor=77; 5-HT2A/5-HT2B selectivity factor=160). When tested at the other 5-HT receptors, compound 2-1 showed a lack of agonist activity up to the highest concentrations tested across all except for the 5-HT5A receptor. At the 5-HT5A receptor, compound 2-1 demonstrated nanomolar potency but partial agonist activity. Overall, the in vitro activity tested across these 5-HT receptors indicates that compound 2-1 is a potent and selective agonist at human 5-HT2A receptor in the in vitro assays tested. In Table 2, 5-HT receptor selectivity was calculated using $\Delta\Delta \log(E_{mx}/EC_{50})$. Assay reference α-Me-5-HT or 5-HT was used for normalization at each receptor (5-HT2A/5-HT2B selectivity 1; 5-HT2A/5-HT2C selectivity 1). ND in Table 2 indicates, not determined, plateau was not reached within the concentration range tested to determine $E_{max}$.

TABLE 2

In vitro binding, activity, and selectivity profiles of compound 2-1 at 5-HT receptors
compound 2-1

| Assay | Target (human) | Readout | Value |
|---|---|---|---|
| Radioligand Binding | 5-HT2A | $IC_{50}$ (nM) | 42.38 |
|  |  | Max % inhibition | 96.93 |
|  | 5-HT2B | $IC_{50}$ (nM) | 84.86 |
|  |  | Max % inhibition | 102.5 |
| Ca++ | 5-HT2A | $EC_{50}$ (nM) | 4.24 |
|  |  | Emax (%5-HT) | 93.26 |
|  | 5-HT2C | $EC_{50}$ (nM) | 42.16 |
|  |  | Emax (%5-HT) | 82.04 |
|  |  | 5-HT2A/5-HT2C Selectivity | 77 |
| IPOne | 5-HT2A | $EC_{50}$ (nM) | 2.802 |
|  |  | Emax (% α-Me-5-HT) | 99.36 |
|  | 5-HT2B | $EC_{50}$ (nM) | 34.73 |
|  |  | Emax (% α-Me-5-HT) | 77.57 |
|  |  | 5-HT2A/5-HT2B Selectivity | 160 |
| β-Arrestin | 5-HT2A | $EC_{50}$ (nM) | 17.20 |
|  |  | Emax (%5-HT) | 89.35 |
| cAMP | 5-HT1A | $EC_{50}$ (nM) | >20000 |
|  |  | Emax (%5-HT) | ND |
|  | 5-HT1B | $EC_{50}$ (nM) | >100000 |
|  |  | Emax (%5-HT) | ND |
|  | 5-HT1F | $EC_{50}$ (nM) | >9000 |
|  |  | Emax (%5-HT) | ND |
|  | 5-HT5A | $EC_{50}$ (nM) | 25.2 |
|  |  | Emax (%5-HT) | 44.37 |
|  | 5-HT7D | $EC_{50}$ (nM) | >100000 |
|  |  | Emax (%5-HT) | ND |

Further in vitro activity profiling was performed for compound 2-1 at rodent 5-HT2A and 5-HT2B receptors. As shown in Table 3, compound 2-1 demonstrated full agonist activity at rat 5-HT2A receptor with similar potency compared to at the human 5-HT2A receptor. compound 2-1 was inactive at rat 5-HT2B receptor, in contrast to full agonist activity at the human 5-HT2B receptor. In the G protein-independent signaling assay (β-arrestin) at the mouse 5-HT2A receptor, compound 2-1 showed similar nanomolar potency, but reduced efficacy compared to at the human 5-HT2A receptor with the same assay readout. Overall, in vitro activity at rodent 5-HT2A and 5-HT2B receptors is consistent with the human receptor results, with compound 2-1 acting as a potent and selective 5-HT2A agonist.

TABLE 3

In vitro activity and selectivity profiles of compound 2-1 at rodent 5-HT receptors
compound 2-1

| Assay | Target (rodent) | Readout | Value |
|---|---|---|---|
| IPOne | 5-HT2A (rat) | $EC_{50}$ (nM) | 3.06 |
|  |  | Emax (% α-Me-5-HT) | 99.53 |

TABLE 3-continued

In vitro activity and selectivity profiles of
compound 2-1 at rodent 5-HT receptors
compound 2-1

| Assay | Target (rodent) | Readout | Value |
|---|---|---|---|
| | 5-HT2B (rat) | $EC_{50}$ (nM) | >1000 |
| | | Emax (% α-Me-5-HT) | ND |
| | | 5-HT2A/5-HT2B Selectivity (rat) | >100000 |
| β-Arrestin | 5-HT2A (mouse) | $EC_{50}$ (nM) | 4.37 |
| | | Emax (%5-HT) | 64.96 |

Example 2

Effect of Compound 2-1 on Mouse Head Twitch Response

Figure 1B:
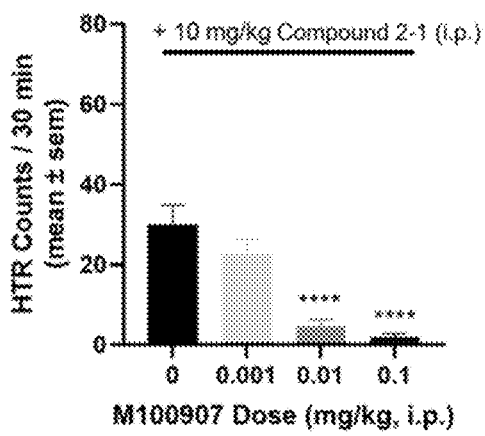
FIG. 1B is a graph showing mouse head twitch response (HTR) data following administration of compound 2-1 i.p. in the presence of M100907.
Figure 1C:
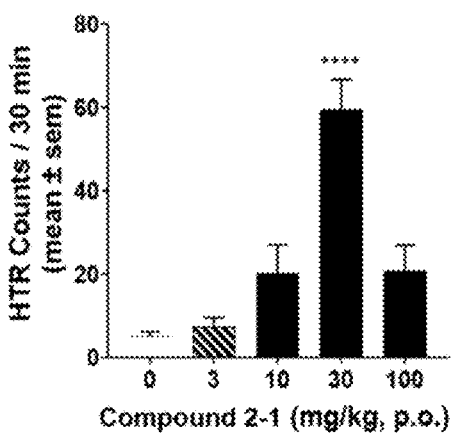
FIG. 1C is a graph showing HTR data following oral administration.

The head twitch response (HTR) assay in rodents is commonly used as a behavioral proxy for 5-HT2A receptor activation. For classical serotonergic psychedelics, mouse HTR potency correlates with potency of subjective effects in humans. The ability of compound 2-1 to induce HTR in mice was assessed using a validated and automated detection system. Briefly, adult male C57BL/6J mice surgically prepared with a small neodymium magnet (4.57 mm×4.57 mm×2.03 mm) attached to the cranium were injected intraperitoneally (i.p.) with single doses of compound 2-1 (0.3, 1, 3, 10, 30 mg/kg, based on weight of the free base) or 40% (w/v) 2-HPBCD (hydroxypropyl-beta-cyclodextrin) vehicle (n=5-6 mice per treatment). In a 5-HT2A receptor antagonism study, M100907, a 5-HT receptor antagonist (0.001, 0.01, 0.1 mg/kg, i.p.) was administered 20 minutes prior to compound 2-1. Immediately after compound 2-1 injection, the mouse was placed individually in a glass cylinder surrounded by a magnetometer coil. HTR were recorded for 30 minutes and analyzed using a validated technique based on artificial intelligence. Individual mice were assessed for HTR on multiple test occasions, performed at least 7 days apart. compound 2-1 exhibited an inverted "U"-shaped dose-response curve on HTR (FIG. 1A), similar to that reported for psilocin in the same assay (Klein et al., 2021). compound 2-1 (3 and 10 mg/kg, i.p.) significantly increased HTR compared to the 40% (w/v) 2-HPBCD vehicle group with a 50% effective dose (ED50) of 1.7 mg/kg i.p., a potency that is lower than psilocin (ED50=0.17 mg/kg i.p.). 5-HT2A receptor activation was confirmed to underpin the compound 2-1 HTR based on significant dose-dependent attenuation of the response by M100907 (FIG. 1B). Oral compound 2-1 also increased HTR significantly at 30 mg/kg, with an ED50 of 15.7 mg/kg p.o. (FIG. 1C). These data indicate that compound 2-1 produced behavioral effects in the intact mouse consistent with in vivo 5-HT2A receptor activation-mediated activity. In FIG. 1A, FIG. 1B, and FIG. 1C, HTR data were analyzed using a 1-way Analysis of Variance (ANOVA) followed by Dunnett's test $p<0.01$, *$p<0.001$, ****$p<0.0001$ vs. vehicle).

Example 3

Effect of Compound 2-1 in Rat Forced Swim Test (FST)

Figure 2:
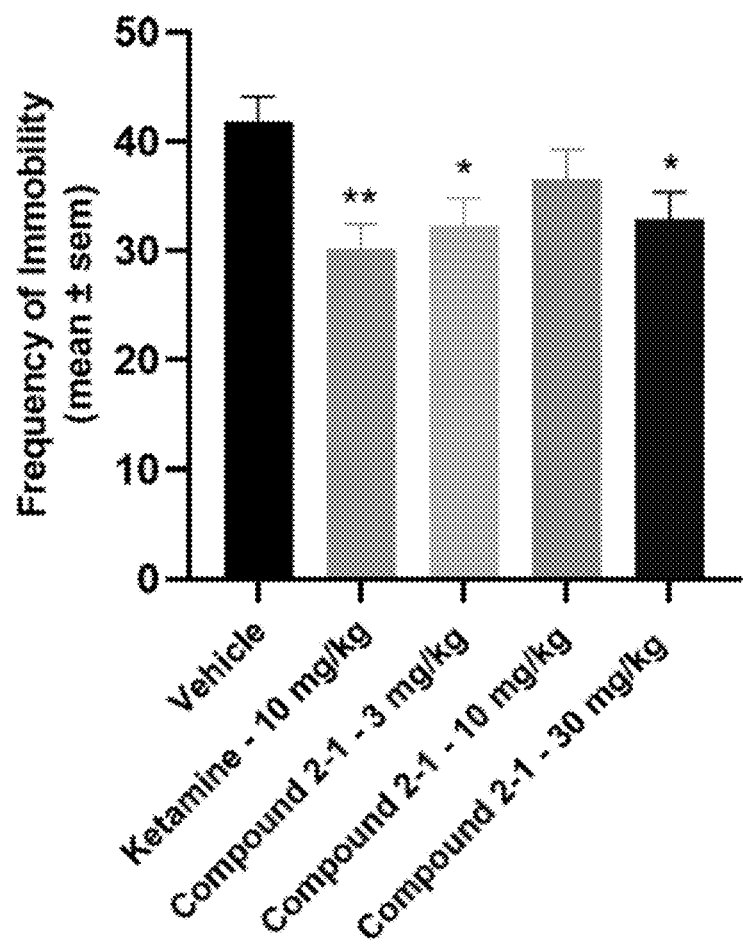
FIG. 2 is a graph showing rat FST immobility frequency during a 5-minute test following administration of vehicle, ketamine, or compound 2-1. The data were plotted as the mean±sem for each treatment group.

The FST in rodents is commonly used to screen for in vivo antidepressant-like activity, as acute administration of clinically relevant antidepressant drugs has been shown to reduce immobility in the test, indicative of predictive validity. Male Sprague-Dawley rats were placed individually in clear acrylic swim chambers (40 cm height×20.3 cm diameter) filled to 16 cm for a 15-minute pre-swim session on day 1 and filled to 30 cm for a 5-minute swim test session 24 hours later. Rats (n=10 per treatment group) were administered compound 2-1 (3, 10, 30 mg/kg, i.p., 1 mL/kg, based on weight of the free base) or vehicle (40% (w/v) 2-HPBCD in water, i.p.) at 23.5, 16 and 0.5 hours prior to the swim test. The rapid-acting antidepressant, ketamine (10 mg/kg, i.p.), was included in the study as a positive control condition and injected once 24 hours prior to the swim test. The presence of immobility behavior was assessed every 5 seconds during the 5-minute swim test. compound 2-1 (3 and 30 mg/kg, i.p.) significantly decreased the frequency of immobility compared to the vehicle group (FIG. 2). Ketamine significantly decreased immobility compared to vehicle, indicating the robustness of the experiment to detect a significant antidepressant-like effect. These data suggest that compound 2-1 exhibits in vivo antidepressant-like activity in rats.

Example 4

Primary In Vitro Pharmacology of Compound 2-2

In vitro pharmacology studies were performed to evaluate the effects of compound 2-2 on functional activity at several 5-HT receptors using recombinant target overexpression cell culture systems. The effect of compound 2-2 on G protein-dependent signaling was investigated at 5-HT2A, 5-HT2B, and 5-HT2C receptors with calcium mobilization and IPOne assays; and at 5-HT1A, 5-HT1B, 5-HT1F, 5-HT5A, and 5-HT7D receptors with a cAMP assay. G protein-independent signaling was investigated at the 5-HT2A receptor with a β-arrestin assay. As shown in Table 4, compound 2-2 demonstrated 5-HT2A receptor binding and full agonism in both G protein-dependent and -independent functional assays with nanomolar potency. compound 2-2 also showed full agonist activity at 5-HT2C receptors, as well as binding and partial agonist activity at 5-HT2B receptors, with nanomolar potencies in the assays tested, but demonstrated higher selectivity for the 5-HT2A receptor (5-HT2A/5-HT2C selectivity factor=56; 5-HT2A/5-HT2B selectivity factor=177). When tested at the other 5-HT receptors, compound 2-2 showed a lack of agonist activity up to the highest concentrations tested. Overall, the in vitro activity tested across these 5-HT receptors indicates that compound 2-2 is a potent and selective agonist at the human 5-HT2A receptor in the in vitro assays tested. In Table 4, 5-HT receptor selectivity was calculated using $\Delta\Delta\log(E_{max}/EC_{50})$. Assay reference α-Me-5-HT or 5-HT was used for normalization at each receptor (5-HT2A/5-HT2B selectivity=1; 5-HT2A/5-HT2C selectivity=1). ND in Table 4 indicates, not determined, plateau was not reached within the concentration range tested to determine $E_{max}$.

TABLE 4

In vitro binding, activity, and selectivity profiles
of compound 2-2 at human 5-HT receptors
compound 2-2

| Assay | Target (human) | Readout | Value |
|---|---|---|---|
| Radioligand Binding | 5-HT2A | $IC_{50}$ (nM) | 105.3 |
| | | Max % inhibition | 99 |

TABLE 4-continued

In vitro binding, activity, and selectivity profiles
of compound 2-2 at human 5-HT receptors
compound 2-2

| Assay | Target (human) | Readout | Value |
|---|---|---|---|
| | 5-HT2B | $IC_{50}$ (nM) | 321 |
| | | Max % inhibition | 99.56 |
| Ca++ | 5-HT2A | $EC_{50}$ (nM) | 9.00 |
| | | $E_{max}$ (%5-HT) | 87.95 |
| | 5-HT2C | $EC_{50}$ (nM) | 73.50 |
| | | $E_{max}$ (%5-HT) | 88.24 |
| | | 5-HT2A/5-HT2C Selectivity | 56 |
| IPOne | 5-HT2A | $EC_{50}$ (nM) | 9.19 |
| | | Emax (% α-Me-5-HT) | 97.94 |
| | 5-HT2B | EC50 (nM) | 81.14 |
| | | Emax (% α-Me-5-HT) | 49.3 |
| | | 5-HT2A/5-HT2B Selectivity | 177 |
| β-Arrestin | 5-HT2A | EC50 (nM) | 25.79 |
| | | Emax (%5-HT) | 82.11 |
| cAMP | 5-HT1A | EC50 (nM) | >1000 |
| | | Emax (%5-HT) | ND |
| | 5-HT1B | EC50 (nM) | >100000 |
| | | Emax (%5-HT) | ND |
| | 5-HT1F | EC50 (nM) | >25000 |
| | | Emax (%5-HT) | ND |
| | 5-HT5A | EC50 (nM) | >30000 |
| | | Emax (%5-HT) | ND |
| | 5-HT7D | EC50 (nM) | >100000 |
| | | Emax (%5-HT) | ND |

Further in vitro activity profiling was performed for compound 2-2 at rodent 5-HT2A and 5-HT21B receptors. As shown in Table 5, compound 2-2 demonstrated full agonist activity at rat 5-HT2A receptor with similar potency compared to at the human 5-HT2A receptor. compound 2-2 did not exhibit agonist activity at rat 5-HT21B receptor, in contrast to partial agonist activity at the human 5-HT21B receptor. In the G protein-independent signaling assay (β-arrestin) at the mouse 5-HT2A receptor, compound 2-2 showed similar nanomolar potency, but reduced efficacy compared to at the human 5-HT2A receptor with the same assay readout. Overall, in vitro activity at rodent 5-HT2A and 5-HT21B receptors is consistent with the human receptor results, with compound 2-2 acting as a potent and selective 5-HT2A agonist. In Table 5, ND indicates not determined.

TABLE 5

In vitro activity and selectivity profiles of
compound 2-2 at rodent 5-HT receptors
compound 2-2

| Assay | Target (rodent) | Readout | Value |
|---|---|---|---|
| IPOne | 5-HT2A (rat) | $EC_{50}$ (nM) | 7.2 |
| | | $E_{max}$ (% α-Me-5-HT) | 105.43 |
| | 5-HT2B (rat) | $EC_{50}$ (nM) | >1000 |
| | | $E_{max}$ (% α-Me-5-HT) | ND |
| | | 5-HT2A/5-HT2B Selectivity (rat) | >100000 |
| β-Arrestin | 5-HT2A (mouse) | $EC_{50}$ (nM) | 21.8 |
| | | $E_{max}$ (%5-HT) | 60.24 |

Example 5

Effect of Compound 2-2 on Mouse Head Twitch Response (HTR)

Figure 3A:
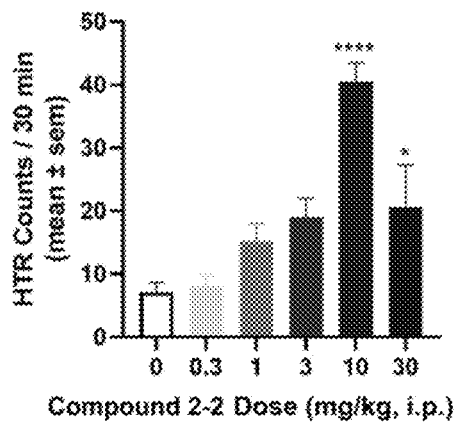
FIG. 3A is a graph showing mouse head twitch response (HTR) data following administration of compound 2-2 i.p. alone.
Figure 3B:
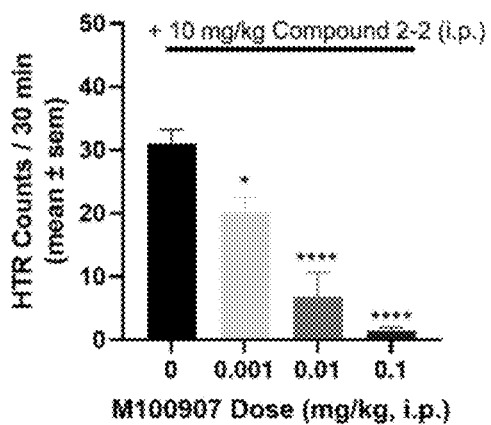
FIG. 3B is a graph showing mouse head twitch response (HTR) data following administration of compound 2-2 i.p. in the presence of M100907.
Figure 3C:
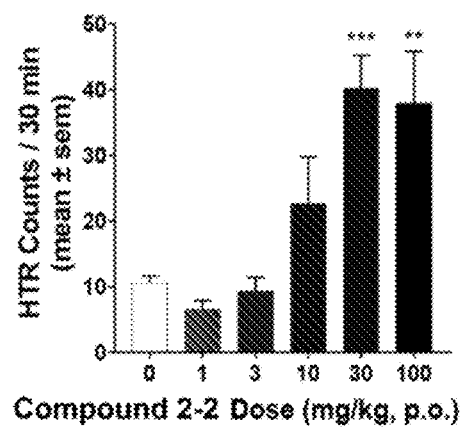
FIG. 3C is a graph showing HTR data following oral administration.

The HTR assay in rodents is commonly used as a behavioral proxy for 5-HT2A receptor activation. For classical serotonergic psychedelics, mouse HTR potency correlates with potency of subjective effects in humans. The ability of compound 2-2 to induce HTR in mice was assessed using a validated and automated detection system. Briefly, adult male C57BL/6J mice surgically prepared with a small neodymium magnet (4.57 mm×4.57 mm×2.03 mm) attached to the cranium were injected intraperitoneally (i.p.) with single doses of compound 2-2 (0.3, 1, 3, 10, 30 mg/kg, based on weight of the free base) or 40% (w/v) 2-HPBCD vehicle (n=5-6 mice per treatment). In a 5-HT2A receptor antagonism study, M100907 (0.001, 0.01, 0.1 mg/kg, i.p.) was administered 20 minutes prior to compound 2-2. Immediately after compound 2-2 injection, the mouse was placed individually in a glass cylinder surrounded by a magnetometer coil. HTR were recorded for 30 minutes and analyzed using a validated technique based on artificial intelligence. Individual mice were assessed for HTR on multiple test occasions, performed at least 7 days apart. compound 2-2 exhibited an inverted "U"-shaped dose-response curve on HTR (FIG. 3A), similar to that reported for psilocin in the same assay. compound 2-2 (10 and 30 mg/kg, i.p.) significantly increased HTR compared to the 40% (w/v) 2-HPBCD vehicle group with a 50% effective dose ($ED_{50}$) of 3.2 mg/kg i.p., a potency that is lower than psilocin ($ED_{50}$=0.17 mg/kg i.p., Klein et al., 2021). 5-HT2A receptor activation was confirmed to underpin the compound 2-2 (i.p.) HTR based on significant dose-dependent attenuation of the response by M100907 (FIG. 3B). Orally administered compound 2-2 also increased HTR significantly at 30 and 100 mg/kg, with an ED50 of 13.7 mg/kg p.o. (FIG. 3C). These data indicate that compound 2-2 produced behavioral effects in the intact mouse consistent with in vivo 5-HT2A receptor activation-mediated activity. HTR were analyzed using a 1-way Analysis of Variance (ANOVA) followed by Dunnett's test (*p<0.05, p<0.01, *p<0.001, ****p<0.0001 vs. vehicle).

Example 6

Effect of Compound 2-2 in Rat Forced Swim Test (FST)

Figure 4:
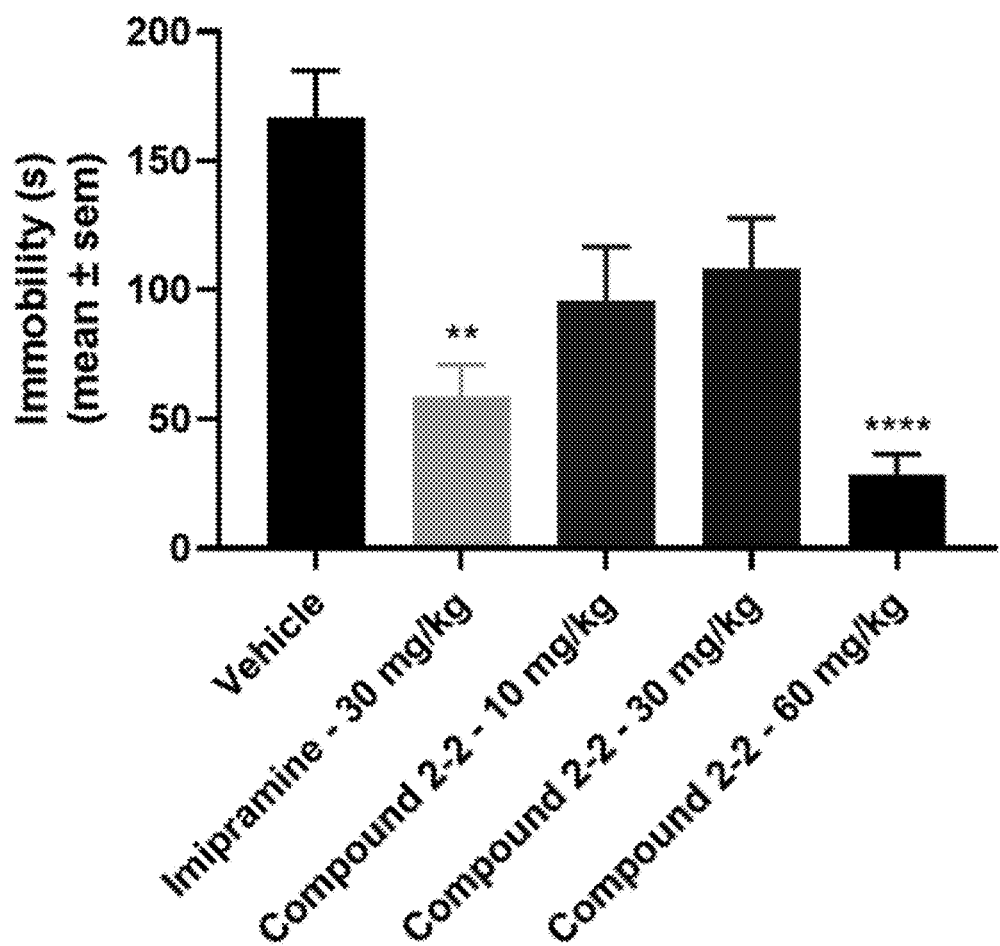
FIG. 4 is a bar graph showing rat FST immobility duration during a 5-minute test following i.p. administration of vehicle, imipramine, or compound 2-2.

The FST in rodents is commonly used to screen for in vivo antidepressant-like activity, as acute administration of clinically relevant antidepressant drugs has been shown to reduce immobility in the test, indicative of predictive validity. Male adult Sprague-Dawley rats were placed individually in clear acrylic swim chambers (45 cm height×21.5 cm diameter) filled to 30 cm with water for a 15-minute pre-swim session on day 1 and a 5-minute swim test session 24 hours later. Rats (n=10-14 per treatment group) were administered vehicle (40% (w/v) 2-HPBCD in water, i.p.), compound 2-2 (10, 30 or 60 mg/kg, i.p., based on weight of the free base) or the positive control antidepressant drug imipramine (30 mg/kg, i.p.) in a volume of 5 mL/kg at 23.5, 16 and 0.25 hours prior to the swim test. The duration of immobility behavior was measured during the 5-minute swim test. compound 2-2 (60 mg/kg, i.p.) significantly decreased the duration of immobility compared to the vehicle group. Imipramine significantly decreased immobility compared to vehicle, indicating the robustness of the experiment to detect a significant antidepressant-like effect (FIG. 4). These data suggest that compound 2-2 exhibits in vivo antidepressant-like activity in rats. In FIG. 4, data were analyzed using a 1-way ANOVA followed by Dunnett's test ($p<0.01$, **$p<0.0001$ vs. vehicle).

Example 7

Effect of Compound 2-1 and Compound 2-2 on Sleep-Wake Behavior and EEG Brain Oscillatory Power The aim of the current study was to investigate the dose-dependent effects of compound 2-1 and compound 2-2 on sleep-wake behavior and EEG brain oscillatory power in rats, across the circadian cycle. Psilocybin was used as a positive control.

Male WKY rats (n=7, 289-388 g at the start of dosing) were housed in groups of 2-3 animals per cage with standard housing conditions. For implantation of the EEG electrodes and radio transmitter, the animals were anesthetized with isoflurane (2-5% in oxygen at 1l/min) throughout the procedure. The scalp, neck and right flank were cleared of hair using clippers and cleaned using diluted Hibitane (chlorhexidine, 50% (v/v) in water). A non-steroidal anti-inflammatory agent was administered (carprofen 5 mg/kg, s.c.) and the animals placed on a homeothermic blanket (37° C.) with the head fixed in a stereotaxic frame. Incisions were made in the scalp and neck, as well as in the right flank. Blunt dissection of the abdominal muscle was then made to gain access to the peritoneal cavity. A radio transmitter (HD-S02, Data Sciences International) was implanted in the peritoneal cavity and secured to the muscle wall with non-absorbable sutures. The wires of the transmitter were passed using a 19G needle through the muscle wall and then sub-dermally to the scalp to act as Electroencephalogram (EEG)/Electromyograph (EMG) electrodes. The scalp was cleared of connective tissue and two craniotomies were made with a trepanning drill (fronto-parietal coordinates; Bregma+2 mm anterior, midline+1.0 mm lateral and Lambda 0 mm, +1.5 mm lateral). The positive EEG electrode was attached to the anterior craniotomy and the negative EEG electrode to the posterior craniotomy. Both electrodes were secured in place using a suitable adhesive agent (cyanoacrylate gel, RS components). A second set of electrodes were sutured into the nuchal muscle to act as EMG electrodes. All incisions were closed using absorbable suture.

All animals were allowed to recover in a warm environment and given 5 ml of saline subcutaneously (s.c.). Animals were kept singly in the cage until the next day, then pair housed for the duration of post-surgical recovery (minimum 7 days). During the recovery period, the rats received 5 days of standard post-operative care with no further experimental procedures until the pre-operative body weight was regained. The animals were maintained on a 12/12 hour light dark cycle (08:00 am lights on) after the surgery. Home cages and post-operative cages contained bedding and nesting material, along with environmental enrichment such as wooden chew-sticks and plastic tunnels.

On test days, ~60 minutes after lights-on, animals were placed in recording boxes similar to their home-cages, except that environmental enrichment was restricted to a large bundle of nesting and bedding material, to avoid interference with the telemeter signals. Then, data acquisition was initiated for confirmation of signal quality. EEG and EMG data were acquired using intraperitoneal HD-S02 transmitters (DSI, New Brighton, MN) and Spike2 software (CED). EEG and EMG signals were digitized 500 samples/second, amplified 1000× and bandpass filtered at 0.5-100 Hertz (Hz). After 60 minutes of habituation, each animal was briefly removed from its box and dosed via the intraperitoneal (i.p.) route in a volume of 2 mL/kg. Test conditions included saline vehicle, psilocybin (10 mg/kg) positive control, compound 2-1 at 3, 10 and 30 mg/kg and compound 2-2 at 10, 17 and 30 mg/kg. Doses were based on the molecular weight of the free bases. compound 2-1 and compound 2-2 dosing solutions were prepared in 40% (w/v) hydroxypropyl-beta-cyclodextrin. After dosing, animals were immediately put back into the recording boxes, the experimenter left the room, and recordings continued uninterrupted for 23 hours. At the end of the recording session, the transmitters were turned off and the animals were returned to their home cages. All animals received all treatment conditions in a pseudo randomized cross-over fashion with a minimum washout period of 7 days between doses.

All data was aligned to zero (the time of dosing), with epochs defined as non-overlapping 10-second time segments. EEG was analyzed using short-time fast Fourier transform (FFT) (amplitude/second, 1-second non-overlapping, unpadded Hann windows), producing 1-100 Hz spectra with 1 Hz frequency resolution. For each epoch, the resulting spectra were reduced to the median value for each frequency, and the area under the curve was used to estimate qEEG values for the following bands: delta (1-4 Hz), theta (4-7 Hz), alpha (8-12 Hz), beta (14-30 Hz), low gamma (30-50 Hz) and high gamma (50-100 Hz). EMG data was digitally bandpass filtered (50-150 Hz), rectified, and median values were calculated for each epoch.

10-second epochs were scored as wake, non-REM (NREM) sleep, or REM sleep. Briefly, "waking" was defined as active movement, or high muscle tone (EMG) with high EEG gamma power. Non-REM sleep was defined as inactivity combined with lower muscle tone and low EEG gamma power. REM sleep was defined as inactivity combined with very-low muscle tone and high EEG gamma power.

In 30-minute bins, qEEG epoch averages and the percentage of time spent in each vigilance state were estimated across the entire recording period. These half-hourly values were used to determine the pharmacodynamic profile of the compounds being tested, and to determine the appropriate time window and bin-size to use for statistical analysis.

Non-REM sleep latency was defined as the time after dosing at which the first occurrence of 6 consecutive non-REM sleep epochs occurred, allowing for a single epoch of another type to interrupt the sequence. For REM sleep, the criterion was 3 consecutive epochs.

Signal loss during acquisition was defined as two or more consecutive samples of value "0" (for both EEG and EMG). EEG spectral estimates for a 1-second window were invalidated if more than 10% of the samples in that window were missing.

Effects of treatment and time were assessed with 2-way repeated-measures ANOVA (R version 3.6.3) following multiple-imputation (if required) to handle missing cases and using the Greenhouse-Geisser correction for violations of sphericity. Results for the compound 2-1 and compound 2-2 dose-series were analyzed separately, but the same vehicle and psilocybin data were included in both analyses. For qEEG, separate analyses were conducted for each vigilance state. Post-hoc analysis of interaction contrasts was performed to compare each treatment with the control (Vehicle), with Dunnett's correction applied. Post-hoc results were only reported if either the main effect of treatment or the treatment×time interaction was significant.

Initial data-inspection suggested that the effects of compound 2-1 and compound 2-2, where present, were largely restricted to the first 6 hours after dosing. Consequently, most statistical analyses were performed on data averaged in 2-hour bins spanning this period. Results for the compound 2-1 and compound 2-2 dose-series were analyzed separately, but the same vehicle and psilocybin data were included in both analyses, and in the respective figures. All data are presented as mean±SEM (standard error of the mean). Statistical significance relative to control (Vehicle) is represented as stars: *$p<0.05$, $p<0.01$, and *$p<0.001$. Where data is presented as a time-series, labels refer to the beginning of the time-bin relative to dosing-time. Dose labels in all figures indicate mg/kg, i.p.

Figure 5A:
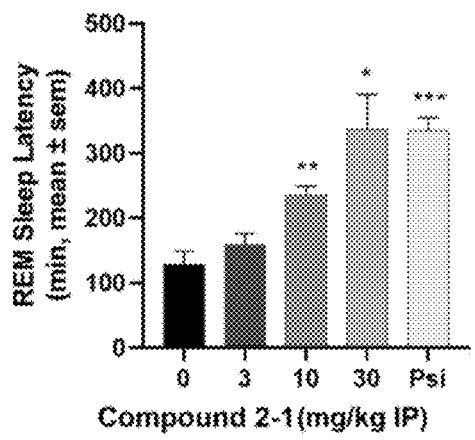
FIG. 5A is a graph showing the effects of compound 2-1 on REM sleep latency.
Figure 5B:
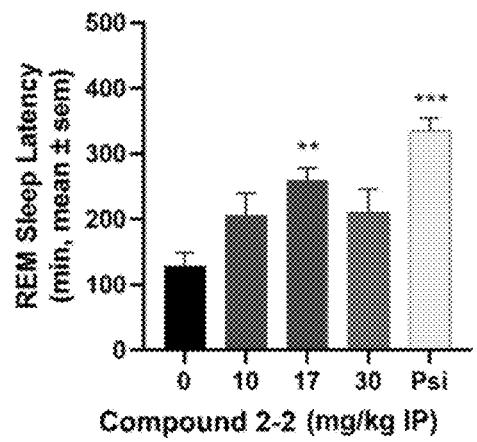
FIG. 5B is a graph showing the effects of compound 2-2 on REM sleep latency.

Both compound 2-1 (10 and 30 mg/kg) and compound 2-2 (17 mg/kg) significantly increased the latency to REM sleep, similar to the psilocybin (Psi) positive control, indicating an antidepressant drug-like response (FIG. 5A and FIG. 5B).

Figure 6A:
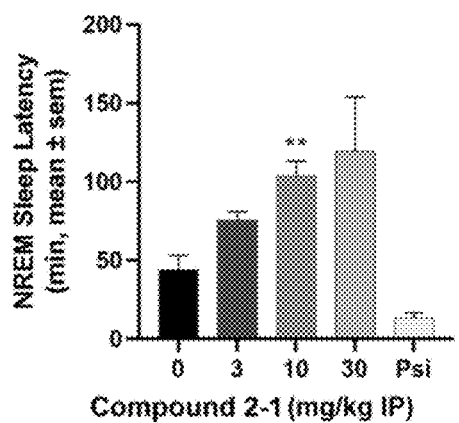
FIG. 6A is a graph showing the effects of compound 2-1 on non-REM sleep latency.
Figure 6B:
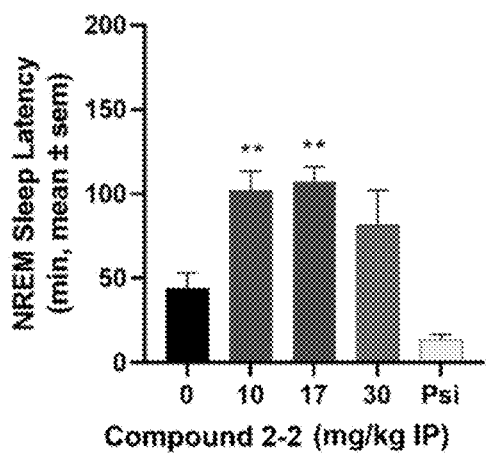
FIG. 6B is a graph showing the effects of compound 2-2 on non-REM sleep latency.
Figure 7A:
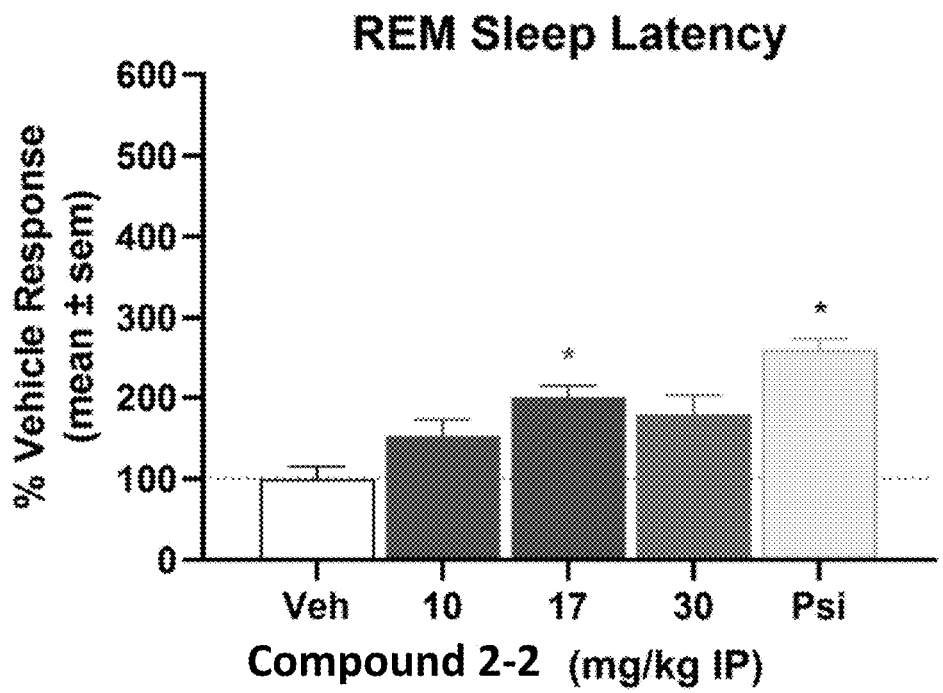
FIG. 7A is a graph showing the effects of compound 2-2 on REM sleep latency relative to the vehicle response.
Figure 7B:
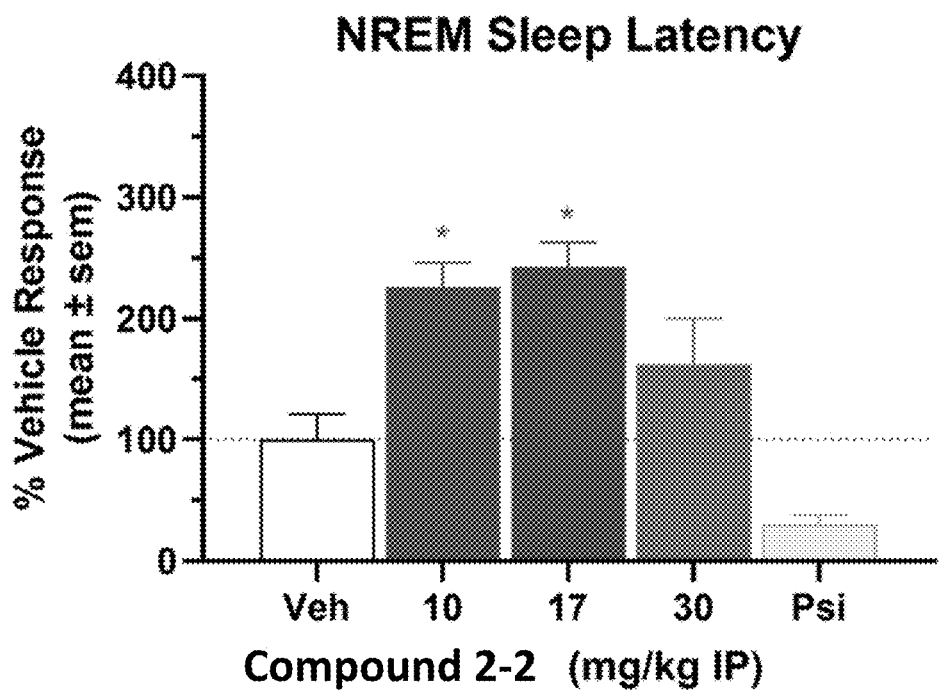
FIG. 7B is a graph showing the effects of compound 2-2 on non-REM (NREM) sleep latency relative to the vehicle response.

Both compound 2-1 (10 mg/kg) and compound 2-2 (10 and 17 mg/kg) significantly increased the latency to non-REM (NREM) sleep, in contrast to the psilocybin (Psi) reference control (FIG. 6A and FIG. 6B). FIGS. 7A-B depict compound 2-2's effects on REM and NREM sleep latencies relative to the vehicle response.

Figure 8A:
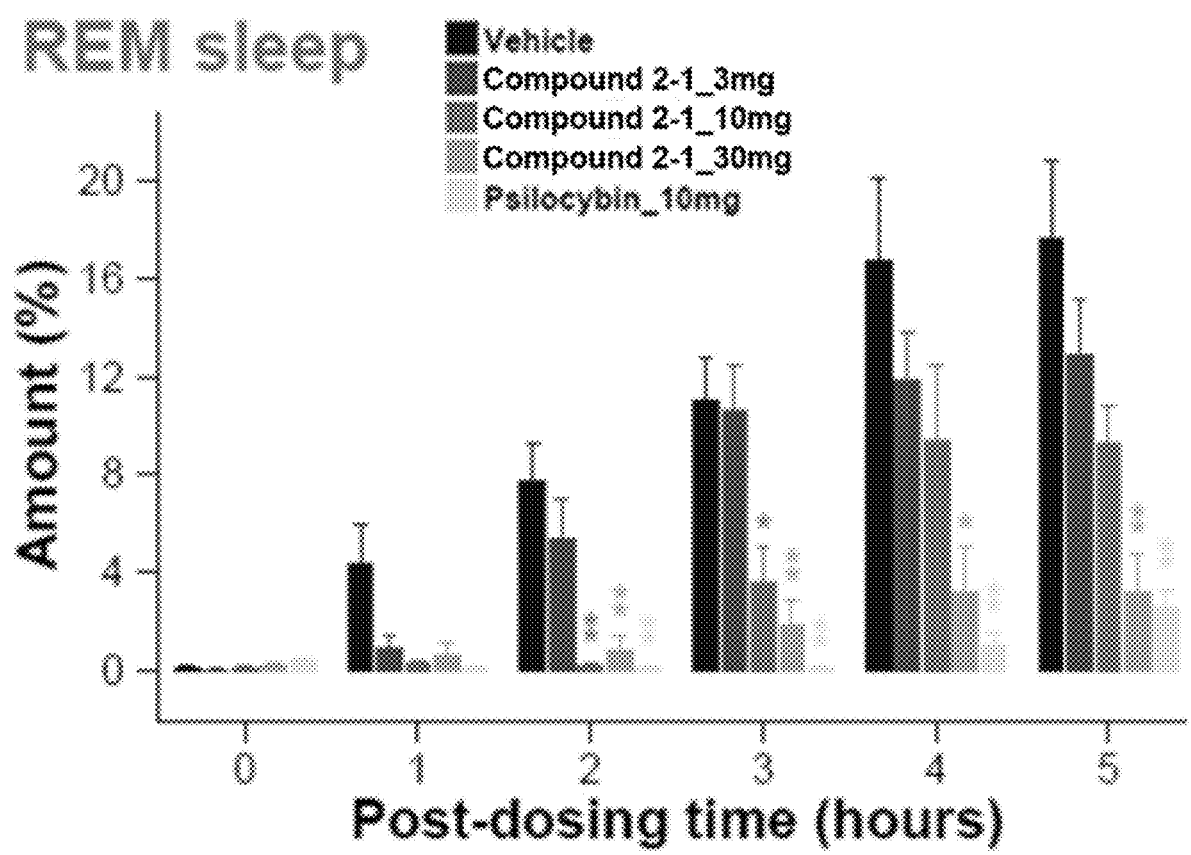
FIG. 8A is a graph showing the effects of compound 2-1 on amount (%) of REM sleep.
Figure 8B:
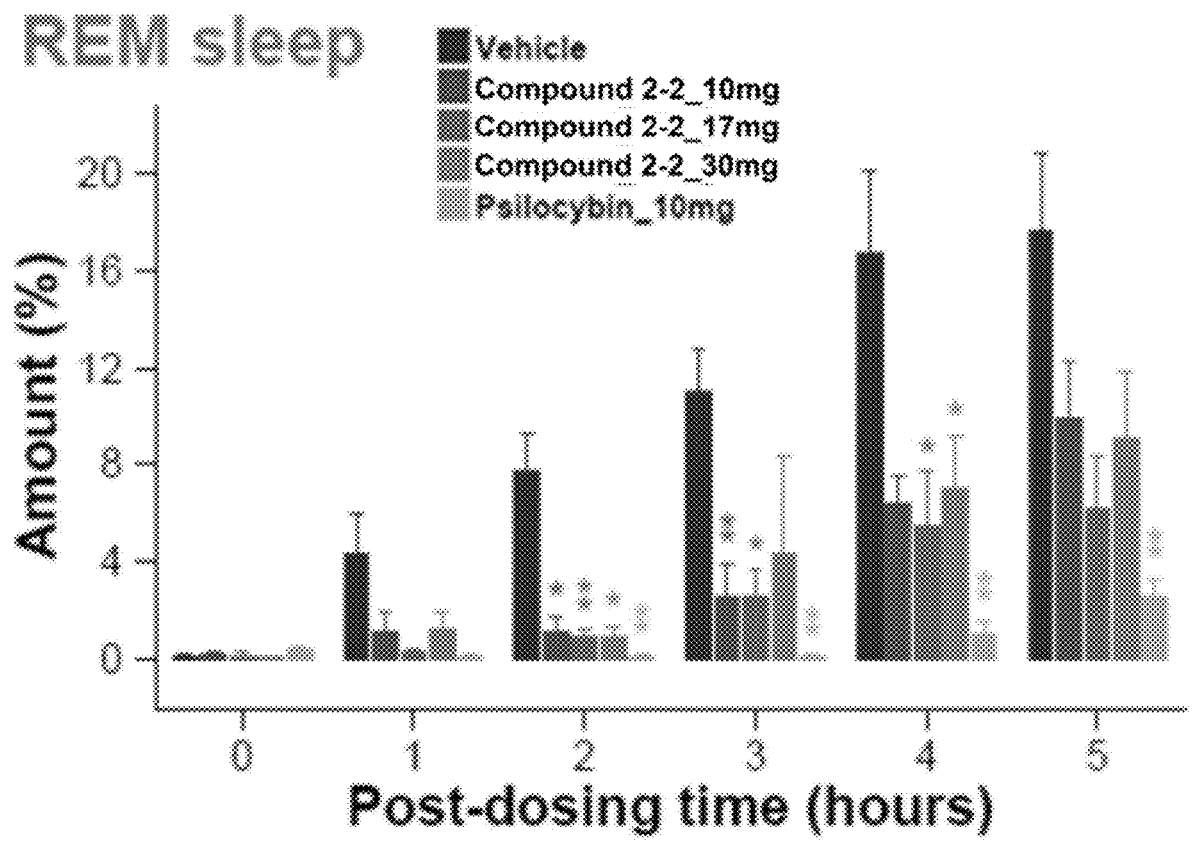
FIG. 8B is a graph showing the effects of compound 2-2 on amount (%) of REM sleep.

Both compound 2-1 (10 and 30 mg/kg) and compound 2-2 (10, 17 and 30 mg/kg) significantly decreased the amount of time spent in REM sleep starting in the third hour post dose (indicated in the figures as post-dosing time 2 hours), similar to the psilocybin positive control, indicating an antidepressant drug-like response (FIG. 8A and FIG. 8B).

Figure 9A:
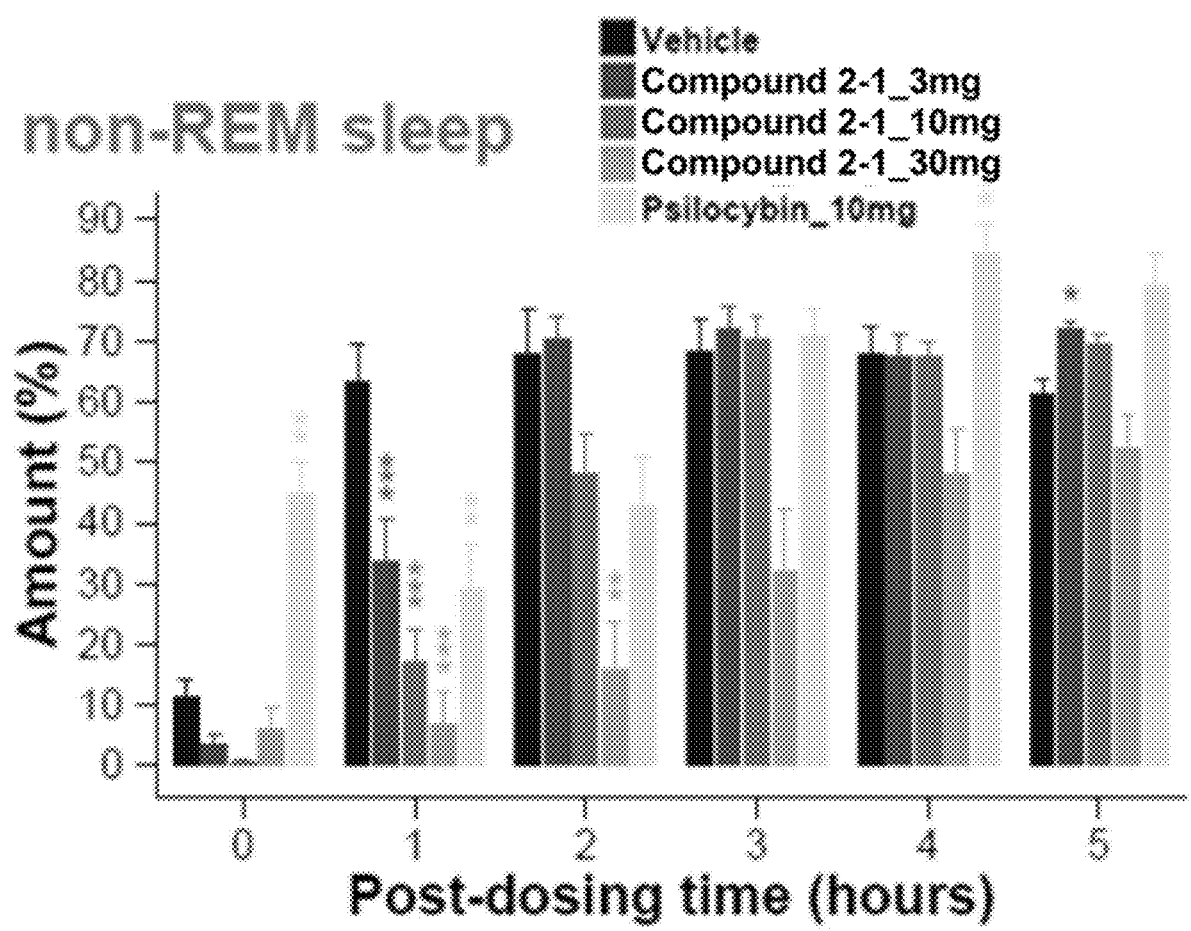
FIG. 9A is a graph showing the effects of compound 2-1 on amount (%) of non-REM sleep.
Figure 9B:
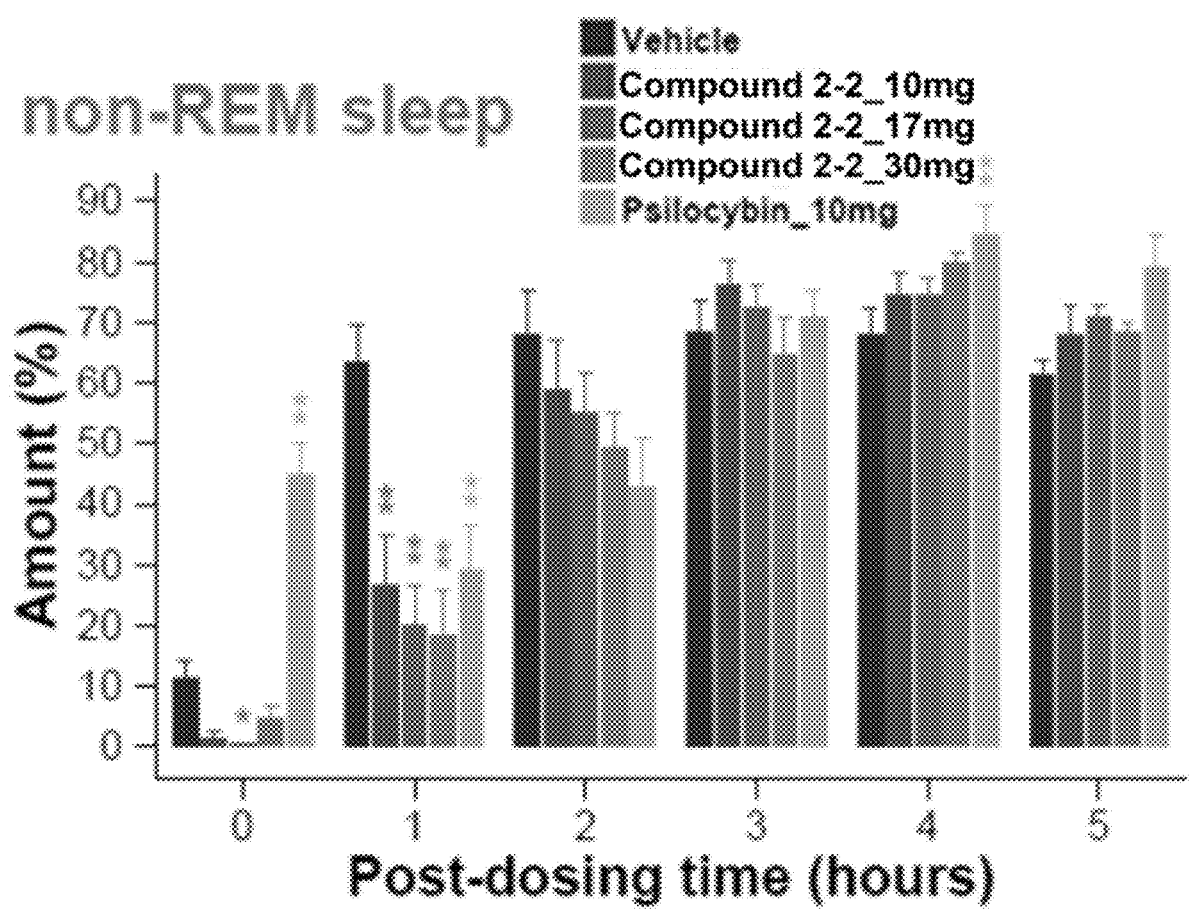
FIG. 9B is a graph showing the effects of compound 2-2 on amount (%) of non-REM sleep.
Figure 10A:
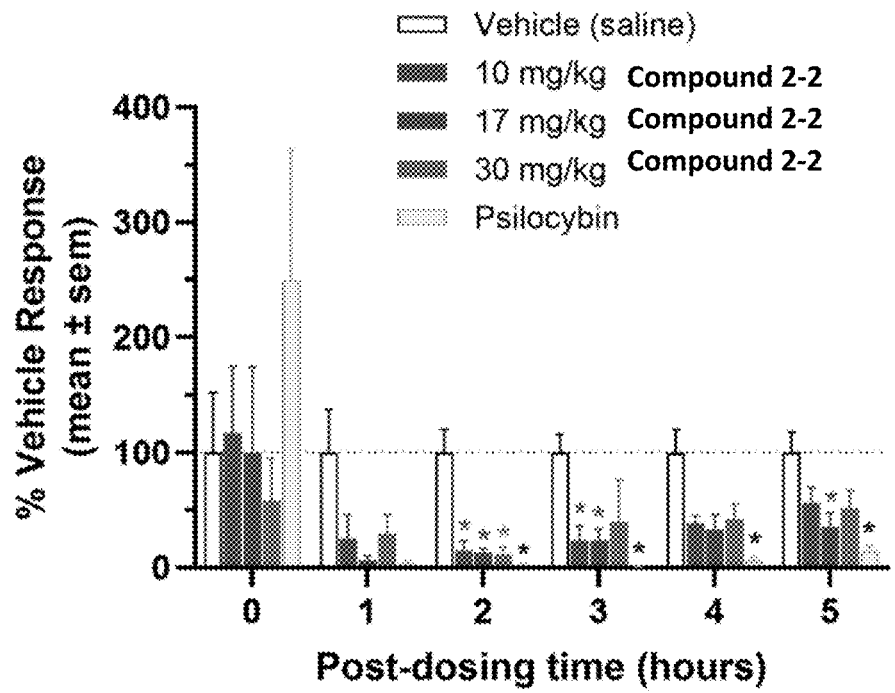
FIG. 10A is a graph showing the effects of compound 2-2 on REM sleep amounts relative to the vehicle response.
Figure 10B:
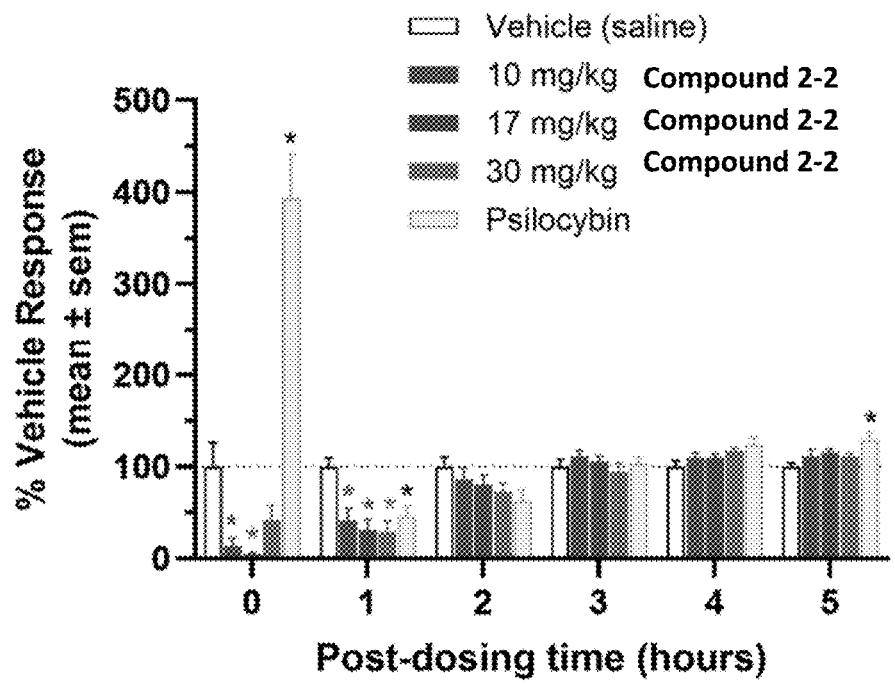
FIG. 10B is a graph showing the effects of compound 2-2 on NREM sleep amounts relative to the vehicle response.

Both compound 2-1 (3, 10 and 30 mg/kg) and compound 2-2 (10, 17 and 30 mg/kg) significantly decreased the amount of time spent in non-REM sleep in the first 3 hours after administration (indicated in the figures as post-dose period 0-2 hours), with a similar effect of the psilocybin reference control in the hour interval starting at 1 hour post dose. However, compound 2-1 (3 mg/kg) in the interval starting at 5 hours post dose, and psilocybin in the intervals starting at 0 and 4 hours post dose, also significantly increased non-REM sleep amount (FIG. 9A and FIG. 9B). FIGS. 10A-B depict compound 2-2's effects on REM and NREM sleep amounts relative to the vehicle response. Sleep amounts are percent of time within a specific period that an animal spends in a specific state (e.g., wake, NREM or REM).

Figure 11A:
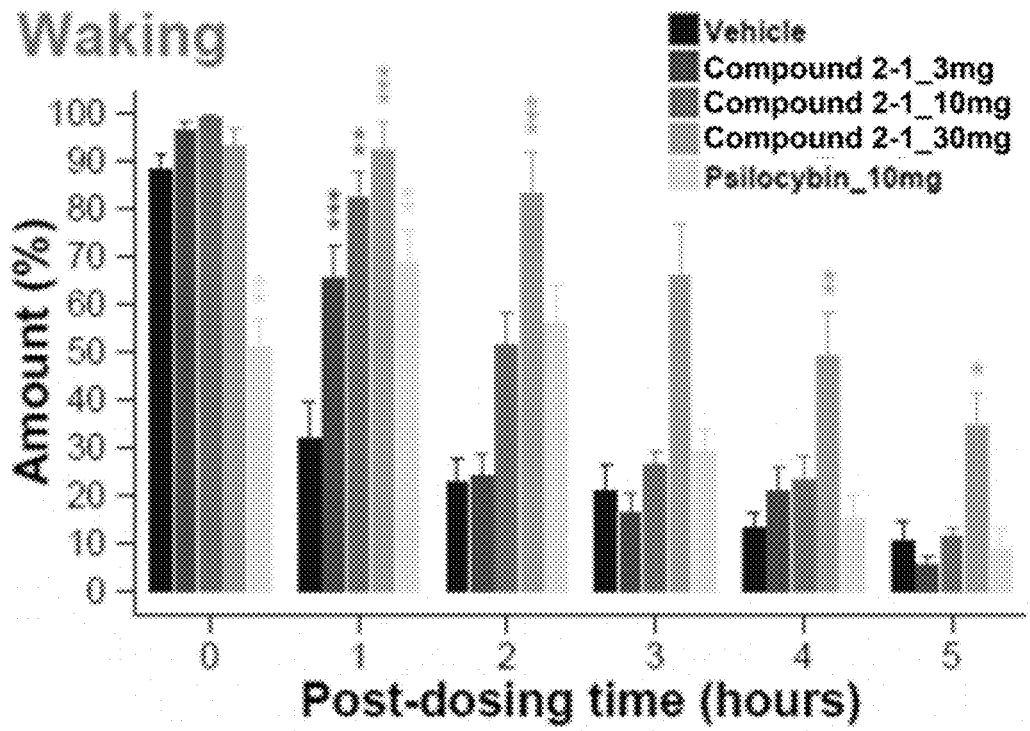
FIG. 11A is a graph showing the effects of compound 2-1 on amount (%) of time spent in wake.
Figure 11B:
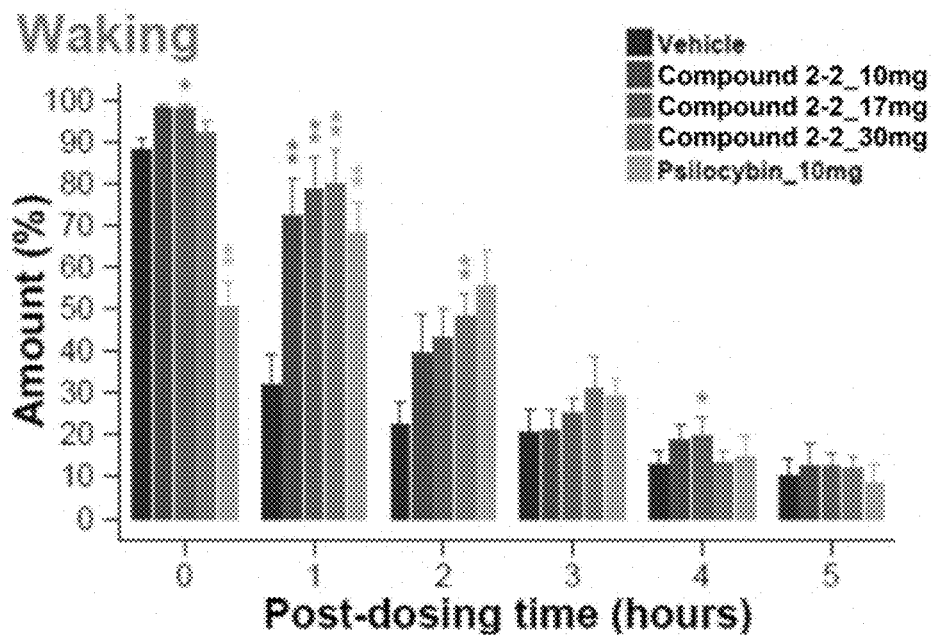
FIG. 11B is a graph showing the effects of compound 2-2 on amount (%) of time spent in wake.
Figure 12:
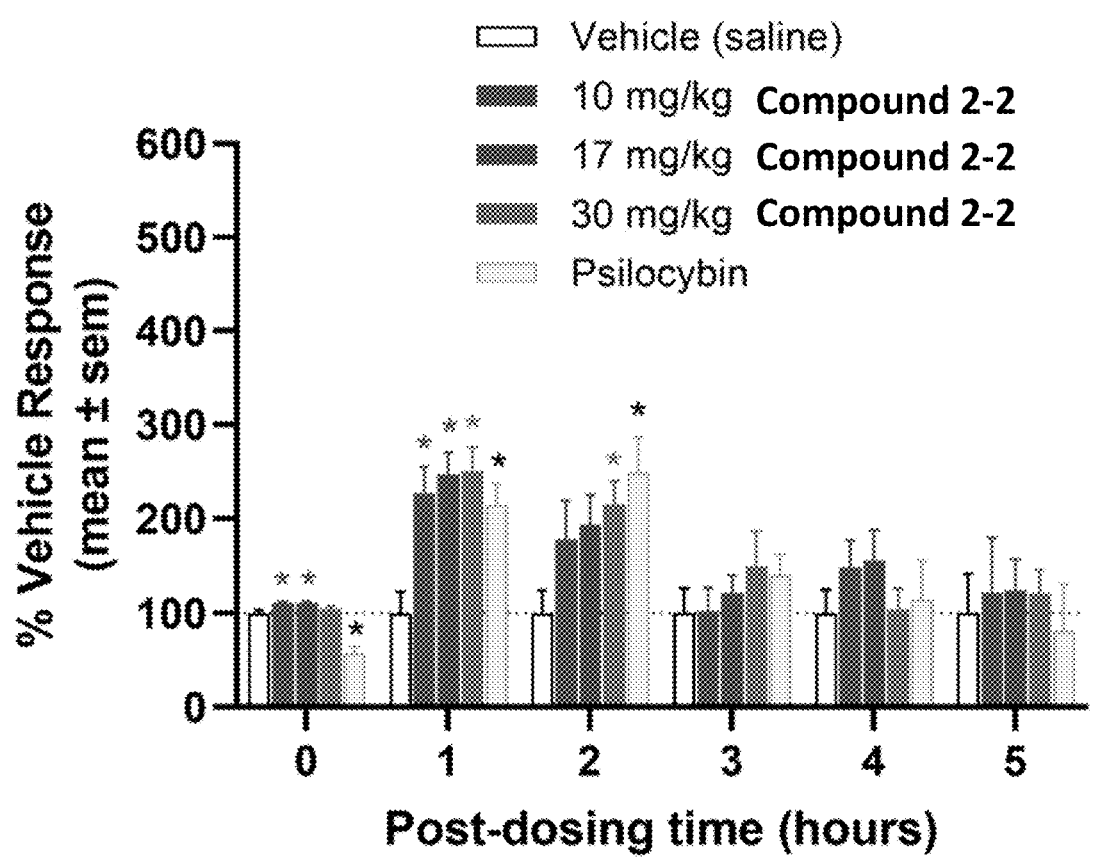
FIG. 12 is a graph showing the effects of compound 2-2 on amount of time spent in wake relative to the vehicle response.

Both compound 2-1 (3, 10 and 30 mg/kg) and compound 2-2 (10, 17 and 30 mg/kg) significantly increased the amount of time spent in wake, with a similar effect of the psilocybin reference control in the hour interval starting immediately after dosing (0 hour). However, psilocybin also significantly decreased the amount of waking in the 0 hour interval (FIG. 11A and FIG. 11B). FIG. 12 shows the effects of compound 2-2 on amount of time spent in wake relative to the vehicle response.

Figure 13A:
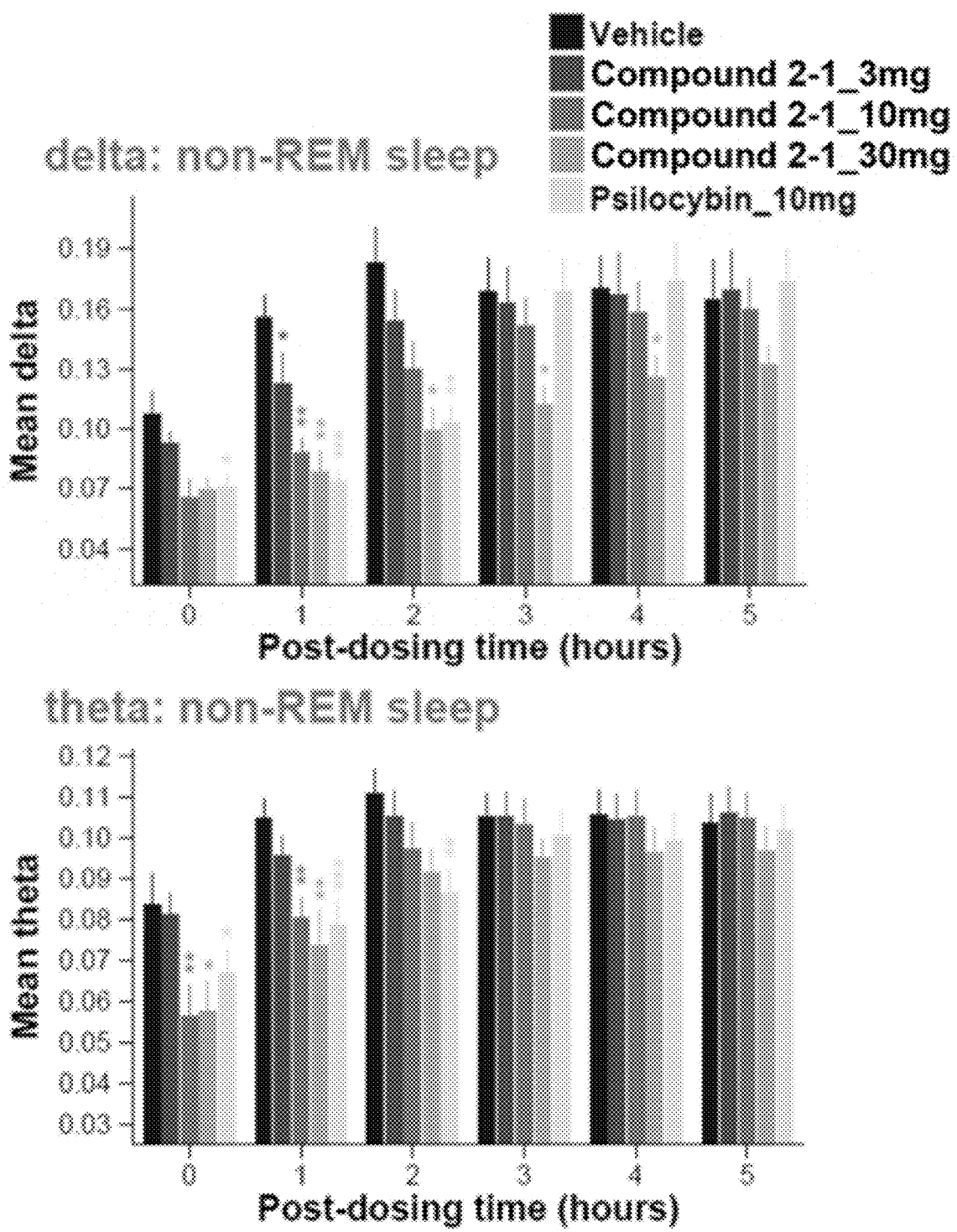
FIG. 13A is a graph showing the effects of compound 2-1 on mean delta and mean theta power during non-REM sleep.
Figure 13B:
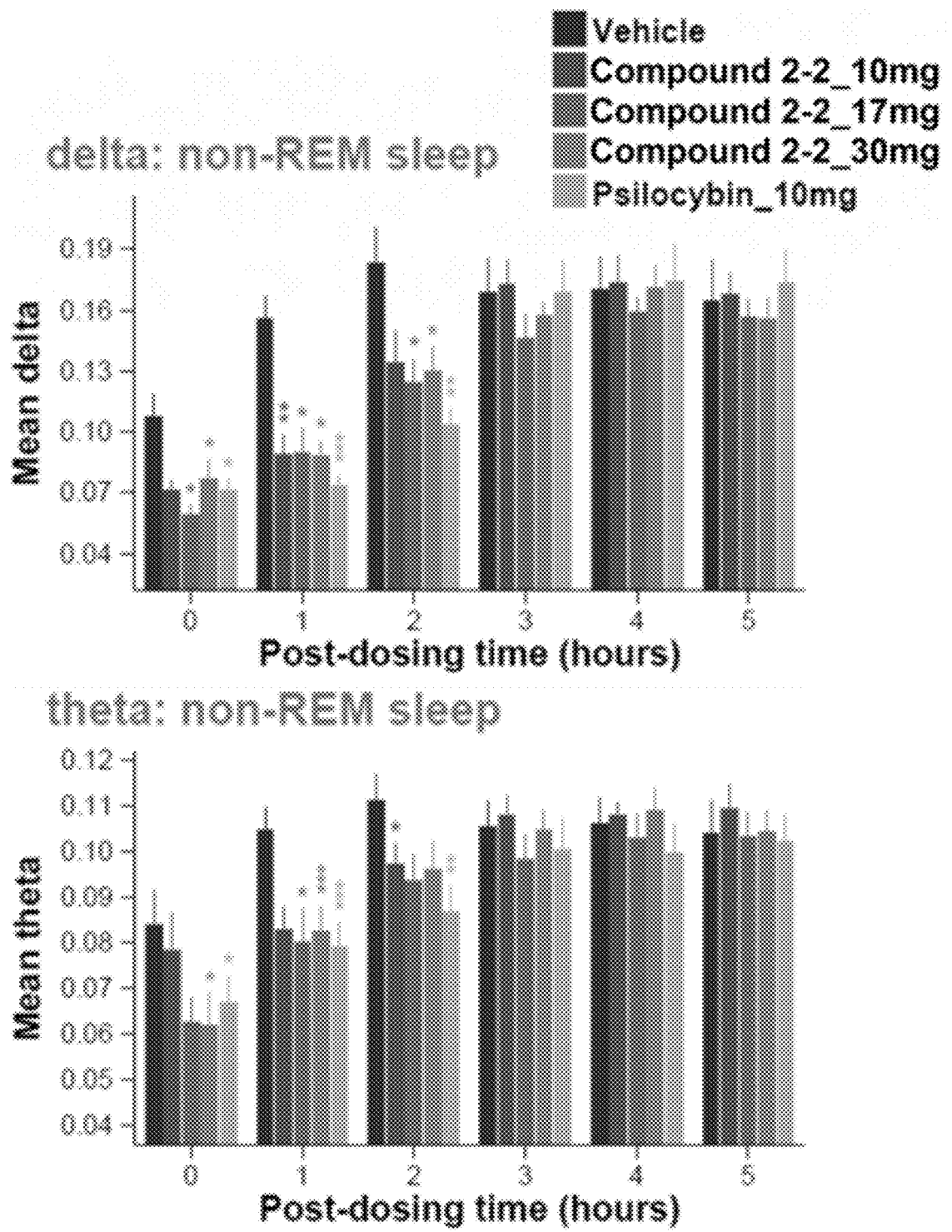
FIG. 13B is a graph showing the effects of compound 2-2 on mean delta and mean theta power during non-REM sleep.
Figure 14A:
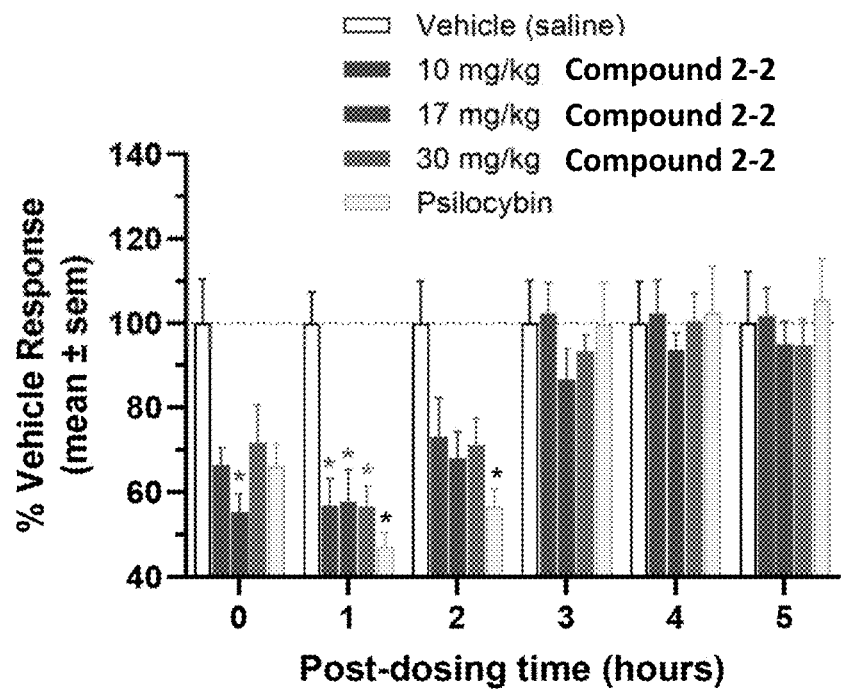
FIG. 14A is a graph showing the effects of compound 2-2 on mean delta power during non-REM sleep relative to the vehicle response.
Figure 14B:
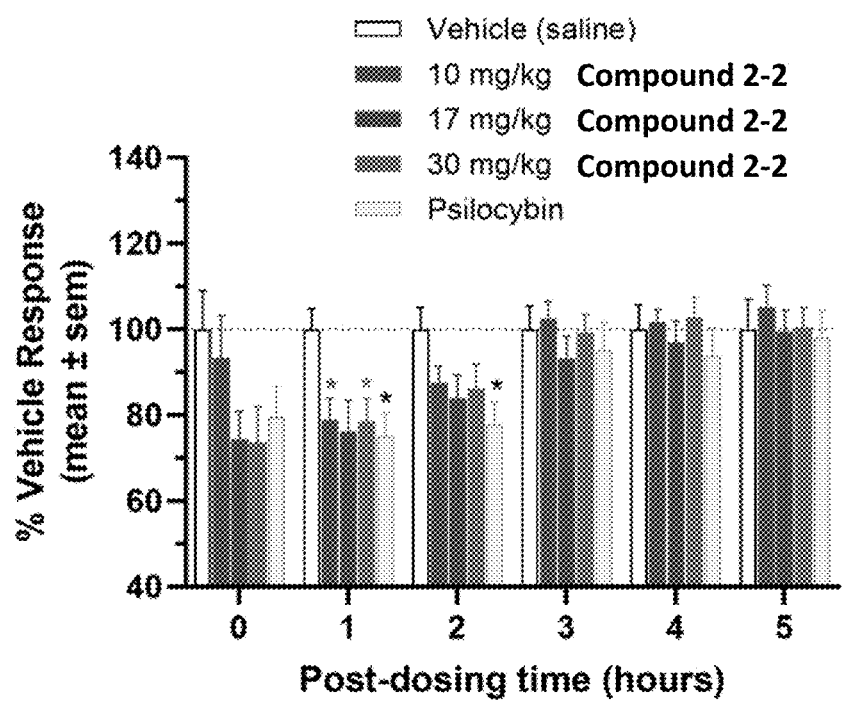
FIG. 14B is a graph showing the effects of compound 2-2 on mean theta power during non-REM sleep relative to the vehicle response.

Both compound 2-1 (3, 10 and 30 mg/kg) and compound 2-2 (10, 17 and 30 mg/kg) significantly decreased low frequency (delta and theta) power during non-REM sleep primarily in the post-dose period covering 0-2 hours, similar to the psilocybin reference control. The significant effect of compound 2-1 (30 mg/kg) on delta power persisted through the period starting at 4 hours post dose (FIG. 13A and FIG. 13B). FIGS. 14A-B depict compound 2-2's effects on mean delta and mean theta power during non-REM sleep relative to the vehicle response.

Figure 15A:
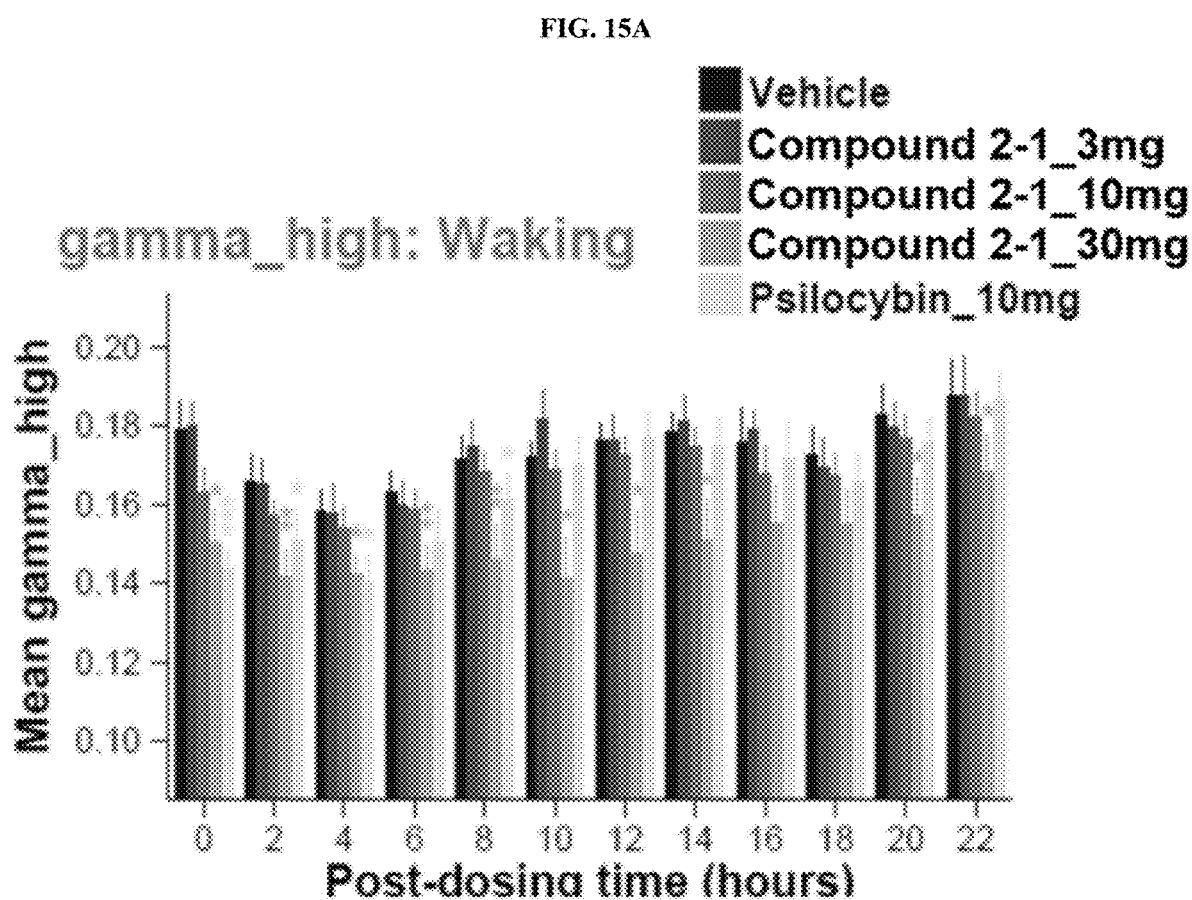
FIG. 15A is a graph showing the effects of compound 2-1 on mean high gamma power during waking.
Figure 15B:
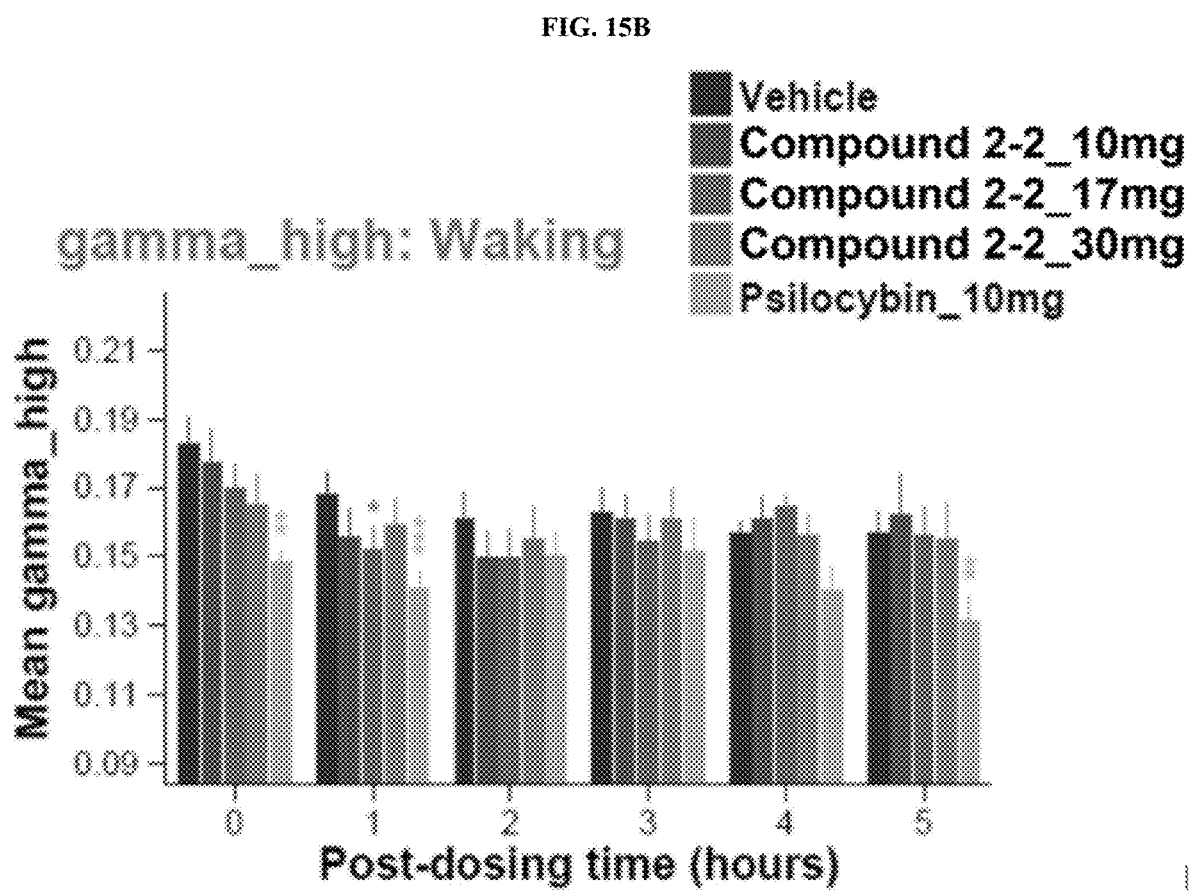
FIG. 15B is a graph showing the effects of compound 2-2 on mean high gamma power during waking.

Compound 2-1 (30 mg/kg) exhibited a significant and lasting decrease of high gamma power during waking over 24 hours post dose. compound 2-2 showed a 3-hour trend for reduced high gamma power during waking, with limited statistical significance (17 mg/kg). The psilocybin reference control significantly decreased high gamma power during waking, with a more limited time course than compound 2-1 (FIG. 15A and FIG. 15B).

Figure 16:
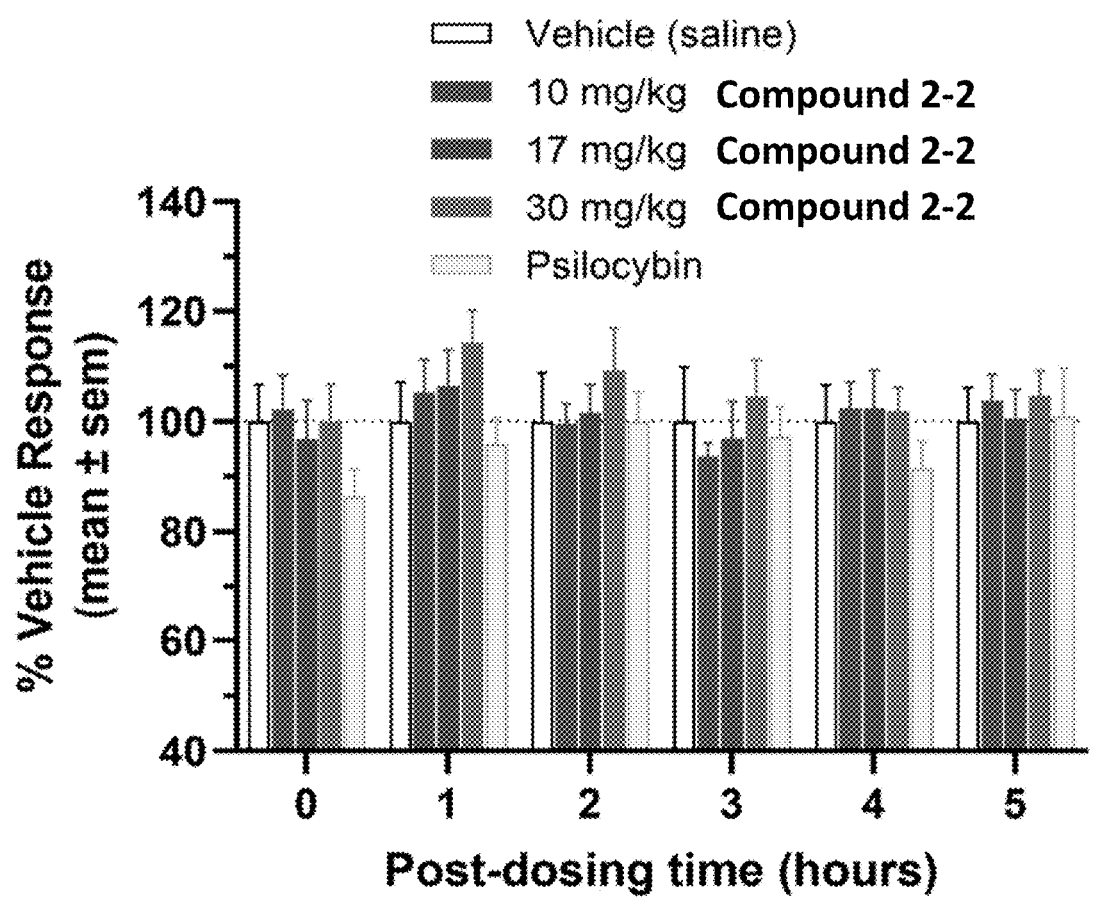
FIG. 16 is a graph showing the effects of compound 2-2 on brain oscillations in the alpha frequency (8-12 Hz) range during waking.
Figure 17:
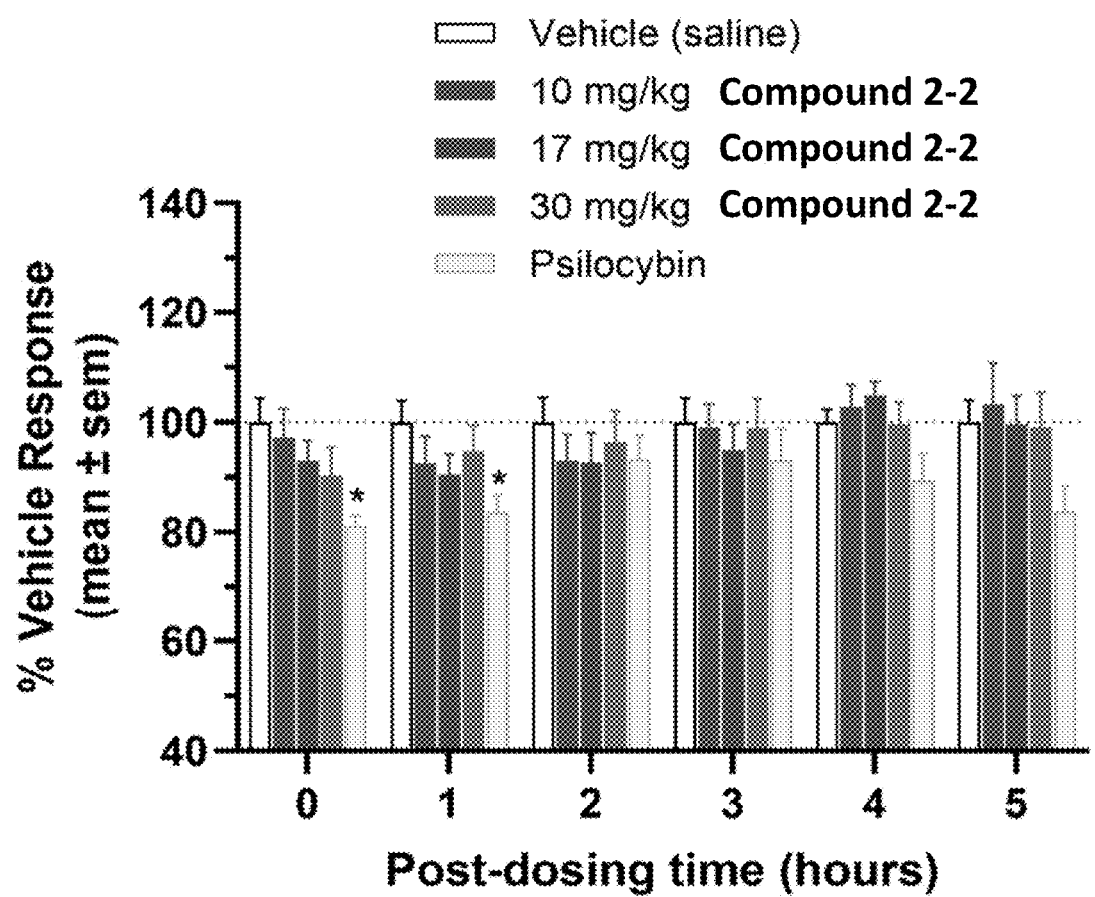
FIG. 17 is a graph showing the effects of compound 2-2 on brain oscillations in the high-frequency gamma (50-100 Hz) range during waking relative to the vehicle response.

Compound 2-2 and psilocybin did not show significant effects on brain oscillations in the alpha frequency (8-12 Hz) range during waking (FIG. 16). Compound 2-2 did not show psilocybin-like effects on brain oscillations in the high-frequency gamma (50-100 Hz) range during waking (FIG. 17).

The finding of compound effects on/normalization of translational EEG-based spectral power and/or sleep/wake measures in the WKY rat model of treatment-resistant depression supports a) REM and non-REM sleep-reducing effects, b) antidepressant drug-like effects on intact brain functional activity, c) compound prioritization for advancement to clinical development, and d) selection of clinical biomarkers related to target engagement and antidepressant-like activity.

Although the invention has been described with reference to the above examples, it will be understood that modifications and variations are encompassed within the spirit and scope of the invention. Accordingly, the invention is limited only by the following claims.

Example 8

Brain and Plasma Concentrations of Compound 2-1 (EGX-A) and Compound 2-2 (EGX-B)

Figure 18:
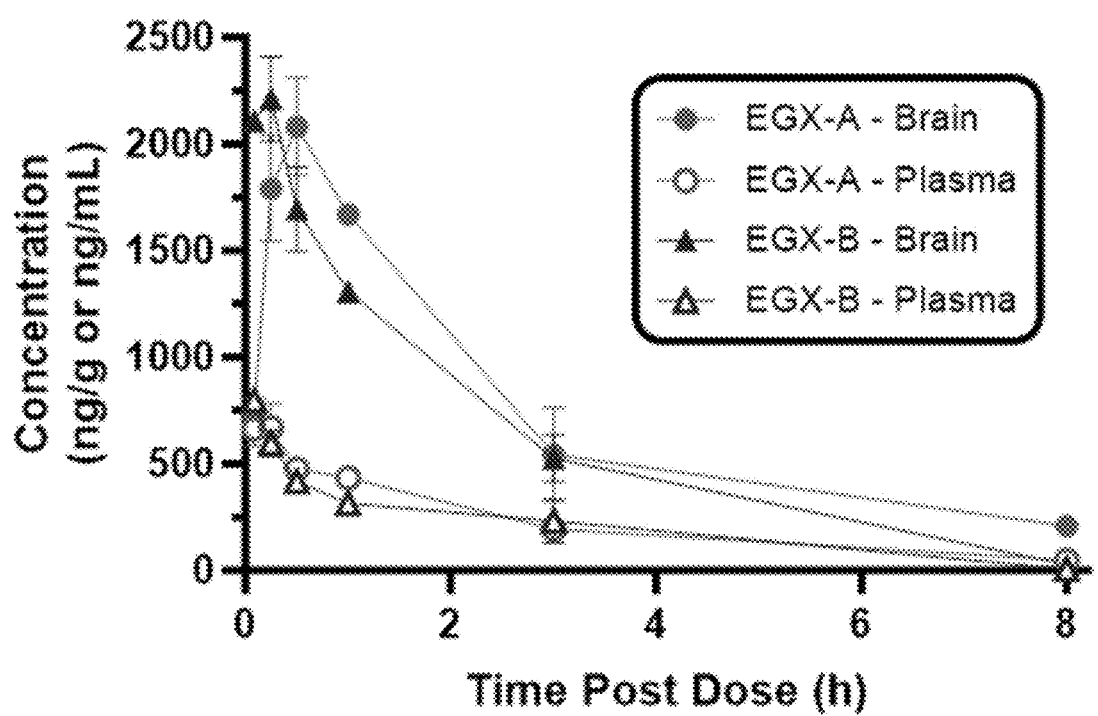
FIG. 18 is a graph showing brain (ng/g) and plasma (ng/mL) concentrations (mean±sem) over time following administration of 10 mg/kg compound 2-1 (EGX-A) or compound 2-2 (EGX-B) IP to male Sprague-Dawley rats.

Brain and plasma concentrations of compound 2-1 (EGX-A) and compound 2-2 (EGX-B) were determined. EGX-A and EGX-B showed similarly high brain relative to plasma concentrations for ~6-8h following dosing of 10 mg/kg IP to male rats. Thus, analyses of compound effects were focused on the initial 4-6 hours post dosing. Results are shown in FIG. 18.

Example 9

Sleep and Wake Effects of Compound 2-1 (EGX-A) and Compound 2-2 (EGX-B)

Adult male WKY rats (n=7) were implanted with an EEG dipole electrode (frontal positive, occipital negative) and EMG (nuchal muscle) electrodes. An intraperitoneal radio transmitter was used to transmit signals.

One hour after lights-on, animals were placed individually in recording boxes similar to their home cages (with food, water and limited environmental enrichment). After 1 hour of habituation, each animal was briefly removed from its box to be dosed and then recordings continued uninterrupted for 23 hours.

All animals received all 8 treatments in a pseudo randomized cross-over design with a minimum of 7 days washout between doses. Each treatment condition was represented during each weekly test session. Treatment conditions included: Vehicle negative control, Psilocybin positive control (10 mg/kg IP), EGX-A (3, 10, 30 mg/kg IP) or EGX-B (10, 17, 30 mg/kg IP). Novel compound doses were based on the free base weights and prepared in 40% (w/v) hydroxypropyl-b-cyclodextrin in water.

Automatic scoring of wake and REM sleep was performed on 10-second epochs of EEG/EMG recordings using proprietary software. Compound effects on the percentage of time spent in REM sleep were analyzed over the initial 6 hours of EEG recording post-dosing.

REM sleep latencies were defined as the time (minutes) after dosing at which the first 3 consecutive REM sleep epochs occurred.

Quantitative EEG (qEEG) spectra (Delta (1-4 Hz), Theta (4-7 Hz), Alpha (8-12 Hz), Beta (14-30 Hz), Low Gamma (30-50 Hz), High Gamma (50-100 Hz)) were computed using fast Fourier Transformation on 1-second non-overlapping consecutive epochs (unpadded Hann windows, 1 Hz resolution) and bandpass filtered at 0.5-100 Hz. Compound effects on waking qEEG power were analyzed as the average of the initial 4 hours post-dosing.

Body temperature and locomotor activity (EMG data) were computed using 10-second epoch values. Compound effects were analyzed over the initial 6 hours of recording post-dosing.

Data were analyzed by 1- or 2-way repeated measures Analysis of Variance (ANOVA, R version 3.6.3 or GraphPad Prism version 10.0.3) followed by Dunnett's test to compare test articles to the vehicle group. The level of significance was set at $p<0.05$.

Figure 19A:
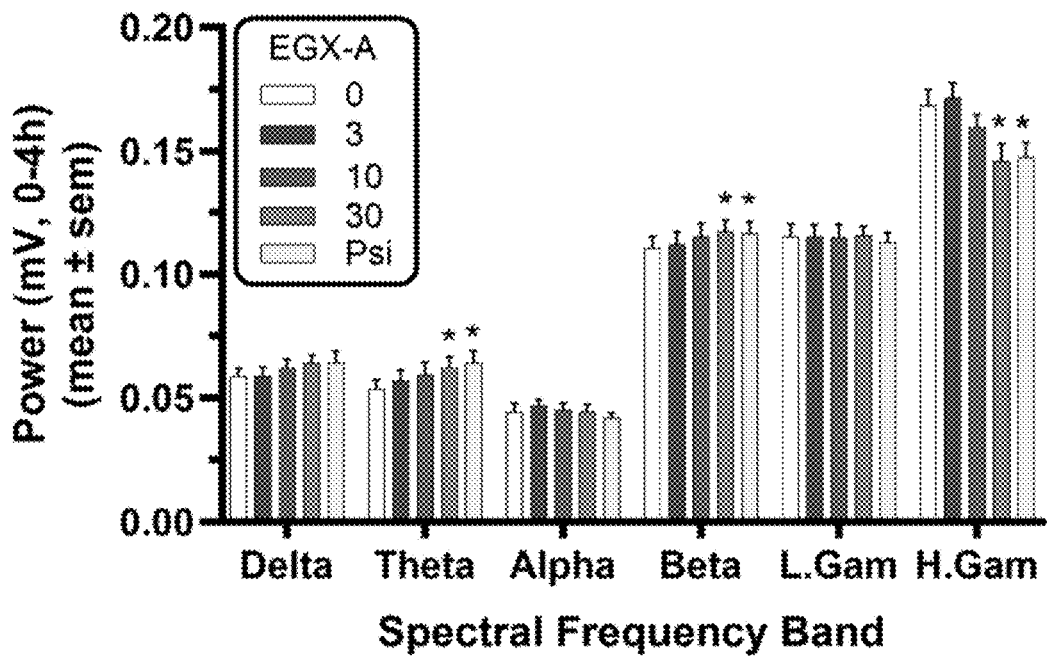
FIG. 19A is a graph of Mean (±sem) spectral frequency band power (mV) during wake over the initial 4 hours following administration of EGX-A (3, 10, 30 mg/kg IP, 19A) or Psilocybin (10 mg/kg IP) to male WKY rats.
Figure 19B:
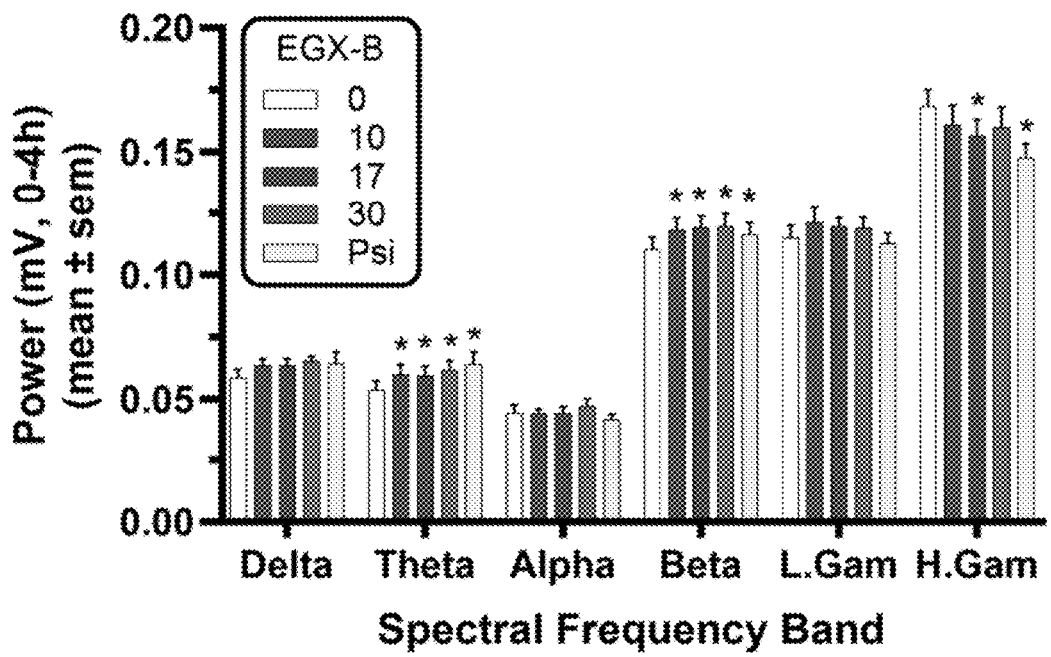
FIG. 19 B is a graph of Mean (±sem) spectral frequency band power (mV) during wake over the initial 4 hours following administration of EGX-B (10, 17, 30 mg/kg IP, 19B) or Psilocybin (10 mg/kg IP) to male WKY rats.

As shown in FIGS. 19A (EGX-A) and 19B (EGX-B), EGX-A and EGX-B significantly increased waking theta and beta power, and decreased high gamma power, over the initial 4 hours following dosing to male WKY rats, consistent with the effects of Psilocybin (Psi).

Figure 20:
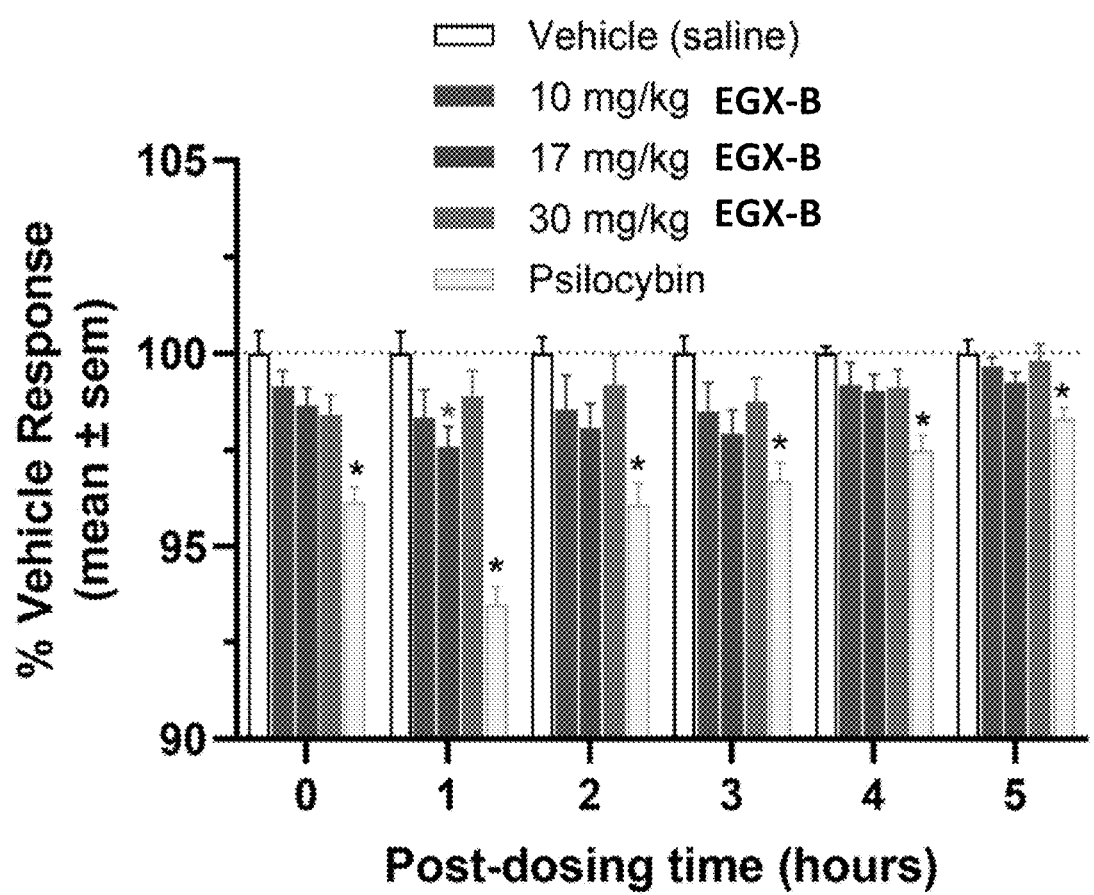
FIG. 20 is a graph showing the effects of compound 2-2 (EGX-B) on body temperature relative to the vehicle response in WKY rats.
Figure 21:
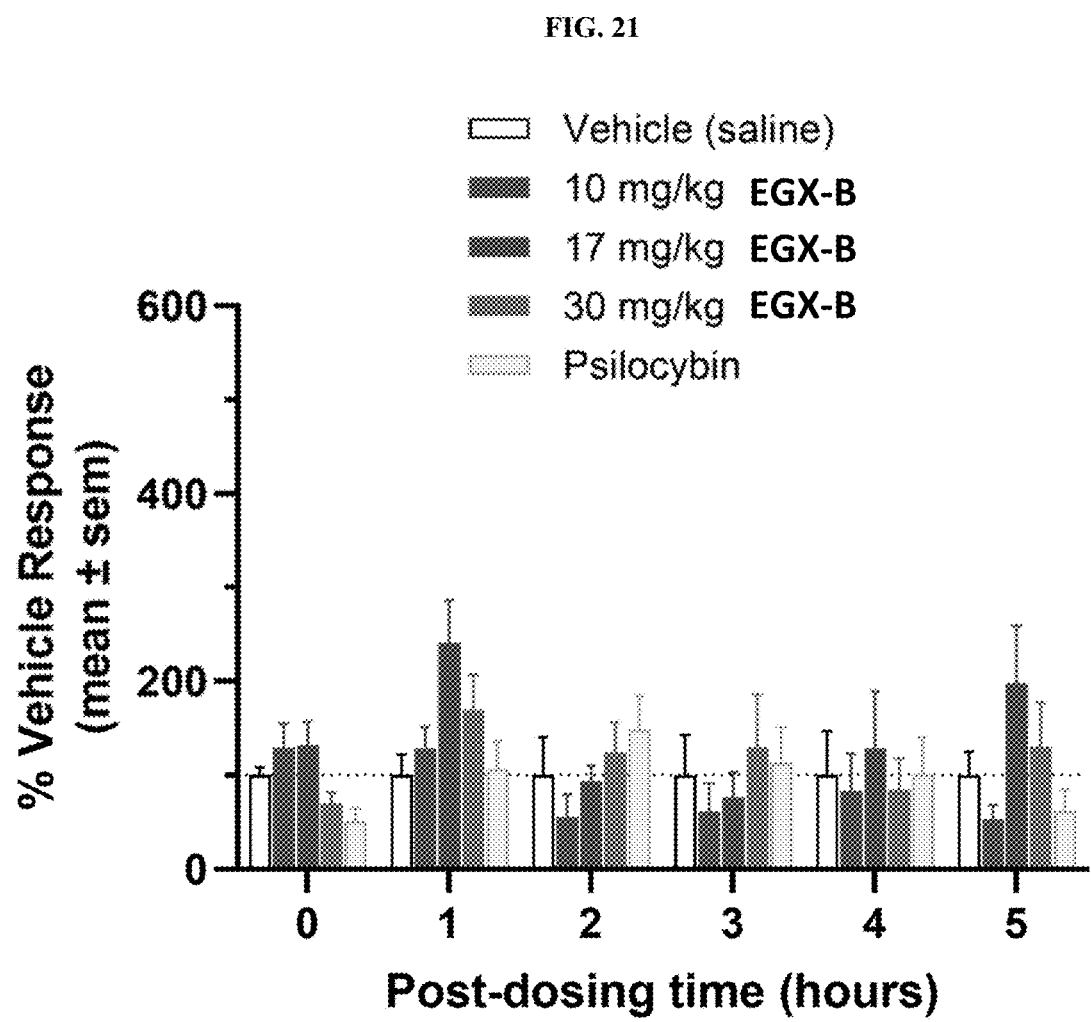
FIG. 21 is a graph showing the effects of compound 2-2 (EGX-B) on locomotion relative to the vehicle response in WKY rats.

As shown in table 6 (raw data) and FIGS. 20 and 21 (normalized data), EGX-B exhibited minimal effects on body temperature and locomotor activity in male WKY rats.

TABLE 6

Compound Effects over 6 Hours Post Dose

| Measure | EGX-A | EGX-B | Psilocybin |
| --- | --- | --- | --- |
| Body temperature | ↓ (for 6 h) | ↓(2 h) | ↓(for 6 h) |
| Locomotor activity | ↓(1 h)/↑ (2 h) | No Δ | ↓(1 h) |

↓ Significant decrease;
↑ Significant increase;
No Δ No significant change

Example 10

Acute Antidepressant-Like Activity of Single Administration of Compound 2-1 or Compound 2-2 in the Forced Swim Test (FST) in Mice Young adult C57BL/6J male mice (8-9 weeks old at arrival; n=113) were purchased from Charles River (DE). All $C_{57}BL/6J$ mice were housed in groups of 4 per cage. Mice were maintained under controlled conditions (21±2° C., 50±1% humidity, 12/12 h light/dark cycles, lights on at 7 a.m.) with food and water available ad libitum.

Experimental Design: The experimental procedures were in accordance with the European Communities Council Directive (Directive 2010/63 EU into the Polish Directives (Journal of Laws of 2021, item 1331, as amended)) and approved by the Local Ethic Committee in Olsztyn (Approval No. 27/203 from 22 Mar. 2023). Animals were subjected to a single injection of either vehicle, psilocybin (5 mg/kg i.p), compound 2-1 (3, 10 or 30 mg/kg, i.p.) or compound 2-2 (3, 10 or 30 mg/kg, i.p.). 24 hrs later, each mouse was tested in the forced swim test.

Experimental Groups:
Group 1: CTRL-Vehicle (HPBCD 40% (w/v) in water); n=14.
Group 2: Psilocybin 5 mg/kg in 0.9% NaCl; n=14.
Group 3: 2-1 3 mg/kg; n=14.
Group 4: 2-1 10 mg/kg; n=14.
Group 5: 2-1 30 mg/kg; n=14.
Group 6: 2-2 3 mg/kg; n=14.
Group 7: 2-2 10 mg/kg; n=14.
Group 8: 2-2 30 mg/kg; n=15.

Forced Swim Test: After 17 days of acclimatization (11-12 weeks old), all mice were randomly assigned to experimental groups (n=14-15/group). Sample size (n=14 per group) was determined based on G-power calculations using alpha 0.05, t-test and effect size calculation based on mean and SD from vehicle and positive control groups. Animals were subjected to single administration of test compound and, 24 hr later, the forced swim test. The FST was performed under 55-60 lux light conditions. Briefly, mice were individually placed into a glass cylinder (280 mm high, 135 mm diameter) containing 12 cm of water at 25±1° C. for a 6 min test session. Because little immobility is observed during the first 2 minutes of the FST, only immobility occurring during the last 4 minutes was scored and analyzed. A mouse was judged immobile when it stopped struggling and remained floating in the water, making only movements necessary to keep its head above water. All test sessions were recorded using a video camera placed on the side of the cylinder for subsequent behavioral analysis by scorers blinded to the treatment conditions. At the end of the FST, animals were removed from the water, carefully dried and placed under a heating lamp for up to 6 min.

Data Analysis: Data for each compound have been analyzed separately using the GraphPad Prism 9 statistical software. For compound 2-1, immobility time in the forced swim test was analyzed by ordinary one way ANOVA. Shapiro-Wilk test confirmed the data normality. For compound 2-2, immobility time in the forced swim test was analyzed by Kruskal-Wallis test followed by Dunn's multiple comparisons test, as the data did not pass the normality test (Shapiro-Wilk). Acute effect of reference substance (psilocybin 5 mg/kg, 24 hr) on immobility time in the FST was determined by unpaired t test. An alpha level of 0.05 was used as criterion for statistical significance. All data are presented as mean±SEM (standard error of the mean). Outliers were removed from statistical analysis using the ROUT method (Q=5%).

Figure 22:
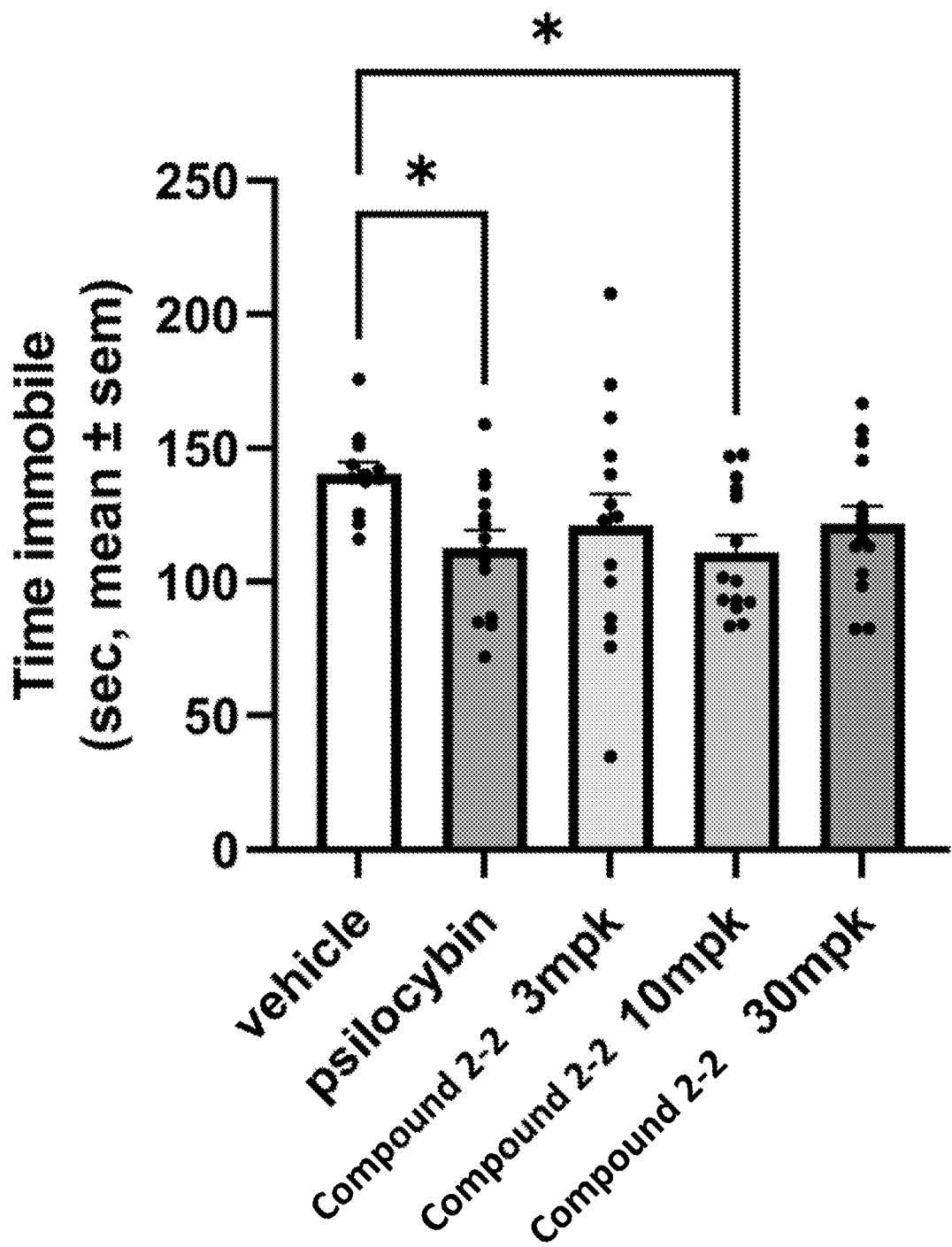
FIG. 22 is a graph showing the Acute effect of compound 2-2 (24 hr pretreatment) on immobility time in the mouse forced swim test.

Results: An overall non-significant 1-way ANOVA on vehicle, psilocybin and compound 2-1 time immobile data indicated a lack of robust differences among the treatment groups (F (4,62)=1.744, p=0.1518). A separate unpaired t test confirmed a significant reduction in time immobile by the reference substance, psilocybin, compared to vehicle (t=3.332, p=0.0028). An overall non-significant Kruskal-Wallis test on vehicle, psilocybin and compound 2-2 time immobile data indicated a strong trend toward significant differences among the treatment groups (Kruskal-Wallis statistic=9.219, p=0.0558, FIG. 22). Dunn's multiple comparisons test indicated this trend was driven by the effects of psilocybin and 10 mg/kg of compound 2-2, which exhibited similar reductions in immobility time.

Conclusion: A single dose of the reference substance, psilocybin (5 mg/kg, i.p.), demonstrated a significant reduction in immobility time in the mouse FST 24 hr post-administration, indicating antidepressant-like activity. Neither compound 2-1 (3, 10 & 30 mg/kg) nor compound 2-2 (3 & 30 mg/kg) showed significant reductions in immobility time in the FST 24 hr post-administration. The compound 2-2 statistical analysis indicated a trend toward significance, with a dose of 10 mg/kg showing a strong tendency to reduce immobility time in the FST (similar to the effect of the reference substance, psilocybin) and, thus, compound 2-2 might be considered as having antidepressant-like activity in the FST 24 hr post-administration.

Example 11

Evaluation of the Effects of a Low Dose of Compound 2-2 on Sleep, Locomotor Activity, Body Temperature and qEEG in the Male Wistar Kyoto Rat The aim of the current study was to identify a minimal effective dose of compound by testing a series of lower doses (1, 3 and 10 mg/kg). The study was carried out similarly to Examples 7 and 9 with differences noted below. Male WKY rats (n=8, 255-296 g at the start of dosing) were housed in groups of 2-3 animals per cage with standard housing conditions. Specifics of the study design are shown in Table 7.

TABLE 7

Treatment Conditions

1. Vehicle (40% w/v HPBCD in water, IP)
2. Psilocybin (10 mg/kg in saline, IP)
3. Compound 2-2 (1 mg/kg in 40% w/v HPBCD in water, IP)
4. Compound 2-2 (3 mg/kg in 40% w/v HPBCD in water, IP)
5. Compound 2-2 (10 mg/kg in 40% w/v HPBCD in water, IP)

Figure 23A:
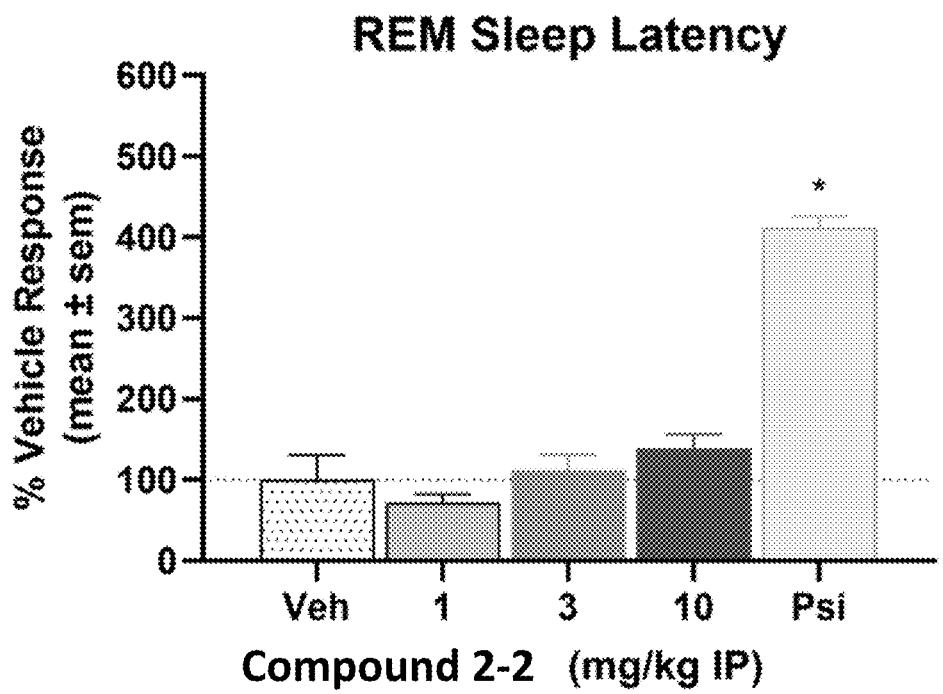
FIG. 23A is a graph showing the effects of compound 2-2 on REM sleep latency relative to the vehicle response in WKY rats.
Figure 23B:
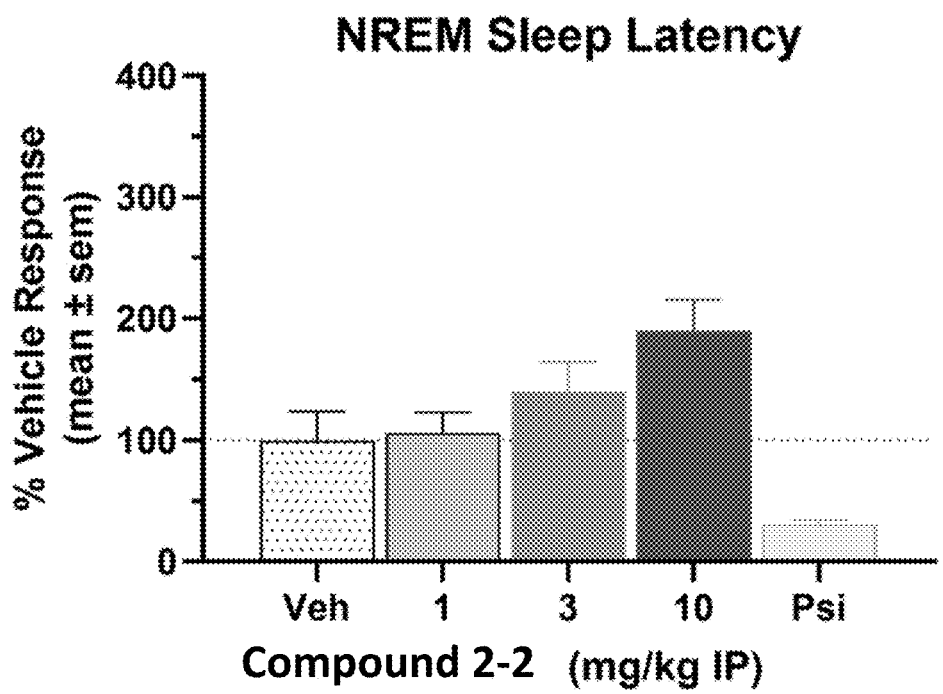
FIG. 23B is a graph showing the effects of compound 2-2 on NREM sleep latency relative to the vehicle response in WKY rats.
Figure 24A:
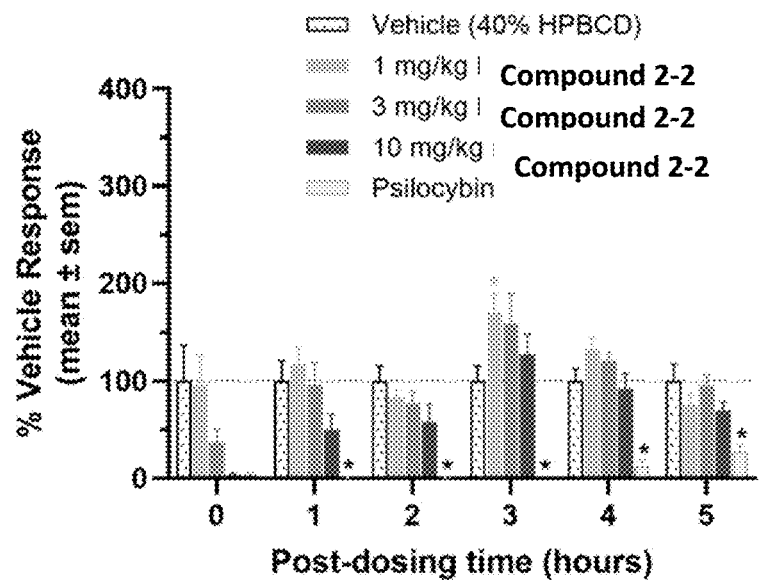
FIG. 24A is a graph showing the effects of compound 2-2 on REM sleep amounts in WKY rats.
Figure 24B:
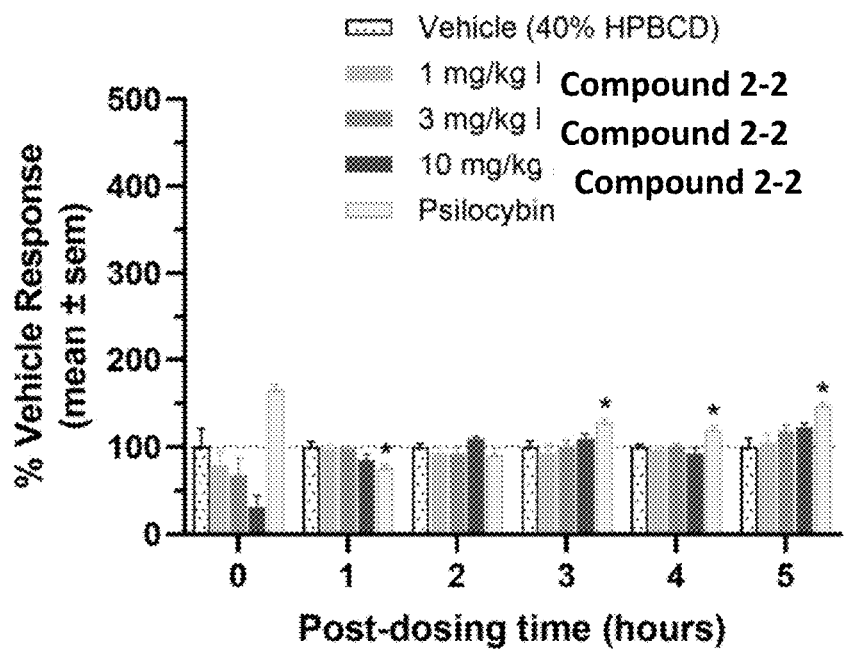
FIG. 24B is a graph showing the effects of compound 2-2 on NREM sleep amounts in WKY rats.

Results:

Compound 2-2 did not affect latencies to both REM and NREM sleep (FIGS. 23A-B). Compound 2-2 increased REM sleep amount during only the 4th hour after dosing (post dosing time 3h) and did not affect NREM sleep amounts (FIGS. 24A-B) in WKY rats.

Figure 25:
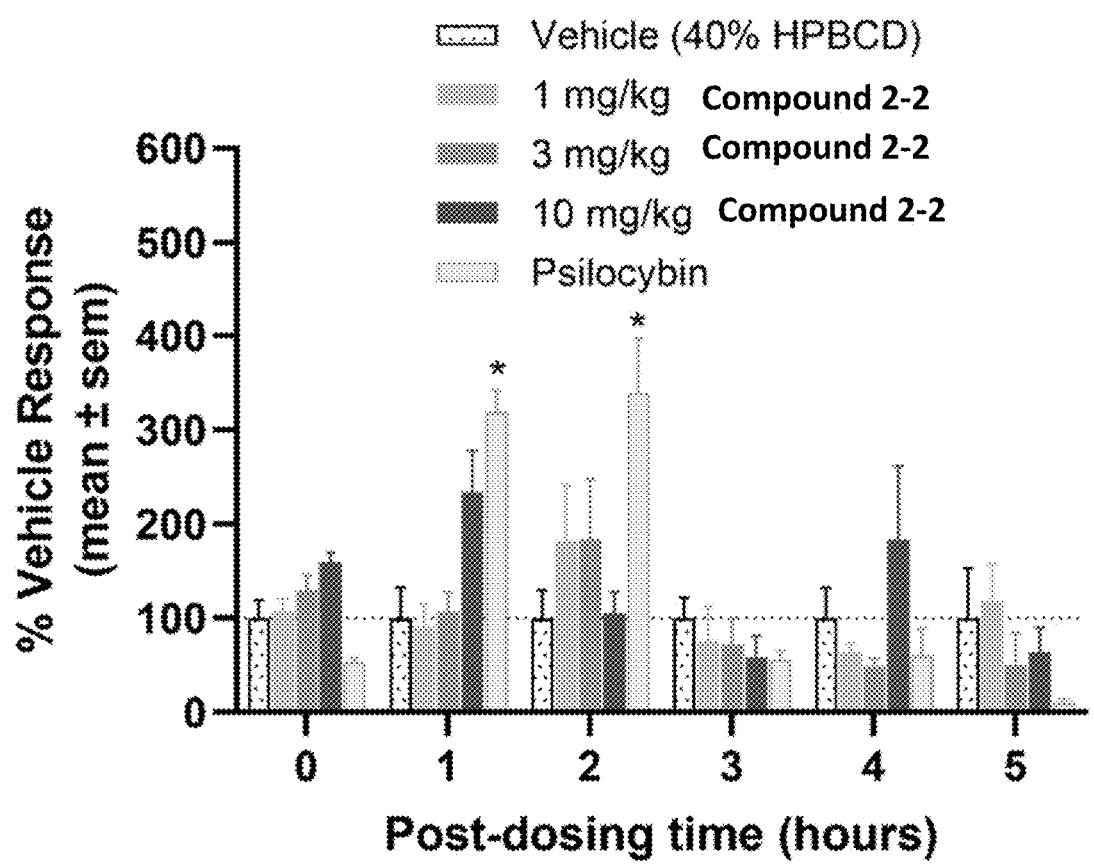
FIG. 25 is a graph showing the effects of compound 2-2 on waking relative to the vehicle response in WKY rats.

Compound 2-2 did not affect the amount of waking in WKY rats (FIG. 25).

Figure 26A:
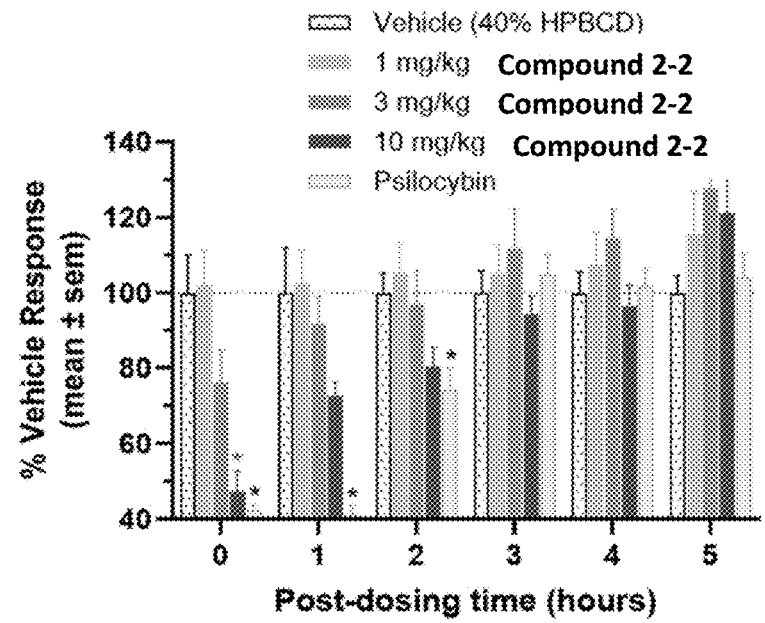
FIG. 26A is a graph showing the effects of compound 2-2 on brain oscillations in the delta frequency (1-4 Hz) range during NREM sleep relative to the vehicle response.
Figure 26B:
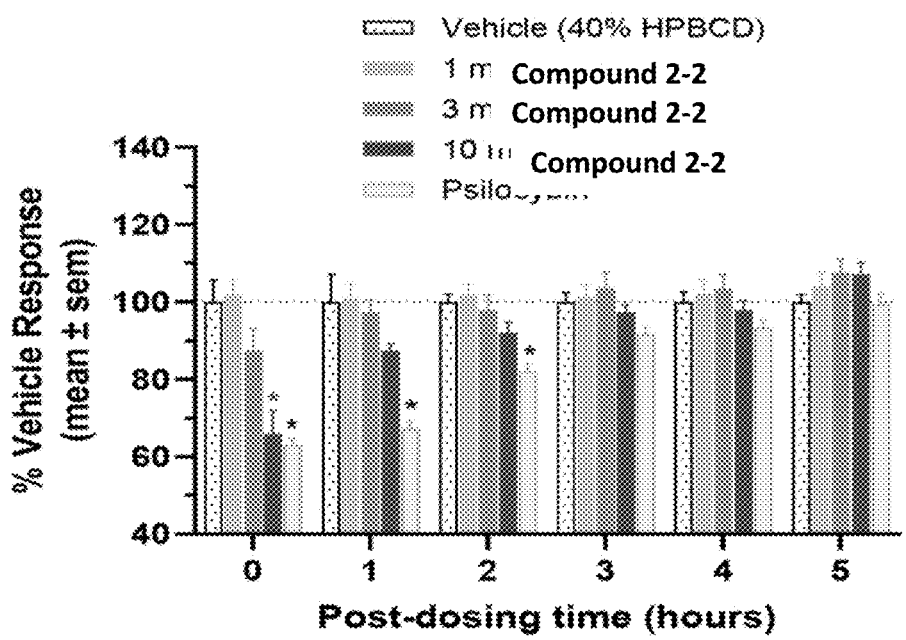
FIG. 26B is a graph showing the effects of compound 2-2 on brain oscillations in the theta frequency (4-7 Hz) range during NREM sleep relative to the vehicle response.

Compound 2-2 exhibited psilocybin-like effects on low-frequency brain oscillations during NREM sleep (delta power, 1-4 Hz; theta power, 4-7 Hz; FIGS. 26A and 26B).

Figure 27A:
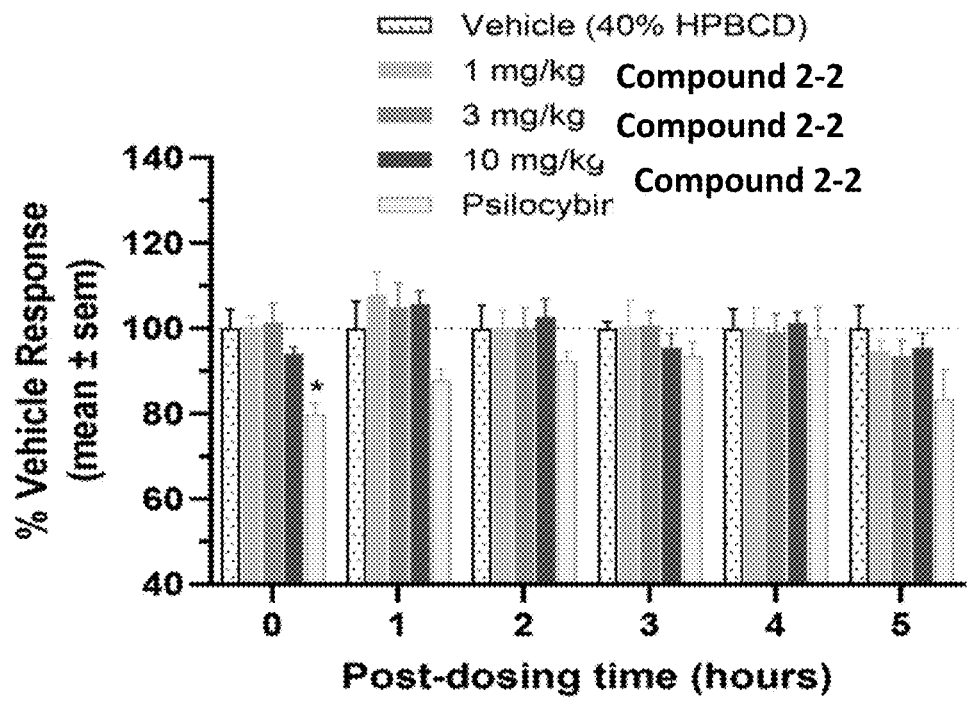
FIG. 27A is a graph showing the effects of compound 2-2 on brain oscillations in the alpha frequency (8-12 Hz) range during waking relative to the vehicle response.
Figure 27B:
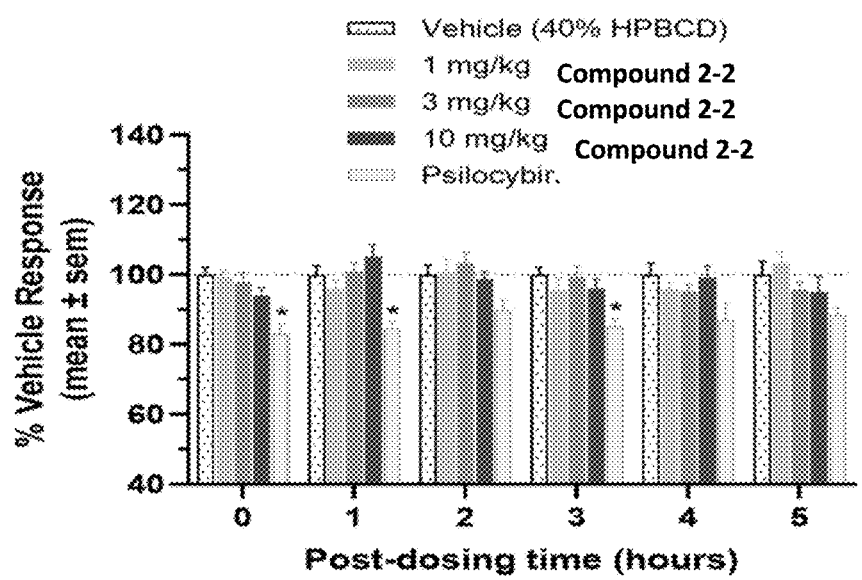
FIG. 27B is a graph showing the effects of compound 2-2 on brain oscillations in the high-frequency gamma (50-100 Hz) range during waking relative to the vehicle response.

Compound 2-2 did not show psilocybin-like effects on brain oscillations in the alpha frequency (8-12 Hz) range during waking (FIG. 27A) or on brain oscillations in the high-frequency gamma (50-100 Hz) range during waking (FIG. 27B).

Figure 28:
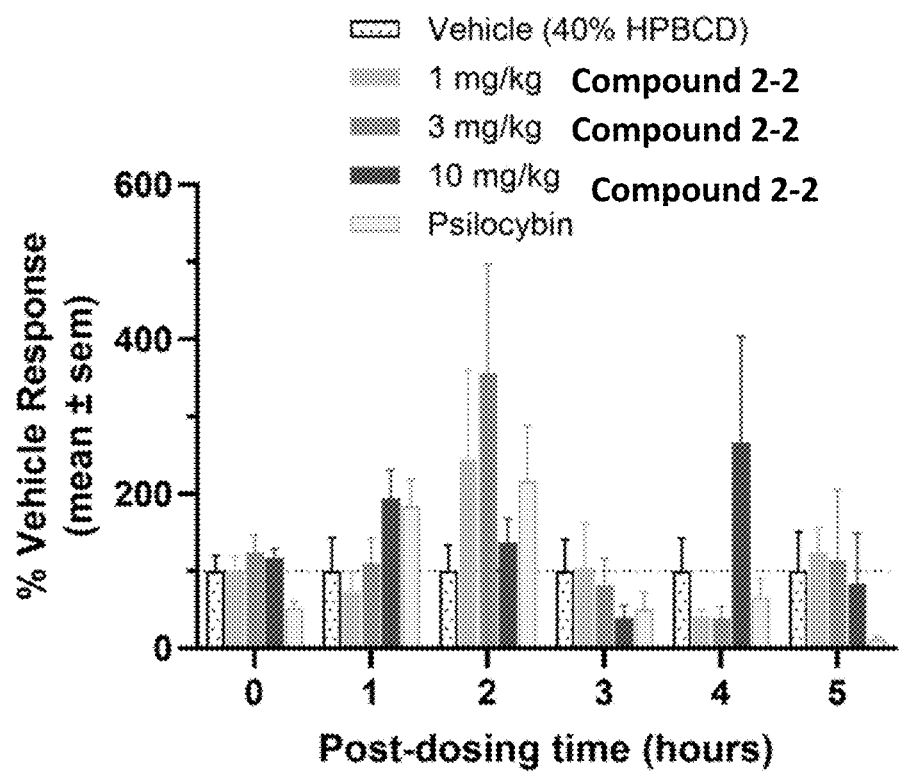
FIG. 28 is a graph showing the effects of compound 2-2 on locomotion relative to the vehicle response in WKY rats.

Compound 2-2 did not affect locomotion in WKY rats (FIG. 28).

Figure 29:
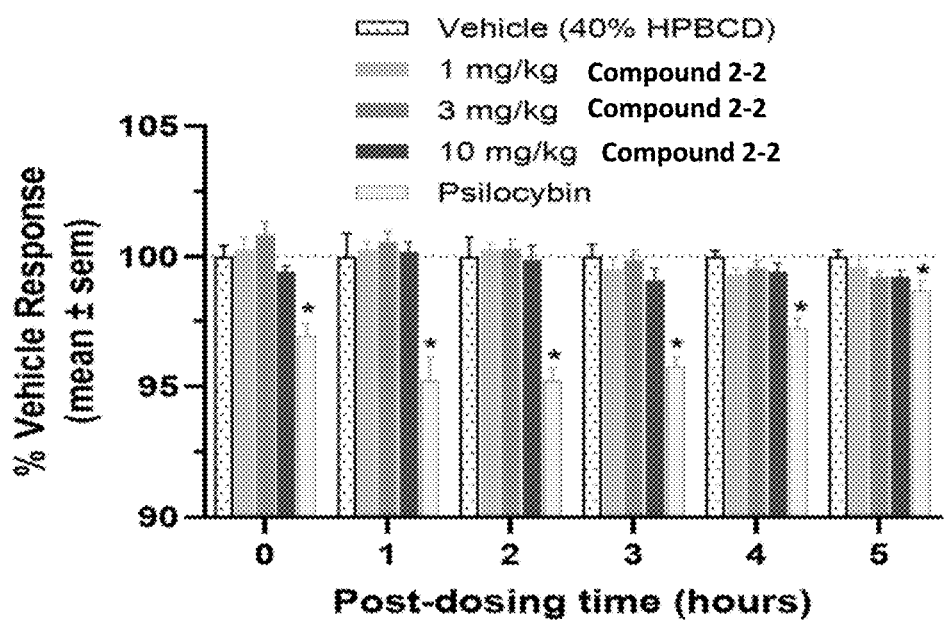
FIG. 29 is a graph showing the effects of compound 2-2 on body temperature relative to the vehicle response in WKY rats.
Figure 30A:
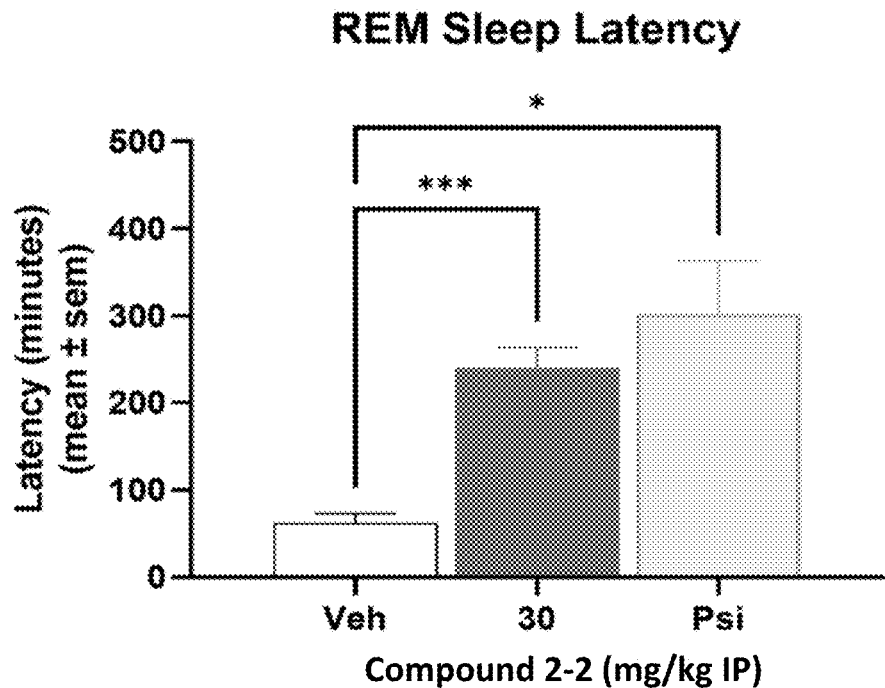
FIG. 30A is a graph showing the effects of compound 2-2 on REM sleep latency in WKY rats.
Figure 30B:
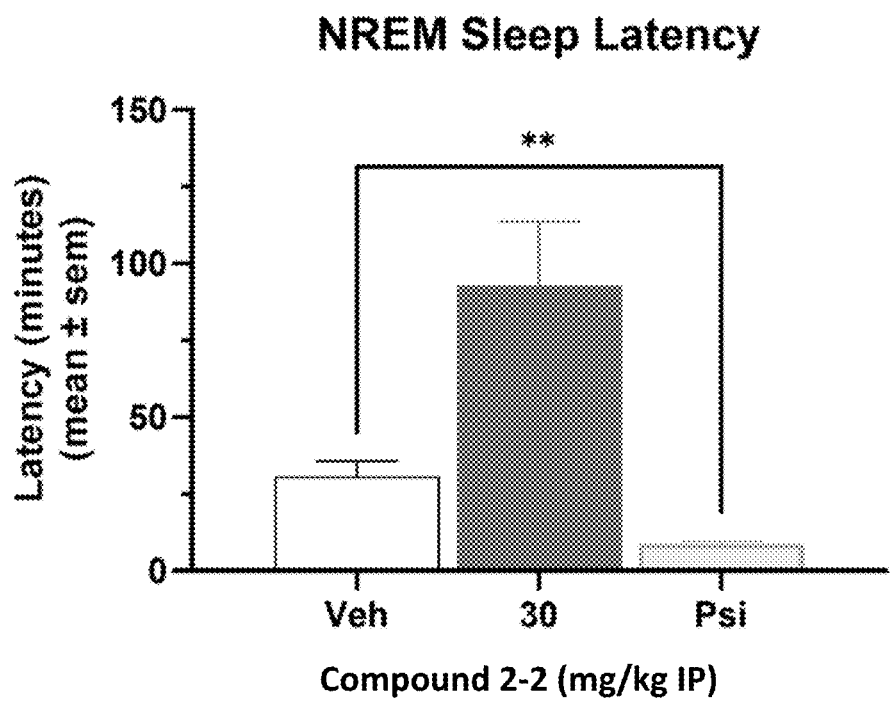
FIG. 30B is a graph showing the effects of compound 2-2 on NREM sleep latency in WKY rats.
Figure 31A:
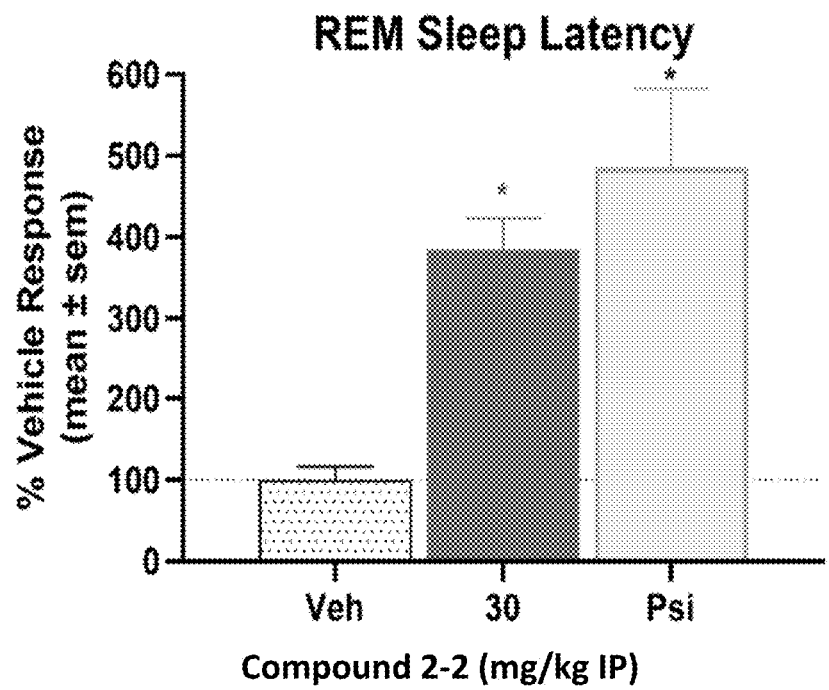
FIG. 31A is a graph showing the effects of compound 2-2 on REM sleep latency relative to the vehicle response in WKY rats.
Figure 31B:
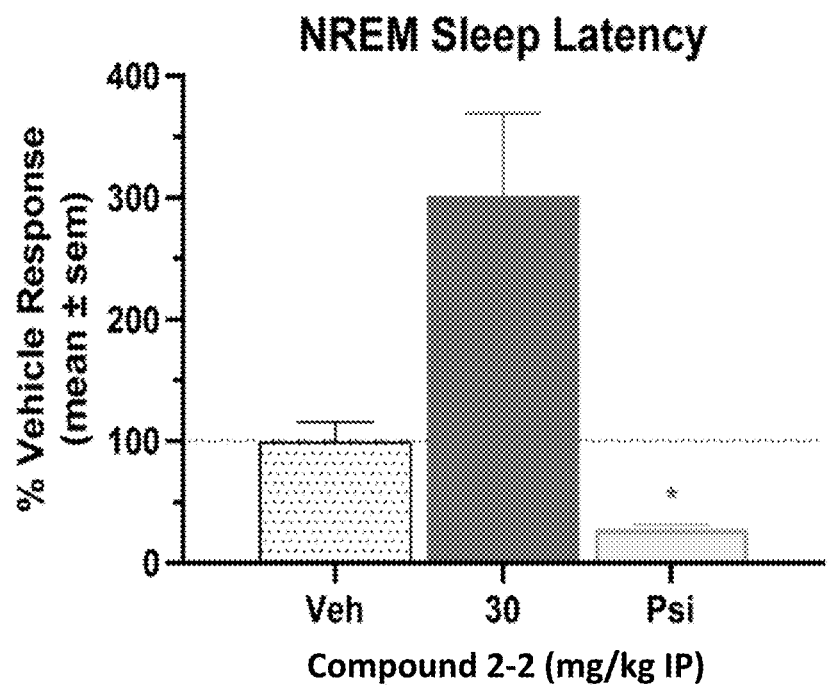
FIG. 31B is a graph showing the effects of compound 2-2 on NREM sleep latency relative to the vehicle response in WKY rats.
Figure 32A:
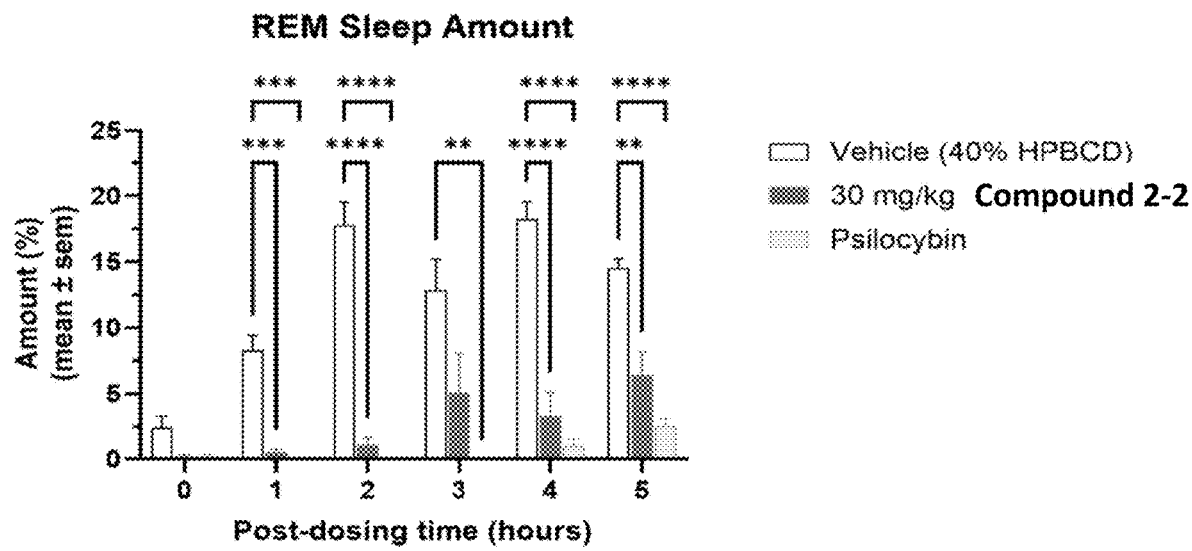
FIG. 32A is a graph showing the effects of compound 2-2 on REM sleep amounts in WKY rats.
Figure 32B:
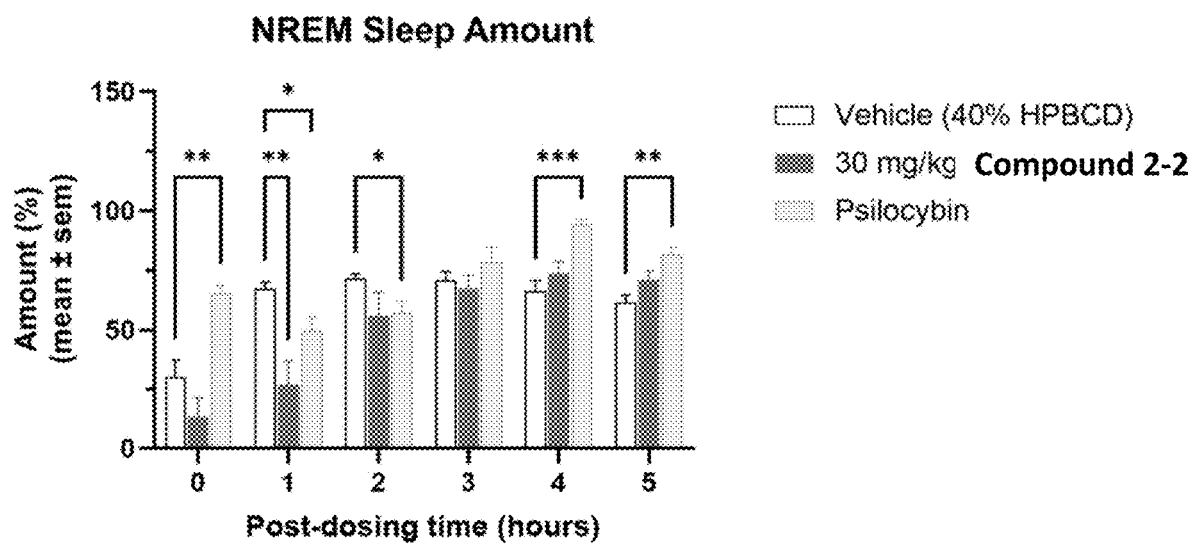
FIG. 32B is a graph showing the effects of compound 2-2 on NREM sleep amounts in WKY rats.
Figure 33A:
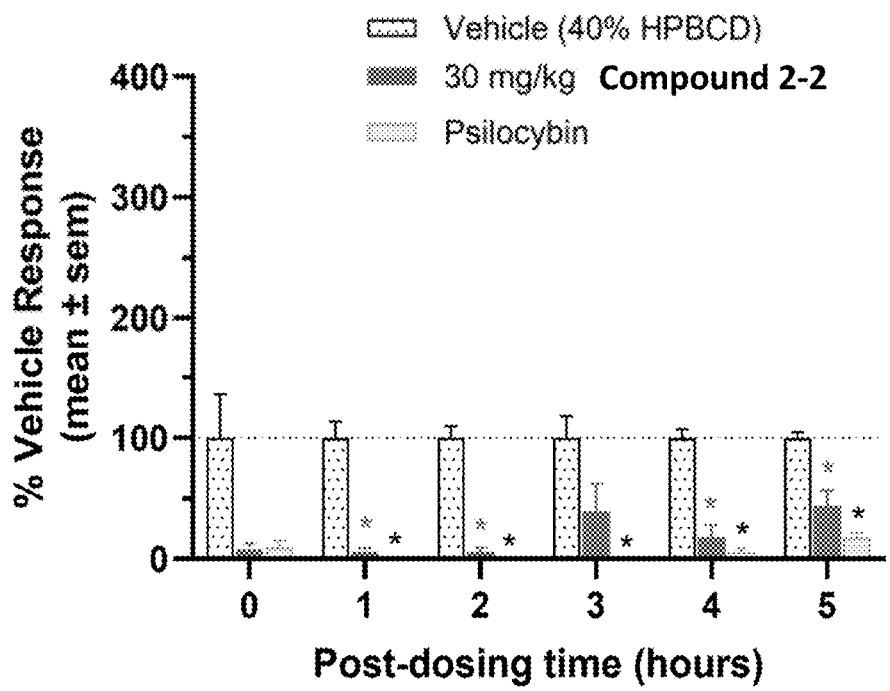
FIG. 33A is a graph showing the effects of compound 2-2 on REM sleep amounts relative to the vehicle response in WKY rats.
Figure 33B:
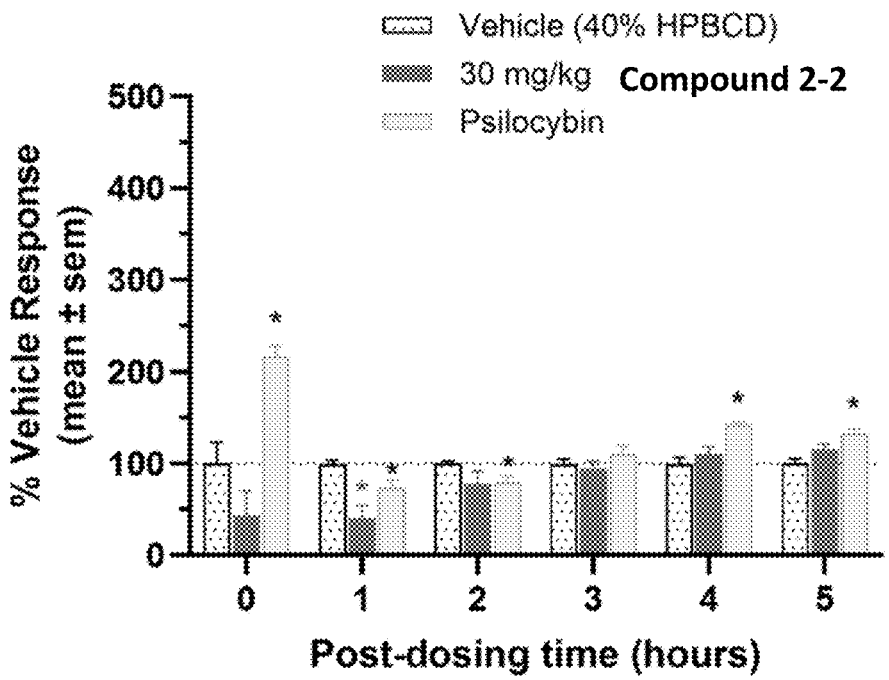
FIG. 33B is a graph showing the effects of compound 2-2 on NREM sleep amounts relative to the vehicle response in WKY rats.

Compound 2-2 did not affect body temperature in WKY Rats (FIG. 29).

Example 12

Evaluation of the Effects of Compound 2-2 on Sleep, Locomotor Activity, Body Temperature and qEEG in the Male Wistar Kyoto Rat The aim of the current study was to confirm the effects of compound 2-2 (30 mg/kg) on sleep-wake behavior and EEG brain oscillatory power in an independent cohort of male Wistar Kyoto rats. The study was carried out similarly to Examples 7 and 9 with differences noted below. Male WKY rats (n=8, 323-352 g at the start of dosing) were housed in groups of 2-3 animals per cage with standard housing conditions. Specifics of the study design are shown in Table 8.

TABLE 8

Treatment Conditions

1. Vehicle (40% w/v HPBCD in water, IP)
2. Psilocybin (10 mg/kg in saline, IP)
3. Compound 2-2 (30 mg/kg in 40% w/v HPBCD in water, IP)

Results:

Compound 2-2 increased REM sleep latency but had no significant effect on NREM sleep latency (FIGS. 30A-B and 31A-B) and decreased both REM and NREM sleep amounts (FIGS. 32A-B and 33A-B) in WKY rats.

Figure 34:
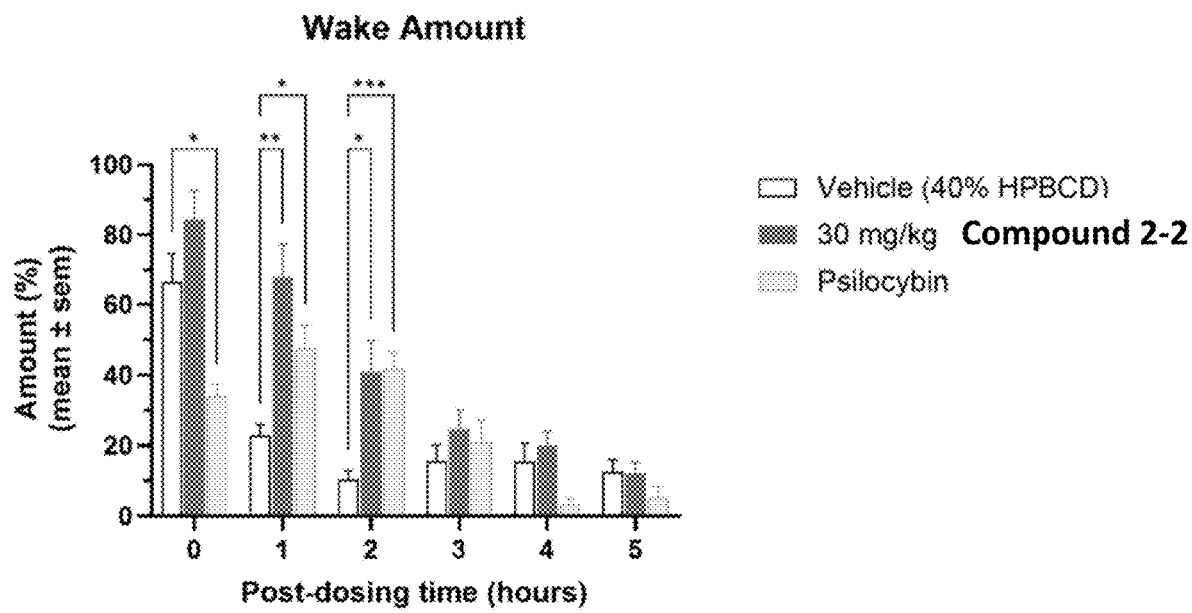
FIG. 34 is a graph showing the effects of compound 2-2 on wake amounts in WKY rats.

Compound 2-2 increased the amount of waking in WKY rats (FIG. 34).

Figure 35:
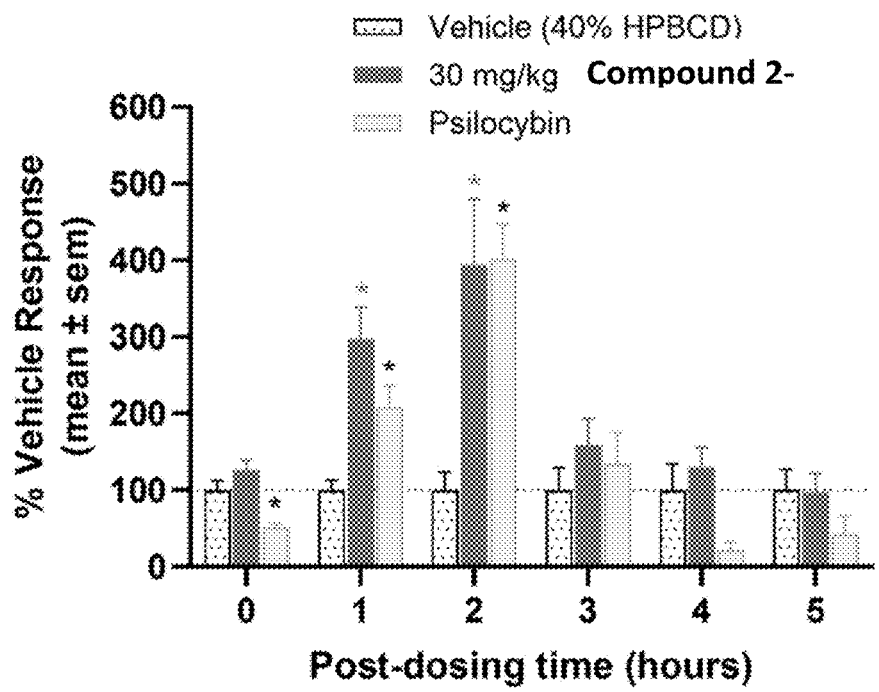
FIG. 35 is a graph showing the effects of compound 2-2 on waking relative to the vehicle response in WKY rats.
Figure 36A:
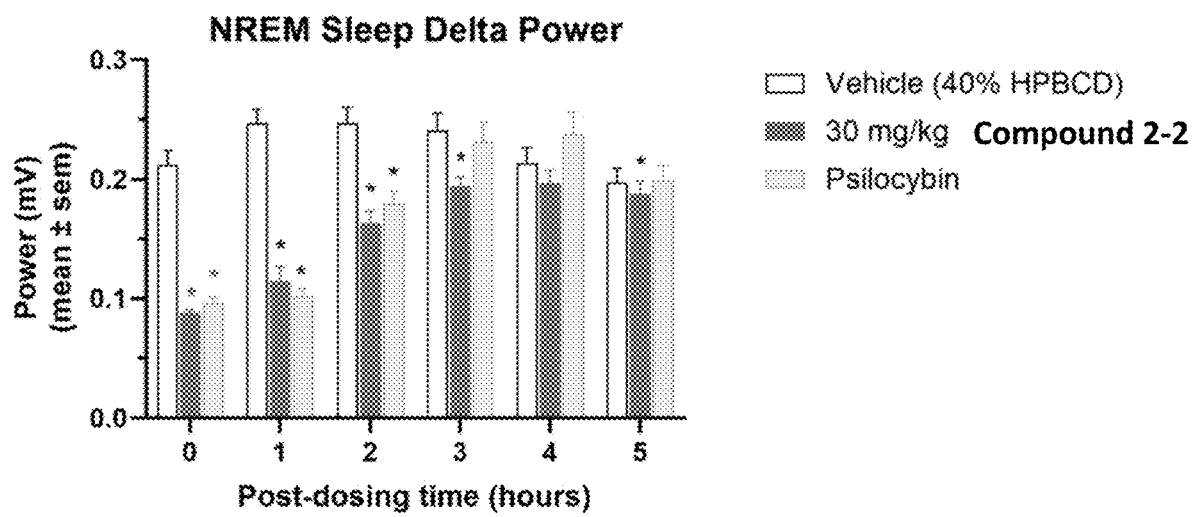
FIG. 36A is a graph showing the effects of compound 2-2 on brain oscillations in the delta frequency (1-4 Hz) range during NREM sleep.
Figure 36B:
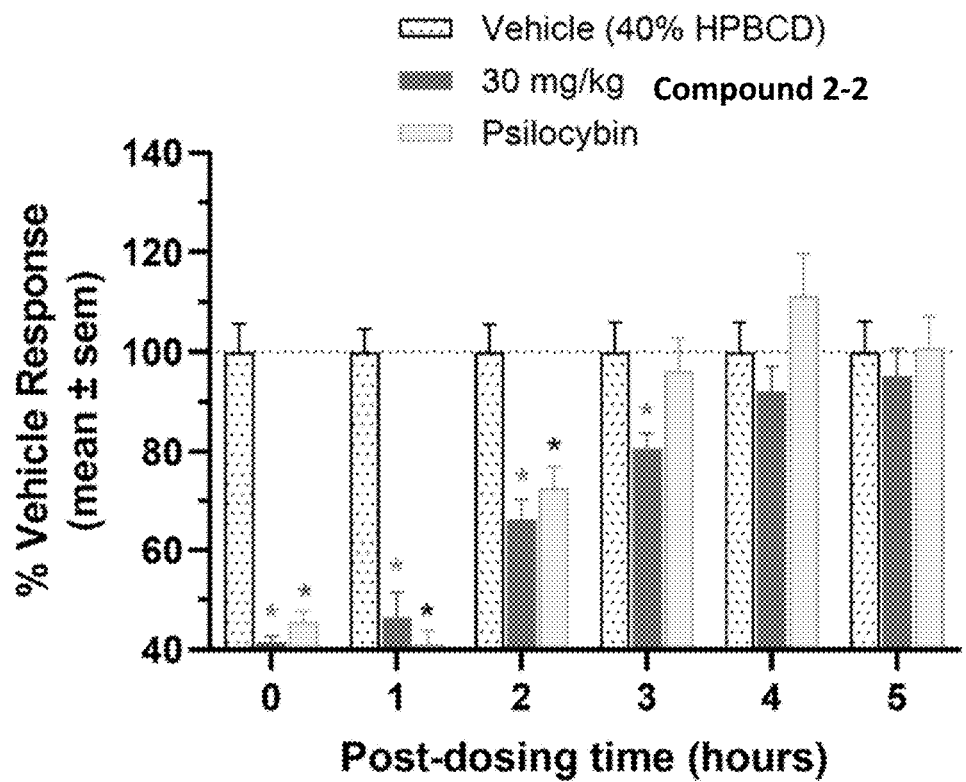
FIG. 36B is a graph showing the effects of compound 2-2 on brain oscillations in the delta frequency (1-4 Hz) range during NREM sleep relative to the vehicle response.
Figure 37A:
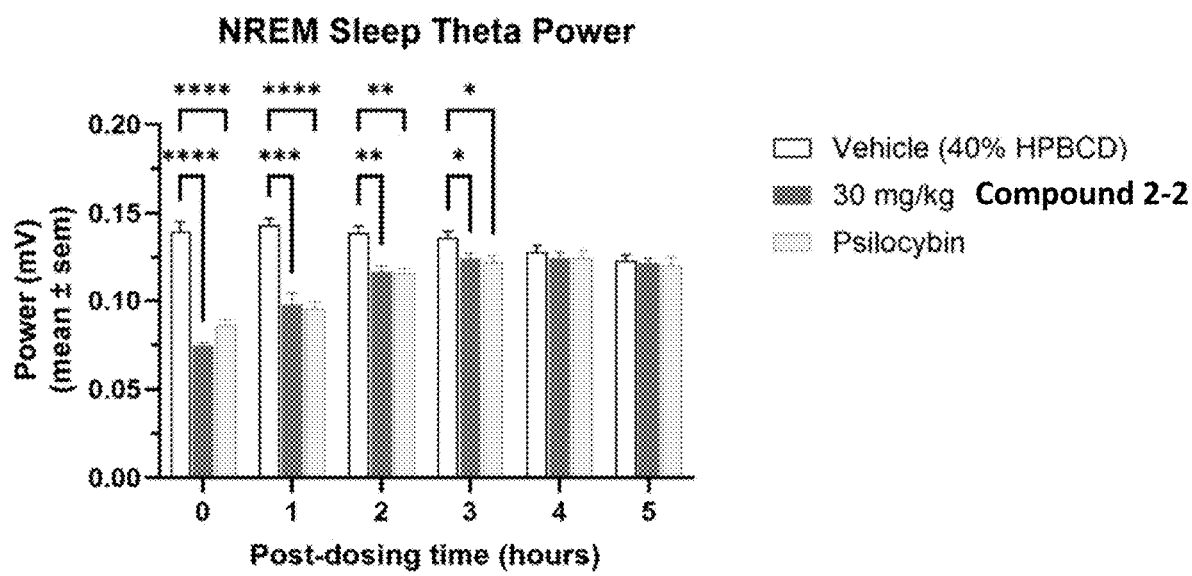
FIG. 37A is a graph showing the effects of compound 2-2 on brain oscillations in the theta frequency (4-7 Hz) range during NREM sleep.
Figure 37B:
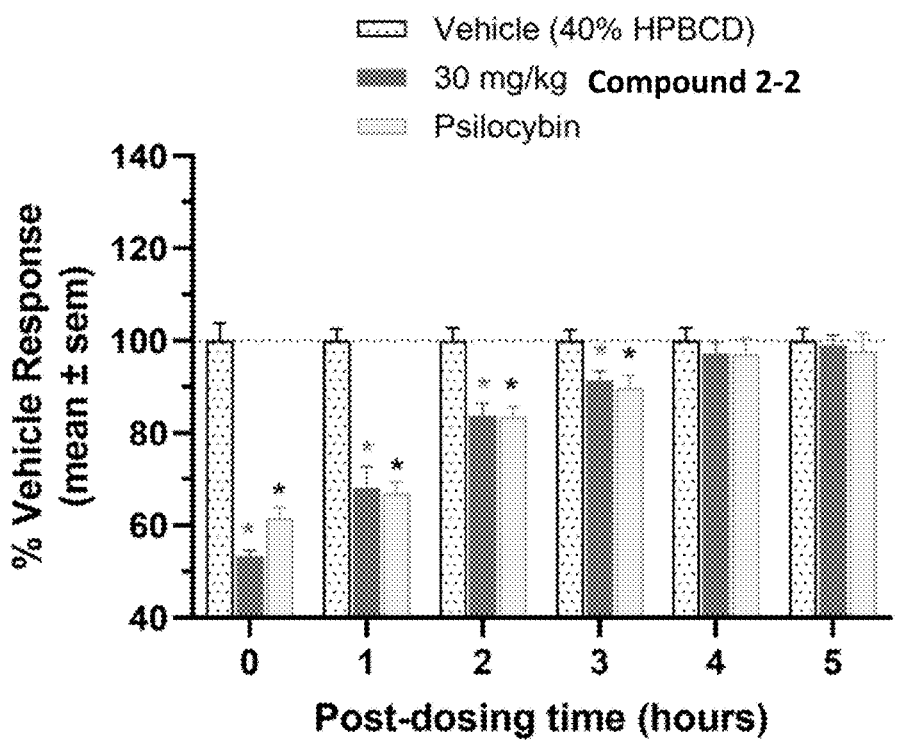
FIG. 37B is a graph showing the effects of compound 2-2 on brain oscillations in the theta frequency (4-7 Hz) range during NREM sleep relative to the vehicle response.
Figure 38A:
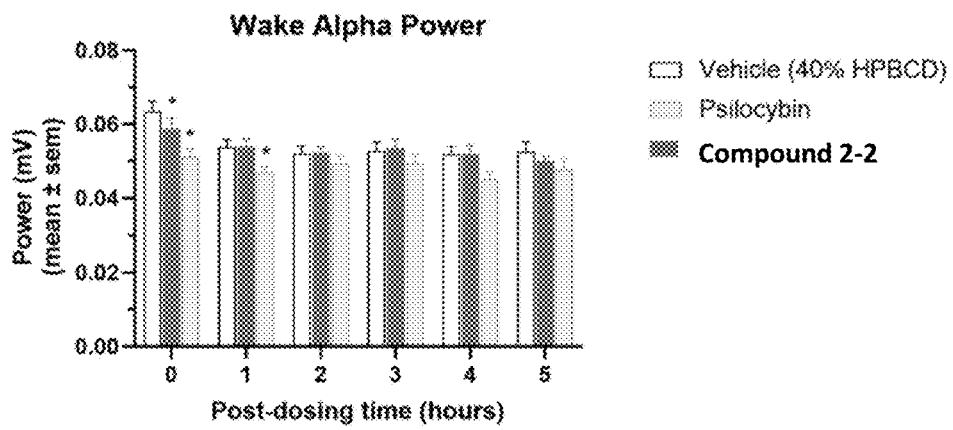
FIG. 38A is a graph showing the effects of compound 2-2 on brain oscillations in the alpha range during waking.
Figure 38B:
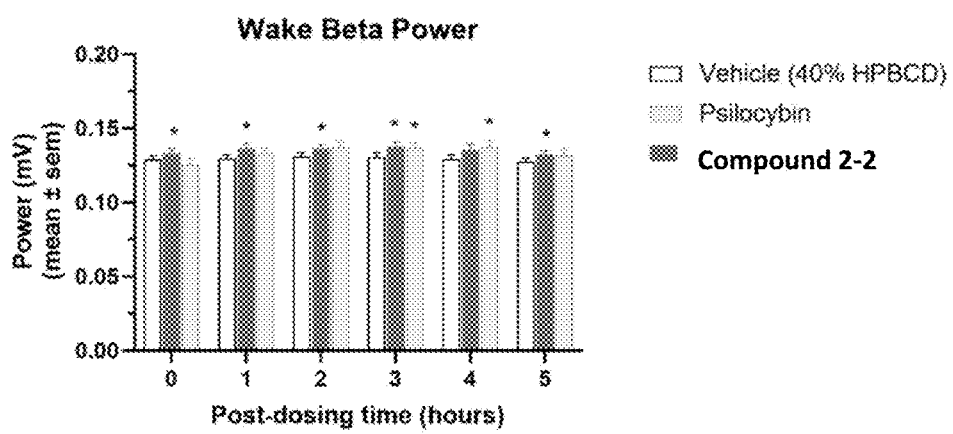
FIG. 38B is a graph showing the effects of compound 2-2 on brain oscillations in the beta range during waking.
Figure 38C:
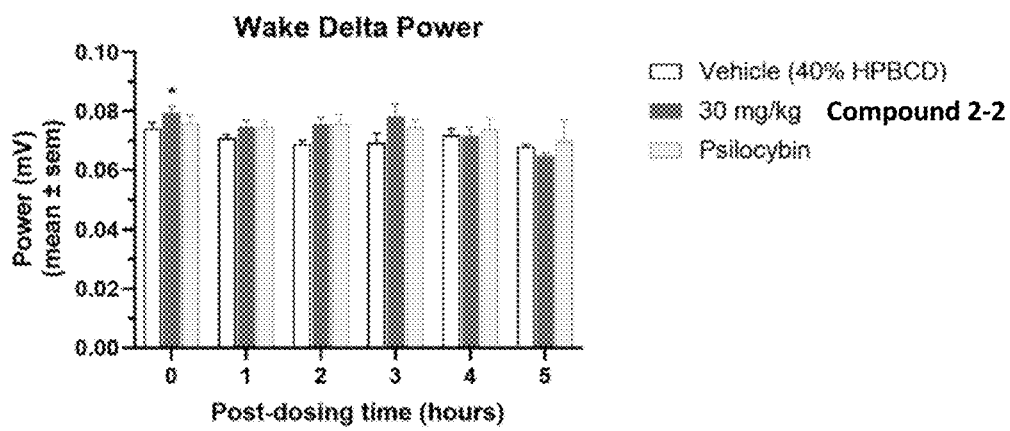
FIG. 38C is a graph showing the effects of compound 2-2 on brain oscillations in the delta range during waking.
Figure 38D:
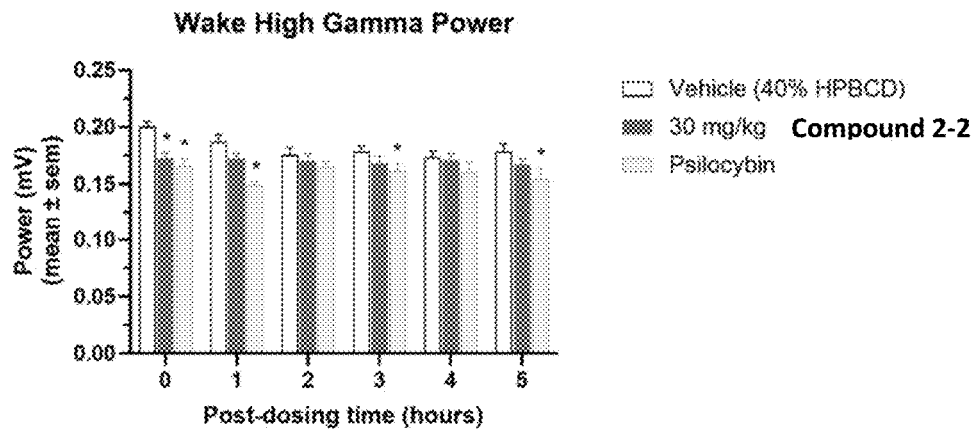
FIG. 38D is a graph showing the effects of compound 2-2 on brain oscillations in the high-gamma range during waking.
Figure 38E:
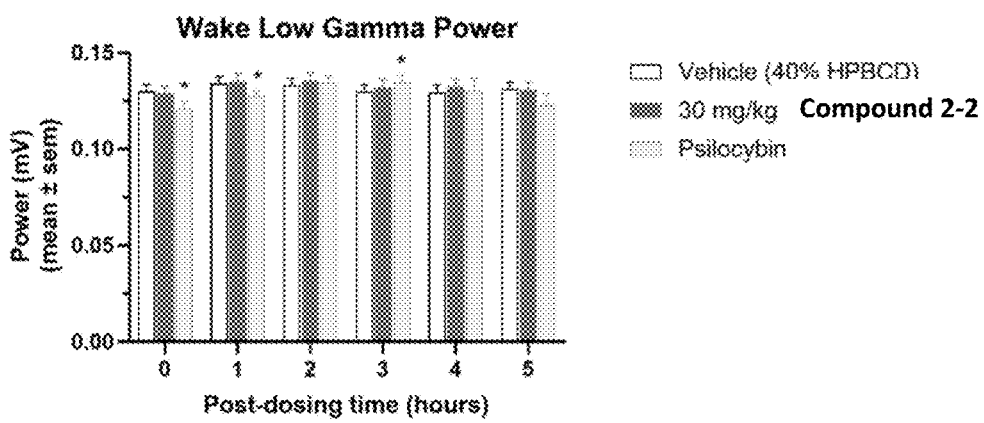
FIG. 38E is a graph showing the effects of compound 2-2 on brain oscillations in the low-gamma range during waking.
Figure 38F:
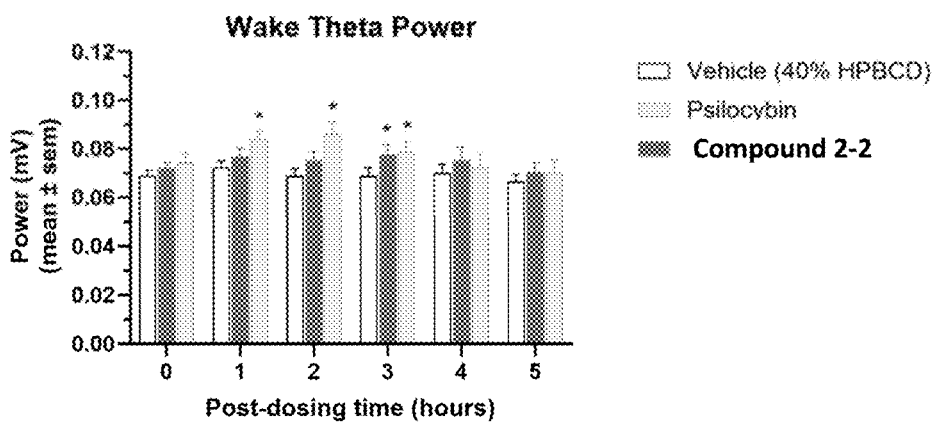
FIG. 38F is a graph showing the effects of compound 2-2 on brain oscillations in the theta range during waking.

The effects of compound 2-2 on wake amount relative to the vehicle response is shown in FIG. 35.

Compound 2-2 exhibited psilocybin-like effects on low-frequency brain oscillations during NREM sleep (delta power, 1-4 Hz; theta power, 4-7 Hz; FIGS. 36A, 36B, 37A, and 37B).

Compound 2-2's effects on brain oscillations in the alpha, beta, delta, high-gamma, low-gamma, and theta range during waking are shown in FIGS. 38A-F.

Figure 39A:
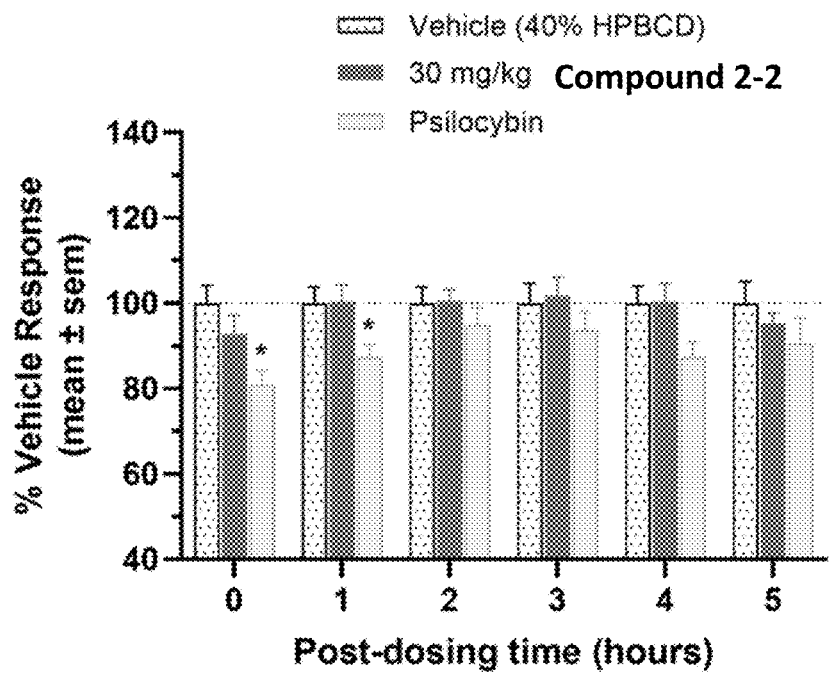
FIG. 39A is a graph showing the effects of compound 2-2 on brain oscillations in the alpha frequency (8-12 Hz) range during waking relative to the vehicle response.
Figure 39B:
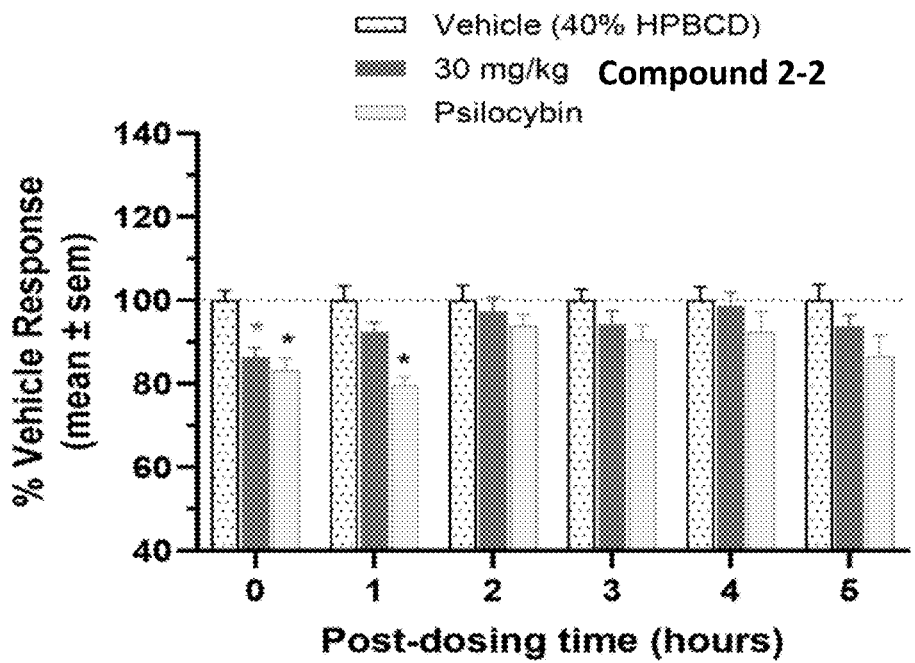
FIG. 39B is a graph showing the effects of compound 2-2 on brain oscillations in the high-frequency gamma (50-100 Hz) range during waking relative to the vehicle response.

Compound 2-2 did not show psilocybin-like effects on brain oscillations in the alpha frequency (8-12 Hz) range during waking (FIG. 39A) but did show psilocybin-like effects on brain oscillations in the high-frequency gamma (50-100 Hz) range during waking (FIG. 39B).

Figure 40A:
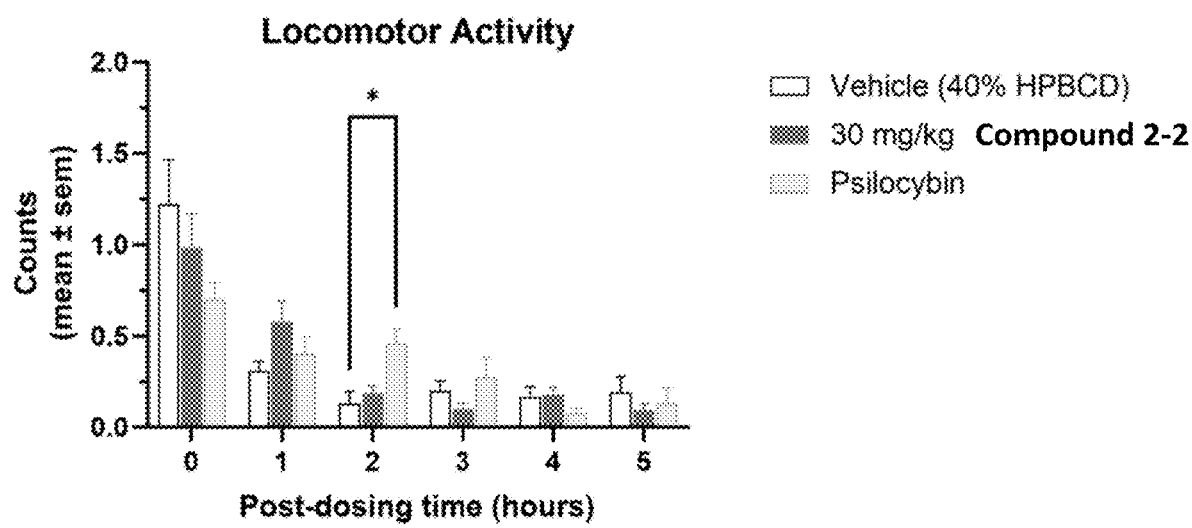
FIG. 40A is a graph showing the effects of compound 2-2 on locomotion in WKY rats.
Figure 40B:
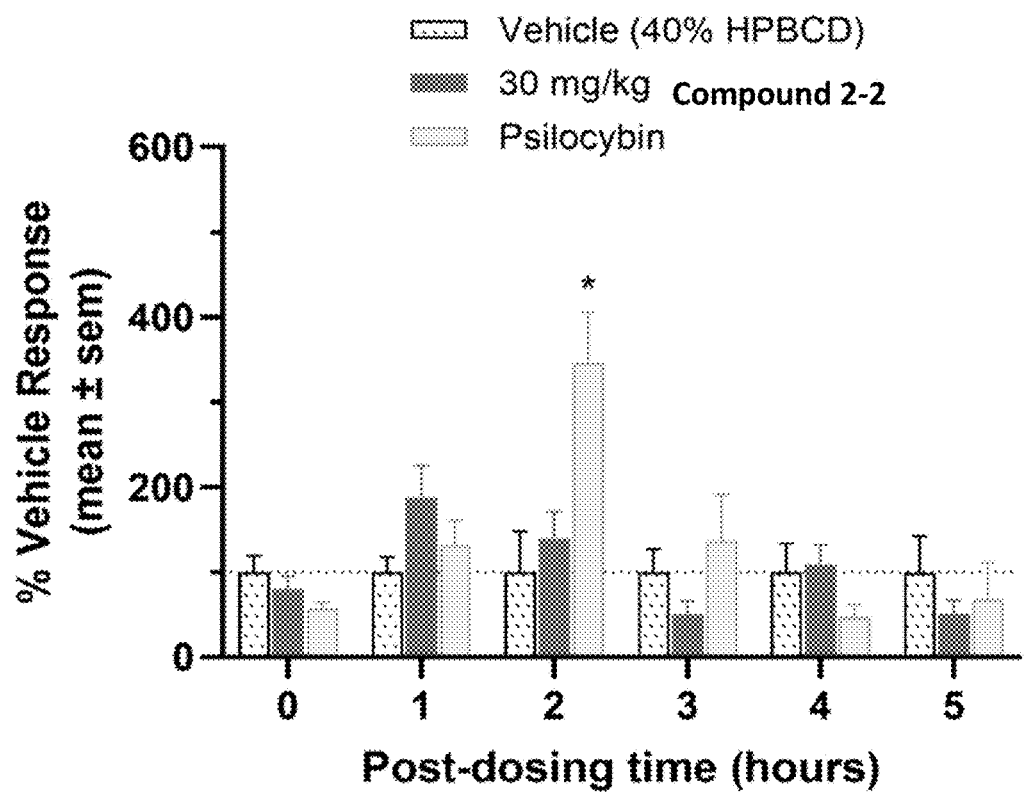
FIG. 40B is a graph showing the effects of compound 2-2 on locomotion relative to the vehicle response in WKY rats.

Compound 2-2 did not affect locomotion in WKY rats (FIGS. 40A and 40B).

Figure 41A:
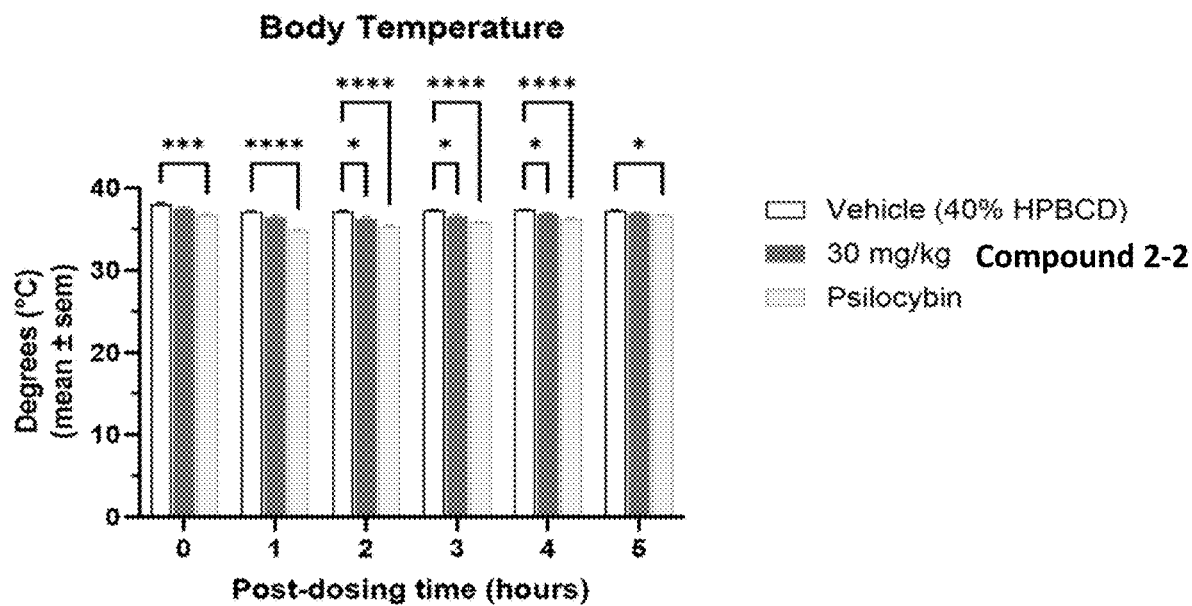
FIG. 41A is a graph showing the effects of compound 2-2 on body temperature in WKY rats.
Figure 41B:
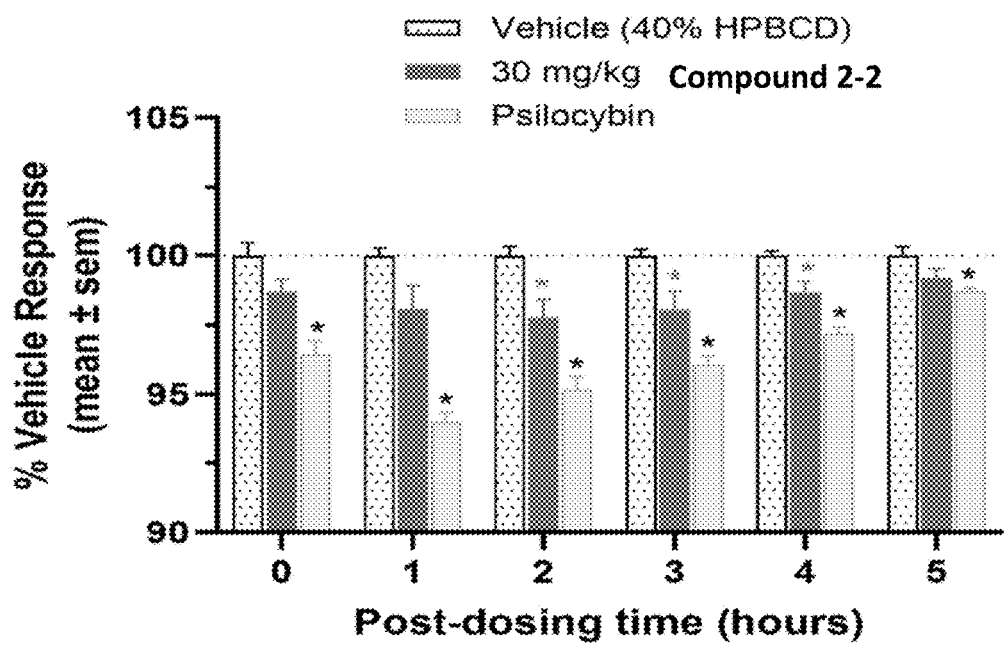
FIG. 41B is a graph showing the effects of compound 2-2 on body temperature relative to the vehicle response in WKY rats.

Compound 2-2 transiently reduced body temperature in WKY Rats (FIGS. 41A and 41B).

Example 13

Effect of Compound 2-2 and Psilocybin on 5-HT2A Receptor Occupancy in Mice

Twenty seven (25 study plus 2 spare) male C57BL/6J mice (8-9 weeks of age, 22-28 g upon arrival). Animals were group housed (2 or 3 per cage) in polypropylene cages. Mice were maintained on a normal phase 12 h light-dark cycle (lights on: 07:00-19:00 h) with free access to standard rodent maintenance diet (standard pelleted diet Envigo 2018) and filtered tap water. The holding room was maintained at a temperature of 21±2° C. and relative humidity will typically be 55±15% with prolonged periods below 40% RH or above 70% RH were avoided. For enrichment each cage contained sawdust, sizzlenest, a red plastic house and tunnel, plastic chew stick and a nestlet so that the mice can make nests and facilitate warmth.

Prior to the onset of procedures, animals were weighed and allocated into 5 groups by a statistician based on body weight. Animals sharing a cage were dosed with the same drug treatments to avoid cross contamination between groups. Animals were dosed intraperitoneally with psilocybin (3 mg/kg), or one of 3 doses of compound 2-2 (1 mg/kg, 3 mg/kg, 10 mg/kg). Dosing was to a timed scheduled. Animals were weighed prior to dosing and the body weight recorded. Food and water intake were not monitored. The animals were dosed at time "0" and then returned to the home cage. Behaviors of note after dosing were recorded. Each animal was humanely killed (by exposure to increasing $CO_2$ concentration and confirmation of death by cervical dislocation) to allow terminal blood sampling to take place 15 minutes after dosing. The brain sampling was performed immediately after blood sampling was completed for each animal.

Post-mortem blood samples (approx. 0.5 ml) were collected from all animals by cardiac puncture for DMPK analysis, dispensed into a LH-coated tube. The blood samples were gently inverted, centrifuged promptly (2400 g for 5 minutes at 4° C.) and 150 µl of plasma from each animal was placed into a 96-well plate. Plasma samples from group B were stabilized with DTT (50 mM; 1:10). All plasma samples were frozen on dry ice and stored at approximately −80° C. prior to analysis. Whole brains were removed from all animals, rinsed briefly with saline and blot dried. The left and right frontal cortices (~25 mg each frontal cortex) were dissected separately from the brain, weighed, placed in microtubes, frozen on dry ice and stored at −20° C. to measure receptor occupancy. The remaining brain tissue was weighed, placed in homogenization tubes, frozen on dry ice, and stored at −80° C. prior to transferring (on dry ice) to Signature DMPK with the plasma samples.

Left frontal cortices from each animal were homogenized individually (3.75 mg/ml weight of tissue) in ice cold assay buffer using a tight-fitting glass/Teflon homogenizer and used immediately in the binding assay. Left cortical membranes (400 µl; equivalent to 1.5 mg wet weight of tissue/tube) were incubated with 50 µl of 0.075 nM [$^3$H]cimbi-36 and either 50 µl of buffer (total binding) or 50 µl of 1 µM 25CN—NBOH (to define non-specific binding) for 30 mins at 25° C. The homogenate and assay and buffer will consist of 50 mM Tris, pH 7.4 containing 4 mM $CaCl_2$ and wash buffer will consist of 50 mM Tris, pH 7.4. For each animal there were two tubes for the determination of total binding and two tubes for the determination of non-specific binding. Membrane bound radioactivity was recovered by filtration under vacuum through Whatman GF/A filters, presoaked in 0.5% polyethyleneimine (PEI) using a cell harvester. Filters were rapidly washed with ice-cold buffer (wash setting 9,9,0) and radioactivity determined by liquid scintillation counting.

A value for specific binding (dpm) was generated by the subtraction of mean non-specific binding (dpm) from mean total binding (dpm) for each animal. Data is presented as mean specific binding (dpm), as a percentage of the vehicle-treated control taken as 100% and as percentage receptor occupancy. Statistical analysis was by one-way analysis of variance of square root transformed data, with each treatment/time combination as a separate group, followed by appropriate multiple comparison tests to compare each treatment to the combined vehicle group. A p value of less than 0.05 will be considered statistically significant. The statistics was performed in-house by a qualified statistician. 5-HT2A ex vivo binding, plasma and brain drug levels will be correlated for individual animals. $ED_{SOS}$ (the dose where there is 50% occupancy) was calculated, where appropriate, by non-linear regression. Also, $EC_{SOS}$ was calculated, where appropriate, for plasma and brain concentrations.

Figure 42A:
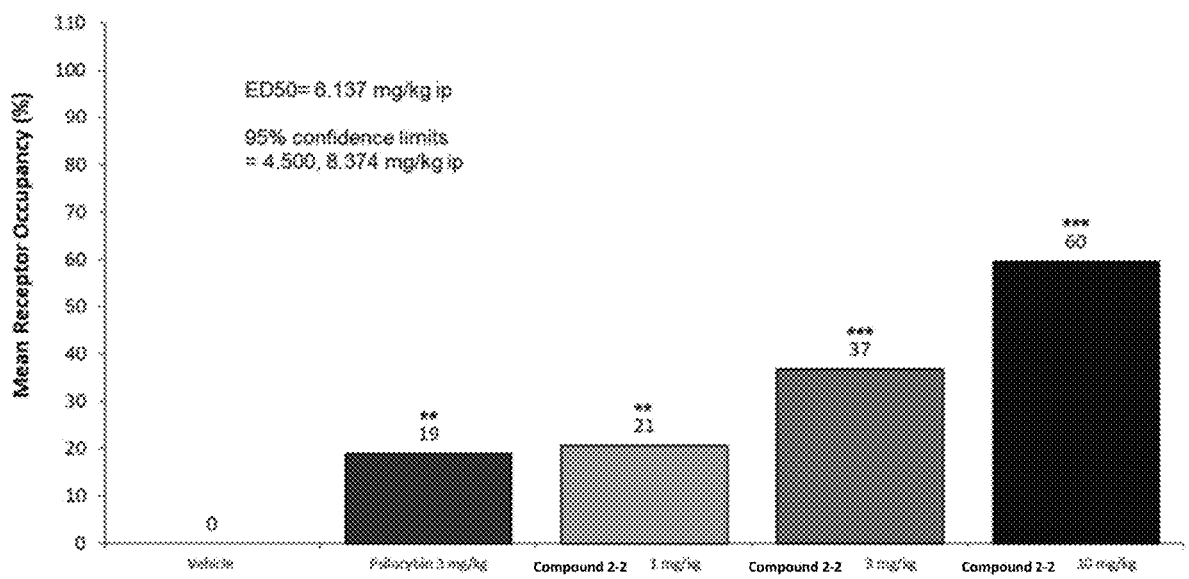
FIG. 42A is a graph showing the dose-dependent & significant 5-HT2A receptor occupancy in mouse frontal cortex of compound 2-2.
Figure 42B:
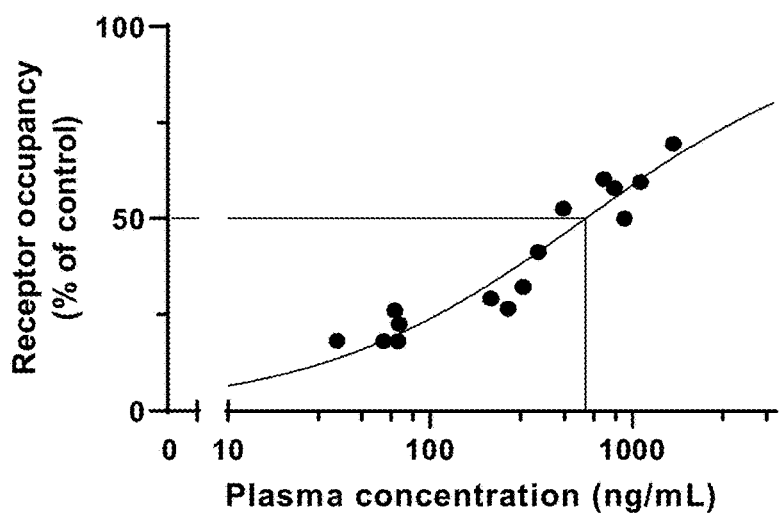
FIG. 42B is a graph showing compound 2-2's 5-HT2A receptor occupancy in mouse frontal cortex related to plasma exposure.
Figure 43:
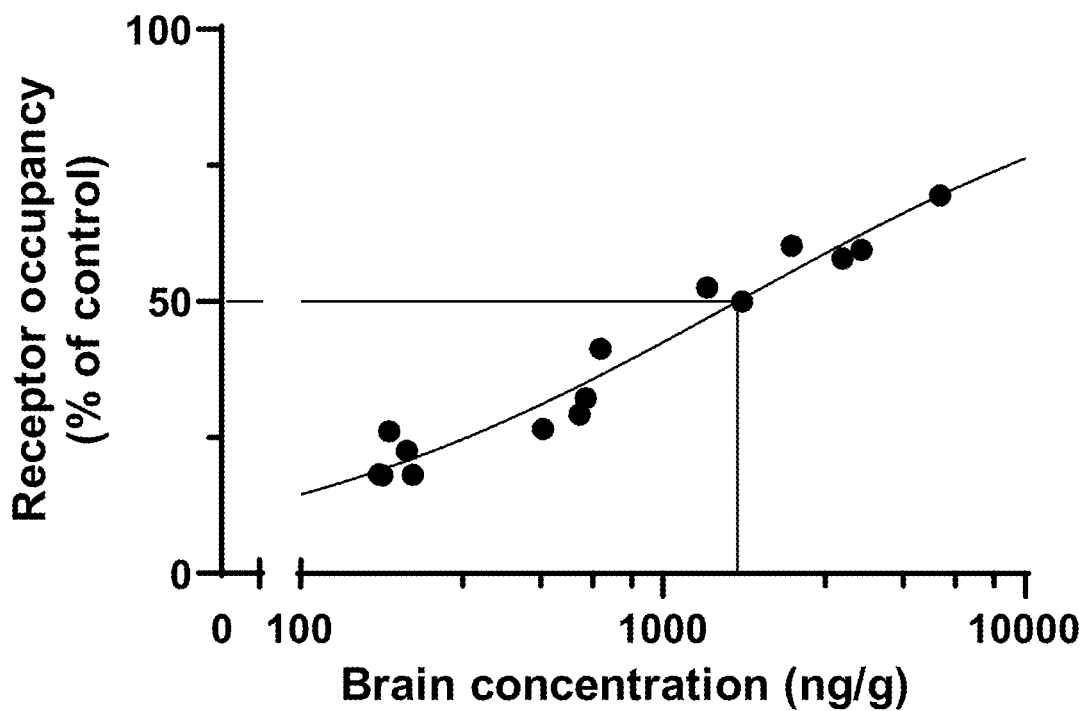
FIG. 43 is a graph showing compound 2-2's 5-HT2A receptor occupancy in mouse frontal cortex related to brain exposure.
Figure 44A:
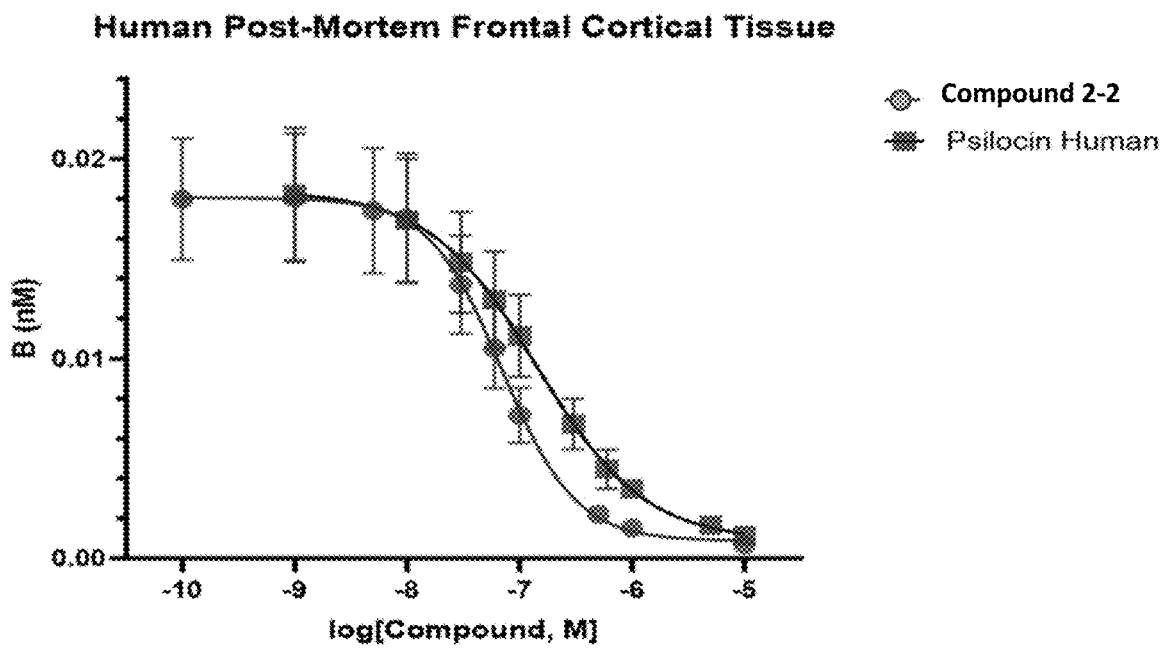
FIG. 44A is a graph showing compound 2-2 and psilocin 5-HT2A receptor binding in human post-mortem frontal cortical tissue.
Figure 44B:
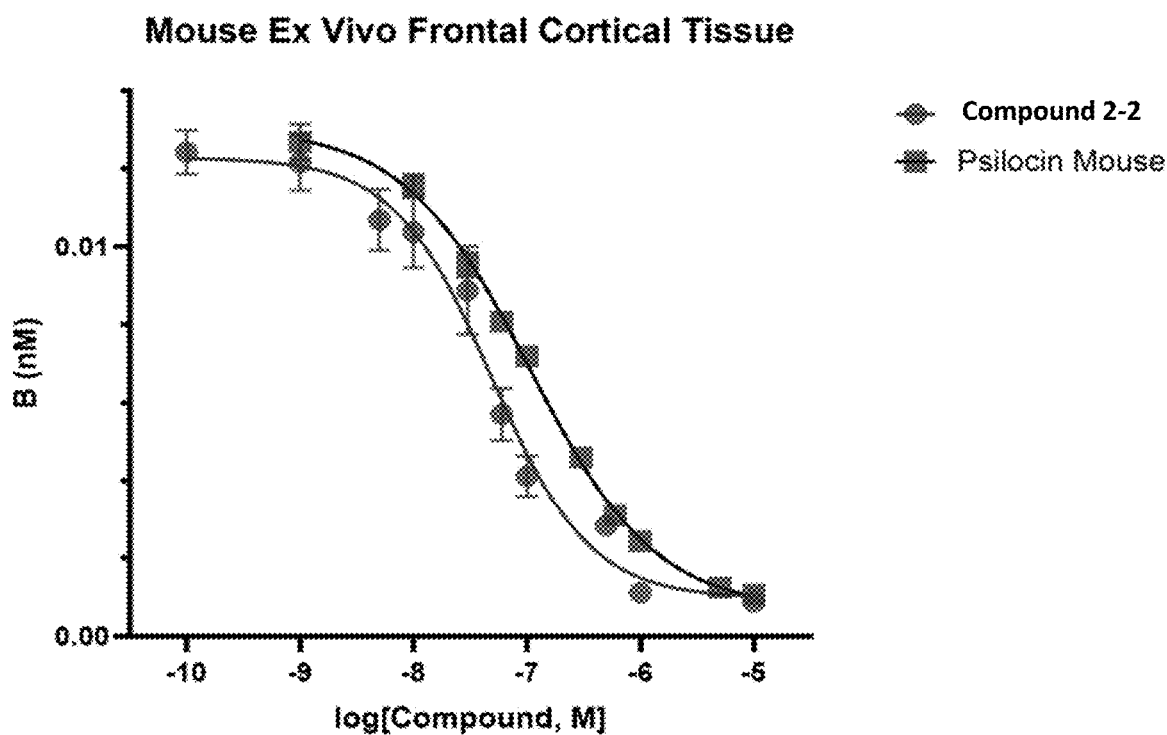
FIG. 44B is a graph showing compound 2-2 and psilocin 5-HT2A receptor binding in mouse ex vivo frontal cortical tissue.
Figure 45:
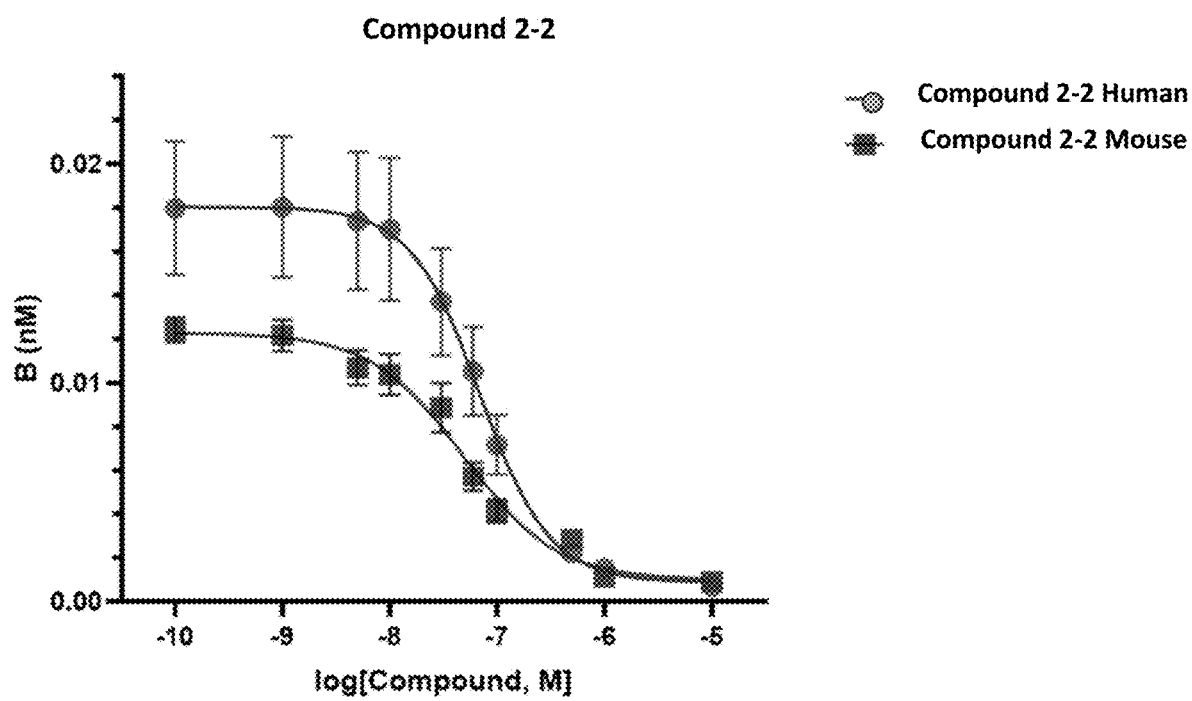
FIG. 45 is a graph showing the overlay of compound 2-2's 5-HT2A receptor binding in human post-mortem frontal cortical tissue and mouse ex vivo frontal cortical tissue.
Figure 46:
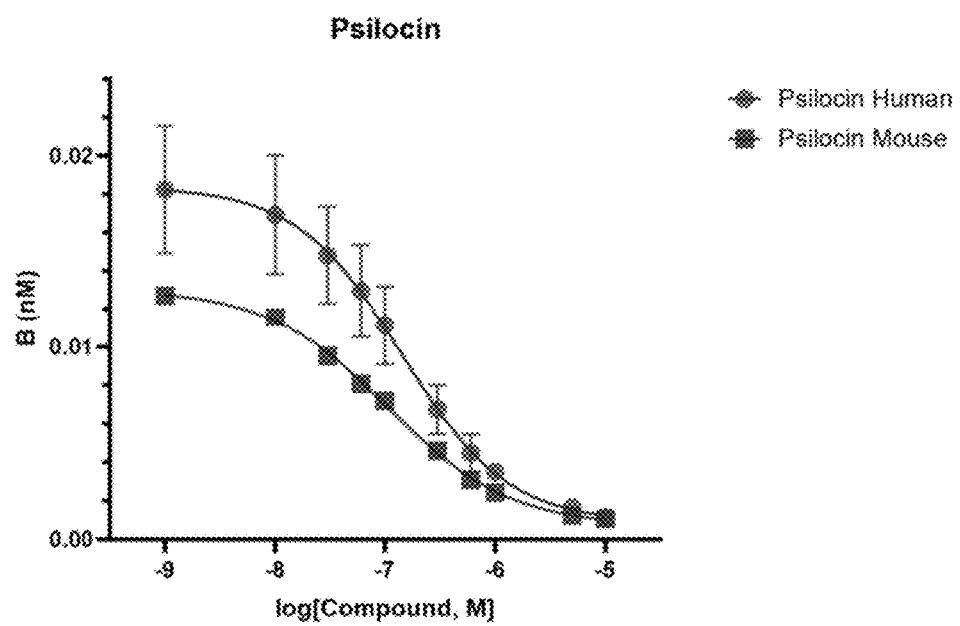
FIG. 46 is a graph showing the overlay of psilocin's 5-HT2A receptor binding in human post-mortem frontal cortical tissue and mouse ex vivo frontal cortical tissue.

Results are shown in tables 9-12 and FIGS. 42A, 42B, and 43. Compound 2-2 (1, 3, 10 mg/kg IP) demonstrated dose-dependent & significant ex vivo occupancy of 5-HT2A receptors in the mouse frontal cortex (21-60% RO). 50% 5-HT2A RO at: 6.137 mg/kg compound 2-2 IP, 585 ng/mL compound 2-2 in plasma, 1608 ng/g compound 2-2 in brain. The positive control, psilocybin (3 mg/kg IP), exhibited significant ex vivo binding to/occupancy of 5-HT2A receptors in the mouse frontal cortex (19% RO).

TABLE 9

| Treatment | N | Mean SB | SEM | % of Control Binding | % Receptor Occupancy (RO) | p value |
|---|---|---|---|---|---|---|
| Vehicle | 5 | 1390 | 28 | 100 | 0 | |
| Psilocybin, 3 mg/kg | 5 | 1128 | 45 | 81 | 19 | 0.003** |
| Compound 2-2, 1 mg/kg | 5 | 1104 | 23 | 79 | 21 | 0.001** |
| Compound 2-2, 3 mg/kg | 5 | 880 | 68 | 63 | 37 | <0.001*** |
| Compound 2-2, 10 mg/kg | 5 | 562 | 44 | 40 | 60 | <0.001*** |

Data was square-root transformed and analysed by one-way ANOVA followed by the multiple t test to compare Psilocybin to vehicle and Williams' test to compare EGX-121 to vehicle.
**p < 0.01,
***p < 0.001.

TABLE 10

| Treatment | N | Terminal Plasma Conc (ng/mL) at 15 min | | | Terminal Brain Conc (ng/g) at 15 min | | |
|---|---|---|---|---|---|---|---|
| | | Mean | SD | SEM | Mean | SD | SEM |
| Psilocybin, 3 mg/kg | 5 | 869 | 49.2 | 22.0 | 521 | 87.3 | 39.0 |
| Compound 2-2, 1 mg/kg | 5 | 60.1 | 14.9 | 6.67 | 182 | 17.5 | 7.84 |
| Compound 2-2, 3 mg/kg | 5 | 305 | 98.7 | 44.2 | 734 | 339 | 152 |
| Compound 2-2, 10 mg/kg | 5 | 1025 | 348 | 156 | 3279 | 1599 | 715 |

15 minutes post IP dosing, Vehicle: 40% w/v HPBCD (Trappsol ®) in water, Psilocybin formulated in saline;
SB: Specific Binding, determined by Inhibition of 0.077 nM [$^3$H]Cimbi-36 (5-HT2A agonist) binding

TABLE 11

| Treatment | N | Terminal Plasma Total Concentration (uM) at 15 min | | | Terminal Brain Total Concentration (uM) at 15 min | | |
|---|---|---|---|---|---|---|---|
| | | Mean | SD | SEM | Mean | SD | SEM |
| Psilocybin, 3 mg/kg | 5 | 4.25 | 0.24 | 0.11 | 2.55 | 0.43 | 0.19 |
| Compound 2-2, 1 mg/kg | 5 | 0.20 | 0.05 | 0.02 | 0.60 | 0.06 | 0.03 |
| Compound 2-2, 3 mg/kg | 5 | 1.00 | 0.33 | 0.15 | 2.42 | 1.12 | 0.50 |
| Compound 2-2, 10 mg/kg | 5 | 3.38 | 1.15 | 0.51 | 10.81 | 5.27 | 2.36 |

TABLE 12

| Treatment | N | Terminal Plasma Free Concentration (uM) at 15 min | | | Terminal Brain Free Concentration (uM) at 15 min | | |
|---|---|---|---|---|---|---|---|
| | | Mean | SD | SEM | Mean | SD | SEM |
| Compound 2-2, 1 mg/kg | 5 | 0.016 | 0.004 | 0.002 | 0.010 | 0.001 | 0.0004 |
| Compound 2-2, 3 mg/kg | 5 | 0.082 | 0.027 | 0.012 | 0.039 | 0.018 | 0.008 |
| Compound 2-2, 10 mg/kg | 5 | 0.277 | 0.094 | 0.042 | 0.175 | 0.085 | 0.038 |

Example 14

Effect of Compound 2-2 and Psilocybin on 5-HT2A Receptor Binding in Post-Mortem Human and Mouse Frontal Cortical Tissue In vitro activity profiling was performed for compound 2-2 and psilocybin in post-mortem human frontal cortical and mouse frontal cortical tissue preparations. Results are shown in table 13 and FIGS. 44A, 44B, 45, and 46.

TABLE 13

|  | Mean (Mouse) | SEM (Mouse) | N | Mean (Human) | SEM (Human) | N |
|---|---|---|---|---|---|---|
| Psilocin |  |  |  |  |  |  |
| Ki (nM) | 45.05 | 1.02 | 5 | 60.03 | 3.06 | 3 |
| pKi | 7.34 | 0.010 |  | 7.22 | 0.023 |  |
| IC$_{50}$ (nM) | 99.00 | 1.02 |  | 142.46 | 5.87 |  |
| pIC$_{50}$ | 7.00 | 0.008 |  | 6.85 | 0.018 |  |
| Compound 2-2 |  |  |  |  |  |  |
| Ki (nM) | 9.60 | 1.24 | 3 | 30.79 | 1.02 | 3 |
| pKi | 8.02 | 0.092 |  | 7.51 | 0.008 |  |
| IC$_{50}$ (nM) | 20.84 | 1.23 |  | 68.97 | 1.04 |  |
| pIC$_{50}$ | 7.68 | 0.090 |  | 7.16 | 0.016 |  |

Compound 2-2 has greater binding potency at mouse and human 5-HT2A receptors than psilocin. Both compounds appear to have greater binding potency at 5-HT2A receptors in mouse frontal cortex tissue compared to human post-mortem frontal cortex tissue.

Example 15

Effect of Compound 2-2 and Psilocybin on 5-HT2A/2C/1A-Mediated Behaviors, Locomotor Activity (LMA), and Body Temperature Forty (40) male Sprague-Dawley rats were used as test subjects in this study. Animals were dosed with vehicle (IP), one of 3 doses of compound 2-2 (3 mg/kg, 10 mg/kg, 30 mg/kg IP) or psilocybin (1 mg/kg SC) and, following the appropriate pre-treatment time, were placed in locomotor activity boxes and continuously monitored for a 1 hr period with data collected into 10-minute time bins. Animals were visually assed for overt behavioral signs, including biomarkers for 5-HT2A receptor target engagement (i.e. wet dog shakes, back muscle contractions and stereotypic behaviors), 5-HT2C receptor activation (yawning, penile grooming), and 5-HT1A behaviors (forepaw treading, hindlimb abduction). Additional behavioral and somatic signs characteristic of 5-HT syndrome (i.e. tremor, salivation, flat body posture) also were measured. Core body temperature change was determined at 0 hr (pre-dose), 1 hr, and 2 hr. Simultaneously, the spontaneous locomotor activity of the rats was measured using automated Med Associates activity test chambers. Activity data collected included total distance travelled, rearing counts, and ambulatory episodes. LMA was measured for a total of 2 hours (i.e. the first hour to include visual assessments of behavioral signs, and the second hour the animals will not be assessed for behavioral signs) with data collected into 10 minute time bins. The tracking arena measured 17" W×17" L×12" H, sensor bars were secured 1" above the floor to track distance travelled, and a second set of sensor bars were placed ~5" above the floor to measure vertical movement and rearing activity. The parameters set on the tracking software were as follows: resolution −50 ms, box size −4 beams, resting delay −500 ms, and ambulatory trigger −3.

Table 14 outlines receptor activity and related behavioral and/or physiological measures.

TABLE 14

| Receptor activity | Related Measures |
|---|---|
| 5-HT2A agonism | Wet dog shakes (WDS) |
|  | Back muscle contractions (BMC) |
|  | Core body temperature - increase |
| 5-HT2C agonism | Penile grooming (PG) |
|  | Yawning |
| 5-HT1A agonism | Forepaw treading (FPT) |
|  | Hindlimb abduction (HLA) |
|  | Flat body posture |
|  | Core body temperature - decrease |
| Excess 5-HT agonism | Tremor |
| (5-HT syndrome) | Salivation |
|  | Flat body posture |
| Mixed/non-selective | Locomotor activity |

Figure 47A:
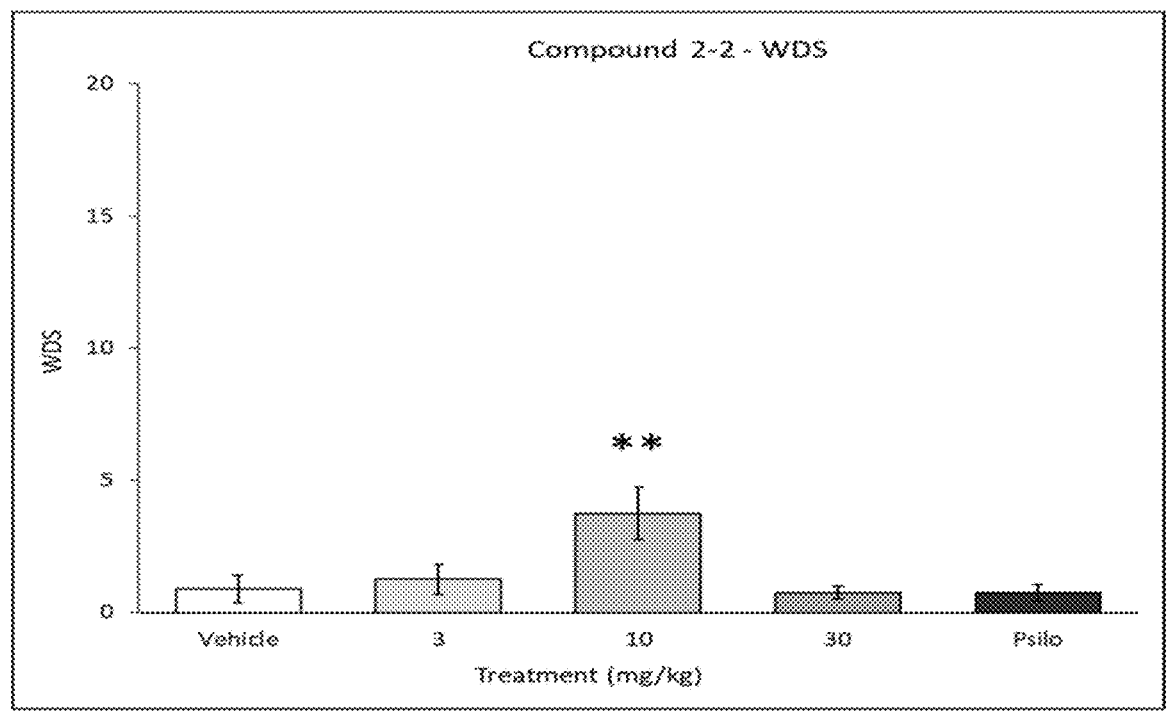
FIG. 47A is a graph showing the effects of compound 2-2 on WDS.
Figure 47B:
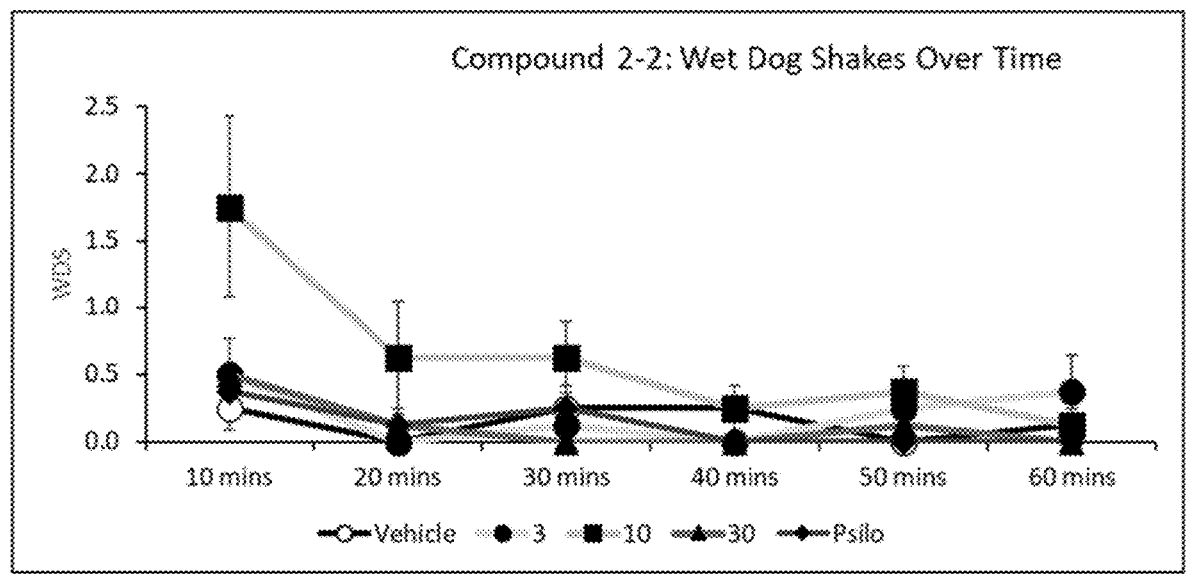
FIG. 47B is a graph showing the effects of compound 2-2 on WDS over time.
Figure 48A:
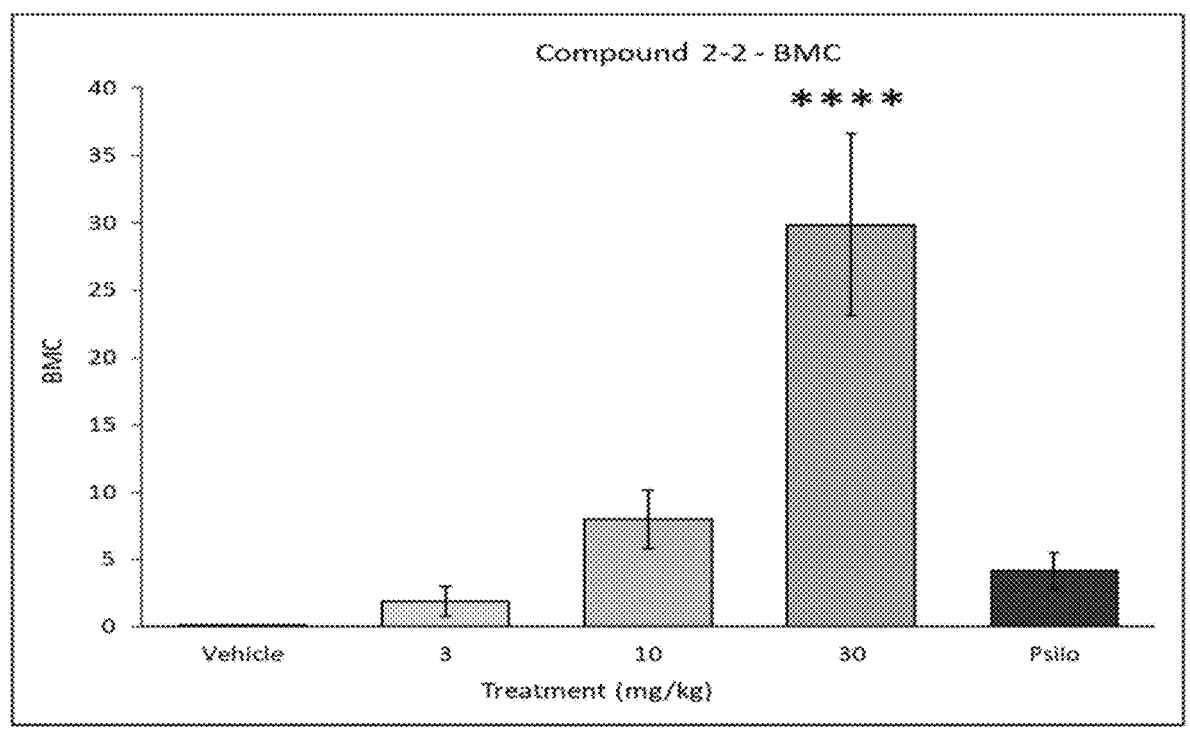
FIG. 48A is a graph showing the effects of compound 2-2 on BMC.
Figure 48B:
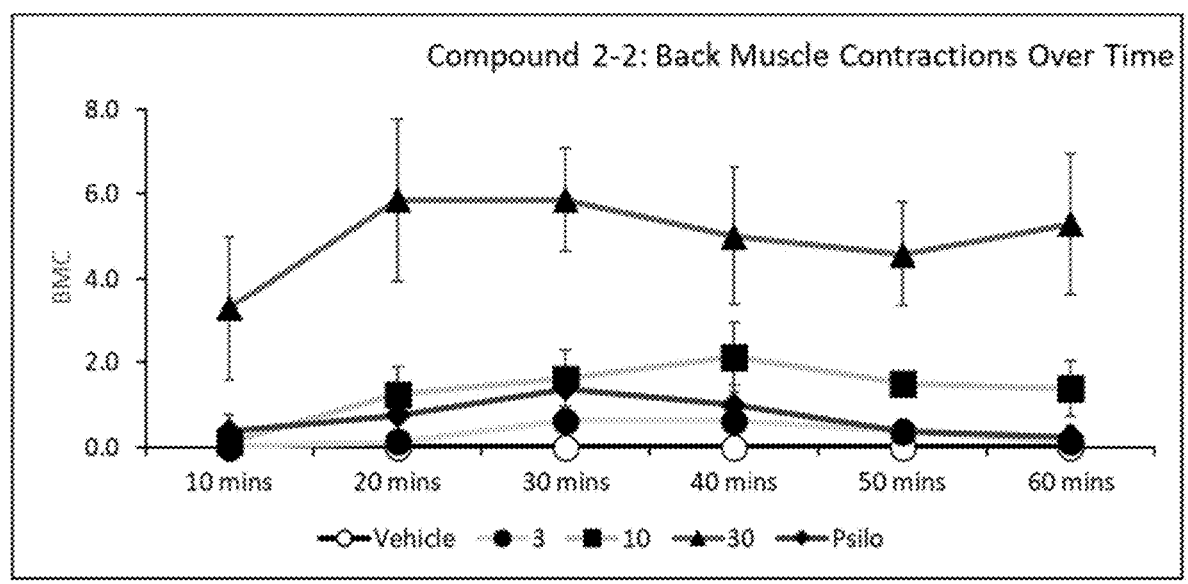
FIG. 48B is a graph showing the effects of compound 2-2 on BMC over time.
Figure 49:
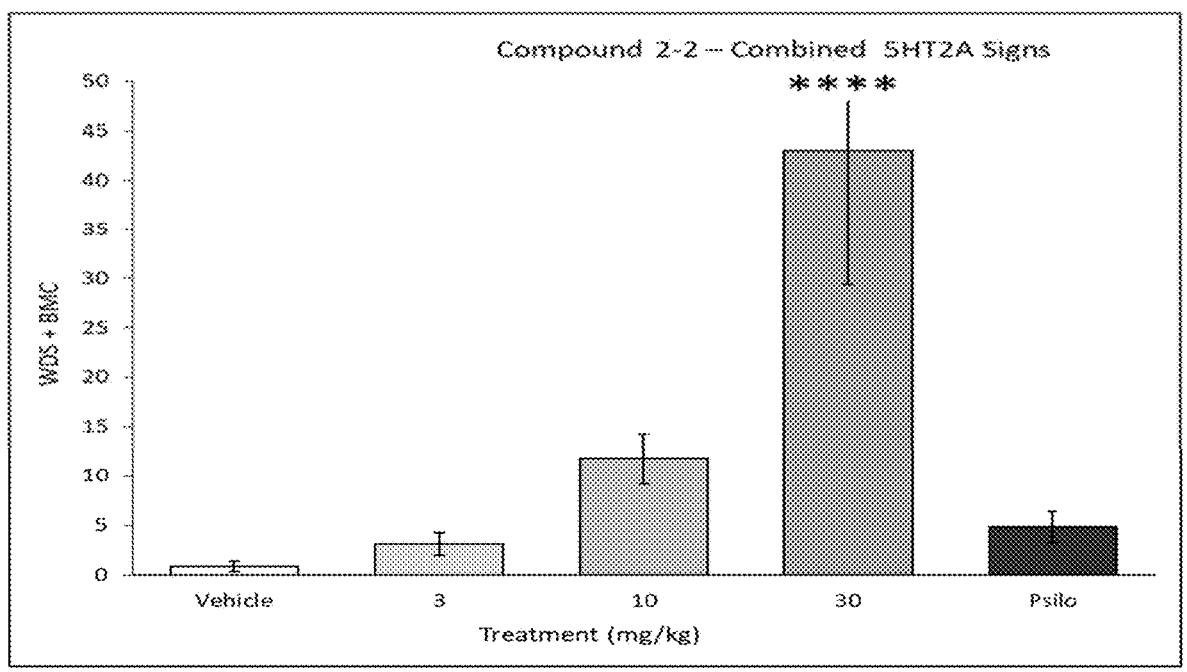
FIG. 49 is a graph showing the combined effects of compound 2-2 on 5-HT2A signs as compared to the psilocybin reference.

Compound 2-2 exhibited robust 5-HT2A-mediated effects in rats. Compound 2-2 exhibited significant dose-related increases in WDS (FIGS. 47A and 47B) and BMC (FIGS. 48A and 48B), which are 5-HT2A agonism-mediated effects. Compound 2-2 5-HT2A agonist effects were more pronounced than the psilocybin reference (1 mg/kg SC, FIG. 49).

Figure 50A:
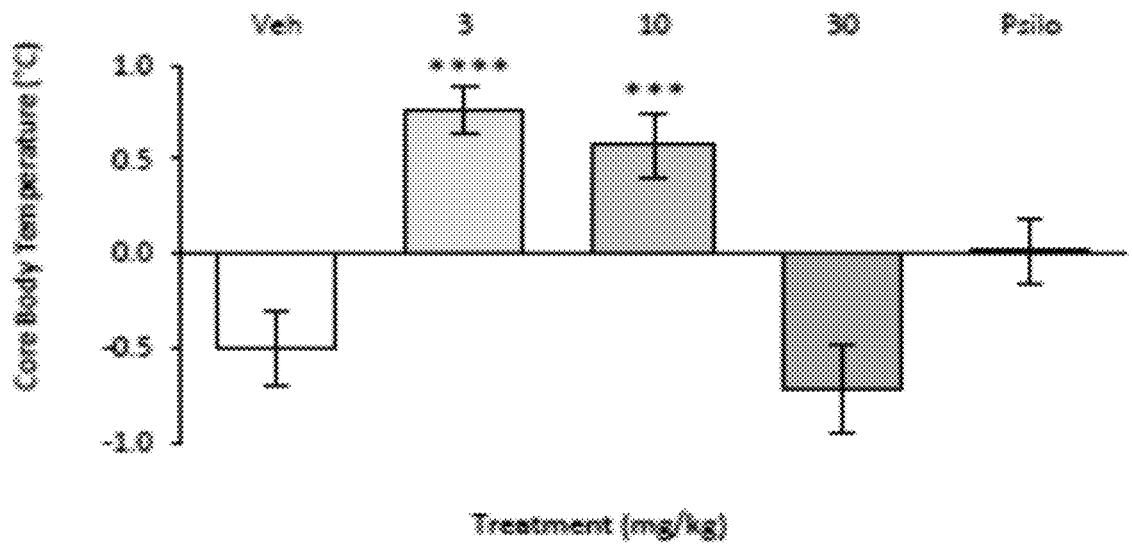
FIG. 50A is a graph showing the effects of compound 2-2 on body temperature at 1 hour.
Figure 50B:
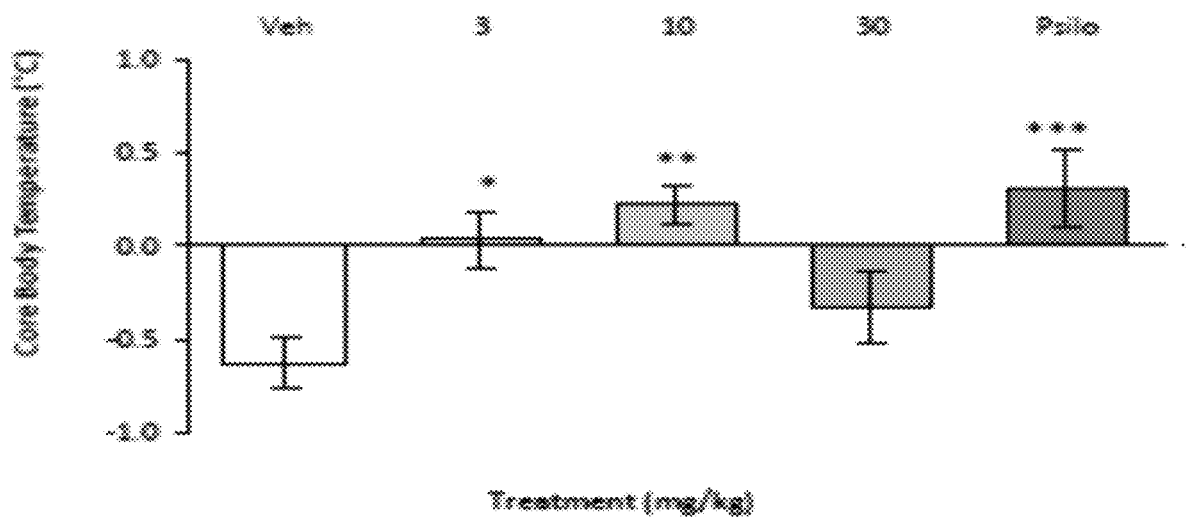
FIG. 50B is a graph showing the effects of compound 2-2 on body temperature at 2 hour.

Compound 2-2 exhibited significant increases in core body temperature, which is a 5-HT2A agonism-mediated effect. Body temperature increases were more pronounced after the $1^{st}$ hour than the $2^{nd}$ hour post dosing. Body temperature effects were larger in magnitude than the psilocybin reference (1 mg/kg SC) over the 2h assessment period. See FIGS. 50A and 50B.

Figure 51:
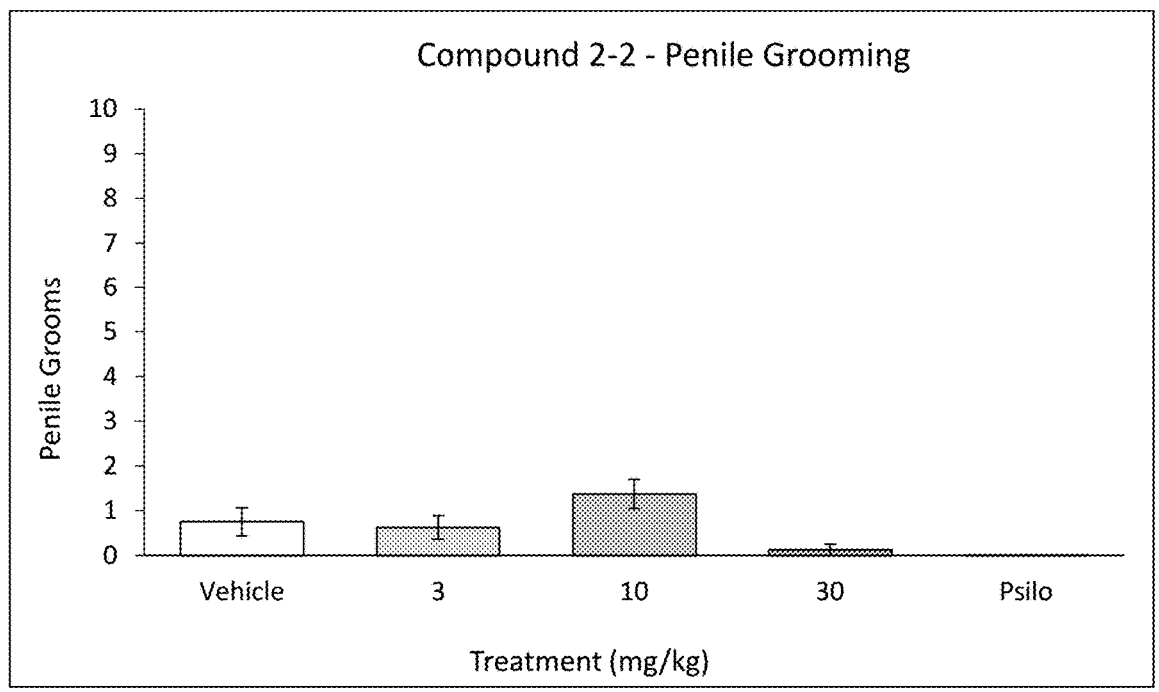
FIG. 51 is a graph showing the effects of compound 2-2 on penile grooming.
Figure 52:
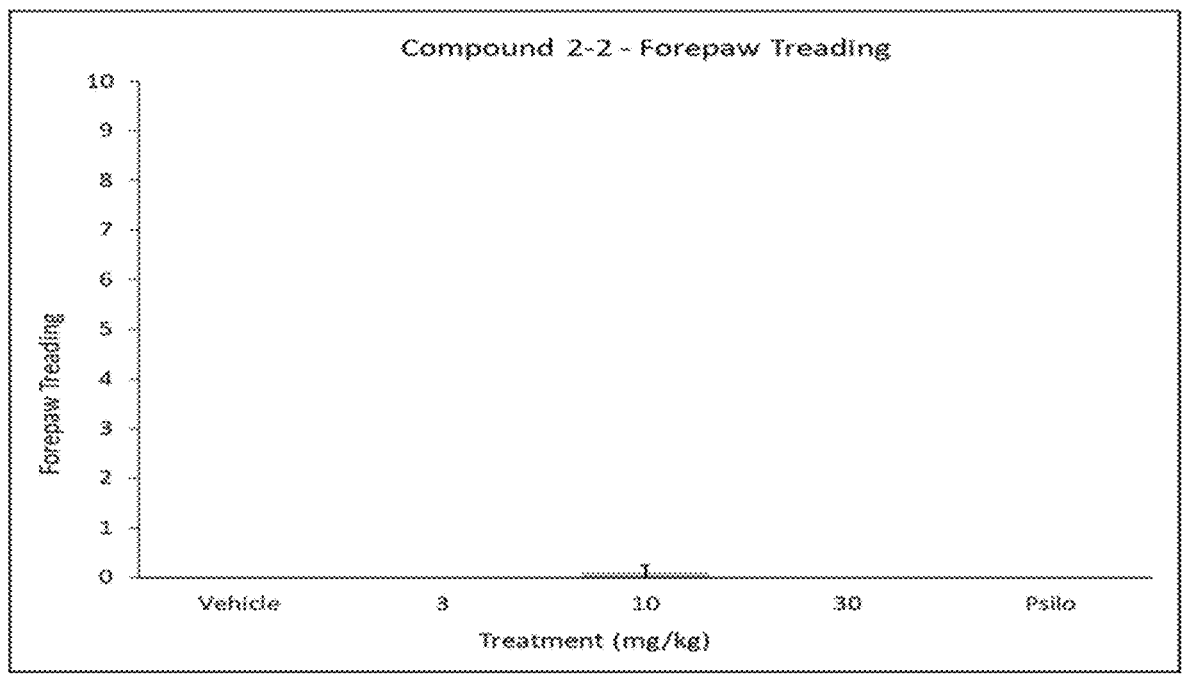
FIG. 52 is a graph showing the effects of compound 2-2 on forepaw treading.
Figure 53:
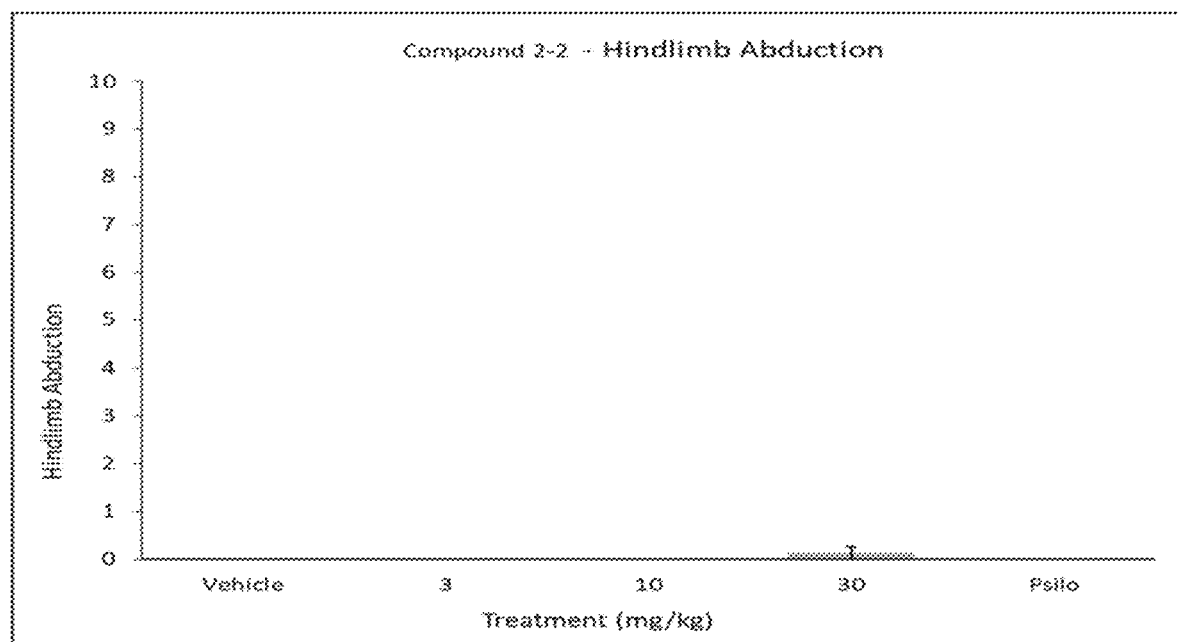
FIG. 53 is a graph showing the effects of compound 2-2 on hindlimb abduction.
Figure 54:
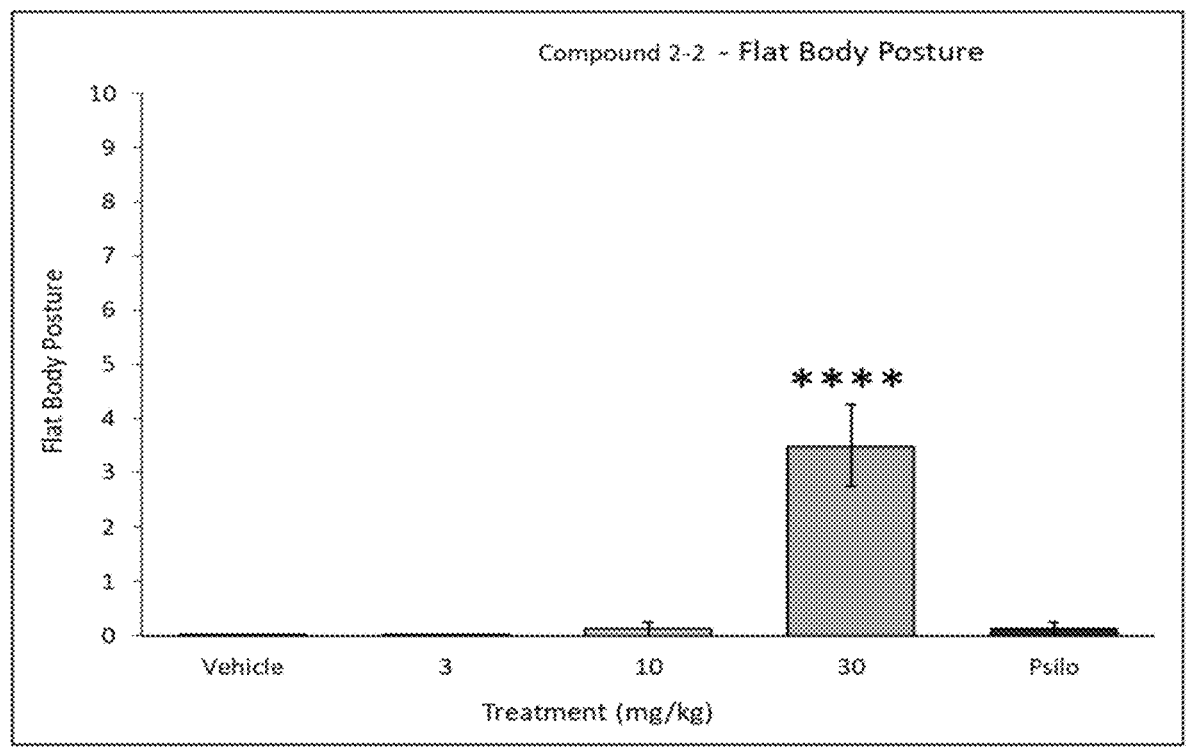
FIG. 54 is a graph showing the effects of compound 2-2 on flat body posture.
Figure 55:
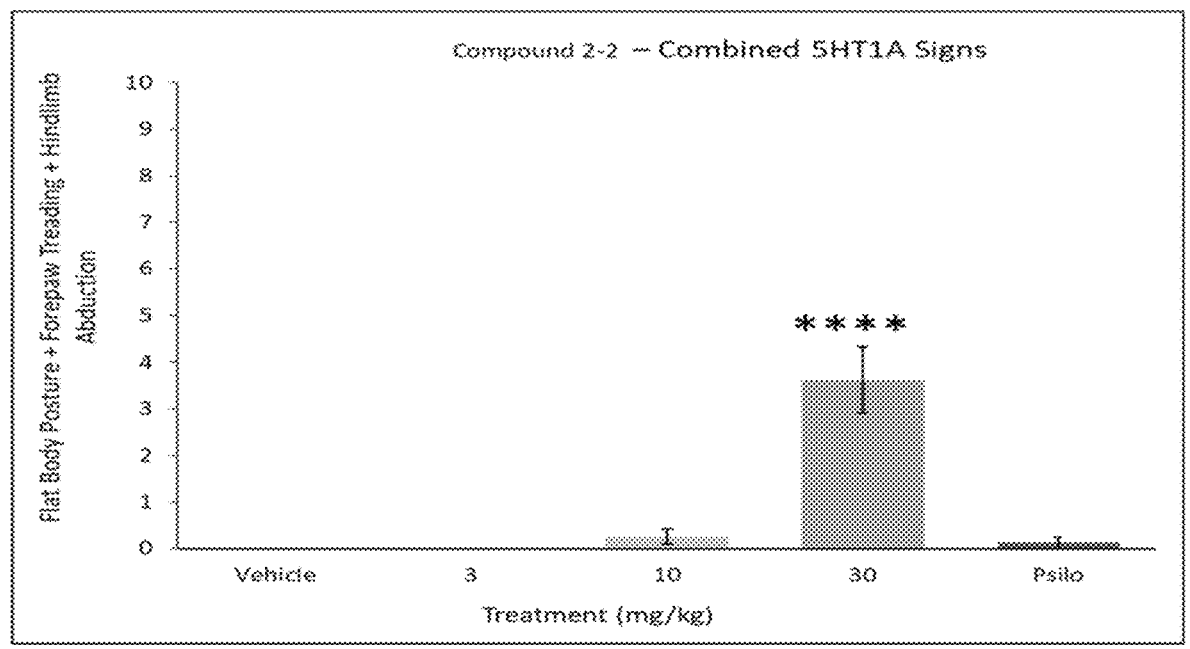
FIG. 55 is a graph showing the combined effects of compound 2-2 on 5-HT1A signs as compared to the psilocybin reference.

Compound 2-2 did not exhibit 5-HT2C-mediated effects in rats. 5-HT2C agonist effects of compound 2-2 may be masked by predominating 5-HT2A agonist effects. See FIG. 51.

Compound 2-2 may exhibit limited 5-HT1A-mediated effects in rats. Compound 2-2 induced flat body posture at the highest dose tested, which may be 5-HT1A agonist-related. This effect distinguished compound 2-2 from the psilocybin reference (1 mg/kg SC). See FIGS. 52-55. As body temperature decreases at 30 mg/kg compound 2-2 were similar to the vehicle responses, this effect cannot be concluded to be indicative of 5-HT1A agonist-mediated activity. See FIGS. 50A and 50B.

Compound 2-2 exhibited limited signs of excess 5-HT agonism in rats. Compound 2-2 induced flat body posture at the highest dose tested. This effect distinguished compound 2-2 from the psilocybin reference (1 mg/kg SC). No other signs of excess 5-HT agonism were observed during the study. See FIG. 54.

Figure 56A:
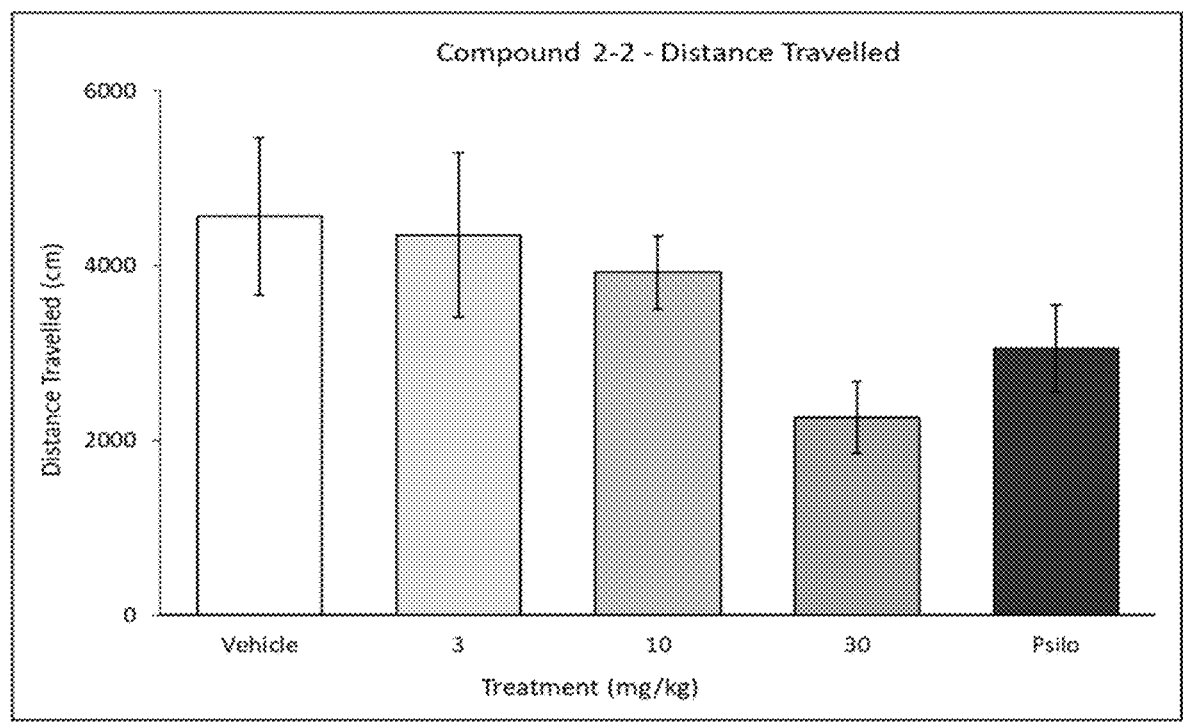
FIG. 56A is a graph showing the effects of compound 2-2 on distance travelled.
Figure 56B:
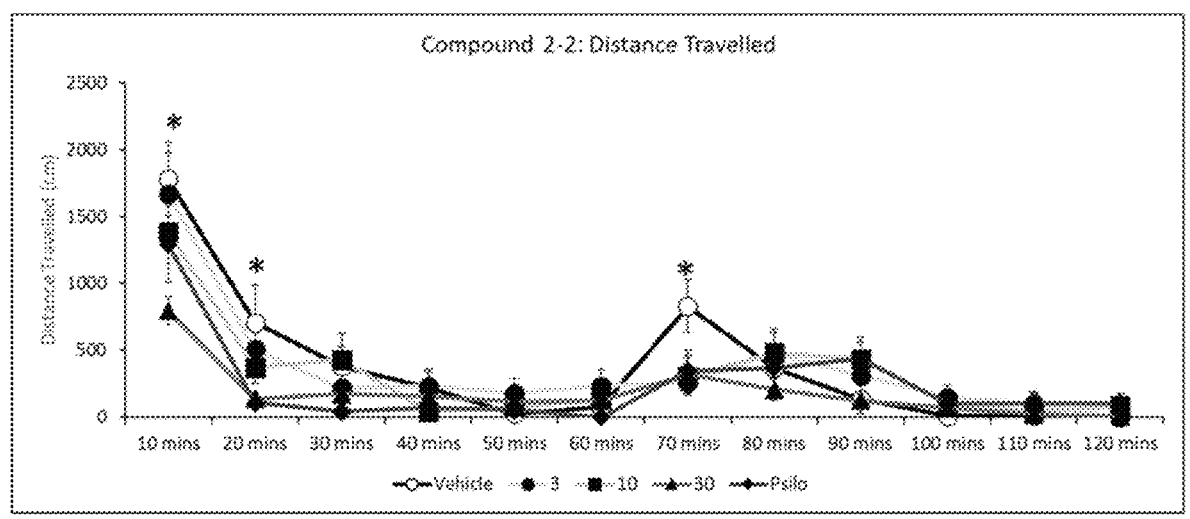
FIG. 56B is a graph showing the effects of compound 2-2 on distance travelled over time.
Figure 57:
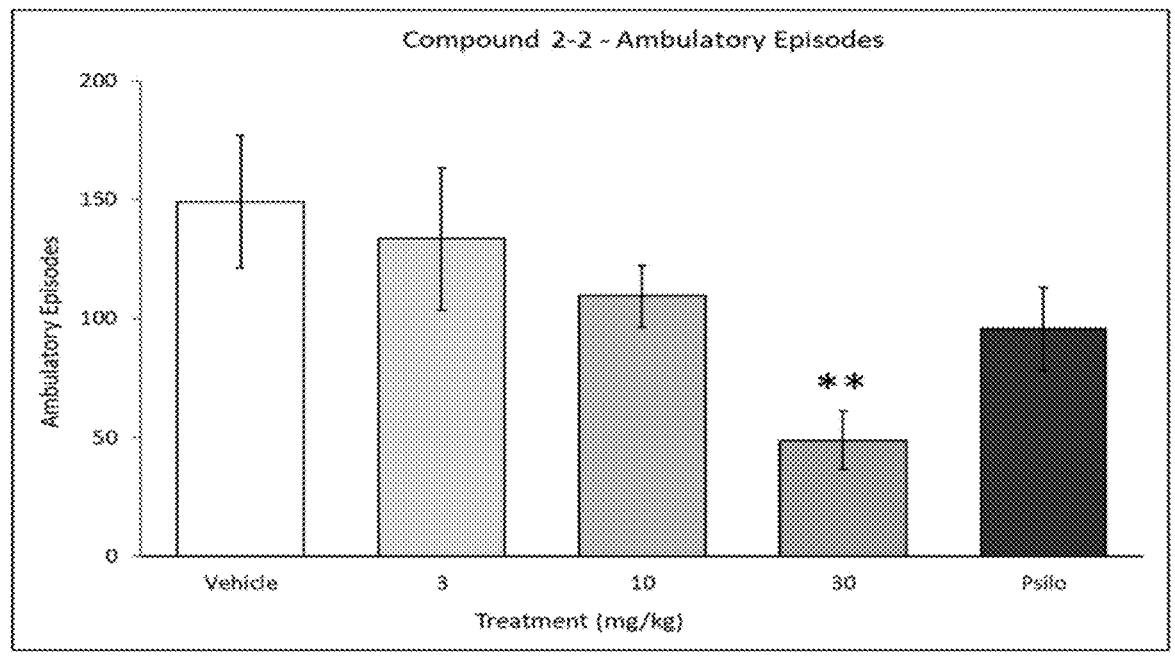
FIG. 57 is a graph showing the effects of compound 2-2 on ambulatory episodes.
Figure 58:
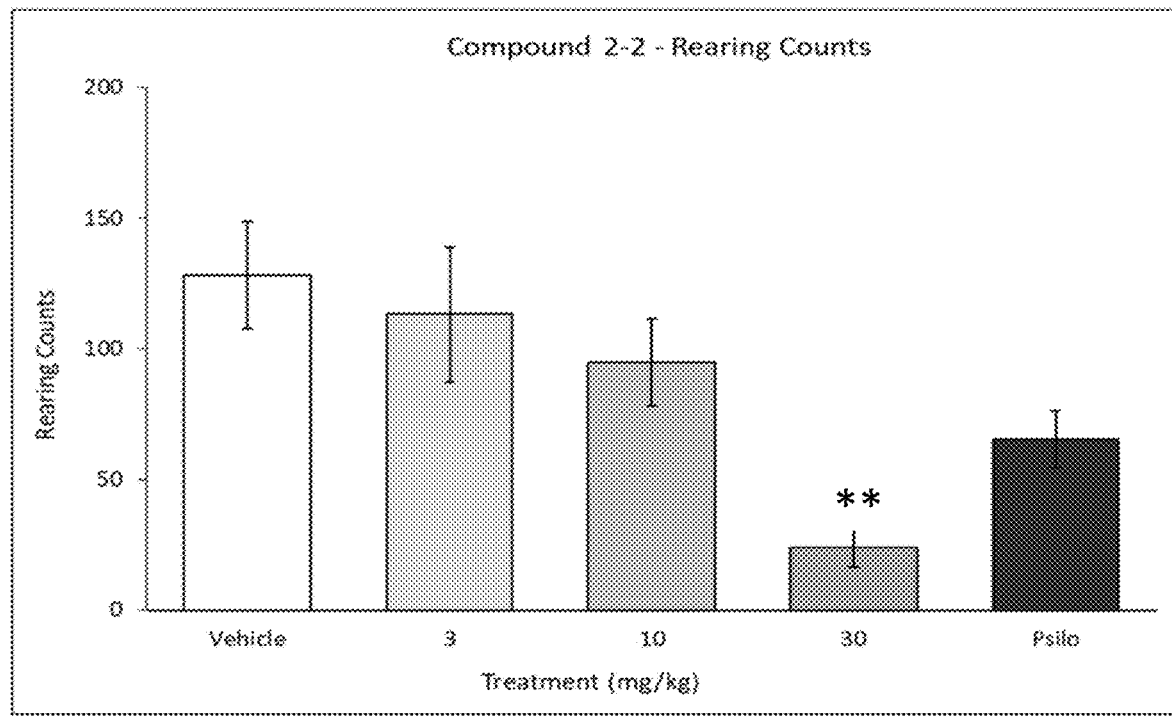
FIG. 58 is a graph showing the effects of compound 2-2 on rearing counts.

Compound 2-2 significantly reduced some measures of locomotor activity in rats. Although compound 2-2 did not affect total distance travelled, the highest dose tested (30 mg/kg IP) decreased distance travelled during the first 20 minutes of the 2 hour test. Compound 2-2 (30 mg/kg IP) also decreased total ambulatory episodes and total rearing counts. The psilocybin reference (1 mg/kg SC) decreased distance travelled during the first 20 minutes of the 2 hour test, but it did not affect any of the total locomotor activity measures. See FIGS. 56A, 56B, 57, and -58.

Vehicle and Psilocybin control responses were as expected for all of the measures. Compound 2-2 exhibited significant 5-HT2A- and possibly 5-HT1A-activation-related signs. Compound 2-2 did not exhibit significant 5-HT2C-activation-related signs. Table 15 summarized the results of the study.

TABLE 15

| Receptor activity | Related Measures | Compound 2-2 Effect |
|---|---|---|
| 5-HT2A agonism | Wet dog shakes (WDS) | Significant Increase (10 mg/kg IP) |
| | Back muscle contractions (BMC) | Significant Increase (30 mg/kg IP) |
| | Core body temperature (increase) | Significant Increase (3, 10 mg/kg IP) |
| 5-HT2C agonism | Penile grooming (PG) | No effect |
| | Yawning | No effect |
| 5-HT1A agonism | Forepaw treading (FPT) | No effect |
| | Hindlimb abduction (HLA) | No effect |
| | Flat body posture | Significant Increase (30 mg/kg IP) |
| | Core body temperature (decrease) | No effect (decrease similar to vehicle) |
| Excess | Tremor | No effect |
| 5-HT agonism | Salivation | No effect |
| (5-HT syndrome) | Flat body posture | Significant Increase (30 mg/kg IP) |
| Mixed/non-selective | Locomotor activity | Significant decrease (30 mg/kg IP) |

Example 16

The Effect of Compound 2-2 in Rats Trained to Discriminate Psilocybin in an Operant Drug Discrimination Task Thirty-six (36) male Sprague Dawley rats served as subjects. Rats had been trained to lever press for food in standard operant conditioning chambers controlled by Med-PC software (Med. Associates Inc., St. Albans, VT) followed by training to associate the right lever to a psilocybin stimulus (0.5 mg/kg, SC), and the left lever to a neutral stimulus (saline, SC). The sequence of psilocybin and saline injections were administered under a randomized design where neither condition was administered for more than 3 consecutive days. All training sessions were complete after 30 min or 50 pellets were delivered under an FR10 schedule, i.e., every 10th response on the designated lever resulted in delivery of a food pellet. Any incorrect lever response did not reset the number of responses on correct lever to zero. The rats continued to receive a daily food ration (~18 g at day end) with ad libitum access to water in their home cages.

On test days, both levers were designated active, i.e., every 10th response on either lever resulted in delivery of a food pellet. Test sessions continued until 50 pellets had been obtained or 30 min had elapsed. During these sessions, response rate was also measured. Three types of tests were conducted:

1. Dose-response profile for compound 2-2 to generalize to the psilocybin cue. On test days, rats received a single compound 2-2 dose (1, 3, or 10 mg/kg, IP) 10 min prior to test. The distribution of vehicle vs. drug-paired lever presses was recorded as well as the rate of lever response.
2. Effect of the 5-HT subtype selective antagonists, M100907 (5-HT2A receptor selective; Kehne et al, 1996) and SB242084 (5-HT2C receptor selective, Kennett et al, 1997) against the generalization of compound 2-2. On test days, the rats received a single dose (0.5 mg/kg IP) of either antagonist 30 min before compound 2-2 (10 mg/kg, IP), which was administered 10 min prior to testing. The distribution of vehicle vs. drug-paired lever presses was recorded as well as the rate of lever response.
3. Time-course profile for compound 2-2 (10 mg/kg IP) to generalize to the psilocybin cue. On test days, the rats received a single compound 2-2 dose (10 mg/kg, IP) at various pretreatment times (i.e., 10 min, 30 min, 1 h, 2 h, 4 h, 8 h) prior to test. The distribution of vehicle vs. drug-paired lever presses was recorded as well as the rate of lever response.

These studies were conducted in the same pool of psilocybin-trained rats, i.e., rats were tested on multiple occasions based on demonstrating appropriate stimulus control (defined as six consecutive sessions where animals made no more than 16 lever presses before the delivery of the first reward, and at least 95% total responses on the appropriate lever). Drug testing was conducted on a Tuesday and Friday with the animals run on either vehicle or training drug (psilocybin 0.5 mg/kg, SC) on intervening weekdays. Group sizes varied among doses and pretreatment times and tended to be higher under situations where the choice response was more variable. This adjustment was made in an attempt to get as reliable a measure of drug vs. vehicle discrimination as possible at that specific dose or pretreatment time.

Results:

Compound 2-2 substitution test: Compound 2-2 evoked full generalization to the psilocybin cue over the dose range 1-10 mg/kg IP. At the highest dose tested (10 mg/kg), compound 2-2 evoked 91+8% generalization to the psilocybin cue. Across this dose range, there were minor effects on response rate, a slight increase over vehicle at the 3 mg/kg dose, transitioning to a slight decrease at 10 mg/kg. It is important to note that the decrease in rate was not accompanied by any obvious motor impairment per se, rather the animals were behaviorally quiet.

Figure 59:
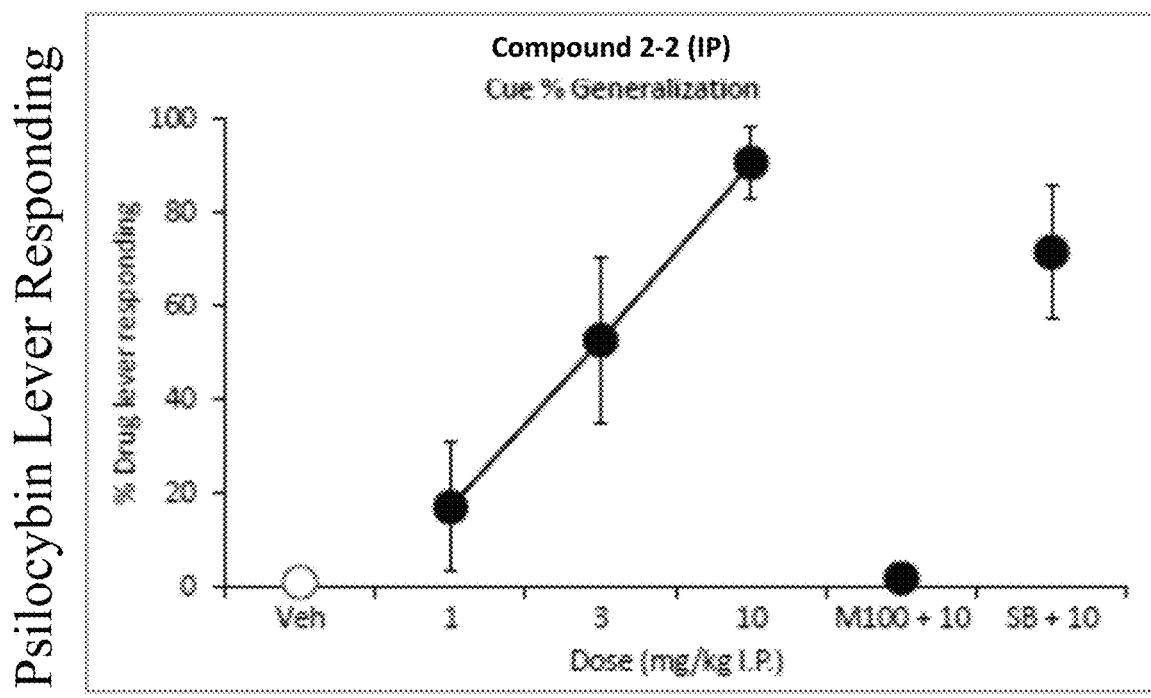
FIG. 59 is a graph showing the effects of compound 2-2 on cue generalization (%), alone or in combination with M100907 or SB-242084.
Figure 60:
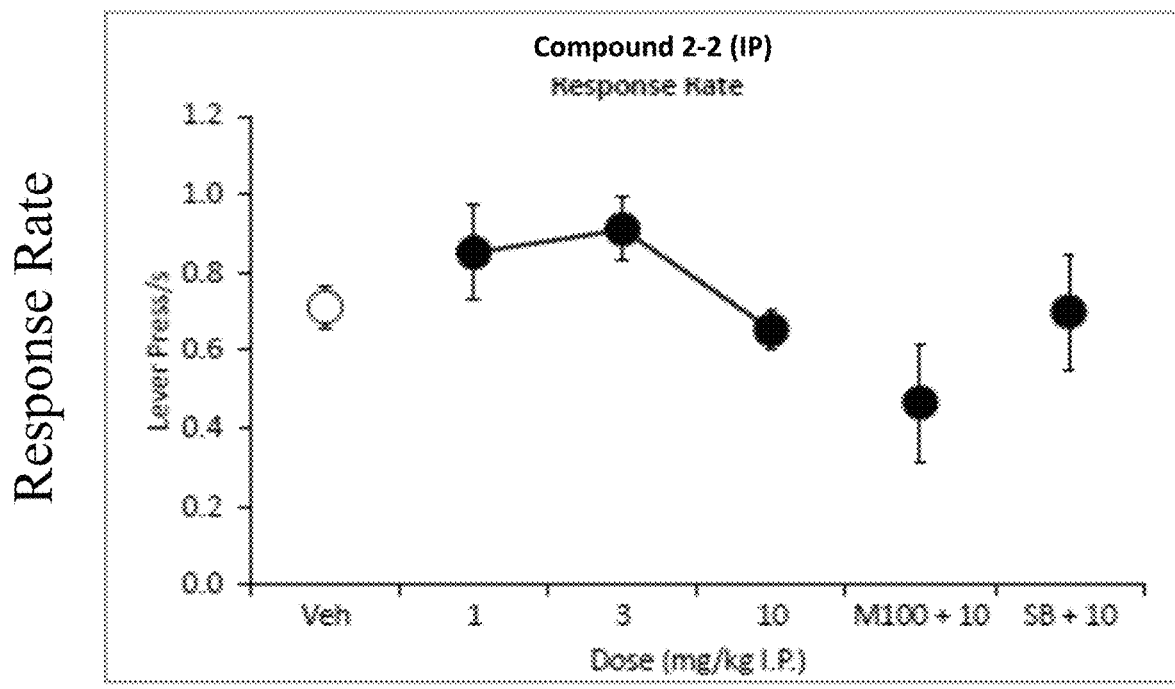
FIG. 60 is a graph showing the effects of compound 2-2 on response rate, alone or in combination with M100907 or SB-242084.

Compound 2-2 antagonist test: The effect of single doses of the selective 5-HT2A receptor antagonist, M100907, and the selective 5-HT2C receptor antagonist, SB242084, to influence the generalization produced by compound 2-2 (10 mg/kg) was examined. M100907 (0.5 mg/kg) completely blocked the generalization (i.e., Veh+Compound 2-2: 91+8% generalization; M100+Compound 2-2: 2+1% generalization; P<0.01), which is consistent with a dominant 5-HT2A receptor mediation of the psilocybin cue and compound 2-2 generalization. These data support a direct agonist property of compound 2-2 at the 5-HT2A receptor. In contrast, the selective 5-HT2C receptor antagonist SB242084 produced only a minor attenuation of compound 2-2 generalization (Veh+Compound 2-2: 91+8%; SB+Compound 2-2: 71+14%; NS). The magnitude of this effect, relative to the marked effect of M100907, would suggest a negligible effect of any 5-HT2C receptor agonist effect of compound 2-2 as contributing to generalization. Following antagonist pretreatment, there was no significant effect on response rate. See FIGS. 59 and 60.

Figure 61:
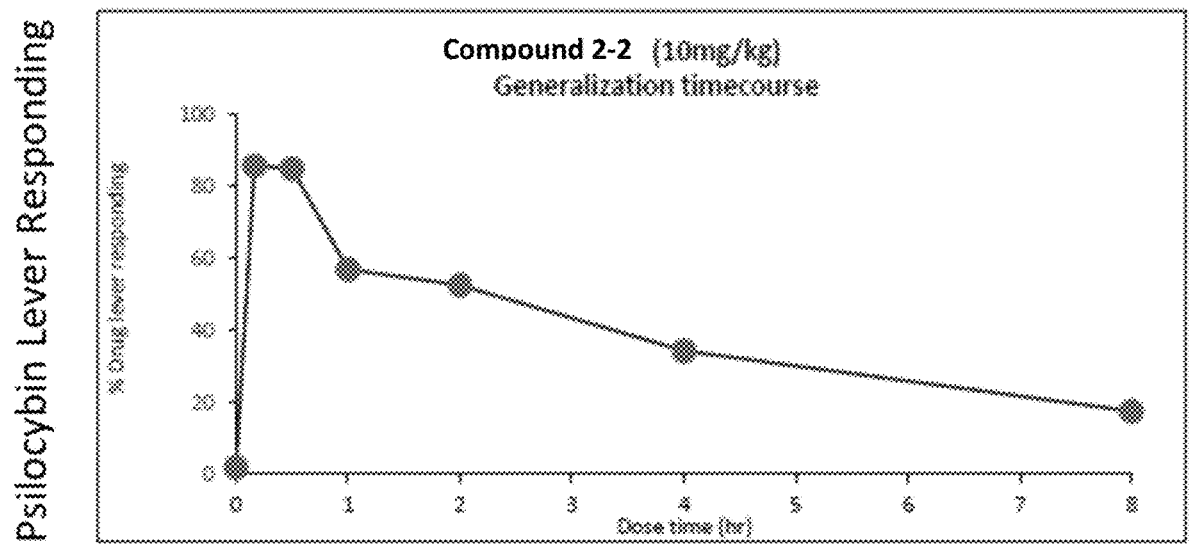
FIG. 61 is a graph showing the effects of compound 2-2 on the generalization time course.
Figure 62:
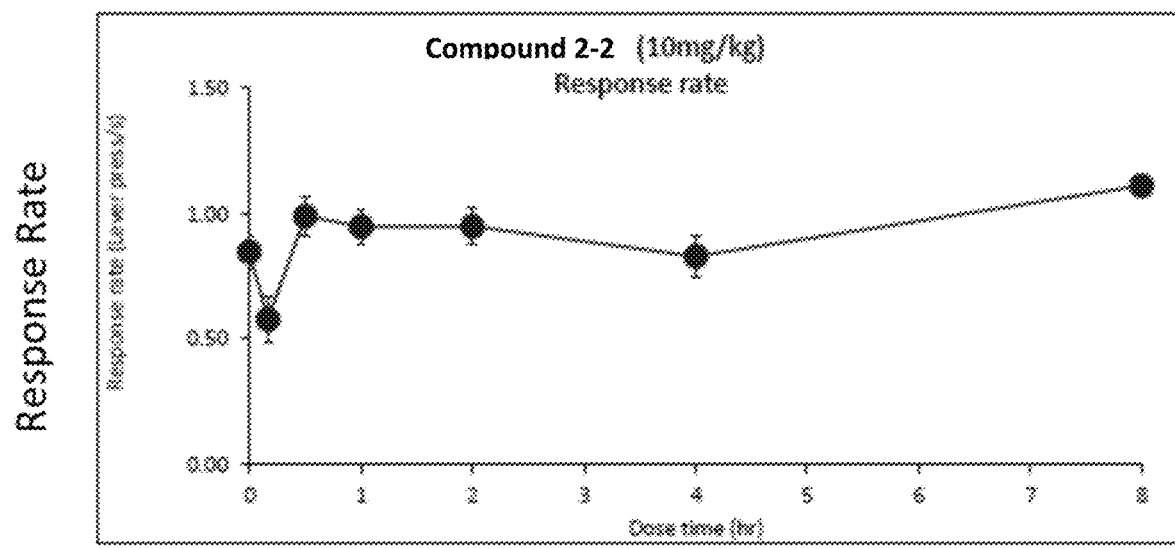
FIG. 62 is a graph showing the effects of compound 2-2 on response rate over time.

Compound 2-2 time course: Robust (~80%) generalization following compound 2-2 (10 mg/kg, IP) pretreatment times of 10 and 30 min was noted. At longer pretreatment times (1-4 h) there was a gradual decline in compound 2-2 generalization, such that at 4 h generalization was in the range of 35%. Sample size was increased at these longer timepoints for the purpose of trying to define this descending phase. Across these pretreatment times, there was a minor effect on response rate, with a slight increase over vehicle at the 8 h time point. See FIGS. 61 and 62.

Compound 2-2 (IP) fully substituted for a psilocybin (0.5 mg/kg SC) discriminative stimulus in a dose-dependent manner, suggesting psilocybin-like subjective effects. Compound 2-2 (10 mg/kg IP) fully substituted for psilocybin in a 5-HT2AR agonist-dependent manner (effect completely blocked by 5-HT2AR antagonist, 0.5 mg/kg M100907 IP) with a modest role for 5-HT2CR agonism (effect modestly attenuated by 5-HT2CR antagonist, 0.5 mg/kg SB-242084 IP). See FIGS. 59 and 60.

Compound 2-2 (10 mg/kg IP) fully substituted for psilocybin for 30 min post dose, suggesting full psilocybin-like subjective effects were time-limited, and partially substituted from 1-4 h post dose, with no substitution by 8 h post dose. Compound 2-2 modestly suppressed rate of responding only at 10 min post dose. See FIGS. 61 and 62.

Example 17

Synaptogenesis Assay in Primary Cortical Rat Neurons

The aim of the study was to assess synaptogenesis in primary cortical neurons upon treatment with Compound 2-2 and the reference item fibroblast growth factor (FGF).

Pregnant rats for this study were purchased from a commercial breeder. Primary cortical neurons from E17/E18 rat pups were isolated and seeded in 96-well plates. Cells were treated with compound 2-2, FGF (Reference item) or vehicle. After incubation with the respective treatment, cortical neurons were stained for synapsin and tubulin using immunofluorescence.

Stained cells were imaged with the Cytation 5 Multimode reader. From each well, 9 images were taken at 10× magnification. Digital images from cortical neurons were analyzed for the following parameter using a software-supported automatic quantification method: Number of synapsin positive objects. Analysis was performed using Gen5 software. The experiment was run in n=10 technical replicates per condition. Vehicle control and FGF were included on each plate totaling n=20 technical replicates.

The overall setup of the experiment is detailed in table 16.

TABLE 16

| Experimental Day | Days in vitro | Description |
| --- | --- | --- |
| Day1 | DIV1 | Preparation and seeding of cells 1.5 × 104 cells/well in 96-well plates Treatment with compound 2-2/FGF or vehicle |
| Day5 | DIV5 | Half medium change Re-treatment with Compound 2-2 (0.1 mM/0.5 mM/1 mM)/FGF/ Vehicle |
| Day10 | DIV10 | Fixation and Immunocytochemistry start |

Primary cortical neurons were prepared from timed pregnant Spargue Dawley rats at E17/E18. Animals were sacrificed (see section 3.3.1) and embryos were dissected in Calcium and Magnesium free Hanks Balanced Salt Solution (CMF-HBSS) containing 15 mM HEPES and 10 mM NaHCO3, pH 7.2. Embryos were decapitated, skin and skull gently removed and hemispheres were separated. After removing meninges and brain stem, the cortices were isolated, chopped with a sterile razor blade in Chop solution (Hibernate-E without Calcium containing 2% B-27) and digested in 2 mg/mL papain (Worthington) dissolved in Hibernate-E without Calcium for 30 minutes (±5 min) at 30° C. The cortices of the embryos from the two rats were pooled and processed together.

Cortices were triturated for 10-15 times with a fire-polished silanized Pasteur pipette in Hibernate-E without Calcium containing 2% B-27, 0.01% DNaseI, 1 mg/mL BSA, and 1 mg/mL Ovomucoid Inhibitor. Undispersed pieces were allowed to settle by gravity for 3 min and the supernatant was centrifuged for 3 min at 228 g. The pellet was resuspended in Hibernate-E containing 2% B-27, 0.01% DNaseI, 1 mg/ml BSA, 1 mg/mL Ovomucoid Inhibitor and diluted with Hibernate-E containing 2% B-27. After the second centrifugation step (3 min at 228 g), the pellet was resuspended in nutrition medium (Neurobasal, 2% B-27, 0.5 mM glutamine, 1% Penicillin-Streptomycin).

Cells were counted in a hemacytometer and seeded in nutrition medium on poly-D-lysine pre-coated 96-well plates at a density of 1.5×104 cells/well. Cells were cultured at 37° C.; 95% humidity and 5% CO2. All wells were handled the same way. The experiment was performed in n=10 technical replicates for all groups.

On the day of preparation (DIV1), rat cortical neurons were seeded on poly-D-lysine pre-coated 96-well plates at a density of 1.5×104 cells per well.

Immediately on DIV1, cells were treated with compound 2-2 at 3 concentrations (0.1 μM/0.5 μM/1 μM) and 40 ng/mL of the FGF or vehicle control (VC). On DIV5, a half medium change was carried out and cells were re-treated with the compound 2-2 at 3 concentrations (0.1 μM/0.5p M/1 μM), the FGF or vehicle for further until DIV10.

The experiment was carried out with n=10 technical replicates per condition. In each plate n=5 technical replicates per VC and FGF were added. Vehicle treated cells served as control.

Treated primary neurons were fixed on DIV10 by addition of equal volume 4% paraformaldehyde (PFA) to the medium at room temperature (RT) for 30 minutes. Fixed cells were stored in PBS at 4° C. until further use for immunocytochemistry (ICC).

Cells were rinsed two times with PBS and were permeabilized with 0.1% Triton X-100 in PBS for 30 minutes at RT. Next, cells were blocked for 90 min at RT with 20% horse serum, 0.1% Triton X-100 in PBS.

Then, samples were incubated with the primary antibody (Table 17) against Beta Tubulin Isotype III (neuron specific marker) and Synapsin (synaptic marker) at 4° C. overnight (for at least 16 h).

TABLE 17

| Antibody | QPS ID | target | Host | Dilution |
| --- | --- | --- | --- | --- |
| Primary | 63 | tubulin III | mouse | 1:1000 |
|  | 380 | Synapsin I | rabbit | 1:450 |
| Secondary | 598 | Anti-mouse | donkey | 1:750 |
|  | 385 | Texas Red Anti-Rabbit Alex Fluor555 | donkey | 1:500 |

Next day, cells were further incubated for another 2 h at RT. After three washing steps with PBS, cells were incubated with a fluorescently labelled secondary antibody (Table 17) and DAPI (nucleus marker to determine the presence of cells) for 1.5 hours at RT in the darkness. Cells were again rinsed four times with PBS and imaged with the Cytation 5 Multimode reader. From each well, 9 images were taken at 10× magnification.

Digital images from cortical neurons were analyzed for number of synapsin positive objects using the Gen5 software.

Basic statistical analysis was performed using GraphPad Prism version 10. The presence of outliers was tested using ROUT (Q=1%) method (This method is based on the False Discovery Rate (FDR), Q being the maximum desired false discovery rate. A value of Q equal to 1% means that no more than 1% of the identified outliers are false and that at least 99% are real outliers). Data was tested for normal distribution using Kolmogorov-Smirnov test. One-way ANOVA followed by Dunnett's multiple comparison test (post hoc test) was used to analyze group differences for normally distributed data. If data were not normally distributed, either Kruskal-Wallis Test followed by Dunn's Multiple Comparison Test and/or Mann-Whitney test were chosen. Unpaired Student's t-tests were used to compare 40 ng/mL R.I. to vehicle control conditions. Data collected included total number of synapsin positive objects and total tubulin III area. Data were displayed as total number of synapsin positive objects (absolute value) normalized to total tubulin III area and presented as bar graphs with aligned dot blots as mean+SEM (n=10 or n=20 per group). *p<0.05; p<0.01; *p<0.001.

This study was performed to assess synaptogenesis in primary cortical neurons upon treatment with 4 different compounds as well as FGF as reference item.

Therefore, primary cortical neurons were prepared and seeded in 96-well plates. Afterwards, cells were treated with compound 2-2 at 3 concentrations (0.1p M/0.5 µM/1 µM), FGF (R.I.) or vehicle. On DIV5, a half medium change was carried out and cells were re-treated with the 4 compounds, the R.I. or vehicle for further until DIV10.

On DIV10 cells were fixed and subject to indirect immunofluorescence analysis. Experiment was designed with 10 replicates of Compound 2-2 or N,N-DMT. condition. In each plate 5 replicates of VC and R.I. were included resulting in a total of 20 replicates of each control. When data was normalized an outlier from vehicle (VC) group was identified and was therefore excluded from the statistical analysis.

Figure 63A:
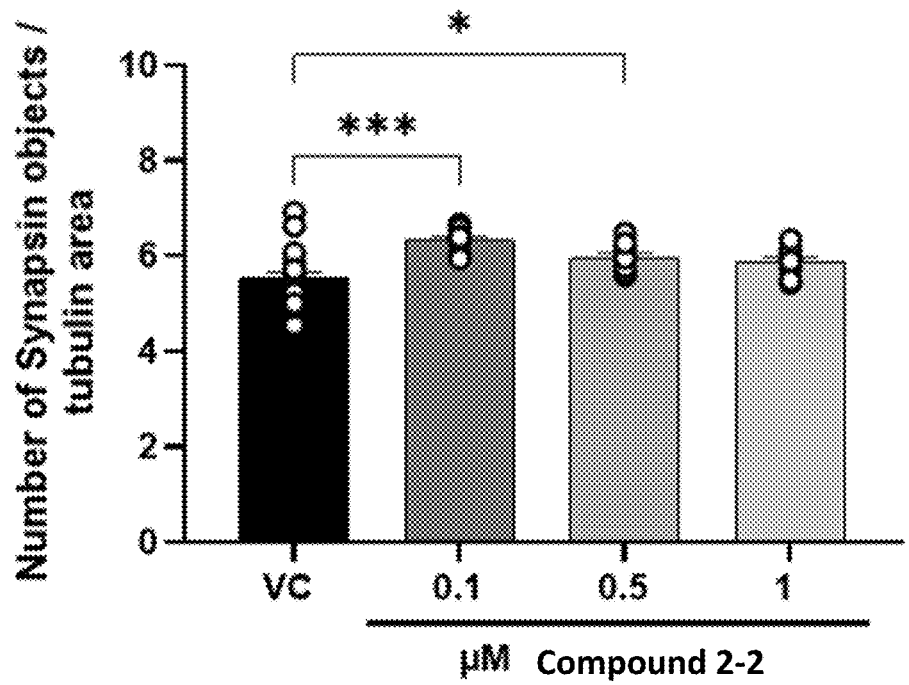
FIG. 63A is a graph showing the effect of compound 2-2 on synaptogenesis in treated cortical rat neurons.

Treatment of primary cortical neurons with compound 2-2 lead to significant changes in synaptogenesis as it is observed in FIG. 63A.

In the case of Compound 2-2 a significant increase in synaptogenesis compared to VC was observed at 0.5 µM and 0.1 µM, while the highest test concentration (1 µM) did not have any significant effect (FIG. 63A).

Figure 63B:
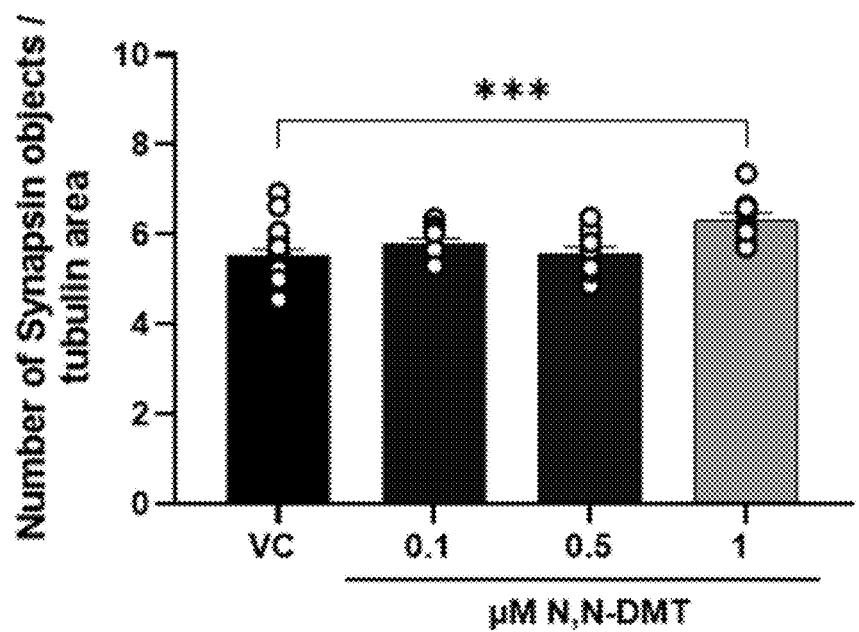
FIG. 63B is a graph showing the effect of N,N-DMT on synaptogenesis in treated cortical rat neurons.

Treatment with N,N-DMT at the highest concentration (1 µM) caused a significant increase in synaptogenesis (total number of synapsin positive objects normalized to the total tubulin III area) compared to VC, while no significance was detected at lower concentrations (FIG. 63B).

Figure 63C:
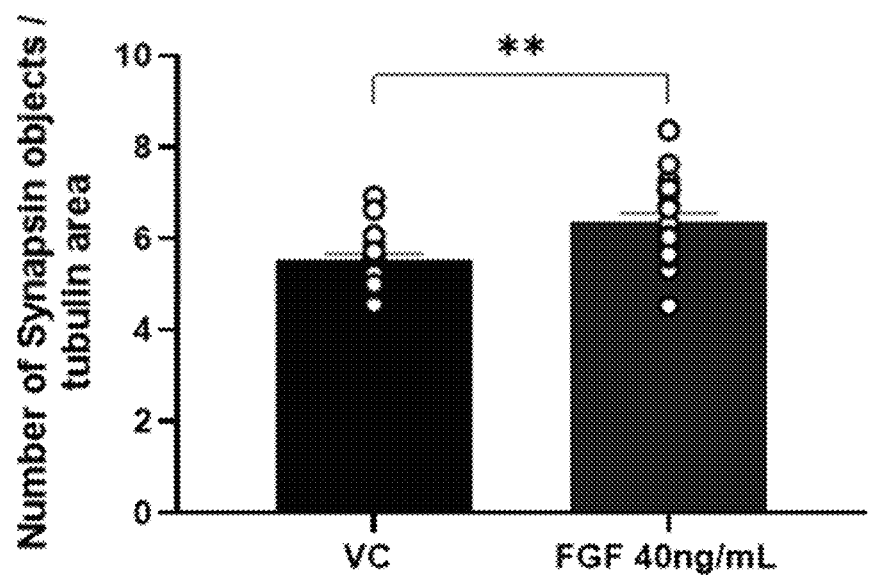
FIG. 63C is a graph showing the effect of FGF (R.I.) on synaptogenesis in treated cortical rat neurons.

Treatment of primary cortical neurons with R.I. FGF showed a significant increase in the total number of synapsin positive objects normalized to the total tubulin III area compared to VC, indicative of synaptogenesis (FIG. 63C).

Although the invention has been described with reference to the above examples, it will be understood that modifications and variations are encompassed within the spirit and scope of the invention. Accordingly, the invention is limited only by the following claims.

What is claimed is:

1. A method of treating a sleep dysfunction or a sleep disorder in a subject comprising administering to the subject a compound of Formula (I):

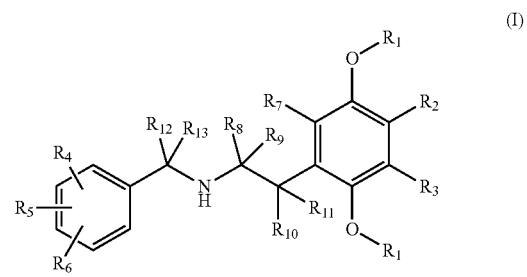

or a pharmaceutically acceptable salt thereof; wherein $R_1$ is independently at each position hydrogen, $C_1$-$C_6$ alkyl, or $C_1$-$C_6$ haloalkyl;

$R_2$, $R_3$ and $R_7$ are independently hydrogen, heterocycle, $C_1$-$C_6$ alkyl, $C_1$-$C_6$ haloalkyl, halogen, cyano, $OR_1$, $S(O)(=NH)R_1$, $S(O)_2R_1$, $S(O)R_1$ or $SR_1$, wherein at least one of $R_2$ and $R_3$ is hydrogen;

$R_4$, $R_5$ and $R_6$ are independently hydrogen, $C_1$-$C_6$ alkyl, $C_1$-$C_6$ haloalkyl, halogen, cyano, $OR_1$, $SR_1$, $(C=O)(R_{14})$, $O(C=O)(R_{14})$, $NO_2$, or $NH(C=O)(R_{14})$, wherein $R_{14}$ is $C_1$-$C_6$ alkyl, OH, or $OC_1$-$C_6$ alkyl;

$R_8$ and $R_9$ are independently hydrogen, $C_1$-$C_6$ alkyl, $C_1$-$C_4$ alkyl, $C_3$-$C_6$ cycloalkyl, $C_3$-$C_{10}$ cycloalkyl, $CH_2OH$, or $CH_2O$—$C_1$-$C_4$ alkyl;

$R_{10}$ and $R_{11}$ are independently hydrogen, halogen, $C_1$-$C_6$ alkyl, OH, $C_1$-$C_4$ alkyl, $C_3$-$C_6$ cycloalkyl, or $CH_2O$—$C_1$-$C_4$ alkyl;

$R_{12}$ is hydrogen, $CH_2OH$, $CH_2O$—$C_1$-$C_9$ alkyl, $C_3$-$C_{10}$ cycloalkyl, $CH_2OH$, or $CH_2O$—$C_1$-$C_4$ alkyl; and $R_{13}$ is hydrogen, $C_1$-$C_9$ alkyl, $C_3$-$C_{10}$ cycloalkyl, $CH_2OH$, or $CH_2O$—$C_1$-$C_4$ alkyl, thereby treating the sleep dysfunction or the sleep disorder in the subject.

2. The method of claim 1, wherein the sleep dysfunction or sleep disorder is a hypersomnia or a circadian rhythm sleep disorder.

3. The method of claim 2, wherein the hypersomnia is narcolepsy, long sleeper disorder, Kleine-Levine Syndrome, or a combination thereof.

4. The method of claim 3, wherein the hypersomnia is narcolepsy.

5. The method of claim 3, wherein the hypersomnia is long sleeper disorder.

6. The method of claim 3, wherein the hypersomnia is Kleine-Levine Syndrome.

7. The method of claim 2, wherein the circadian rhythm sleep disorder is delayed sleep-wake phase disorder, advanced sleep-wake phase disorder, a non-24 sleep wake rhythm, or a combination thereof.

8. The method of claim 7, wherein the circadian rhythm sleep disorder is delayed sleep-wake phase disorder.

9. The method of claim 7, wherein the circadian rhythm sleep disorder is advanced sleep-wake phase disorder.

10. The method of claim 7, wherein the circadian rhythm sleep disorder is a non-24 sleep wake rhythm.

11. The method of claim 1, wherein the compound is

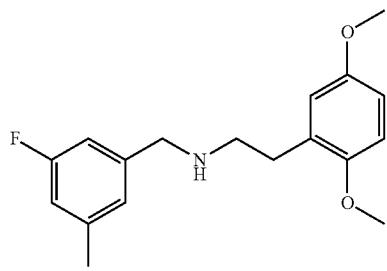

or a pharmaceutically acceptable salt thereof.

12. The method of claim 1, wherein the compound is:

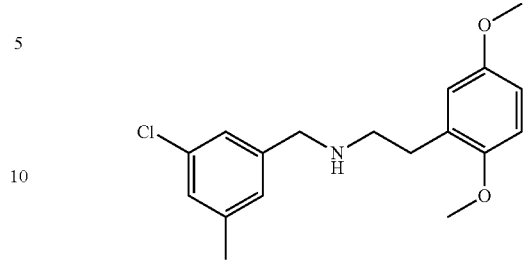

or a pharmaceutically acceptable salt thereof.

13. The method of claim 1, wherein the administering comprises sublingual, intracutaneous, subcutaneous, intramuscular, intraperitoneal, intravenous, intraarterial, intradermal, transdermal, oral, buccal, or nasal route of administration.

* * * * *